US012629331B2

(12) United States Patent
Proehl et al.

(10) Patent No.: US 12,629,331 B2
(45) Date of Patent: May 19, 2026

(54) COMPOSITIONS FOR THE TREATMENT OF SKIN CONDITIONS

(71) Applicant: Dermata Therapeutics, Inc., San Diego, CA (US)

(72) Inventors: Gerald Thomas Proehl, San Diego, CA (US); Christopher Joseph Nardo, San Diego, CA (US)

(73) Assignee: Dermata Therapeutics, Inc., San Diego, CA (US)

( * ) Notice: Subject to any disclaimer, the term of this patent is extended or adjusted under 35 U.S.C. 154(b) by 0 days.

(21) Appl. No.: 17/546,001

(22) Filed: Dec. 8, 2021

(65) Prior Publication Data

US 2022/0175660 A1     Jun. 9, 2022

Related U.S. Application Data

(60) Provisional application No. 63/281,526, filed on Nov. 19, 2021, provisional application No. 63/123,113, filed on Dec. 9, 2020.

(51) Int. Cl.
*A61K 8/98* (2006.01)
*A61K 8/02* (2006.01)
*A61K 8/66* (2006.01)
*A61Q 19/02* (2006.01)
*A61Q 19/08* (2006.01)

(52) U.S. Cl.
CPC ............ *A61K 8/987* (2013.01); *A61K 8/0245* (2013.01); *A61K 8/66* (2013.01); *A61Q 19/02* (2013.01); *A61Q 19/08* (2013.01)

(58) Field of Classification Search
None
See application file for complete search history.

(56) References Cited

U.S. PATENT DOCUMENTS

| | | | |
|---|---|---|---|
| 7,226,605 | B2 | 6/2007 | Suskind et al. |
| 7,824,693 | B2 | 11/2010 | Sanders |
| 11,311,496 | B2 | 4/2022 | Edelson |
| 2005/0196414 | A1* | 9/2005 | Dake ...................... A61P 17/14 |
| | | | 530/395 |
| 2008/0081049 | A1* | 4/2008 | Sanders ................. A61Q 19/08 |
| | | | 424/239.1 |
| 2010/0080853 | A1* | 4/2010 | Villani ................... A61K 8/987 |
| | | | 424/520 |
| 2010/0297095 | A1 | 11/2010 | Villani |
| 2016/0051646 | A1 | 2/2016 | Dake et al. |
| 2019/0185523 | A1 | 6/2019 | Jacky et al. |
| 2024/0099962 | A1 | 3/2024 | Proehl et al. |

FOREIGN PATENT DOCUMENTS

| | | |
|---|---|---|
| RU | 2176511 C1 | 12/2001 |
| RU | 2182820 C1 | 5/2002 |
| RU | 2183967 C1 | 6/2002 |
| RU | 2345782 C2 | 2/2009 |
| WO | 2019241296 A1 | 12/2019 |
| WO | 2020117698 A1 | 6/2020 |

OTHER PUBLICATIONS

Iriarte, C., et al. 2017 Clinical, Cosmetic and Investigational Dermatology 10: 289-298. (Year: 2017).*
Aquino, K.A.d.S. (2012 Sterilization by Gamma Irradiation, Gamma Radiation, Prof. Feriz Adrovic (Ed.), ISBN: 978-953-51-0316-5, InTech: pp. 171-206). (Year: 2012).*
Landau Marina (2006) "Combination of Chemical Peelings With Botulinum Toxin Injections and Dermal Fillers", Journal of Cosmetic Dermatology, 5(2):121-126.
Satriyasa B K. (2019) "Botulinum Toxin (Botox) A for Reducing the Appearance of Facial Wrinkles: A Literature Review of Clinical Use and Pharmacological Aspect", Clinical Cosmetic and Investigational Dermatology, 12:223-228.
Aoki et al. (Dec. 2001) "A Comparison of the Safety Margins of Botulinum Neurotoxin Serotypes A, B, and F in Mice", Toxicon, 39(12):1815-1820.
Beer et al. (Feb. 2006) "Comparative Evaluation of the Safety and Efficacy of Botulinum Toxin Type A and Topical Creams for Treating Moderate-to-Severe Glabellar Rhytides", Dermatologic Surgery, 32(2):184-197.

(Continued)

*Primary Examiner* — Marsha Tsay
(74) *Attorney, Agent, or Firm* — Mintz, Levin, Cohn, Ferris Glovsky and Popeo, P.C.

(57) ABSTRACT

The present disclosure relates to the treatment of a skin condition in a subject, including but not limited to one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles, comprising applying to the skin of the subject a first composition derived from one or more sponges, and a second composition comprising one or more botulinum toxins. Also provided are compositions for use in the treatment of a skin condition in a subject, including but not limited to hyperhidrosis, comprising a first composition and a second composition, wherein (a) the first composition comprises Spongilla; and (b) the second composition comprises one or more botulinum toxins. Also provided are kits, including kits for the treatment of a skin condition in a subject including but not limited to hyperhidrosis, comprising a first composition and a second composition, wherein the first composition comprises Spongilla, and the second composition comprises one or more botulinum toxins.

13 Claims, 5 Drawing Sheets

(56)               References Cited

OTHER PUBLICATIONS

Blitzer et al. (Sep. 1993) "Botulinum Toxin for the Treatment of Hyperfunctional Lines of the Face", Archives of Otorhinolaryngology-Head & Neck Surgery, 119:1018-1022.

Brin et al. (Dec. 2009) "Safety and Tolerability of OnabotulinumtoxinA in the Treatment of Facial Lines: A Meta-Analysis of Individual Patient Data From Global Clinical Registration Studies in 1678 Participants", Journal of the American Academy of Dermatology, 61(6):961-970.

Cox et al. (2005) "Social Implications of Hyperdynamic Facial Lines and Patient Satisfaction Outcomes.", International ophthalmology clinics, 45:13-24.

Fernandez et al. (Nov. 2012) "Botulinum Neurotoxin Serotype a Specific Cell-Based Potency Assay to Replace the Mouse Bioassay", PLOS ONE, 7(11):e49516.

Fleiss (Jun. 2013) "Statistical Methods for Rates and Proportions, 3rd Edition", Wiley and Sons, 800 pages.

Garcia et al. (Jan. 1996) "Cosmetic Denervation of the Muscles of Facial Expression with Botulinum Toxin A Dose-Response Study", Dermatologic Surgery, 22(1):39-43.

Glaser et al. (Jan. 2018) "Topical Glycopyrronium Tosylate for the Treatment of Primary Axillary Hyperhidrosis: Results from the ATMOS-1 and ATMOS-2 Phase 3 Randomized Controlled Trials", Journal of the American Academy of Dermatology.

Goschel et al. (Sep. 1997) "Botulinum A Toxin Therapy: Neutralizing and Nonneutralizing Antibodies—Therapeutic Consequences", Experimental Neurology, 147;96-102.

Hambleton (Jan. 1992) "Clostridium Botulinum Toxins: A General Review of Involvement in Disease, Structure, Mode of Action and Preparation for Clinical Use", Journal of Neurology, 239:16-20.

Huber et al. (May 2008) "The Intercostal NMJ Assay: A New Alternative to the Conventional LD50 Assay for the Determination of the Therapeutic Potency of Botulinum Toxin Preparations", Alternatives to Laboratory Animals, 36(2):141-152.

Khan (Jan. 2001) "Aesthetic Surgery: Diagnosing and Healing the Miscues of Human Facial Expression", Ophthalmic plastic and reconstructive surgery, 17(1):4-6.

Koblenzer (Oct. 2005) "The Emotional Impact of Chronic and Disabling Skin Disease: A Psychoanalytic Perspective", Dermatologic Clinics, 23(4):619-627.

Musnier et al. (Feb. 2004) "Visual Evaluation in Vivo of Complexion Radiance Using the CLBT Sensory Methodology", Skin Research and Technology, 10(1):50-56.

Rasetti-Escargucil et al. (Apr. 2009) "Measurement of Botulinum Types A, B and E Neurotoxicity Using the Phrenic Nerve-Hemidiaphragm: Improved Precision With In-Bred Mice", Toxicon, 53;503-511.

Sesardic et al. (May 1996) "Refinement and Validation of an Alternative Bioassay for Potency Testing of Therapeutic Botulinum type A Toxin", Pharmacology Toxicology, 78;283-288.

Trussell et al. (2011) "Contraceptive Efficacy", Contraceptive Technology: Twentieth Revised Edition. New York NY: Ardent Media, 779-863 pages.

Extended European Search Report for EP Application No. 21904337.9, mailed on Apr. 24, 2025, 10 pages.

Krupska et al. (Aug. 4, 2020) "1 H NMR Spectroscopy Study of Structural Water in Rehydrated Biocomposite of Spongilla Lacustris Freshwater Demosponge Origin", Applied Physics A, 126(8): 667 (7 Pages).

Udompataikul (Dec. 1, 2012) "The Study on Effects and Safety of Spongilla lacustris in 3% Hydrogen Peroxide Solution on Rat Skin", Journal of the Medical Association of Thailand, 95 (Suppl.12):S15-S20.

* cited by examiner

Large biomolecule (>100 kD)

Spicule creates channel for large biomolecules

Botulinum toxin (~900kD) penetrates stratum corneum into dermis

FIG. 3A
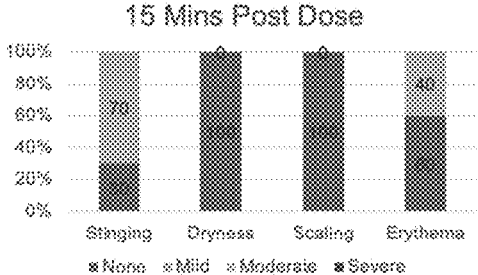
FIG. 3B
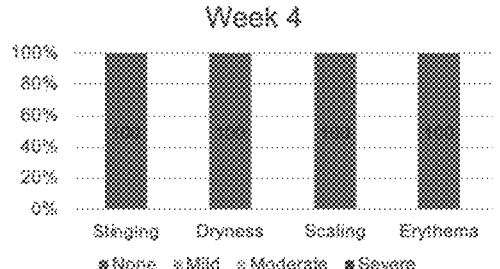
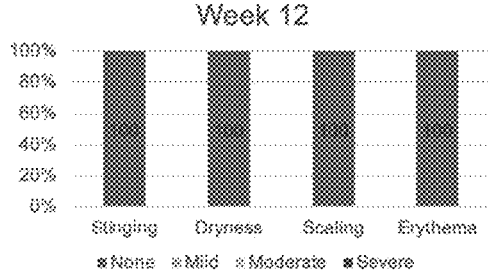
FIG. 3C
FIG. 3D
FIG. 4A
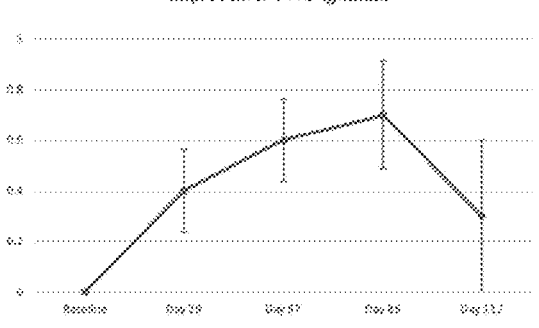
Range of improvement from 1 to 5 points
FIG. 4B
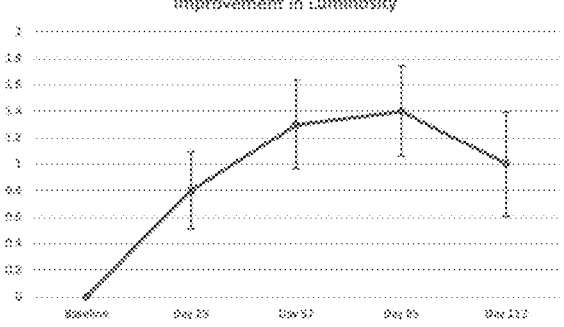

FIG. 5A
FIG. 5B
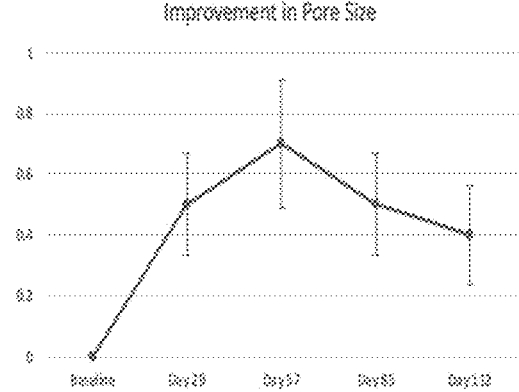
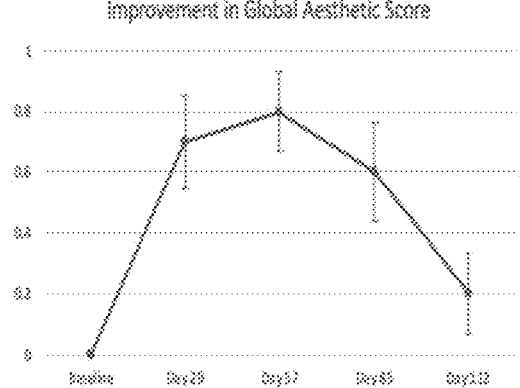
FIG. 6A
FIG. 6B
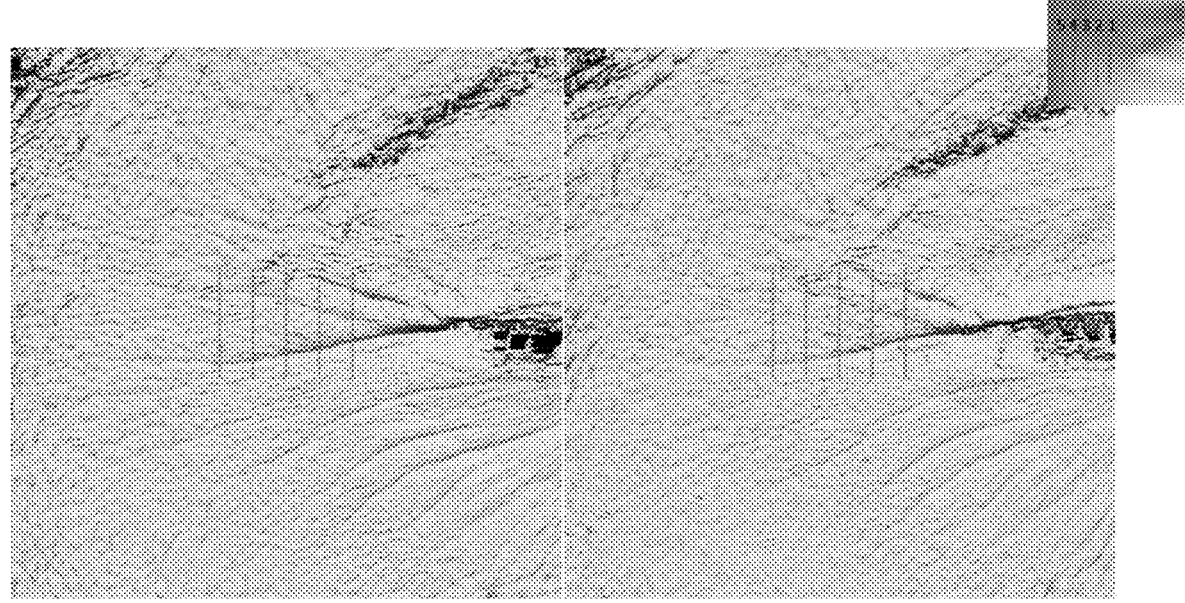

COMPOSITIONS FOR THE TREATMENT OF SKIN CONDITIONS

CROSS REFERENCE TO RELATED APPLICATIONS

This application claims priority to U.S. Provisional Application No. 63/123,113, filed Dec. 9, 2020, and U.S. Provisional Application No. 63/281,526, filed Nov. 19, 2021, which are hereby incorporated by reference in their entirety and for all purposes.

FIELD

The present disclosure relates to the treatment of a skin condition in a subject. The skin conditions can include, but are not limited to, luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, forehead wrinkles, and the like. The treatments can include, for example, applying to the skin of the subject a first composition derived from one or more sponges, and a second composition comprising one or more botulinum toxins.

In some embodiments, the present disclosure relates to the treatment of a skin condition as described herein in a subject, for example, by a method that includes applying to the skin of the subject a first composition comprising Spongilla, and a second composition comprising one or more botulinum toxins. The disclosure also relates to a products or kits for the treatment of skin conditions, as described herein, in a subject, the kit including for example, a first composition comprising Spongilla, and a second composition comprising one or more botulinum toxins. The disclosure also relates to a first composition comprising Spongilla for use in a method of treating a condition as set forth herein, wherein the method comprises administering to the subject an effective amount of the first composition in combination with an effective amount of a second composition, the second composition comprising one or more botulinum toxins.

BACKGROUND

Skin conditions in subjects, including human subjects, such as luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, forehead wrinkles, and the like can be difficult to treat. Embodiments described herein generally relate to methods of treatment, kits and compositions that address challenges in treating conditions such as those described above.

SUMMARY OF THE INVENTION

Generally, embodiments described herein relate to improved methods of treating skin conditions, as well as compositions and kits related to the same. As already noted, skin conditions in subjects, including human subjects, such as luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, forehead wrinkles, and the like can be difficult to treat. In some cases, topical treatment of these skin conditions is successful, but proper usage of topical therapies is often more complex and may require injections or other procedures administered by health care or cosmetic providers. As a result, adherence and full treatment completion may be a particularly significant issue for such topical therapies. Poor subject adherence to treatment regimens using topical therapies, development of resistance to medications, and increased costs may contribute to treatment failure. Furthermore, over-the-counter and other topicals applied or administered by the patients can be less than effective due to limitations of the products. Thus, a method of treating these skin conditions in subjects using topical products having simple usage paradigms, for example that is applied over a certain interval or frequency may have the opportunity to exhibit greater treatment success due to improved subject adherence.

A number of skin conditions in subjects have been treated with the topical application of materials derived from naturally occurring sponges, such as Spongilla *lacustris*. Some materials derived from Spongilla are promoted for the treatment of certain skin conditions, such as acne vulgaris, for example. The Spongilla contains organic and inorganic compounds. The total lipid content is approximately 5% of the biomass of the dried sponge and the protein is composed of spongin or sclerotized collagen. The polysaccharides and N-acetyl-D-glucosamine (NAG) are part of chitin and chitosan that has been reported to be an important component within the skeletal fibers of Spongilla *lacustris* and detected $750\pm1.5$ µg N-acetyl-D-glucosamine per 1 mg of spicule-free skeleton. Chitin and chitosan are described as a family of linear polysaccharides consisting of varying amounts of α or β (1-4) linked residues of N-acetyl-2 amino-2-deoxy-D-glucose and 2-amino-2-deoxy-D glucose residues. In α-chitin, the chains are arranged in sheets or stacks, the chains in any one sheet having the same direction or 'sense'. In β-chitin, adjacent sheets along the c axis have the same direction; the sheets are parallel, while in α-chitin adjacent sheets along the c axis have the opposite direction, they are antiparallel. Chitin is deacetylated into chitosan and can be further degraded into N-acetyl-D-glucosamine (NAG) units. Chitosan preparations are classified into native chitosan, chitosan formulations, complexes and derivatives with other substances. Chitosan can be used to prevent or treat wound and burn infections not only because of its intrinsic antimicrobial properties, but also by virtue of its ability to deliver extrinsic antimicrobial agents to wounds and burns. Chitosan is water-insoluble and highly viscous in dilute acidic solutions. Soluble chitosan oligosaccharides were found to be instrumental in suppressing the LPS-induced nuclear factor kappa-light-chain-enhancer of activated B cell (NF-κB)-dependent inflammatory gene expression, and this was associated with reduced nuclear translocation of NF-κB. Chitosan has also been demonstrated to have an antimicrobial effect against *P. acnes* and *S. aureus*. Chitosan of differing molecular weight (MW) were tested on antibacterial activity, chitosan of low MW (50-190 kDa), medium MW (190-310 kDa), and high MW (310-375+kDa). Concentrations of 2.5, 5, 10, and 20 µg/mL were tested against *P. acnes* with high molecular weight having a greater effect against the gram-positive bacteria *P. acnes* demonstrated in a clinical study that with acne vulgaris subjects, NAG quickly reduced the number of acne lesions over an 8-week period and was better tolerated by the subjects than 10% benzoyl peroxide.

Skin conditions such as luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, forehead wrinkles, and the like can be difficult to effectively and conveniently treat. Treatment of these conditions can be limited by the ability of the administered treatment material, such as a botulinum toxin, to adequately penetrate the skin when applied through typical topical approaches. More aggressive approaches to penetrate the skin, such as injections for example, can produce injection site pain and discomfort. Given the nature of the target tissue for many of the conditions described herein, there is no adequate treatment that provides efficacy and for that has good patient compliance. Thus, a topical product with a simple usage paradigm, that would allow for adequate penetration of botulinum toxin, for example, past the stratum corneum and into the dermis, may exhibit greater compliance and adoption due to improved efficacy and tolerability of the treatment.

The inventors of the subject matter disclosed herein have discovered that an important component of materials derived from Spongilla are the siliceous spicules that comprise the skeletal structure of Spongilla. The inventors have discovered the spicules penetrate the stratum corneum of the skin of a subject during application and promote sloughing of the keratinocytes. The inventors of the subject matter disclosed herein have also discovered that the spicules derived from Spongilla are useful in facilitating and permitting certain therapeutic compounds and compositions to penetrate into the skin of subjects to which the spicules are applied, which compounds and compositions would otherwise not be able to penetrate the skin of the subject in order to reach their therapeutic targets and treat certain skin conditions. Among the compounds and compositions that may better penetrate the skin in the presence of materials derived from Spongilla are products containing botulinum toxins.

Products containing botulinum toxins have been demonstrated to be useful for the treatment of a number of medical conditions, including those affecting the skin of subjects. For example, products containing botulinum toxins have been approved for the treatment of subjects suffering from hyperhidrosis (excessive sweating). There have also been reports that the topical application of products containing a botulinum toxin might be useful in the treatment of subjects suffering from acne (see, for example, U.S. Pat. No. 7,226, 605). However, the difficulties of using products containing one or more botulinum toxins for the topical treatment of skin conditions in subjects is well known. One difficulty in the topical use of botulinum toxin-containing products is the recognition that the endogenous non-toxin proteins in a botulinum toxin complex obtained from *Clostridium botulinum* bacteria (viz., the non-toxic hemagglutinin and non-hemagglutinin proteins) decrease the ability of the toxin to diffuse through the skin epithelium. These effects can be further exacerbated when an exogenous stabilizer, such as albumin, binds to botulinum toxin during conventional manufacturing processes. Therefore, the application of compositions comprising Spongilla, for example in the form of a powder, to the skin of a subject will help facilitate the penetration of topically-applied products containing one or more botulinum toxins into the skin of the subject, leading to the use of new treatment regimens for sometimes difficult to treat skin conditions.

In one aspect is provided a method of treating a skin condition in a subject, comprising applying to the skin of the subject a first composition comprising Spongilla, and a second composition comprising one or more botulinum toxins.

In one aspect is provided a method of treating a skin condition in a subject, comprising applying to the skin of the subject a first composition comprising one or more sponges, and a second composition comprising one or more botulinum toxins. In one aspect, the compositions are derived from one or more sponges. In another aspect, the one or more sponges may be marine sponges or freshwater sponges. In another aspect, the one or more sponges is a marine sponge. In another aspect, the sponge is a freshwater sponge. In another aspect, the compositions are derived from sponges of the phylum Porifera. In another aspect, the compositions are derived from sponges of the class Demospongiae. In another aspect, the compositions are derived from sponges of the order Spongdilla. In another aspect, the compositions are derived from sponges of the family Spongillidae. In another aspect, the compositions are derived from sponges of the genus Spongilla. In another aspect, the compositions are derived from sponges of the species Spongilla *lacustris*. In another aspect, the compositions are derived from sponges of the order Haplosclerida. In another aspect, the compositions are derived from sponges of the family Chalinidea. In another aspect, the compositions are derived from sponges of the genus Halciona.

In one aspect is provided a method of treating a skin condition in a subject, comprising applying to the skin of the subject a first composition comprising one or more sponges, and a second composition comprising one or more botulinum toxins, wherein (a) the second composition is comprises one or more botulinum toxin type selected from botulinum toxin type A, botulinum toxin type B, botulinum toxin type C1, botulinum toxin type C2, botulinum toxin type D, botulinum toxin type E, botulinum toxin type F and botulinum toxin type G; and (b) the skin condition in the subject is selected from luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, forehead wrinkles, acne vulgaris, acne rosacea type 1, acne rosacea type 2, psoriasis, hyperhidrosis, alopecia areata, androgenic alopecia, keloids, and hypertrophic scars, hidradenitis suppurativa, Raynaud phenomenon, post-herpetic neuralgia, Hailey-Hailey disease, IgA bullous dermatosis, epidermolysis bullosa Simplex Weber-Cockane, Darier disease, pachyonchia congenita, aquagenic keratoderma, notalgia paresthetic, pompholyx (dyshidrotic eczema), chromhidrosis and bromhidrosis, eccrine nevus, facial rhytides, atrophic acne scars, and melasma. In another aspect, the one or more sponges may be marine sponges or freshwater sponges. In another aspect, the one or more sponges is a marine sponge. In another aspect, the sponge is a freshwater sponge. In another aspect, the compositions are derived from sponges of the phylum Porifera. In another aspect, the compositions are derived from sponges of the class Demospongiae. In another aspect, the compositions are derived from sponges of the order Spongdilla. In another aspect, the compositions are derived from sponges of the family Spongillidae. In another aspect, the compositions are derived from sponges of the genus Spongilla. In another aspect, the compositions are derived from sponges of the species Spongilla *lacustris*. In another aspect, the compositions are derived from sponges of the order Haplosclerida. In another aspect, the compositions are derived from sponges of the family Chalinidea. In another aspect, the compositions are derived from sponges of the genus Halciona.

In one aspect is provided a method of treating a skin condition in a subject, comprising applying to the skin of the subject a first composition and a second composition, wherein (a) the first composition comprises one or more sponges; (b) the second composition is comprises one or more botulinum toxin type selected from botulinum toxin type A, botulinum toxin type B, and botulinum toxin type E; and (c) the skin condition in the subject is selected from luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, forehead wrinkles, acne vulgaris, acne rosacea type 1, acne rosacea type 2, psoriasis, hyperhidrosis, alopecia areata, androgenic alopecia, keloids, and hypertrophic scars, hidradenitis suppurativa, Raynaud phenomenon, post-herpetic neuralgia, Hailey-Hailey disease, IgA bullous dermatosis, epidermolysis bullosa Simplex Weber-Cockane, Darier disease, pachyonchia congenita, aquagenic keratoderma, notalgia paresthetic, pompholyx (dyshidrotic eczema), chromhidrosis and bromhidrosis, eccrine nevus, facial rhytides, atrophic acne scars, and melasma. In another aspect, the one or more sponges may be marine sponges or freshwater sponges. In another aspect, the one or more sponges is a marine sponge. In another aspect, the sponge is a freshwater sponge. In another aspect, the compositions are derived from sponges of the phylum Porifera. In another aspect, the compositions are derived from sponges of the class Demospongide. picIn another aspect, the compositions are derived from sponges of the family Spongillidae. In another aspect, the compositions are derived from sponges of the genus Spongilla. In another aspect, the compositions are derived from sponges of the species Spongilla *lacustris*. In another aspect, the compositions are derived from sponges of the order Haplosclerida. In another aspect, the compositions are derived from sponges of the family Chalinidea. In another aspect, the compositions are derived from sponges of the genus Halciona.

In another aspect is provided a kit, comprising a first composition and a second composition, wherein (a) the first composition comprises one or more sponges; and (b) the second composition comprises one or more botulinum toxins. In another aspect is provided a kit comprising a first composition and a second composition, wherein (a) the first composition comprises a Spongilla; and (b) the second composition comprises one or more botulinum toxins, wherein the kit is used for the treatment of a skin condition in a subject. In another aspect is provided a kit comprising a first composition and a second composition, wherein (a) the first composition comprises a Spongilla; and (b) the second composition comprises one or more botulinum toxins, wherein the kit is for use in the treatment of a skin condition in a subject. In another aspect is provided a kit as described herein, wherein the skin condition in the subject is selected from luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, forehead wrinkles, acne vulgaris, acne rosacea type 1, acne rosacea type 2, psoriasis, hyperhidrosis, alopecia areata, androgenic alopecia, keloids, and hypertrophic scars, hidradenitis suppurativa, Raynaud phenomenon, post-herpetic neuralgia, Hailey-Hailey disease, IgA bullous dermatosis, epidermolysis bullosa Simplex Weber-Cockane, Darier disease, pachyonchia congenita, aquagenic keratoderma, notalgia paresthetic, pompholyx (dyshidrotic eczema), chromhidrosis and bromhidrosis, eccrine nevus, facial rhytides, atrophic acne scars, and melasma. In another aspect, the one or more sponges may be marine sponges or freshwater sponges. In another aspect, the one or more sponges is a marine sponge. In another aspect, the sponge is a freshwater sponge. In another aspect, the compositions are derived from sponges of the phylum Porifera. In another aspect, the compositions are derived from sponges of the class Demospongiae. In another aspect, the compositions are derived from sponges of the order Spongdilla. In another aspect, the compositions are derived from sponges of the family Spongillidae. In another aspect, the compositions are derived from sponges of the genus Spongilla. In another aspect, the compositions are derived from sponges of the species Spongilla *lacustris*. In another aspect, the compositions are derived from sponges of the order Haplosclerida. In another aspect, the compositions are derived from sponges of the family Chalinidea. In another aspect, the compositions are derived from sponges of the genus Halciona.

In another aspect is provided a composition comprising a first composition and a second composition for use as a medicament, wherein the (a) the first composition comprises one or more sponges; and (b) the second composition one or more botulinum toxins. In another aspect is provided a composition comprising a first composition and a second composition for use as a medicament, wherein the (a) the first composition comprises a Spongilla *lacustris*; and (b) the second composition one or more botulinum toxins. In another aspect is provided such compositions for use as a medicament for the treatment of a skin condition in a subject. In another aspect is such combinations for use as a medicament for the treatment of a skin condition in a subject, wherein the skin condition in the subject is selected from luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, forehead wrinkles, acne vulgaris, acne rosacea type 1, acne rosacea type 2, psoriasis, hyperhidrosis, alopecia areata, androgenic alope-cia, keloids, and hypertrophic scars, hidradenitis suppura-tiva, Raynaud phenomenon, post-herpetic neuralgia, Hailey-Hailey disease, IgA bullous dermatosis, epidermolysis bullosa Simplex Weber-Cockane, Darier disease, pachyon-chia congenita, aquagenic keratoderma, notalgia paresthetic, pompholyx (dyshidrotic eczema), chromhidrosis and bro-mhidrosis, eccrine nevus, facial rhytides, atrophic acne scars, and melasma. In another aspect, the one or more sponges may be marine sponges or freshwater sponges. In another aspect, the one or more sponges is a marine sponge. In another aspect, the sponge is a freshwater sponge. In another aspect, the compositions are derived from sponges of the phylum Porifera. In another aspect, the compositions are derived from sponges of the class Demospongiae. In another aspect, the compositions are derived from sponges of the order Spongdilla. In another aspect, the compositions are derived from sponges of the family Spongillidae. In another aspect, the compositions are derived from sponges of the genus Spongilla. In another aspect, the compositions are derived from sponges of the species Spongilla *lacustris*. In another aspect, the compositions are derived from sponges of the order Haplosclerida. In another aspect, the compositions are derived from sponges of the family Chalinidea. In another aspect, the compositions are derived from sponges of the genus Halciona.

In another aspect is provided a composition comprising a first composition and a second composition for use in the treatment of a skin condition in a subject, wherein (a) the first composition comprises one or more sponges; and (b) the second composition one or more botulinum toxins. In another aspect is provided a combination comprising a first composition and a second composition for use in the treat-ment of a skin condition in a subject, wherein (a) the first composition comprising a sponge; and (b) the second com-position one or more botulinum toxins. In another aspect is such compositions for use in the treatment of a skin condi-tion in a subject, wherein the skin condition in the subject is selected from luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, cor-rection of facila depressions, either due to injury or age-related, perioral wrinkles, lip commissures, crow's feet, forehead wrinkles, acne vulgaris, acne rosacea type 1, acne rosacea type 2, psoriasis, hyperhidrosis, alopecia areata, androgenic alopecia, keloids, and hypertrophic scars, hidradenitis suppurativa, Raynaud phenomenon, post-her-petic neuralgia, Hailey-Hailey disease, IgA bullous derma-tosis, epidermolysis bullosa Simplex Weber-Cockane, Darier disease, pachyonchia congenita, aquagenic kerato-derma, notalgia paresthetic, pompholyx (dyshidrotic eczema), chromhidrosis and bromhidrosis, eccrine nevus, facial rhytides, atrophic acne scars, and melasma. In another aspect, the one or more sponges may be marine sponges or freshwater sponges. In another aspect, the one or more sponges is a marine sponge. In another aspect, the sponge is a freshwater sponge. In another aspect, the compositions are derived from sponges of the phylum Porifera. In another aspect, the compositions are derived from sponges of the class Demospongiae. In another aspect, the compositions are derived from sponges of the order Spongdilla. In another aspect, the compositions are derived from sponges of the family Spongillidae. In another aspect, the compositions are derived from sponges of the genus Spongilla. In another aspect, the compositions are derived from sponges of the species Spongilla *lacustris*. In another aspect, the composi-tions are derived from sponges of the order Haplosclerida. In another aspect, the compositions are derived from sponges of the family Chalinidea. In another aspect, the compositions are derived from sponges of the genus Halciona.

In another aspect is provided a composition for the manufacture of a medicament for the treatment of a skin condition in a subject, wherein the composition comprises a first composition and a second composition wherein (a) the first composition comprises one or more sponges; and (b) the second composition one or more botulinum toxins. In another aspect is provided a composition for the manufac-ture of a medicament for the treatment of a skin condition in a subject, wherein the composition comprises a first com-position and a second composition wherein (a) the first composition comprising a Spongilla *lacustris*; and (b) the second composition one or more botulinum toxins. In another aspect is provided a composition for the manufac-ture of a medicament for the treatment of a skin condition in a subject, wherein the skin condition in the subject is selected from luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, cor-rection of facila depressions, either due to injury or age-related, perioral wrinkles, lip commissures, crow's feet, forehead wrinkles, acne vulgaris, acne rosacea type 1, acne rosacea type 2, psoriasis, hyperhidrosis, alopecia areata, androgenic alopecia, keloids, and hypertrophic scars, hidradenitis suppurativa, Raynaud phenomenon, post-her-petic neuralgia, Hailey-Hailey disease, IgA bullous derma-tosis, epidermolysis bullosa Simplex Weber-Cockane, Darier disease, pachyonchia congenita, aquagenic kerato-derma, notalgia paresthetic, pompholyx (dyshidrotic eczema), chromhidrosis and bromhidrosis, eccrine nevus, facial rhytides, atrophic acne scars, and melasma. In another aspect, the one or more sponges may be marine sponges or freshwater sponges. In another aspect, the one or more sponges is a marine sponge. In another aspect, the sponge is a freshwater sponge. In another aspect, the compositions are derived from sponges of the phylum Porifera. In another aspect, the compositions are derived from sponges of the class Demospongiae. In another aspect, the compositions are derived from sponges of the order Spongdilla. In another aspect, the compositions are derived from sponges of the family Spongillidae. In another aspect, the compositions are derived from sponges of the genus Spongilla. In another aspect, the compositions are derived from sponges of the species Spongilla *lacustris*. In another aspect, the composi-tions are derived from sponges of the order Haplosclerida. In another aspect, the compositions are derived from sponges of the family Chalinidea. In another aspect, the compositions are derived from sponges of the genus Halciona.

In one aspect is provided a method of treating a skin condition in a subject, comprising applying to the skin of the subject a first composition comprising Spongilla, and a second composition comprising one or more botulinum toxins, wherein (a) the second composition is comprises one or more botulinum toxin type selected from botulinum toxin type A, botulinum toxin type B, botulinum toxin type C1, botulinum toxin type C2, botulinum toxin type D, botulinum toxin type E, botulinum toxin type F and botulinum toxin type G; and (b) the skin condition in the subject is selected from luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, forehead wrinkles, acne vulgaris, acne rosacea type 1, acne rosacea type 2, psoriasis, hyperhidrosis, alopecia areata, androgenic alopecia, keloids, and hypertrophic scars, hidradenitis suppurativa, Raynaud phenomenon, post-herpetic neuralgia, Hailey-Hailey disease, IgA bullous dermatosis, epidermolysis bullosa Simplex Weber-Cockane, Darier disease, pachyonchia congenita, aquagenic keratoderma, notalgia paresthetic, pompholyx (dyshidrotic eczema), chromhidrosis and bromhidrosis, eccrine nevus, facial rhytides, atrophic acne scars, and melasma.

In one aspect is provided a method of treating a skin condition in a subject, comprising applying to the skin of the subject a first composition and a second composition, wherein (a) the first composition comprises Spongilla powder; (b) the second composition is comprises one or more botulinum toxin type selected from botulinum toxin type A, botulinum toxin type B, and botulinum toxin type E; and (c) the skin condition in the subject is selected from luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, forehead wrinkles, acne vulgaris, acne rosacea type 1, acne rosacea type 2, psoriasis, hyperhidrosis, alopecia areata, androgenic alopecia, keloids, and hypertrophic scars, hidradenitis suppurativa, Raynaud phenomenon, post-herpetic neuralgia, Hailey-Hailey disease, IgA bullous dermatosis, epidermolysis bullosa Simplex Weber-Cockane, Darier disease, pachyonchia congenita, aquagenic keratoderma, notalgia paresthetic, pompholyx (dyshidrotic eczema), chromhidrosis and bromhidrosis, eccrine nevus, facial rhytides, atrophic acne scars, and melasma.

In another aspect is provided a kit, comprising a first composition and a second composition, wherein (a) the first composition comprises a Spongilla; and (b) the second composition comprises one or more botulinum toxins. In another aspect is provided a kit comprising a first composition and a second composition, wherein (a) the first composition comprises a Spongilla; and (b) the second composition comprises one or more botulinum toxins, wherein the kit is used for the treatment of a skin condition in a subject. In another aspect is provided a kit comprising a first composition and a second composition, wherein (a) the first composition comprises a Spongilla; and (b) the second composition comprises one or more botulinum toxins, wherein the kit is for use in the treatment of a skin condition in a subject. In another aspect is provided a kit as described herein, wherein the skin condition in the subject is selected from luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, forehead wrinkles, acne vulgaris, acne rosacea type 1, acne rosacea type 2, psoriasis, hyperhidrosis, alopecia areata, androgenic alopecia, keloids, and hypertrophic scars, hidradenitis suppurativa, Raynaud phenomenon, post-herpetic neuralgia, Hailey-Hailey disease, IgA bullous dermatosis, epidermolysis bullosa Simplex Weber-Cockane, Darier disease, pachyonchia congenita, aquagenic keratoderma, notalgia paresthetic, pompholyx (dyshidrotic eczema), chromhidrosis and bromhidrosis, eccrine nevus, facial rhytides, atrophic acne scars, and melasma.

In another aspect is provided a composition comprising a first composition and a second composition for use as a medicament, wherein the (a) the first composition comprises a Spongilla; and (b) the second composition one or more botulinum toxins. In another aspect is provided a composition comprising a first composition and a second composition for use as a medicament, wherein the (a) the first composition comprises a Spongilla lacustris; and (b) the second composition one or more botulinum toxins. In another aspect is provided such compositions for use as a medicament for the treatment of a skin condition in a subject. In another aspect is such combinations for use as a medicament for the treatment of a skin condition in a subject, wherein the skin condition in the subject is selected from luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, forehead wrinkles, acne vulgaris, acne rosacea type 1, acne rosacea type 2, psoriasis, hyperhidrosis, alopecia areata, androgenic alopecia, keloids, and hypertrophic scars, hidradenitis suppurativa, Raynaud phenomenon, post-herpetic neuralgia, Hailey-Hailey disease, IgA bullous dermatosis, epidermolysis bullosa Simplex Weber-Cockane, Darier disease, pachyonchia congenita, aquagenic keratoderma, notalgia paresthetic, pompholyx (dyshidrotic eczema), chromhidrosis and bromhidrosis, eccrine nevus, facial rhytides, atrophic acne scars, and melasma.

In another aspect is provided a composition comprising a first composition and a second composition for use in the treatment of a skin condition in a subject, wherein (a) the first composition comprising a Spongilla; and (b) the second composition one or more botulinum toxins. In another aspect is provided a combination comprising a first composition and a second composition for use in the treatment of a skin condition in a subject, wherein (a) the first composition comprising a Spongilla *lacustris*; and (b) the second composition one or more botulinum toxins. In another aspect is such compositions for use in the treatment of a skin condition in a subject, wherein the skin condition in the subject is selected from luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, forehead wrinkles, acne vulgaris, acne rosacea type 1, acne rosacea type 2, psoriasis, hyperhidrosis, alopecia areata, androgenic alopecia, keloids, and hypertrophic scars, hidradenitis suppurativa, Raynaud phenomenon, post-herpetic neuralgia, Hailey-Hailey disease, IgA bullous dermatosis, epidermolysis bullosa Simplex Weber-Cockane, Darier disease, pachyonchia congenita, aquagenic keratoderma, notalgia paresthetic, pompholyx (dyshidrotic eczema), chromhidrosis and bromhidrosis, eccrine nevus, facial rhytides, atrophic acne scars, and melasma.

In another aspect is provided a composition for the manufacture of a medicament for the treatment of a skin condition in a subject, wherein the composition comprises a first composition and a second composition wherein (a) the first composition comprising a Spongilla; and (b) the second composition one or more botulinum toxins. In another aspect is provided a composition for the manufacture of a medicament for the treatment of a skin condition in a subject, wherein the composition comprises a first composition and a second composition wherein (a) the first composition comprising a Spongilla *lacustris*; and (b) the second composition one or more botulinum toxins. In another aspect is provided a composition for the manufacture of a medicament for the treatment of a skin condition in a subject, wherein the skin condition in the subject is selected from luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, forehead wrinkles, acne vulgaris, acne rosacea type 1, acne rosacea type 2, psoriasis, hyperhidrosis, alopecia areata, androgenic alopecia, keloids, and hypertrophic scars, hidradenitis suppurativa, Raynaud phenomenon, post-herpetic neuralgia, Hailey-Hailey disease, IgA bullous dermatosis, epidermolysis bullosa Simplex Weber-Cockane, Darier disease, pachyonchia congenita, aquagenic keratoderma, notalgia paresthetic, pompholyx (dyshidrotic eczema), chromhidrosis and bromhidrosis, eccrine nevus, facial rhytides, atrophic acne scars, and melasma.

BRIEF DESCRIPTION OF THE DRAWINGS

FIGS. 3A-3D show graphs illustrating local tolerability of compounds and formulations consistent with the present disclosure at 15 minutes post dose (FIG. 3A), 4 weeks post dose (FIG. 3B), 8 weeks post dose (FIG. 3C), and 12 weeks post dose (FIG. 3D).

FIGS. 4A-4B show graphs illustrating mean improvements in skin brightness (FIG. 4A) and luminosity (FIG. 4B) after treatment with compounds and formulations consistent with the present disclosure.

FIGS. 5A-5B show graphs illustrating mean improvements in pore size (FIG. 5A) and global aesthetic score (FIG. 5B) after treatment with compounds and formulations consistent with the present disclosure.

FIGS. 6A-6B are images of a facial wrinkles at a second visit (FIG. 6A) and a fourth visit (FIG. 6B) for treatment with compounds and formulations consistent with the present disclosure.

DETAILED DESCRIPTION

Figure 1:
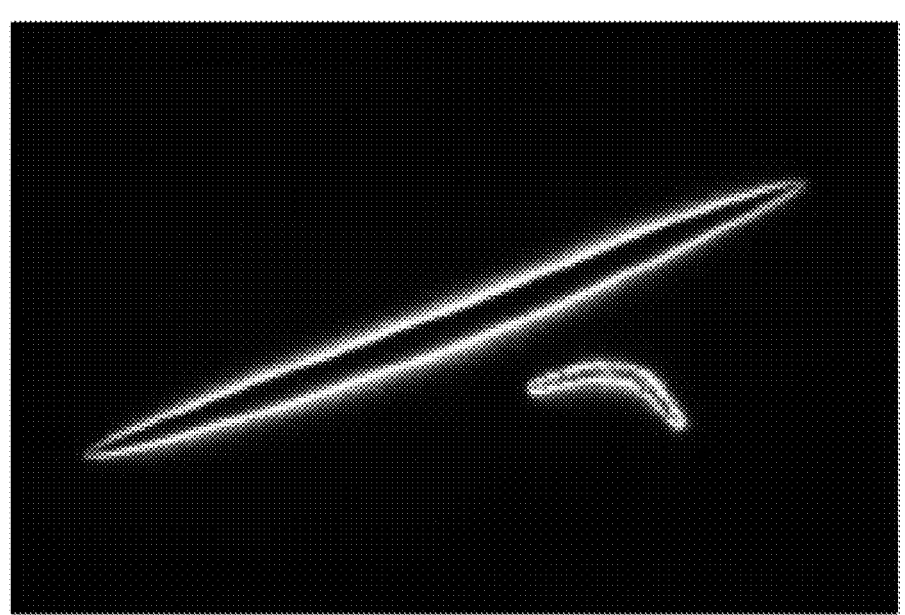
FIG. 1 shows the structure of inorganic siliceous spicules.

The singular form "a", "an", and "the" include plural references unless the context clearly dictates otherwise. For example, the term "a cell" includes one or more cells, including mixtures thereof. "A and/or B" is used herein to include all of the following alternatives: "A", "B", "A or B", and "A and B".

As used herein, the term "about" means either within plus or minus 10% of the provided value, or rounded to the nearest significant figure, in all cases inclusive of the provided value. Where ranges are provided, they are inclusive of the boundary values.

As used herein, the terms "applied," "applying," "administration," "administering," and "used" means the delivery of a composition disclosed herein to a subject, in particular to the skin of the subject, by an administration route including, but not limited to, intraperitoneal, subcutaneous, intramuscular, topically, or any combinations thereof. In some embodiments disclosed herein, the compositions disclosed herein are administered to the subject, in particular to the skin of the subject, by topical administration. In some embodiments application or applied to the skin includes or consists of delivering to the area of the skin condition. For example, in the case of luminosity and brightness, applying the material to the area where the improvement in luminosity and brightness is desired. As another example, in the case of fine lines under the eye, delivering or applying the material to the skin under the eye that has the fine lines.

As used herein, the term "aspect ratio" means with respect to the particles of Spongilla described herein the ratio between the average length of the particles to the average diameter of the particles.

As used herein, the term "botulinum toxin" means a protein produced by the bacterium *Clostridium botulinum* and related species. As used herein, the term "botulinum toxin type A" means a protein known to those of ordinary skill in the art as the protein also referred to as "BoNT/A" or "botA," and having representative UniProt reference numbers BXA1 CLOBH (strain Hall), BXA1_CLOBO, BXA2_CLOBO, or variants thereof. As used herein, the term "botulinum toxin type B" means a protein known to those of ordinary skill in the art as the protein also referred to as "BoNT/B" or "botB," and having representative Uni-Prot reference number BXB_CLOBO, or variants thereof. As used herein, the term "botulinum toxin type C1" means a protein known to those of ordinary skill in the art as the protein also referred to as "BoNT/C1" and having representative UniProt reference numbers BXC1_CLOBO, or variants thereof. As used herein, the term "botulinum toxin type C2" means a protein known to those of ordinary skill in the art as the protein referred to as botulinum toxin type C2. As used herein, the term "botulinum toxin type D" means a protein known to those of ordinary skill in the art as the protein also referred to as "BoNT/D" or "botD," and having representative UniProt reference number BXD_CLOBO, or variants thereof. As used herein, the term "botulinum toxin type E" means a protein known to those of ordinary skill in the art as the protein also referred to as "BoNT/E" and having representative UniProt reference number BXE_CLOBO, or variants thereof. As used herein, the term "botulinum toxin type F" means a protein known to those of ordinary skill in the art as the protein also referred to as "BoNT/F" or "botF," and having representative UniProt reference number BXF_CLOBO, or variants thereof. As used herein, the term "botulinum toxin type G" means a protein known to those of ordinary skill in the art as the protein also referred to as "BoNT/E" or "botG," and having representative UniProt reference number BXG_CLOBO, or variants thereof. As used herein, the term "variants" means proteins having 70%, 75%, 80%, 85%, 90%, 91%, 92%, 93%, 94%, 95%, 96%, 97%, 98% or 99% or any percentage in between homology.

As used herein, the terms "combination" and "in combination with" mean the application, use, or administration of one or more of the compositions disclosed herein, sequentially or simultaneously. It includes dosing simultaneously, or within minutes or hours of each other, or on the same day, or on alternating days, or using the compositions disclosed herein on a daily basis, or multiple days per week, or weekly basis, for example, while administering another composition on the same day or alternating days or weeks or on a periodic basis during a time simultaneous therewith or concurrent therewith, or at least a part of the time during which the composition disclosed herein is applied, used or administered. For example, one or more of the compositions disclosed herein, could be applied, used, or administered to a subject every day or several days a week while the additional composition is applied, used or dosed on alternating days or alternating weeks or other periods of time, such as every 1, 2, 3, 4, 5, 6, 7, 8, 9, 10, 11, 12, 13, 14 or more days.

The term "abobotulinumtoxinA" as used herein means the botulinum toxin type A product approved by the FDA under BLA No. 125274.

The term "Chalinidea" as used herein means one or more sponges of the family Chalinidea.

The term "daxibotulinumtoxinA" means daxibotulinum-toxinA 150 kiloDalton (kDa) purified botulinum toxin type A complex currently in development by Revance Therapeutics, Inc.

The term "Demospongiae" means one or more sponges of the class Demospongiae.

The term "EB-001A" as used herein means the botulinum toxin type E product being developed by Bonti, Inc. of Orange County, California.

The term "EB-001T" as used herein means the botulinum toxin type E product being developed by Bonti, Inc. of Orange County, California.

The term "Halciona" as used herein means one or more sponges from the genus Halciona.

The term "Haplosclerida" as used herein means one or more sponges of the order Haplosclerida.

The term "incobotulinumtoxinA" as used herein, means the botulinum toxin type A product approved by the FDA under BLA No. 125360.

The term "onabotulinumtoxinA" as used herein means the botulinum toxin type A product approved by the United States Food and Drug Administration ("FDA") under Biologics License Application ("BLA") No. 103000.

The term "rimabotulintoxin B" as used herein means the botulinum toxin type B product approved by the FDA under BLA No. 103846.

The term "Porifera" as used herein means one or more sponge members of the phylum Porifera.

The term "prabotulinumtoxinA" means prabotulinum-toxinA 900 kiloDalton (kDa) purified botulinum toxin type A complex currently in development by Evolus, Inc. and Daewoong Pharmaceutical Co. Ltd.

The term "Spongilla" as used herein means a genus of freshwater sponges in the family Spongillidae, including, but not limited to, Spongilla lacustris, S. fragilis Leidy, and Ephydatia fluviatilis. The term "Spongilla lacustris" as used herein means a species of sponge of the freshwater sponge family Spongillidae.

The terms "composition comprising one or more sponges," "powders comprising one or more sponges, "materials comprising one or more sponges," "sponge in the form of a powder," and the like, as used herein, mean materials derived from one or more sponges that is harvested and processed and may include all the various components of the sponge following harvest, including all organic and/or inorganic compounds and materials that are part of the naturally-occurring sponge, or any sponges that are specially grown or adapted for use in the disclosed compositions, methods and/or kits, or may include only a portion of the organic and/or inorganic compounds and materials that are part of the naturally-occurring sponge. In one aspect is provided any of the methods or kits disclosed herein, wherein the sponge materials comprise all or substantially all the organic and inorganic materials derived from the naturally occurring sponge. In another aspect is provided any of the methods or kits disclosed herein, wherein the sponge materials comprise (a) only the spicules and any materials that are naturally associated with the spicules, or (b) substantially purified spicules and any materials that are naturally associated with the spicules, or (c) purified spicules and any materials that are naturally associated with the spicules that are a component part of naturally-occurring sponge. In another aspect is provided any of the methods or kits disclosed herein, wherein the sponge materials comprise only the spicules and any materials that are naturally associated with the spicules. In another aspect is provided any of the methods or kits disclosed herein, wherein the sponge materials comprise substantially purified spicules and any materials that are naturally associated with the spicules. In another aspect is provided any of the methods or kits disclosed herein, wherein the sponge materials comprise purified spicules and any materials that are naturally associated with the spicules that are a component part of naturally occurring sponge. These terms may be used herein in relation to materials derived from the phylum Porifera. In another aspect, the materials are derived from sponges of the class Demospongiae. In another aspect, the materials are derived from sponges of the order Spongdilla. In another aspect, the materials are derived from sponges of the family Spongillidae. In another aspect, the materials are derived from sponges of the genus Spongilla. In another aspect, the materials are derived from sponges of the species Spongilla *lacustris*. In another aspect, the materials are derived from sponges of the order Haplosclerida. In another aspect, the materials are derived from sponges of the family Chalinidea. In another aspect, the materials are derived from sponges of the genus Halciona.

The terms "composition comprising Spongilla," "powders comprising Spongilla, "materials comprising Spongilla, "Spongilla in the form of a powder," and the like, as used herein, mean materials comprising Spongilla derived from raw Spongilla that is harvested and processed and may include all the various components of the Spongilla following harvest, including all organic and/or inorganic compounds and materials that are part of the naturally-occurring Spongilla, or may include only a portion of the organic and/or inorganic compounds and materials that are part of the naturally-occurring Spongilla. In one aspect is provided any of the methods or kits disclosed herein, wherein the Spongilla materials comprise all or substantially all the organic and inorganic materials derived from the naturally occurring Spongilla. In another aspect is provided any of the methods or kits disclosed herein, wherein the Spongilla materials comprise (a) only the spicules and any materials that are naturally associated with the spicules, or (b) substantially purified spicules and any materials that are naturally associated with the spicules, or (c) purified spicules and any materials that are naturally associated with the spicules that are a component part of naturally-occurring Spongilla. In another aspect is provided any of the methods or kits disclosed herein, wherein the Spongilla materials comprise only the spicules and any materials that are naturally associated with the spicules. In another aspect is provided any of the methods or kits disclosed herein, wherein the Spongilla materials comprise substantially purified spicules and any materials that are naturally associated with the spicules. In another aspect is provided any of the methods or kits disclosed herein, wherein the Spongilla materials comprise purified spicules and any materials that are naturally associated with the spicules that are a component part of naturally occurring Spongilla.

As used herein, the term "subject" has the meaning given to the term by one having ordinary skill in the art and may mean a mammal, including a human, a dog, a cat, cattle, or a pig. In one embodiment, the subject is a human. In one embodiment, the subject is a dog. In one embodiment, the subject is a cat. In one embodiment, the subject is cattle. In one embodiment, the subject is a pig.

As used herein, the term "therapeutically effective amount" means that amount of the composition or combination of compositions being applied, used or administered to a subject that will treat, relieve, or prevent to some extent one or more of the symptoms of the disorder being treated.

Spongilla, including Spongilla *lacustris*, and powders prepared from Spongilla that are utilized in the methods disclosed herein may be obtained, processed and characterized by methods known to those having ordinary skill in the art. For example, U.S. Pat. No. 7,604,821 describes the harvest, processing and characterization of several species of Spongilla, including Spongilla *lacustris*. The disclosure of U.S. Pat. No. 7,604,821 is incorporated herein by reference in its entirety. Sponge materials may be collected using methods commonly known to those skilled in the art of marine biology. For example, sponges can be collected manually using basic under water diving techniques, or in deeper waters larger colonies are harvested using the Agassiz trawl (AGT) or epibenthic sledge (EBS). Under certain environmental conditions, Spongilla colonies occur in a thin crust-like carpet several meters across and must be collected manually, with fork-like tools, and nets. The collected sponge mass is dried, cleaned of gross contamination, such as shells, stems, plants, rocks and other impurities, and is then washed to remove dirt, sand, silt and soluble impurities. The cleaned sponge mass is weighed and dried using methods known to those of ordinary skill in the art, such as air drying and the use of dryers that are used to dehydrate foods and pharmaceuticals. The sponge mass is dried until residual moisture content is less than a desired value as further disclosed herein. Residual moisture measurements can be performed using methods commonly known in the arts of food sciences, analytical chemistry or the pharmaceutical sciences. For example, 10 grams of dried material may be placed on a tared weighing boat and then weighed. The weighed material is then exposed to a heat source such as a drying oven or heat lamp operated at an appropriate temperature, the sample is then cooled in a desiccated chamber and re-weighed. Residual moisture is calculated as the percent difference between the sample weight before drying and the weight after cooling. Following drying, the sponge materials may be packaged in sealed containers, which optionally protect the materials from light, moisture and oxygen. The materials may then be further tested for the presence of pathogens, coliform organisms and organisms that represent a bioburden. The materials may be further heated or irradiated, as disclosed herein, to reduce any pathogens, coliform organisms or other organisms that represent a bioburden. The materials may then be further processed using methods known to those having ordinary skill in the art to provide a powder comprising particles having a desired size. For example, the sponge materials may be ground, and the resulting materials passed through one or more sieves of a defined size to provide a resulting material comprising particles having a uniform, or substantially uniform size. After final processing and sizing processes are completed, the dried sponge material may be packaged in airtight moisture-proof containers and stored at an appropriate temperature, such as at about room or ambient temperature.

Materials derived from sponges other than Spongilla *lacustris* may be prepared according to the methods described above and those known to those of ordinary skill in the art. In particular, these methods may be applied with respect to sponges of the phylum Porifera. In another aspect, these methods may be applied with respect to sponges of the class Demospongiae. In another aspect, these methods may be applied with respect to sponges of the order Spongdilla. In another aspect, these methods may be applied with respect to sponges of the family Spongillidae. In another aspect, these methods may be applied with respect to sponges of the genus Spongilla. In another aspect, these methods may be applied with respect to sponges of the species Spongilla *lacustris*. In another aspect, these methods may be applied with respect to sponges of the order Haplosclerida. In another aspect, these methods may be applied with respect to sponges of the family Chalinidea. In another aspect, these methods may be applied with respect to sponges of the genus Halciona.

In one aspect are provided methods of treating a skin condition in a subject, comprising applying to the skin of the subject in need thereof an effective amount of a first composition comprising Spongilla, and an effective amount of a second composition comprising one or more botulinum toxins, wherein:

(a) the second composition comprises one or more botulinum toxin type selected from botulinum toxin type A, botulinum toxin type B, botulinum toxin type C1, botulinum toxin type C2, botulinum toxin type D, botulinum toxin type E, botulinum toxin type F and botulinum toxin type G; and (b) the skin condition in the subject is selected from luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, forehead wrinkles, acne vulgaris, acne rosacea type 1, acne rosacea type 2, psoriasis, hyperhidrosis, alopecia areata, androgenic alopecia, keloids, and hypertrophic scars, hidradenitis suppurativa, Raynaud phenomenon, post-herpetic neuralgia, Hailey-Hailey disease, IgA bullous dermatosis, epidermolysis bullosa Simplex Weber-Cockane, Darier disease, pachyonchia congenita, aquagenic keratoderma, notalgia paresthetic, pompholyx (dyshidrotic eczema), chromhidrosis and bromhidrosis, eccrine nevus, facial rhytides, atrophic acne scars, and melasma. In another aspect is provided any of the methods, wherein the skin condition in the subject is luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, and/or forehead wrinkles. In one aspect is provided any of the methods, wherein the second composition comprises one or more botulinum toxin type selected from botulinum toxin type A, botulinum toxin type B, botulinum toxin type C1, botulinum toxin type C2, botulinum toxin type D, botulinum toxin type E, botulinum toxin type F and botulinum toxin type G. In another aspect is provided any of the methods disclosed herein, wherein the one or more botulinum toxin type is selected from botulinum toxin type A, botulinum toxin type B, and botulinum toxin type E. In another aspect is provided any of the methods disclosed herein, wherein the one or more botulinum toxin type is botulinum toxin type A. In another aspect is provided any of the methods disclosed herein, wherein the botulinum toxin type A is selected from onabotulinumtoxinA, abobotulinumtoxinA, incobotulinumtoxinA, prabotulinumtoxinA, and daxibotulinumtoxinA. In another aspect is provided any of the methods disclosed herein, wherein the botulinum toxin type A is onabotulinumtoxinA. In another aspect is provided any of the methods disclosed herein, wherein the botulinum toxin type A is abobotulinumtoxinA. In another aspect is provided any of the methods disclosed herein, wherein the botulinum toxin type A is incobotulinumtoxinA. In another aspect is provided any of the methods disclosed herein, wherein the botulinum toxin type A is prabotulinumtoxinA. In another aspect is provided any of the methods disclosed herein, wherein the one or more botulinum toxin type is botulinum toxin type B. In another aspect is provided any of the methods disclosed herein, wherein the one or more botulinum toxin type B is rimabotulinumtoxinB. In another aspect is provided any of the methods disclosed herein, wherein the one or more botulinum toxin type is botulinum toxin type C1. In another aspect is provided any of the methods disclosed herein, wherein the one or more botulinum toxin type is botulinum toxin type C2. In another aspect is provided any of the methods disclosed herein, wherein the one or more botulinum toxin type is botulinum toxin type D. In another aspect is provided any of the methods disclosed herein, wherein the one or more botulinum toxin type is botulinum toxin type E. In another aspect is provided any of the methods disclosed herein, wherein the one or more botulinum toxin type E is EB-001A or EB-001T. In another aspect is provided any of the methods disclosed herein, wherein the one or more botulinum toxin type E is EB-001A. In another aspect is provided any of the methods disclosed herein, wherein the one or more botulinum toxin type E is EB-001T. In another aspect is provided any of the methods disclosed herein, wherein the one or more botulinum toxin type is botulinum toxin type F. In another aspect is provided any of the methods disclosed herein, wherein the one or more botulinum toxin type is botulinum toxin type G. In another aspect is provided any of the methods disclosed herein, wherein the skin condition in the subject is selected from acne vulgaris, acne rosacea type 1, acne rosacea type 2, psoriasis, and hyperhidrosis. In another aspect is provided any of the methods disclosed herein, wherein the skin condition in the subject is acne vulgaris. In another aspect is provided any of the methods disclosed herein, wherein the skin condition in the subject is acne rosacea type 1. In another aspect is provided any of the methods disclosed herein, wherein the skin condition in the subject is acne rosacea type 2. In another aspect is provided any of the methods disclosed herein, wherein the skin condition in the subject is psoriasis. In another aspect is provided any of the methods disclosed herein, wherein the skin condition in the subject is hyperhidrosis. In another aspect is provided any of the methods, wherein the first composition comprising Spongilla is applied to the skin of the subject at least at once per week for at least two weeks, at least at once per week for at least three weeks, at least once per week for at least 4 weeks, at least once per. week for at least 5 weeks, at least once per week for at least 6 weeks, at least once per week for at least 7 weeks, at least once per week for at least 8 weeks, at least once per week for at least 9 weeks, at least once per week for at least 10 weeks, at least once per week for at least 11 weeks, at least once per week for at least 12 weeks, at least once per week for at least 13 weeks, at least once per week for at least 14 weeks, at least once per week for at least 15 weeks, at least once per week for at least 16 weeks, at least once per week for at least 17 weeks, at least once per week for at least 18 weeks, at least once per week for at least 19 weeks, at least once per week for at least 20 weeks, at least once per week for at least 21 weeks, at least once per week for at least 22 weeks, at least once per week for at least 23 weeks, at least once per week for at least 24 weeks. In another aspect is provided any of the methods disclosed herein, wherein the first composition comprising Spongilla is applied to the skin of the subject once per week for 2 weeks. In another aspect is provided any of the methods disclosed herein, wherein the first composition comprising Spongilla is applied to the skin of the subject once per week for 3 weeks. In another aspect is provided any of the methods disclosed herein, wherein the first composition comprising Spongilla is applied to the skin of the subject once per week for 4. weeks. In another aspect is provided any of the methods disclosed herein, wherein the first composition comprising Spongilla is applied to the skin of the subject once per week for 5 weeks. In another aspect is provided any of the methods disclosed herein, wherein the first composition comprising Spongilla is applied to the skin of the subject once per week for 6 weeks. In another aspect is provided any of the methods disclosed herein, wherein the first composition comprising Spongilla is applied to the skin of the subject once per week for 7 weeks. In another aspect is provided any of the methods disclosed herein, wherein the first composition comprising Spongilla is applied to the skin of the subject once per week for 8 weeks.

In one aspect are provided methods of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, and/or forehead wrinkles in a subject, comprising applying to the skin of the subject in need thereof an effective amount of a first composition comprising Spongilla, and an effective amount of a second composition comprising one or more botulinum toxins, wherein the second composition comprises one or more botulinum toxin type selected from botulinum toxin type A, botulinum toxin type B, botulinum toxin type C1, botulinum toxin type C2, botulinum toxin type D, botulinum toxin type E, botulinum toxin type F and botulinum toxin type G. In one aspect is provided any of the methods, wherein the second composition comprises one or more botulinum toxin type selected from botulinum toxin type A, botulinum toxin type B, botulinum toxin type C1, botulinum toxin type C2, botulinum toxin type D, botulinum toxin type E, botulinum toxin type F and botulinum toxin type G. In another aspect is provided any of the methods disclosed herein, wherein the one or more botulinum toxin type is selected from botulinum toxin type A, botulinum toxin type B, and botulinum toxin type E. In another aspect is provided any of the methods disclosed herein, wherein the one or more botulinum toxin type is botulinum toxin type A. In another aspect is provided any of the methods disclosed herein, wherein the botulinum toxin type A is selected from onabotulinumtoxinA, abobotulinumtoxinA, incobotulinumtoxinA, prabotulinumtoxinA, and daxibotulinumtoxinA. In another aspect is provided any of the methods disclosed herein, wherein the botulinum toxin type A is onabotulinumtoxinA. In another aspect is provided any of the methods disclosed herein, wherein the botulinum toxin type A is abobotulinumtoxinA. In another aspect is provided any of the methods disclosed herein, wherein the botulinum toxin type A is incobotulinumtoxinA. In another aspect is provided any of the methods disclosed herein, wherein the botulinum toxin type A is prabotulinumtoxinA. In another aspect is provided any of the methods disclosed herein, wherein the one or more botulinum toxin type is botulinum toxin type B. In another aspect is provided any of the methods disclosed herein, wherein the one or more botulinum toxin type B is rimabotulinumtoxinB. In another aspect is provided any of the methods disclosed herein, wherein the one or more botulinum toxin type is botulinum toxin type C1. In another aspect is provided any of the methods disclosed herein, wherein the one or more botulinum toxin type is botulinum toxin type C2. In another aspect is provided any of the methods disclosed herein, wherein the one or more botulinum toxin type is botulinum toxin type D. In another aspect is provided any of the methods disclosed herein, wherein the one or more botulinum toxin type is botulinum toxin type E. In another aspect is provided any of the methods disclosed herein, wherein the one or more botulinum toxin type E is EB-001A or EB-001T. In another aspect is provided any of the methods disclosed herein, wherein the one or more botulinum toxin type E is EB-001A. In another aspect is provided any of the methods disclosed herein, wherein the one or more botulinum toxin type E is EB-001T. In another aspect is provided any of the methods disclosed herein, wherein the one or more botulinum toxin type is botulinum toxin type F. In another aspect is provided any of the methods disclosed herein, wherein the one or more botulinum toxin type is botulinum toxin type G. In another aspect is provided any of the methods, wherein the first composition comprising Spongilla is applied to the skin of the subject at least at once per week for at least two weeks, at least at once per week for at least three weeks, at least once per week for at least 4 weeks, at least once per week for at least 5 weeks, at least once per week for at least 6 weeks, at least once per week for at least 7 weeks, at least once per week for at least 8 weeks, at least once per week for at least 9 weeks, at least once per week for at least 10 weeks, at least once per week for at least 11 weeks, at least once per week for at least 12 weeks, at least once per week for at least 13 weeks, at least once per week for at least 14 weeks, at least once per week for at least 15 weeks, at least once per week for at least 16 weeks, at least once per week for at least 17 weeks, at least once per week for at least 18 weeks, at least once per week for at least 19 weeks, at least once per week for at least 20 weeks, at least once per week for at least 21 weeks, at least once per week for at least 22 weeks, at least once per week for at least 23 weeks, at least once per week for at least 24 weeks. In another aspect is provided any of the methods disclosed herein, wherein the first composition comprising Spongilla is applied to the skin of the subject once per week for 2 weeks. In another aspect is provided any of the methods disclosed herein, wherein the first composition comprising Spongilla is applied to the skin of the subject once per week for 3 weeks. In another aspect is provided any of the methods disclosed herein, wherein the first composition comprising Spongilla is applied to the skin of the subject once per week for 4 weeks. In another aspect is provided any of the methods disclosed herein, wherein the first composition comprising Spongilla is applied to the skin of the subject once per week for 5 weeks, In another aspect is provided any of the methods disclosed herein, wherein the first composition comprising Spongilla is applied to the skin of the subject once per week for 6 weeks, In another aspect is provided any of the methods disclosed herein, wherein the first composition comprising Spongilla is applied to the skin of the subject once per week for 7 weeks. In another aspect is provided any of the methods disclosed herein, wherein the first composition comprising Spongilla is applied to the skin of the subject once per week for 8 weeks.

In one aspect are provided methods of one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, and forehead wrinkles in a subject, comprising applying to the skin of the subject in need thereof an effective amount of a first composition comprising Spongilla, and an effective amount of a second composition comprising botulinum toxin type A. In another aspect is provided any of the methods disclosed herein, wherein the botulinum toxin type A is selected from onabotulinumtoxinA, abobotulinumtoxinA, incobotulinumtoxinA, prabotulinumtoxinA, and daxibotulinumtoxinA. In another aspect is provided any of the methods disclosed herein, wherein the botulinum toxin type A is onabotulinumtoxinA. In another aspect is provided any of the methods disclosed herein, wherein the botulinum toxin type A is abobotulinumtoxinA. In another aspect is provided any of the methods disclosed herein, wherein the botulinum toxin type A is incobotulinumtoxinA. In another aspect is provided any of the methods disclosed herein, wherein the botulinum toxin type A is prabotulinumtoxinA. In another aspect is provided any of the methods, wherein the first composition comprising Spongilla is applied to the skin of the subject at least at once per week for at least two weeks, at least at once per week for at least three weeks, at least once per week for at least 4 weeks, at least once per week for at least 5 weeks, at least once per week for at least 6 weeks, at least once per week for at least 7 weeks, at least once per week for at least 8 weeks, at least once per week for at least 9 weeks, at least once per week for at least 10 weeks, at least once per week for at least 11 weeks, at least once per week for at least 12 weeks, at least once per week for at least 13 weeks, at least once per week for at least 14 weeks, at least once per week for at least 15 weeks, at least once per week for at least 16 weeks, at least once per week for at least 17 weeks, at least once per week for at least 18 weeks, at least once per week for at least 19 weeks, at least once per week for at least 20 weeks, at least once per week for at least 21 weeks, at least once per week for at least 22 weeks, at least once per week for at least 23 weeks, at least once per week for at least 24 weeks. In another aspect is provided any of the methods disclosed herein, wherein the first composition comprising Spongilla is applied to the skin of the subject once per week for 2 weeks. In another aspect is provided any of the methods disclosed herein, wherein the first composition comprising Spongilla is applied to the skin of the subject once per week for 3 weeks. In another aspect is provided any of the methods disclosed herein, wherein the first composition comprising Spongilla is applied to the skin of the subject once per week for 4 weeks. In another aspect is provided any of the methods disclosed herein, wherein the first composition comprising Spongilla is applied to the skin of the subject once per week for 5 weeks. In another aspect is provided any of the methods disclosed herein, wherein the first composition comprising Spongilla is applied to the skin of the subject once per week for 6 weeks. In another aspect is provided any of the methods disclosed herein, wherein the first composition comprising Spongilla is applied to the skin of the subject once per week for 7 weeks. In another aspect is provided any of the methods disclosed herein, wherein the first composition comprising Spongilla is applied to the skin of the subject once per week for 8 weeks.

A first composition comprising Spongilla for use in a method of treating a skin disease or condition in a subject in need thereof, wherein the method comprises administering to the subject an effective amount of the first composition in combination with an effective amount of a second composition, the second composition comprising one or more botulinum toxin type selected from botulinum toxin type A, botulinum toxin type B, botulinum toxin type C1, botulinum toxin type C2, botulinum toxin type D, botulinum toxin type E, botulinum toxin type F and botulinum toxin type G, and wherein the skin condition in the subject is selected from luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, forehead wrinkles, acne vulgaris, acne rosacea type 1, acne rosacea type 2, psoriasis, hyperhidrosis, alopecia areata, androgenic alopecia, keloids, and hypertrophic scars, hidradenitis suppurativa, Raynaud phenomenon, post-herpetic neuralgia, Hailey-Hailey disease, IgA bullous dermatosis, epidermolysis bullosa Simplex Weber-Cockane, Darier disease, pachyonchia congenita, aquagenic keratoderma, notalgia paresthetic, pompholyx (dyshidrotic eczema), chromhidrosis and bromhidrosis, eccrine nevus, facial rhytides, atrophic acne scars, and melasma. In one aspect is provided such a first composition for use, wherein the second composition comprises one or more botulinum toxin type selected from botulinum toxin type A, botulinum toxin type B, botulinum toxin type C1, botulinum toxin type C2, botulinum toxin type D, botulinum toxin type E, botulinum toxin type F and botulinum toxin type G. In one aspect is provided such a first composition for use wherein the one or more botulinum toxin type is selected from botulinum toxin type A, botulinum toxin type B, and botulinum toxin type E. In one aspect is provided such a first composition for use wherein the one or more botulinum toxin type is botulinum toxin type A. In one aspect is provided such a first composition for use, wherein the botulinum toxin type A is selected from onabotulinumtoxinA, abobotulinumtoxinA, incobotulinumtoxinA, prabotulinumtoxinA, and daxibotulinumtoxinA. In one aspect is provided such a first composition for use wherein the botulinum toxin type A is onabotulinumtoxinA. In one aspect is provided such a first composition for use wherein the botulinum toxin type A is abobotulinumtoxinA. In one aspect is provided such a first composition for use, wherein the botulinum toxin type A is incobotulinumtoxinA. In one aspect is provided such a first composition for use, wherein the botulinum toxin type A is prabotulinumtoxinA. In one aspect is provided such a first composition for use, wherein the one or more botulinum toxin type is botulinum toxin type B. In another aspect is provided any of the methods disclosed herein, wherein the one or more botulinum toxin type B is rimabotulinumtoxinB. In one aspect is provided such a first composition for use, wherein the one or more botulinum toxin type is botulinum toxin type C1. In one aspect is provided such a first composition for use, wherein the one or more botulinum toxin type is botulinum toxin type C2. In one aspect is provided such a first composition for use, wherein the one or more botulinum toxin type is botulinum toxin type D In one aspect is provided such a first composition for use, wherein the one or more botulinum toxin type is botulinum toxin type E. In one aspect is provided such a first composition for use, wherein the one or more botulinum toxin type E is EB-001A or EB-001T. In one aspect is provided such a first composition for use, wherein the one or more botulinum toxin type E is EB-001A. In one aspect is provided such a first composition for use, wherein the one or more botulinum toxin type E is EB-001T. In one aspect is provided such a first composition for use, wherein the one or more botulinum toxin type is botulinum toxin type F. In one aspect is provided such a first composition for use, wherein the one or more botulinum toxin type is botulinum toxin type G. In one aspect is provided such a first composition for use, wherein the skin condition in the subject is selected from one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, and/or forehead wrinkles. In one aspect is provided such a first composition for use, wherein the skin condition in the subject is luminosity and/or brightness. In one aspect is provided such a first composition for use, wherein the skin condition in the subject is skin pore size. In one aspect is provided such a first composition for use, wherein the skin condition in the subject is skin pore count. In one aspect is provided such a first composition for use, wherein the skin condition in the subject is sebum production. In one aspect is provided such a first composition for use, wherein the skin condition in the subject is sebum composition. In one aspect is provided such a first composition for use, wherein the skin condition in the subject is overall skin quality. In one aspect is provided such a first composition for use, wherein the skin condition in the subject is fine lines under the eye. In one aspect is provided such a first composition for use, wherein the skin condition in the subject is fine lines on the face. In one aspect is provided such a first composition for use, wherein the skin condition in the subject is laxity on the face. In one aspect is provided such a first composition for use, wherein the skin condition in the subject is eyelid laxity. In one aspect is provided such a first composition for use, wherein the skin condition in the subject is perioral rhytids. In one aspect is provided such a first composition for use, wherein the skin condition in the subject is moderate to severe facial folds and wrinkles such as nasolabial folds. In one aspect is provided such a first composition for use, wherein the skin condition in the subject is moderate to severe facial wrinkles such as smile lines or marionette lines. In one aspect is provided such a first composition for use, wherein the skin condition in the subject is age-related midface contour deficiencies. In one aspect is provided such a first composition for use, wherein the skin condition in the subject is volume deficit. In one aspect is provided such a first composition for use, wherein the skin condition in the subject is glabellar lines. In one aspect is provided such a first composition for use, wherein the skin condition in the subject is facila depressions, either due to injury or age-related. In one aspect is provided such a first composition for use, wherein the skin condition in the subject is perioral wrinkles. In one aspect is provided such a first composition for use, wherein the skin condition in the subject is lip commissures. In one aspect is provided such a first composition for use, wherein the skin condition in the subject is crow's feet. In one aspect is provided such a first composition for use, wherein the skin condition in the subject is forehead wrinkle. In one aspect is provided such a first composition for use, wherein the first composition comprising Spongilla is applied to the skin of the subject at least at once per week for at least two weeks, at least at once per week for at least three weeks, at least once per week for at least 4 weeks, at least once per week for at least 5 weeks, at least once per week for at least 6 weeks, at least once per week for at least 7 weeks, at least once per week for at least 8 weeks, at least once per week for at least 9 weeks, at least once per week for at least 10 weeks, at least once per week for at least 11 weeks, at least once per week for at least 12 weeks, at least once per week for at least 13 weeks, at least once per week for at least 14 weeks, at least once per week for at least 15 weeks, at least once per week for at least 16 weeks, at least once per week for at least 17 weeks, at least once per week for at least 18 weeks, at least once per week for at least 19 weeks, at least once per week for at least 20 weeks, at least once per week for at least 21 weeks, at least once per week for at least 22 weeks, at least once per week for at least 23 weeks, at least once per week for at least 24 weeks. In one aspect is provided such a first composition for use, wherein the first composition comprising Spongilla is applied to the skin of the subject once per week for 2 weeks. In one aspect is provided such a first composition for use, wherein the first composition comprising Spongilla is applied to the skin of the subject once per week for 3 weeks. In one aspect is provided such a first composition for use, wherein the first composition comprising Spongilla is applied to the skin of the subject once per week for 4 weeks. In one aspect is provided such a first composition for use, wherein the first composition comprising Spongilla is applied to the skin of the subject once per week for 5 weeks. In one aspect is provided such a first composition for use, wherein the first composition comprising Spongilla is applied to the skin of the subject once per week for 6 weeks. In one aspect is provided such a first composition for use, wherein the first composition comprising Spongilla is applied to the skin of the subject once per week for 7 weeks. In one aspect is provided such a first composition for use, wherein the first composition comprising Spongilla is applied to the skin of the subject once per week for 8 weeks.

A first composition comprising Spongilla for use in a method of treating one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, facila depressions, either due to injury or age-related, perioral wrinkles, lip commissures, crow's feet, and forehead wrinkles in a subject in need thereof, wherein the method comprises administering to the subject an effective amount of the first composition in combination with an effective amount of a second composition, the second composition comprising botulinum toxin type A. In one aspect is provided such a first composition for use, wherein the botulinum toxin type A is selected from onabotulinumtoxinA, abobotulinumtoxinA, incobotulinumtoxinA, prabotulinumtoxinA, and daxibotulinumtoxinA. In one aspect is provided such a first composition for use wherein the botulinum toxin type A is onabotulinumtoxinA. In one aspect is provided such a first composition for use wherein the botulinum toxin type A is abobotulinumtoxinA. In one aspect is provided such a first composition for use, wherein the botulinum toxin type A is incobotulinumtoxinA. In one aspect is provided such a first composition for use, wherein the botulinum toxin type A is prabotulinumtoxinA. In one aspect is provided such a first composition for use, wherein the first composition comprising Spongilla is applied to the skin of the subject at least at once per week for at least two weeks, at least at once per week for at least three weeks, at least once per week for at least 4 weeks, at least once per week for at least 5 weeks, at least once per week for at least 6 weeks, at least once per week for at least 7 weeks, at least once per week for at least 8 weeks, at least once per week for at least 9 weeks, at least once per week for at least 10 weeks, at least once per week for at least 11 weeks, at least once per week for at least 12 weeks, at least once per week for at least 13 weeks, at least once per week for at least 14 weeks, at least once per week for at least 15 weeks, at least once per week for at least 16 weeks, at least once per week for at least 17 weeks, at least once per week for at least 18 weeks, at least once per week for at least 19 weeks, at least once per week for at least 20 weeks, at least once per week for at least 21 weeks, at least once per week for at least 22 weeks, at least once per week for at least 23 weeks, at least once per week for at least 24 weeks. In one aspect is provided such a first composition for use, wherein the first composition comprising Spongilla is applied to the skin of the subject once per week for 2 weeks. In one aspect is provided such a first composition for use, wherein the first composition comprising Spongilla is applied to the skin of the subject once per week for 3 weeks. In one aspect is provided such a first composition for use, wherein the first composition comprising Spongilla is applied to the skin of the subject once per week for 4 weeks. In one aspect is provided such a first composition for use, wherein the first composition comprising Spongilla is applied to the skin of the subject once per week for 5 weeks. In one aspect is provided such a first composition for use, wherein the first composition comprising Spongilla is applied to the skin of the subject once per week for 6 weeks. In one aspect is provided such a first composition for use, wherein the first composition comprising Spongilla is applied to the skin of the subject once per week for 7 weeks. In one aspect is provided such a first composition for use, wherein the first composition comprising Spongilla is applied to the skin of the subject once per week for 8 weeks.

A first composition comprising Spongilla for use in a method of treating one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, and forehead wrinkles in a subject in need thereof, wherein the method comprises administering to the subject an effective amount of the first composition in combination with an effective amount of a second composition, the second composition comprising onabotulinumtoxinA. In one aspect is provided such a first composition for use, wherein the first composition comprising Spongilla is applied to the skin of the subject at least at once per week for at least two weeks, at least at once per week for at least three weeks, at least once per week for at least 4 weeks, at least once per week for at least 5 weeks, at least once per week for at least 6 weeks, at least once per week for at least 7 weeks, at least once per week for at least 8 weeks, at least once per week for at least 9 weeks, at least once per week for at least 10 weeks, at least once per week for at least 11 weeks, at least once per week for at least 12 weeks, at least once per week for at least 13 weeks, at least once per week for at least 14 weeks, at least once per week for at least 15 weeks, at least once per week for at least 16 weeks, at least once per week for at least 17 weeks, at least once per week for at least 18 weeks, at least once per week for at least 19 weeks, at least once per week for at least 20 weeks, at least once per week for at least 21 weeks, at least once per week for at least 22 weeks, at least once per week for at least 23 weeks, at least once per week for at least 24 weeks. In one aspect is provided such a first composition for use, wherein the first composition comprising Spongilla is applied to the skin of the subject once per week for 2 weeks. In one aspect is provided such a first composition for use, wherein the first composition comprising Spongilla is applied to the skin of the subject once per week for 3 weeks. In one aspect is provided such a first composition for use, wherein the first composition comprising Spongilla is applied to the skin of the subject once per week for 4 weeks. In one aspect is provided such a first composition for use, wherein the first composition comprising Spongilla is applied to the skin of the subject once per week for 5 weeks. In one aspect is provided such a first composition for use, wherein the first composition comprising Spongilla is applied to the skin of the subject once per week for 6 weeks. In one aspect is provided such a first composition for use, wherein the first composition comprising Spongilla is applied to the skin of the subject once per week for 7 weeks. In one aspect is provided such a first composition for use, wherein the first composition comprising Spongilla is applied to the skin of the subject once per week for 8 weeks.

A composition comprising Spongilla and one or more botulinum toxins for the treatment of a skin condition or disease in a subject in need thereof, wherein the skin condition in the subject is selected from luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, forehead wrinkles, acne vulgaris, acne rosacea type 1, acne rosacea type 2, psoriasis, hyperhidrosis, alopecia areata, androgenic alopecia, keloids, and hypertrophic scars, hidradenitis suppurativa, Raynaud phenomenon, postherpetic neuralgia, Hailey-Hailey disease, IgA bullous dermatosis, epidermolysis bullosa Simplex Weber-Cockane, Darier disease, pachyonchia congenita, aquagenic keratoderma, notalgia paresthetic, pompholyx (dyshidrotic eczema), chromhidrosis and bromhidrosis, eccrine nevus, facial rhytides, atrophic acne scars, and melasma. In another aspect is provided such a first composition for use, wherein the skin condition or condition in the subject is one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, and forehead wrinkles, and wherein the botulinum toxin is selected from botulinum toxin type A, botulinum toxin type B, botulinum toxin type C1, botulinum toxin type C2, botulinum toxin type D, botulinum toxin type E, botulinum toxin type F and botulinum toxin type G, and wherein the skin condition in the subject is selected from one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, forehead wrinkles, acne vulgaris, acne rosacea type 1, acne rosacea type 2, psoriasis, hyperhidrosis, alopecia areata, androgenic alopecia, keloids, and hypertrophic scars, hidradenitis suppurativa, Raynaud phenomenon, post-herpetic neuralgia, Hailey-Hailey disease, IgA bullous dermatosis, epidermolysis bullosa Simplex Weber-Cockane, Darier disease, pachyonchia congenita, aquagenic keratoderma, notalgia paresthetic, pompholyx (dyshidrotic eczema), chromhidrosis and bromhidrosis, eccrine nevus, facial rhytides, atrophic acne scars, and melasma. In another aspect is provided such a composition for use, wherein the skin condition or condition in the subject is one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, and forehead wrinkles. In one aspect is provided such a composition for use, wherein botulinum toxin is selected from botulinum toxin type A, botulinum toxin type B, botulinum toxin type C1, botulinum toxin type C2, botulinum toxin type D, botulinum toxin type E, botulinum toxin type F and botulinum toxin type G. In one aspect is provided such a composition for use wherein the one or more botulinum toxin type is selected from botulinum toxin type A, botulinum toxin type B, and botulinum toxin type E. In one aspect is provided such a composition for use wherein the one or more botulinum toxin type is botulinum toxin type A. In one aspect is provided such a composition for use, wherein the botulinum toxin type A is selected from onabotulinumtoxinA, abobotulinumtoxinA, incobotulinumtoxinA, prabotulinumtoxinA, and daxibotulinumtoxinA. In one aspect is provided such a composition for use wherein the botulinum toxin type A is onabotulinumtoxinA. In one aspect is provided such a composition for use wherein the botulinum toxin type A is abobotulinumtoxinA. In one aspect is provided such a composition for use, wherein the botulinum toxin type A is incobotulinumtoxinA. In one aspect is provided such a composition for use, wherein the botulinum toxin type A is prabotulinumtoxinA. In one aspect is provided such a composition for use, wherein the one or more botulinum toxin type is botulinum toxin type B. In another aspect is provided any of the methods disclosed herein, wherein the one or more botulinum toxin type B is rimabotulinumtoxinB. In one aspect is provided such a composition for use, wherein the one or more botulinum toxin type is botulinum toxin type C1. In one aspect is provided such a composition for use, wherein the one or more botulinum toxin type is botulinum toxin type C2. In one aspect is provided such a composition for use, wherein the one or more botulinum toxin type is botulinum toxin type D. In one aspect is provided such a composition for use, wherein the one or more botulinum toxin type is botulinum toxin type E. In one aspect is provided such a composition for use, wherein the one or more botulinum toxin type E is EB-001A or EB-001T. In one aspect is provided such a composition for use, wherein the one or more botulinum toxin type E is EB-001A. In one aspect is provided such a composition for use, wherein the one or more botulinum toxin type E is EB-001T. In one aspect is provided such a composition for use, wherein the one or more botulinum toxin type is botulinum toxin type F. In one aspect is provided such a composition for use, wherein the one or more botulinum toxin type is botulinum toxin type G. In one aspect is provided such a composition for use, wherein the skin condition in the subject is selected from one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, and forehead wrinkles. In one aspect is provided such a composition for use, wherein the skin condition in the subject is luminosity. In one aspect is provided such a composition for use, wherein the skin condition in the subject is brightness. In one aspect is provided such a composition for use, wherein the skin condition in the subject is skin pore size. In one aspect is provided such a composition for use, wherein the skin condition in the subject is skin pore count. In one aspect is provided such a composition for use, wherein the skin condition in the subject is sebum production. In one aspect is provided a composition for use, wherein the skin condition in the subject is sebum composition. In one aspect is provided such a composition for use, wherein the skin condition in the subject is overall skin quality. In one aspect is provided such a composition for use, wherein the skin condition in the subject is eyelid laxity. In one aspect is provided such a composition for use, wherein the skin condition in the subject is fine lines under the eye. In one aspect is provided such a composition for use, wherein the skin condition in the subject is fine lines on the face. In one aspect is provided such a composition for use, wherein the skin condition in the subject is laxity on the face. In one aspect is provided such a composition for use, wherein the skin condition in the subject is perioral rhytids. In one aspect is provided such a composition for use, wherein the skin condition in the subject is moderate to severe facial folds and wrinkles such as nasolabial folds. In one aspect is provided such a composition for use, wherein the skin condition in the subject is moderate to severe facial wrinkles such as smile lines or marionette lines. In one aspect is provided such a composition for use, wherein the skin condition in the subject is age-related midface contour deficiencies. In one aspect is provided such a composition for use, wherein the skin condition in the subject is dorsal hand to correct volume deficit. In one aspect is provided such a composition for use, wherein the skin condition in the subject is glabellar lines. In one aspect is provided such a composition for use, wherein the skin condition in the subject is facila depressions, either due to injury or age-related. In one aspect is provided such a composition for use, wherein the skin condition in the subject is perioral wrinkles. In one aspect is provided such a composition for use, wherein the skin condition in the subject is lip commissures. In one aspect is provided such a composition for use, wherein the skin condition in the subject is crow's feet. In one aspect is provided such a composition for use, wherein the skin condition in the subject is forehead wrinkles. In one aspect is provided such a composition for use, wherein the composition is applied to the skin of the subject at least at once per week for at least two weeks, at least at once per week for at least three weeks, at least once per week for at least 4 weeks, at least once per week for at least 5 weeks, at least once per week for at least 6 weeks, at least once per week for at least 7 weeks, at least once per week for at least 8 weeks, at least once per week for at least 9 weeks, at least once per week for at least 10 weeks, at least once per week for at least 11 weeks, at least once per week for at least 12 weeks, at least once per week for at least 13 weeks, at least once per week for at least 14 weeks, at least once per week for at least 15 weeks, at least once per week for at least 16 weeks, at least once per week for at least 17 weeks, at least once per week for at least 18 weeks, at least once per week for at least 19 weeks, at least once per week for at least 20 weeks, at least once per week for at least 21 weeks, at least once per week for at least 22 weeks, at least once per week for at least 23 weeks, at least once per week for at least 24 weeks. In one aspect is provided such a composition for use, wherein the composition is applied to the skin of the subject once per week for 2 weeks. In one aspect is provided such a composition for use, wherein the composition is applied to the skin of the subject once per week for 3 weeks. In one aspect is provided such a composition for use, wherein the composition is applied to the skin of the subject once per week for 4 weeks. In one aspect is provided such a composition for use, wherein the composition is applied to the skin of the subject once per week for 5 weeks. In one aspect is provided such a composition for use, wherein the composition comprising Spongilla is applied to the skin of the subject once per week for 6 weeks. In one aspect is provided such a composition for use, wherein the composition is applied to the skin of the subject once per week for 7 weeks. In one aspect is provided such a composition for use, wherein the composition is applied to the skin of the subject once per week for 8 weeks.

A composition comprising Spongilla and one or more botulinum toxins for use in the treatment of hyperhidrosis in a subject in need thereof. In one aspect is provided such a composition for use, wherein botulinum toxin is selected from botulinum toxin type A, botulinum toxin type B, botulinum toxin type C1, botulinum toxin type C2, botulinum toxin type D, botulinum toxin type E, botulinum toxin type F and botulinum toxin type G. In one aspect is provided such a composition for use wherein the one or more botulinum toxin type is selected from botulinum toxin type A, botulinum toxin type B, and botulinum toxin type E. In one aspect is provided such a composition for use wherein the one or more botulinum toxin type is botulinum toxin type A. In one aspect is provided such a composition for use, wherein the botulinum toxin type A is selected from onabotulinumtoxinA, abobotulinumtoxinA, incobotulinumtoxinA, prabotulinumtoxinA, and daxibotulinumtoxinA. In one aspect is provided such a composition for use wherein the botulinum toxin type A is onabotulinumtoxinA. In one aspect is provided such a composition for use wherein the botulinum toxin type A is abobotulinumtoxinA. In one aspect is provided such a composition for use, wherein the botulinum toxin type A is incobotulinumtoxinA. In one aspect is provided such a composition for use, wherein the botulinum toxin type A is prabotulinumtoxinA. In one aspect is provided such a composition for use, wherein the one or more botulinum toxin type is botulinum toxin type B. In another aspect is provided any of the methods disclosed herein, wherein the one or more botulinum toxin type B is rimabotulinumtoxinB. In one aspect is provided such a composition for use, wherein the one or more botulinum toxin type is botulinum toxin type C1. In one aspect is provided such a composition for use, wherein the one or more botulinum toxin type is botulinum toxin type C2. In one aspect is provided such a composition for use, wherein the one or more botulinum toxin type is botulinum toxin type D. In one aspect is provided such a composition for use, wherein the one or more botulinum toxin type is botulinum toxin type E. In one aspect is provided such a composition for use, wherein the one or more botulinum toxin type E is EB-001A or EB-001T. In one aspect is provided such a composition for use, wherein the one or more botulinum toxin type E is EB-001A. In one aspect is provided such a composition for use, wherein the one or more botulinum toxin type E is EB-001T. In one aspect is provided such a composition for use, wherein the one or more botulinum toxin type is botulinum toxin type F. In one aspect is provided such a composition for use, wherein the one or more botulinum toxin type is botulinum toxin type G.

A composition comprising Spongilla and one or more botulinum toxins for use in the treatment of one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, and forehead wrinklesin a subject in need thereof. In one aspect is provided such a composition for use, wherein botulinum toxin is selected from botulinum toxin type A, botulinum toxin type B, botulinum toxin type C1, botulinum toxin type C2, botulinum toxin type D, botulinum toxin type E, botulinum toxin type F and botulinum toxin type G. In one aspect is provided such a composition for use wherein the one or more botulinum toxin type is selected from botulinum toxin type A, botulinum toxin type B, and botulinum toxin type E.

A composition comprising Spongilla and one or more botulinum toxins type A for use in the treatment of one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, and forehead wrinkles in a subject in need thereof, wherein the botulinum toxin type A is selected from onabotulinumtoxinA, abobotulinumtoxinA, incobotulinumtoxinA, prabotulinumtoxinA, and daxibotulinumtoxinA. In one aspect is provided such a composition for use wherein the botulinum toxin type A is onabotulinumtoxinA. In one aspect is provided such a composition for use wherein the botulinum toxin type A is abobotulinumtoxinA. In one aspect is provided such a composition for use, wherein the botulinum toxin type A is incobotulinumtoxinA. In one aspect is provided such a composition for use, wherein the botulinum toxin type A is prabotulinumtoxinA.

A composition comprising Spongilla and onabotulinumtoxinA for use in the treatment of one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, and forehead wrinkles in a subject in need thereof. In another aspect is provided such a composition wherein the composition is applied to the skin of the subject at least at once per week for at least two weeks, at least at once per week for at least three weeks, at least once per week for at least 4 weeks, at least once per week for at least 5 weeks, at least once per week for at least 6 weeks, at least once per week for at least 7 weeks, at least once per week for at least 8 weeks, at least once per week for at least 9 weeks, at least once per week for at least 10 weeks, at least once per week for at least 11 weeks, at least once per week for at least 12 weeks, at least once per week for at least 13 weeks, at least once per week for at least 14 weeks, at least once per week for at least 15 weeks, at least once per week for at least 16 weeks, at least once per week for at least 17 weeks, at least once per week for at least 18 weeks, at least once per week for at least 19 weeks, at least once per week for at least 20 weeks, at least once per week for at least 21 weeks, at least once per week for at least 22 weeks, at least once per week for at least 23 weeks, at least once per week for at least 24 weeks. In another aspect is provided such a composition wherein the composition is applied to the skin of the subject once per week for 2 weeks. In another aspect is provided such a composition wherein the composition is applied to the skin of the subject once per week for 3 weeks. In another aspect is provided such a composition wherein the composition is applied to the skin of the subject once per week for 4 weeks. In another aspect is provided such a composition wherein the composition is applied to the skin of the subject once per week for 5 weeks. In another aspect is provided such a composition wherein the composition is applied to the skin of the subject once per week for 6 weeks. In another aspect is provided such a composition wherein the composition is applied to the skin of the subject once per week for 7 weeks. In another aspect is provided such a composition wherein the composition is applied to the skin of the subject is applied to the skin of the subject once per week for 8 weeks.

A first composition comprising Spongilla for use in improving one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, and forehead wrinkles in a subject wherein the method comprises administering to the subject an effective amount of the first composition in combination with an effective amount of a second composition, the second composition comprising one or more botulinum toxin type selected from botulinum toxin type A, botulinum toxin type B, botulinum toxin type C1, botulinum toxin type C2, botulinum toxin type D, botulinum toxin type E, botulinum toxin type F and botulinum toxin type G. In another aspect is provided such a first composition wherein the subject experiences an improvement in luminosity and brightness as measured on a 0 to 10 scale, skin pore size as measured by standard photography and/or the Global Aesthetic Improvement Scale, sebum production as measured by sebutapes or sebum meter or sebum measuring machine and standard photography, overall skin quality as measured by the Global Aesthetic Improvement Scale, eyelid laxity as measured by the Facial Laxity Rating Scale, fine lines under the eye as measured by the Facial Wrinkle Scale, fine lines on the face as measured by the Facial Wrinkle Scale, laxity on the face as measured by the Facial Laxity Rating Scale, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, and/or forehead wrinkles. In another aspect is provided such a first composition wherein the subject experiences an improvement that is a reduction in one or more of the listed conditions, wherein the reduction is greater than 10%, 20%, 30%, 40%, 50%, 60%, 70%, 80%, 90%, or 95% reduction as measured using the criteria described herein or any other suitable approach utilized to measure, following administration of the first composition and the second composition compared to the subject's situation prior to such administration. In another aspect is provided such a composition for use, wherein the subject experiences an improvement greater than 20%, 30%, 40%, 50%, 60%, 70%, 80%, 90%, or 95% as measured using the criteria described herein or any other suitable approach utilized to measure. In another aspect is provided such a composition for use, wherein the subject experiences a greater 1, 2, 3, 4, 5 or 6 grade improvement.

In one aspect is provided such a first composition for use, wherein the botulinum toxin type A is selected from onabotulinumtoxinA, abobotulinumtoxinA, incobotulinumtoxinA, prabotulinumtoxinA, and daxibotulinumtoxinA. In one aspect is provided such a first composition for use wherein the botulinum toxin type A is onabotulinumtoxinA. In one aspect is provided such a first composition for use wherein the botulinum toxin type A is abobotulinumtoxinA. In one aspect is provided such a first composition for use, wherein the botulinum toxin type A is incobotulinumtoxinA. In one aspect is provided such a first composition for use, wherein the botulinum toxin type A is prabotulinumtoxinA. In another aspect is provided such a composition for use, wherein the subject is treated once per month, twice per month, three times per month, four times per month, five times per month, six times per month, 7 times per month, 8 times per month, 9 times per month, 10 times per month, 11 times per month, 12 times per month, 13 times per month, 14 times per month, 15 times per month, 16 times per month, 17 times per month, 18 times per month, 19 times per month, 20 times per month, 21 times per month, 22 times per month, or 24 times per month. In another aspect is provided such a composition for use, wherein the subject is treated twice per month. In another aspect is provided such a composition for use, wherein the subject is treated three times per month. In another aspect is provided such a composition for use, wherein the subject is treated once per week. In another aspect is provided such a composition for use, wherein the subject is at least 18 years old. In another aspect is provided such a composition for use, wherein the subject is treated once per month, or once every two months, or once every three months, or once every four months, or once every five months, or once every six months, or once every seven months, or once every eight months, or once every nine months, or once every 10 months, or once every 11 months, or once every 12 months. In another aspect is provided such a composition for use, wherein the subject is treated once per month. In another aspect is provided such a composition for use, wherein the subject is treated once every two months. In another aspect is provided such a composition for use, wherein the subject is treated once every three months. In another aspect is provided such a composition for use, wherein the subject is treated once every four months. In another aspect is provided such a composition for use, wherein the subject is treated once every five months. In another aspect is provided such a composition for use, wherein the subject is treated once every six months. In another aspect is provided such a composition for use, wherein the subject is treated once every seven months. In another aspect is provided such a composition for use, wherein the subject is treated once every eight months. In another aspect is provided such a composition for use, wherein the subject is treated once every nine months. In another aspect is provided such a composition for use, wherein the subject is treated once every 10 months. In another aspect is provided such a composition for use, wherein the subject is treated once every 11 months. In another aspect is provided such a composition for use, wherein the subject is treated once every 12 months.

A first composition comprising Spongilla for use in a method of treating hyperhidrosis in a subject in need thereof, wherein the method comprises administering to the subject an effective amount of the first composition in combination with an effective amount of a second composition, the second composition comprising botulinum toxin type A. In one aspect is provided such a first composition for use, wherein the botulinum toxin type A is selected from onabotulinumtoxinA, abobotulinumtoxinA, incobotulinumtoxinA, prabotulinumtoxinA, and daxibotulinumtoxinA. In one aspect is provided such a first composition for use wherein the botulinum toxin type A is onabotulinumtoxinA. In one aspect is provided such a first composition for use wherein the botulinum toxin type A is abobotulinumtoxinA. In one aspect is provided such a first composition for use, wherein the botulinum toxin type A is incobotulinumtoxinA. In one aspect is provided such a first composition for use, wherein the botulinum toxin type A is prabotulinumtoxinA. In one aspect is provided such a first composition for use, wherein the first composition comprising Spongilla is applied to the skin of the subject at least at once per week for at least two weeks, at least at once per week for at least three weeks, at least once per week for at least 4 weeks, at least once per week for at least 5 weeks, at least once per week for at least 6 weeks, at least once per week for at least 7 weeks, at least once per week for at least 8 weeks, at least once per week for at least 9 weeks, at least once per week for at least 10 weeks, at least once per week for at least 11 weeks, at least once per week for at least 12 weeks, at least once per week for at least 13 weeks, at least once per week for at least 14 weeks, at least once per week for at least 15 weeks, at least once per week for at least 16 weeks, at least once per week for at least 17 weeks, at least once per week for at least 18 weeks, at least once per week for at least 19 weeks, at least once per week for at least 20 weeks, at least once per week for at least 21 weeks, at least once per week for at least 22 weeks, at least once per week for at least 23 weeks, at least once per week for at least 24 weeks. In one aspect is provided such a first composition for use, wherein the first composition comprising Spongilla is applied to the skin of the subject once per week for 2 weeks. In one aspect is provided such a first composition for use, wherein the first composition comprising Spongilla is applied to the skin of the subject once per week for 3 weeks. In one aspect is provided such a first composition for use, wherein the first composition comprising Spongilla is applied to the skin of the subject once per week for 4 weeks. In one aspect is provided such a first composition for use, wherein the first composition comprising Spongilla is applied to the skin of the subject once per week for 5 weeks. In one aspect is provided such a first composition for use, wherein the first composition comprising Spongilla is applied to the skin of the subject once per week for 6 weeks. In one aspect is provided such a first composition for use, wherein the first composition comprising Spongilla is applied to the skin of the subject once per week for 7 weeks. In one aspect is provided such a first composition for use, wherein the first composition comprising Spongilla is applied to the skin of the subject once per week for 8 weeks.

A first composition comprising Spongilla for use in a method of treating one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, and forehead wrinkles in a subject in need thereof, wherein the method comprises administering to the subject an effective amount of the first composition in combination with an effective amount of a second composition, the second composition comprising onabotulinumtoxinA. In one aspect is provided such a first composition for use, wherein the first composition comprising Spongilla is applied to the skin of the subject at least at once per week for at least two weeks, at least three weeks, at least once per week for at least 4 weeks, at least once per week for at least 5 weeks, at least once per week for at least 6 weeks, at least once per week for at least 7 weeks, at least at once per week for at least once per week for at least 8 weeks, at least once per week for at least 9 weeks, at least once per week for at least 10 weeks, at least once per week for at least 11 weeks, at least once per week for at least 12 weeks, at least once per week for at least 13 weeks, at least once per week for at least 14 weeks, at least once per week for at least 15 weeks, at least once per week for at least 16 weeks, at least once per week for at least 17 weeks, at least once per week for at least 18 weeks, at least once per week for at least 19 weeks, at least once per week for at least 20 weeks, at least once per week for at least 21 weeks, at least once per week for at least 22 weeks, at least once per week for at least 23 weeks, at least once per week for at least 24 weeks. In one aspect is provided such a first composition for use, wherein the first composition comprising Spongilla is applied to the skin of the subject once per week for 2 weeks. In one aspect is provided such a first composition for use, wherein the first composition comprising Spongilla is applied to the skin of the subject once per week for 3 weeks. In one aspect is provided such a first composition for use, wherein the first composition comprising Spongilla is applied to the skin of the subject once per week for 4 weeks. In one aspect is provided such a first composition for use, wherein the first composition comprising Spongilla is applied to the skin of the subject once per week for 5 weeks. In one aspect is provided such a first composition for use, wherein the first composition comprising Spongilla is applied to the skin of the subject once per week for 6 weeks. In one aspect is provided such a first composition for use, wherein the first composition comprising Spongilla is applied to the skin of the subject once per week for 7 weeks. In one aspect is provided such a first composition for use, wherein the first composition comprising Spongilla is applied to the skin of the subject once per week for 8 weeks.

A composition comprising Spongilla and one or more botulinum toxins for the treatment of a skin condition or disease in a subject in need thereof, wherein the skin condition in the subject is selected from one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, and forehead wrinkles, acne vulgaris, acne rosacea type 1, acne rosacea type 2, psoriasis, hyperhidrosis, alopecia areata, androgenic alopecia, keloids, and hypertrophic scars, hidradenitis suppurativa, Raynaud phenomenon, post-herpetic neuralgia, Hailey-Hailey disease, IgA bullous dermatosis, epidermolysis bullosa Simplex Weber-Cockane, Darier disease, pachyonchia congenita, aquagenic keratoderma, notalgia paresthetic, pompholyx (dyshidrotic eczema), chromhidrosis and bromhidrosis, eccrine nevus, facial rhytides, atrophic acne scars, and melasma. In another aspect is provided such a first composition for use, wherein the skin condition or condition in the subject is one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles, and wherein the botulinum toxin is selected from botulinum toxin type A, botulinum toxin type B, botulinum toxin type C1, botulinum toxin type C2, botulinum toxin type D, botulinum toxin type E, botulinum toxin type F and botulinum toxin type G. In another aspect is provided such a composition for use, wherein the skin condition or condition in the subject is one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles. In one aspect is provided such a composition for use, wherein botulinum toxin is selected from botulinum toxin type A, botulinum toxin type B, botulinum toxin type C1, botulinum toxin type C2, botulinum toxin type D, botulinum toxin type E, botulinum toxin type F and botulinum toxin type G. In one aspect is provided such a composition for use wherein the one or more botulinum toxin type is selected from botulinum toxin type A, botulinum toxin type B, and botulinum toxin type E. In one aspect is provided such a composition for use wherein the one or more botulinum toxin type is botulinum toxin type A. In one aspect is provided such a composition for use, wherein the botulinum toxin type A is selected from onabotulinumtoxinA, abobotulinumtoxinA, incobotulinumtoxinA, prabotulinumtoxinA, and daxibotulinumtoxinA. In one aspect is provided such a composition for use wherein the botulinum toxin type A is onabotulinumtoxinA. In one aspect is provided such a composition for use wherein the botulinum toxin type A is abobotulinumtoxinA. In one aspect is provided such a composition for use, wherein the botulinum toxin type A is incobotulinumtoxinA. In one aspect is provided such a composition for use, wherein the botulinum toxin type A is prabotulinumtoxinA. In one aspect is provided such a composition for use, wherein the one or more botulinum toxin type is botulinum toxin type B. In another aspect is provided any of the methods disclosed herein, wherein the one or more botulinum toxin type B is rimabotulinumtoxinB. In one aspect is provided such a composition for use, wherein the one or more botulinum toxin type is botulinum toxin type C1. In one aspect is provided such a composition for use, wherein the one or more botulinum toxin type is botulinum toxin type C2. In one aspect is provided such a composition for use, wherein the one or more botulinum toxin type is botulinum toxin type D. In one aspect is provided such a composition for use, wherein the one or more botulinum toxin type is botulinum toxin type E. In one aspect is provided such a composition for use, wherein the one or more botulinum toxin type E is EB-001A or EB-001T. In one aspect is provided such a composition for use, wherein the one or more botulinum toxin type E is EB-001A. In one aspect is provided such a composition for use, wherein the one or more botulinum toxin type E is EB-001T. In one aspect is provided such a composition for use, wherein the one or more botulinum toxin type is botulinum toxin type F. In one aspect is provided such a composition for use, wherein the one or more botulinum toxin type is botulinum toxin type G. In one aspect is provided such a composition for use, wherein the skin condition in the subject is selected from one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles. In one aspect is provided such a composition for use, wherein the composition is applied to the skin of the subject at least at once per week for at least two weeks, at least at once per week for at least three weeks, at least once per week for at least 4 weeks, at least once per week for at least 5 weeks, at least once per week for at least 6 weeks, at least once per week for at least 7 weeks, at least once per week for at least 8 weeks, at least once per week for at least 9 weeks, at least once per week for at least 10 weeks, at least once per week for at least 11 weeks, at least once per week for at least 12 weeks, at least once per week for at least 13 weeks, at least once per week for at least 14 weeks, at least once per week for at least 15 weeks, at least once per week for at least 16 weeks, at least once per week for at least 17 weeks, at least once per week for at least 18 weeks, at least once per week for at least 19 weeks, at least once per week for at least 20 weeks, at least once per week for at least 21 weeks, at least once per week for at least 22 weeks, at least once per week for at least 23 weeks, at least once per week for at least 24 weeks. In one aspect is provided such a composition for use, wherein the composition is applied to the skin of the subject once per week for 2 weeks. In one aspect is provided such a composition for use, wherein the composition is applied to the skin of the subject once per week for 3 weeks. In one aspect is provided such a composition for use, wherein the composition is applied to the skin of the subject once per week for 4 weeks. In one aspect is provided such a composition for use, wherein the composition is applied to the skin of the subject once per week for 5 weeks. In one aspect is provided such a composition for use, wherein the composition comprising Spongilla is applied to the skin of the subject once per week for 6 weeks. In one aspect is provided such a composition for use, wherein the composition is applied to the skin of the subject once per week for 7 weeks. In one aspect is provided such a composition for use, wherein the composition is applied to the skin of the subject once per week for 8 weeks.

A composition comprising Spongilla and one or more botulinum toxins for use in the treatment of hyperhidrosis in a subject in need thereof. In one aspect is provided such a composition for use, wherein botulinum toxin is selected from botulinum toxin type A, botulinum toxin type B, botulinum toxin type C1, botulinum toxin type C2, botulinum toxin type D, botulinum toxin type E, botulinum toxin type F and botulinum toxin type G. In one aspect is provided such a composition for use wherein the one or more botulinum toxin type is selected from botulinum toxin type A, botulinum toxin type B, and botulinum toxin type E. In one aspect is provided such a composition for use wherein the one or more botulinum toxin type is botulinum toxin type A. In one aspect is provided such a composition for use, wherein the botulinum toxin type A is selected from onabotulinumtoxinA, abobotulinumtoxinA, incobotulinumtoxinA, prabotulinumtoxinA, and daxibotulinumtoxinA. In one aspect is provided such a composition for use wherein the botulinum toxin type A is onabotulinumtoxinA. In one aspect is provided such a composition for use wherein the botulinum toxin type A is abobotulinumtoxinA. In one aspect is provided such a composition for use, wherein the botulinum toxin type A is incobotulinumtoxinA. In one aspect is provided such a composition for use, wherein the botulinum toxin type A is prabotulinumtoxinA. In one aspect is provided such a composition for use, wherein the one or more botulinum toxin type is botulinum toxin type B. In another aspect is provided any of the methods disclosed herein, wherein the one or more botulinum toxin type B is rimabotulinumtoxinB. In one aspect is provided such a composition for use, wherein the one or more botulinum toxin type is botulinum toxin type C1. In one aspect is provided such a composition for use, wherein the one or more botulinum toxin type is botulinum toxin type C2. In one aspect is provided such a composition for use, wherein the one or more botulinum toxin type is botulinum toxin type D. In one aspect is provided such a composition for use, wherein the one or more botulinum toxin type is botulinum toxin type E. In one aspect is provided such a composition for use, wherein the one or more botulinum toxin type E is EB-001A or EB-001T. In one aspect is provided such a composition for use, wherein the one or more botulinum toxin type E is EB-001A. In one aspect is provided such a composition for use, wherein the one or more botulinum toxin type E is EB-001T. In one aspect is provided such a composition for use, wherein the one or more botulinum toxin type is botulinum toxin type F. In one aspect is provided such a composition for use, wherein the one or more botulinum toxin type is botulinum toxin type G.

A composition comprising one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles and one or more botulinum toxins for use in the treatment of hyperhidrosis in a subject in need thereof. In one aspect is provided such a composition for use, wherein botulinum toxin is selected from botulinum toxin type A, botulinum toxin type B, botulinum toxin type C1, botulinum toxin type C2, botulinum toxin type D, botulinum toxin type E, botulinum toxin type F and botulinum toxin type G. In one aspect is provided such a composition for use wherein the one or more botulinum toxin type is selected from botulinum toxin type A, botulinum toxin type B, and botulinum toxin type E.

A composition comprising Spongilla and one or more botulinum toxins type A for use in the treatment of hyperhidrosis in a subject in need thereof, wherein the botulinum toxin type A is selected from onabotulinumtoxinA, abobotulinumtoxinA, incobotulinumtoxinA, prabotulinumtoxinA, and daxibotulinumtoxinA. In one aspect is provided such a composition for use wherein the botulinum toxin type A is onabotulinumtoxinA. In one aspect is provided such a composition for use wherein the botulinum toxin type A is abobotulinumtoxinA. In one aspect is provided such a composition for use, wherein the botulinum toxin type A is incobotulinumtoxinA. In one aspect is provided such a composition for use, wherein the botulinum toxin type A is prabotulinumtoxinA.

A composition comprising Spongilla and onabotulinumtoxinA for use in the treatment of one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles in a subject in need thereof. In another aspect is provided such a composition wherein the composition is applied to the skin of the subject at least at once per week for at least two weeks, at least at once per week for at least three weeks, at least once per week for at least 4 weeks, at least once per week for at least 5 weeks, at least once per week for at least 6 weeks, at least once per week for at least 7 weeks, at least once per week for at least 8 weeks, at least once per week for at least 9 weeks, at least once per week for at least 10 weeks, at least once per week for at least 11 weeks, at least once per week for at least 12 weeks, at least once per week for at least 13 weeks, at least once per week for at least 14 weeks, at least once per week for at least 15 weeks, at least once per week for at least 16 weeks, at least once per week for at least 17 weeks, at least once per week for at least 18 weeks, at least once per week for at least 19 weeks, at least once per week for at least 20 weeks, at least once per week for at least 21 weeks, at least once per week for at least 22 weeks, at least once per week for at least 23 weeks, at least once per week for at least 24 weeks. In another aspect is provided such a composition wherein the composition is applied to the skin of the subject once per week for 2 weeks. In another aspect is provided such a composition wherein the composition is applied to the skin of the subject once per week for 3 weeks. In another aspect is provided such a composition wherein the composition is applied to the skin of the subject once per week for 4 weeks. In another aspect is provided such a composition wherein the composition is applied to the skin of the subject once per week for 5 weeks. In another aspect is provided such a composition wherein the composition is applied to the skin of the subject once per week for 6 weeks. In another aspect is provided such a composition wherein the composition is applied to the skin of the subject once per week for 7 weeks. In another aspect is provided such a composition wherein the composition is applied to the skin of the subject is applied to the skin of the subject once per week for 8 weeks.

In one aspect are provided methods of one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles in a subject, comprising applying to the skin of the subject in need thereof an effective amount of a first composition comprising Spongilla, and an effective amount of a second composition comprising onabotulinum-toxinA. In another aspect is provided any of the methods, wherein the first composition comprising Spongilla is applied to the skin of the subject at least at once per week for at least two weeks, at least at once per week for at least three weeks, at least once per week for at least 4 weeks, at least once per week for at least 5 weeks, at least once per week for at least 6 weeks, at least once per week for at least 7 weeks, at least once per week for at least 8 weeks, at least once per week for at least 9 weeks, at least once per week for at least 10 weeks, at least once per week for at least 11 weeks, at least once per week for at least 12 weeks, at least once per week for at least 13 weeks, at least once per week for at least 14 weeks, at least once per week for at least 15 weeks, at least once per week for at least 16 weeks, at least once per week for at least 17 weeks, at least once per week for at least 18 weeks, at least once per week for at least 19 weeks, at least once per week for at least 20 weeks, at least once per week for at least 21 weeks, at least once per week for at least 22 weeks, at least once per week for at least 23 weeks, at least once per week for at least 24 weeks. In another aspect is provided any of the methods disclosed herein, wherein the first composition comprising Spongilla is applied to the skin of the subject once per week for 2 weeks. In another aspect is provided any of the methods disclosed herein, wherein the first composition comprising Spongilla is applied to the skin of the subject once per week for 3 weeks. In another aspect is provided any of the methods disclosed herein, wherein the first composition comprising Spongilla is applied to the skin of the subject once per week for 4 weeks. In another aspect is provided any of the methods disclosed herein, wherein the first composition comprising Spongilla is applied to the skin of the subject once per week for 5 weeks. In another aspect is provided any of the methods disclosed herein, wherein the first composition comprising Spongilla is applied to the skin of the subject once per week for 6 weeks. In another aspect is provided any of the methods disclosed herein, wherein the first composition comprising Spongilla is applied to the skin of the subject once per week for 7 weeks. In another aspect is provided any of the methods disclosed herein, wherein the first composition comprising Spongilla is applied to the skin of the subject once per week for 8 weeks.

In another aspect provided herein are any of the disclosed methods, wherein the method comprises comprising applying to the skin of the subject in need thereof an effective amount of a first composition comprising Spongilla, and an effective amount of a second composition comprising one or more botulinum toxins.

In one aspect is provided a method of treating a skin condition in a subject, comprising applying to the skin of the subject a first composition comprising Spongilla, and a second composition comprising one or more botulinum toxins. In another aspect is provided any of the methods disclosed herein, wherein the second composition comprises one or more botulinum toxin type selected from botulinum toxin type A, botulinum toxin type B, botulinum toxin type C1, botulinum toxin type C2, botulinum toxin type D, botulinum toxin type E, botulinum toxin type F and botulinum toxin type G. In another aspect is provided any of the methods disclosed herein, wherein the one or more botulinum toxin type is selected from botulinum toxin type A, botulinum toxin type B, and botulinum toxin type E. In another aspect is provided any of the methods disclosed herein, wherein the one or more botulinum toxin type is botulinum toxin type A. In another aspect is provided any of the methods disclosed herein, wherein the botulinum toxin type A is selected from onabotulinumtoxinA, abobotulinum-toxinA, incobotulinumtoxinA, prabotulinumtoxinA, and daxibotulinumtoxinA. In another aspect is provided any of the methods disclosed herein, wherein the botulinum toxin type A is onabotulinumtoxinA. In another aspect is provided any of the methods disclosed herein, wherein the botulinum toxin type A is abobotulinumtoxinA. In another aspect is provided any of the methods disclosed herein, wherein the botulinum toxin type A is incobotulinumtoxinA. In another aspect is provided any of the methods disclosed herein, wherein the botulinum toxin type A is prabotulinumtoxinA. In another aspect is provided any of the methods disclosed herein, wherein the one or more botulinum toxin type is botulinum toxin type B. In another aspect is provided any of the methods disclosed herein, wherein the one or more botulinum toxin type B is rimabotulinumtoxinB. In another aspect is provided any of the methods disclosed herein, wherein the one or more botulinum toxin type is botulinum toxin type C1. In another aspect is provided any of the methods disclosed herein, wherein the one or more botulinum toxin type is botulinum toxin type C2. In another aspect is provided any of the methods disclosed herein, wherein the one or more botulinum toxin type is botulinum toxin type D. In another aspect is provided any of the methods disclosed herein, wherein the one or more botulinum toxin type is botulinum toxin type E. In another aspect is provided any of the methods disclosed herein, wherein the one or more botulinum toxin type E is EB-001A or EB-001T. In another aspect is provided any of the methods disclosed herein, wherein the one or more botulinum toxin type E is EB-001A. In another aspect is provided any of the methods disclosed herein, wherein the one or more botulinum toxin type E is. EB-001T. In another aspect is provided any of the methods disclosed herein, wherein the one or more botulinum toxin type is botulinum toxin type F. In another aspect is provided any of the methods disclosed herein, wherein the one or more botulinum toxin type is botulinum toxin type G. In another aspect is provided any of the methods disclosed herein, wherein the skin condition in the subject is selected from one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles.

In another aspect is provided a composition comprising a first composition and a second composition for use as a medicament, wherein the (a) the first composition comprises a Spongilla; and (b) the second composition one or more botulinum toxins. In another aspect is provided a composition comprising a first composition and a second composition for use as a medicament, wherein the (a) the first composition comprises a Spongilla *lacustris*; and (b) the second composition one or more botulinum toxins. In another aspect is provided such compositions for use as a medicament for the treatment of a skin condition in a subject. In another aspect is such combinations for use as a medicament for the treatment of a skin condition in a subject, wherein the skin condition in the subject is selected from one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, forehead wrinkles, acne vulgaris, acne rosacea type 1, acne rosacea type 2, psoriasis, hyperhidrosis, alopecia areata, androgenic alopecia, keloids, and hypertrophic scars, hidradenitis suppurativa, Raynaud phenomenon, post-herpetic neuralgia, Hailey-Hailey disease, IgA bullous dermatosis, epidermolysis bullosa Simplex Weber-Cockane, Darier disease, pachyonchia congenita, aquagenic keratoderma, notalgia paresthetic, pompholyx (dyshidrotic eczema), chromhidrosis and bromhidrosis, and eccrine nevus. In another aspect is provided any of the compositions disclosed herein, wherein the second composition comprises one or more botulinum toxin type selected from botulinum toxin type A, botulinum toxin type B, botulinum toxin type C1, botulinum toxin type C2, botulinum toxin type D, botulinum toxin type E, botulinum toxin type F and botulinum toxin type G. In another aspect is provided any of the compositions disclosed herein, wherein the one or more botulinum toxin type is selected from botulinum toxin type A, botulinum toxin type B, and botulinum toxin type E. In another aspect is provided any of the compositions disclosed herein, wherein the one or more botulinum toxin type is botulinum toxin type A. In another aspect is provided any of the compositions disclosed herein, wherein the botulinum toxin type A is selected from onabotulinumtoxinA, abobotulinumtoxinA, incobotulinumtoxinA, prabotulinumtoxinA, and daxibotulinumtoxinA. In another aspect is provided any of the compositions disclosed herein, wherein the botulinum toxin type A is onabotulinumtoxinA. In another aspect is provided any of the compositions disclosed herein, wherein the botulinum toxin type A is abobotulinumtoxinA. In another aspect is provided any of the compositions disclosed herein, wherein the botulinum toxin type A is incobotulinumtoxinA. In another aspect is provided any of the compositions disclosed herein, wherein the botulinum toxin type A is prabotulinumtoxinA. In another aspect is provided any of the compositions disclosed herein, wherein the one or more botulinum toxin type is botulinum toxin type B. In another aspect is provided any of the methods disclosed herein, wherein the one or more botulinum toxin type B is rimabotulinumtoxinB. In another aspect is provided any of the compositions disclosed herein, wherein the one or more botulinum toxin type is botulinum toxin type C1. In another aspect is provided any of the compositions disclosed herein, wherein the one or more botulinum toxin type is botulinum toxin type C2. In another aspect is provided any of the compositions disclosed herein, wherein the one or more botulinum toxin type is botulinum toxin type D. In another aspect is provided any of the compositions disclosed herein, wherein the one or more botulinum toxin type is botulinum toxin type E. In another aspect is provided any of the compositions disclosed herein, wherein the one or more botulinum toxin type E is EB-001A or EB-001T. In another aspect is provided any of the compositions disclosed herein, wherein the one or more botulinum toxin type E is EB-001A. In another aspect is provided any of the compositions disclosed herein, wherein the one or more botulinum toxin type E is EB-001T. In another aspect is provided any of the compositions disclosed herein, wherein the one or more botulinum toxin type is botulinum toxin type F. In another aspect is provided any of the compositions disclosed herein, wherein the one or more botulinum toxin type is botulinum toxin type G. In another aspect is provided any of the compositions disclosed herein, wherein the skin condition in the subject is selected from one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles. In another aspect is provided any of the compositions disclosed herein, wherein the second composition is selected from onabotulinumtoxinA, abobotulinum-toxinA, incobotulinumtoxinA, prabotulinumtoxinA, EB-001A, and EB-001T and the skin condition in the subject is one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles. In another aspect is provided any of the compositions disclosed herein, wherein the second composition is onabotulinumtoxinA, and the skin condition in the subject is one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles.

In another aspect is provided a composition comprising a first composition and a second composition for use in the treatment of a skin condition in a subject, wherein (a) the first composition comprising a Spongilla; and (b) the second composition one or more botulinum toxins. In another aspect is provided a combination comprising a first composition and a second composition for use in the treatment of a skin condition in a subject, wherein (a) the first composition comprising a Spongilla *lacustris*; and (b) the second composition one or more botulinum toxins. In another aspect is such compositions for use in the treatment of a skin condition in a subject, wherein the skin condition in the subject is selected from one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, forehead wrinkles, acne vulgaris, acne rosacea type 1, acne rosacea type 2, psoriasis, hyperhidrosis, alopecia areata, androgenic alopecia, keloids, and hypertrophic scars, hidradenitis suppurativa, Raynaud phenomenon, post-herpetic neuralgia, Hailey-Hailey disease, IgA bullous dermatosis, epidermolysis bullosa Simplex Weber-Cockane, Darier disease, pachyonchia congenita, aquagenic keratoderma, notalgia paresthetic, pompholyx (dyshidrotic eczema), chromhidrosis and bromhidrosis, eccrine nevus, facial rhytides, atrophic acne scars, and melasma. In another aspect is such compositions for use in the treatment of a skin condition in a subject, wherein the skin condition in the subject is selected from one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, forehead wrinkles, acne vulgaris, acne rosacea type 1, acne rosacea type 2, psoriasis, hyperhidrosis, alopecia areata, androgenic alopecia, keloids, and hypertrophic scars, hidradenitis suppurativa, Raynaud phenomenon, post-herpetic neuralgia, Hailey-Hailey disease, IgA bullous dermatosis, epidermolysis bullosa Simplex Weber-Cockane, Darier disease, pachyonchia congenita, aquagenic keratoderma, notalgia paresthetic, pompholyx (dyshidrotic eczema), chromhidrosis and bromhidrosis, eccrine nevus, facial rhytides, atrophic acne scars, and melasma. In another aspect is such compositions for use in the treatment of a skin condition in a subject, wherein the second composition comprises one or more botulinum toxin type selected from botulinum toxin type A, botulinum toxin type B, botulinum toxin type C1, botulinum toxin type C2, botulinum toxin type D, botulinum toxin type E, botulinum toxin type F and botulinum toxin type G. In another aspect is such compositions for use in the treatment of a skin condition in a subject, wherein the one or more botulinum toxin type is selected from botulinum toxin type A, botulinum toxin type B, and botulinum toxin type E. In another aspect is such compositions for use in the treatment of a skin condition in a subject, wherein the one or more botulinum toxin type is botulinum toxin type A. In another aspect is such compositions for use in the treatment of a skin condition in a subject, wherein the botulinum toxin type A is selected from onabotulinumtoxinA, abobotulinumtoxinA, incobotulinumtoxinA, prabotulinumtoxinA, and daxibotulinumtoxinA. In another aspect is such compositions for use in the treatment of a skin condition in a subject, wherein the botulinum toxin type A is onabotulinumtoxinA. In another aspect is such compositions for use in the treatment of a skin condition in a subject, wherein the botulinum toxin type A is abobotulinumtoxinA. In another aspect is such compositions for use in the treatment of a skin condition in a subject, wherein the botulinum toxin type A is incobotulinumtoxinA. In another aspect is such compositions for use in the treatment of a skin condition in a subject, wherein the botulinum toxin type A is prabotulinumtoxinA. In another aspect is such compositions for use in the treatment of a skin condition in a subject, wherein the botulinum toxin type A is daxibotulinumtoxinA. In another aspect is such compositions for use in the treatment of a skin condition in a subject, wherein the one or more botulinum toxin type is botulinum toxin type B. In another aspect is provided any of the methods disclosed herein, wherein the one or more botulinum toxin type B is rimabotulinumtoxinB. In another aspect is such compositions for use in the treatment of a skin condition in a subject, wherein the one or more botulinum toxin type is botulinum toxin type C1. In another aspect is such compositions for use in the treatment of a skin condition in a subject, wherein the one or more botulinum toxin type is botulinum toxin type C2. In another aspect is such compositions for use in the treatment of a skin condition in a subject, wherein the one or more botulinum toxin type is botulinum toxin type D. In another aspect is such compositions for use in the treatment of a skin condition in a subject, wherein the one or more botulinum toxin type is botulinum toxin type E. In another aspect is such compositions for use in the treatment of a skin condition in a subject, wherein the one or more botulinum toxin type E is EB-001A or EB-001T. In another aspect is such compositions for use in the treatment of a skin condition in a subject, wherein the one or more botulinum toxin type E is EB-001A. In another aspect is such compositions for use in the treatment of a skin condition in a subject, wherein the one or more botulinum toxin type E is EB-001T. In another aspect is such compositions for use in the treatment of a skin condition in a subject, wherein the one or more botulinum toxin type is botulinum toxin type F. In another aspect is such compositions for use in the treatment of a skin condition in a subject, wherein the one or more botulinum toxin type is botulinum toxin type G. In another aspect is such compositions for use in the treatment of a skin condition in a subject, wherein the skin condition in the subject is selected from a one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles. In another aspect is such compositions for use in the treatment of a skin condition in a subject, wherein the skin condition in the subject is acne vulgaris. In another aspect is provided any of the compositions disclosed herein, wherein the skin condition in the subject is acne rosacea type 1. In another aspect is such compositions for use in the treatment of a skin condition in a subject, wherein the skin condition in the subject is acne rosacea type 2. In another aspect is such compositions for use in the treatment of a skin condition in a subject, wherein the skin condition in the subject is psoriasis. In another aspect is such compositions for use in the treatment of a skin condition in a subject, wherein the skin condition in the subject is hyperhidrosis. In another aspect is such compositions for use in the treatment of a skin condition in a subject, wherein the second composition is selected from onabotulinumtoxinA, abobotulinumtoxinA, incobotulinumtoxinA, prabotulinumtoxinA, EB-001A, and EB-001T, and the skin condition in the subject is one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles. In another aspect is such compositions for use in the treatment of a skin condition in a subject, wherein the second composition is onabotulinumtoxinA, and the skin condition in the subject is one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles.

In another aspect is provided a composition for the manufacture of a medicament for the treatment of a skin condition in a subject, wherein the composition comprises a first composition and a second composition wherein (a) the first composition comprising a Spongilla; and (b) the second composition one or more botulinum toxins. In another aspect is provided a composition for the manufacture of a medicament for the treatment of a skin condition in a subject, wherein the composition comprises a first composition and a second composition wherein (a) the first composition comprising a Spongilla *lacustris*; and (b) the second composition one or more botulinum toxins. a composition for the manufacture of a medicament for the treatment of a skin condition in a subject, wherein the skin condition in the subject is selected from one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, forehead wrinkles, acne vulgaris, acne rosacea type 1, acne rosacea type 2, psoriasis, hyperhidrosis, alopecia areata, androgenic alopecia, keloids, and hypertrophic scars, hidradenitis suppurativa, Raynaud phenomenon, post-herpetic neuralgia, Hailey-Hailey disease, IgA bullous dermatosis, epidermolysis bullosa Simplex Weber-Cockane, Darier disease, pachyonchia congenita, aquagenic keratoderma, notalgia paresthetic, pompholyx (dyshidrotic eczema), chromhidrosis and bromhidrosis, eccrine nevus, facial rhytides, atrophic acne scars, and melasma. In another aspect is provided a composition for the manufacture of a medicament for the treatment of a skin condition in a subject, wherein the skin condition in the subject is selected from one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, forehead wrinkles, acne vulgaris, acne rosacea type 1, acne rosacea type 2, psoriasis, hyperhidrosis, alopecia areata, androgenic alopecia, keloids, and hypertrophic scars, hidradenitis suppurativa, Raynaud phenomenon, post-herpetic neuralgia, Hailey-Hailey disease, IgA bullous dermatosis, epidermolysis bullosa Simplex Weber-Cockane, Darier disease, pachyonchia congenita, aquagenic keratoderma, notalgia paresthetic, pompholyx (dyshidrotic eczema), chromhidrosis and bromhidrosis, eccrine nevus, facial rhytides, atrophic acne scars, and melasma. In another aspect is provided a composition for the manufacture of a medicament for the treatment of a skin condition in a subject, wherein the skin condition in the subject is selected from one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, forehead wrinkles, acne vulgaris, acne rosacea type 1, acne rosacea type 2, psoriasis, hyperhidrosis, alopecia areata, androgenic alopecia, keloids, and hypertrophic scars, hidradenitis suppurativa, Raynaud phenomenon, post-herpetic neuralgia, Hailey-Hailey disease, IgA bullous dermatosis, epidermolysis bullosa Simplex Weber-Cockane, Darier disease, pachyonchia congenita, aquagenic keratoderma, notalgia paresthetic, pompholyx (dyshidrotic eczema), chromhidrosis and bromhidrosis, eccrine nevus, facial rhytides, atrophic acne scars, and melasma. In another aspect is provided a composition for the manufacture of a medicament for the treatment of a skin condition in a subject, wherein the second composition comprises one or more botulinum toxin type selected from botulinum toxin type A, botulinum toxin type B, botulinum toxin type C1, botulinum toxin type C2, botulinum toxin type D, botulinum toxin type E, botulinum toxin type F and botulinum toxin type G. In another aspect is provided a composition for the manufacture of a medicament for the treatment of a skin condition in a subject, wherein the one or more botulinum toxin type is selected from botulinum toxin type A, botulinum toxin type B, and botulinum toxin type E. In another aspect is provided a composition for the manufacture of a medicament for the treatment of a skin condition in a subject, wherein the one or more botulinum toxin type is botulinum toxin type A. In another aspect is provided a composition for the manufacture of a medicament for the treatment of a skin condition in a subject, wherein the botulinum toxin type A is selected from onabotulinumtoxinA, abobotulinumtoxinA, incobotulinumtoxinA, prabotulinumtoxinA, and daxibotulinumtoxinA. In another aspect is provided a composition for the manufacture of a medicament for the treatment of a skin condition in a subject, wherein the botulinum toxin type A is onabotulinumtoxinA. In another aspect is provided a composition for the manufacture of a medicament for the treatment of a skin condition in a subject, wherein the botulinum toxin type A is abobotulinumtoxinA. In another aspect is provided a composition for the manufacture of a medicament for the treatment of a skin condition in a subject, wherein the botulinum toxin type A is incobotulinumtoxinA. In another aspect is provided a composition for the manufacture of a medicament for the treatment of a skin condition in a subject, wherein the botulinum toxin type A is prabotulinumtoxinA. In another aspect is provided a composition for the manufacture of a medicament for the treatment of a skin condition in a subject, wherein the botulinum toxin type A is daxibotulinumtoxinA. In another aspect is provided a composition for the manufacture of a medicament for the treatment of a skin condition in a subject, wherein the one or more botulinum toxin type is botulinum toxin type B. In another aspect is provided any of the methods disclosed herein, wherein the one or more botulinum toxin type B is rimabotulinumtoxinB. In another aspect is provided a composition for the manufacture of a medicament for the treatment of a skin condition in a subject, wherein the one or more botulinum toxin type is botulinum toxin type C1. In another aspect is provided a composition for the manufacture of a medicament for the treatment of a skin condition in a subject, wherein the one or more botulinum toxin type is botulinum toxin type C2. In another aspect is provided a composition for the manufacture of a medicament for the treatment of a skin condition in a subject, wherein the one or more botulinum toxin type is botulinum toxin type D. In another aspect is provided a composition for the manufacture of a medicament for the treatment of a skin condition in a subject, wherein the one or more botulinum toxin type is botulinum toxin type E. In another aspect is provided a composition for the manufacture of a medicament for the treatment of a skin condition in a subject, wherein the one or more botulinum toxin type E is EB-001A or EB-001T. In another aspect is provided a composition for the manufacture of a medicament for the treatment of a skin condition in a subject, wherein the one or more botulinum toxin type E is EB-001A. In another aspect is provided a composition for the manufacture of a medicament for the treatment of a skin condition in a subject, wherein the one or more botulinum toxin type E is EB-001T. In another aspect is provided a composition for the manufacture of a medicament for the treatment of a skin condition in a subject, wherein the one or more botulinum toxin type is botulinum toxin type F. In another aspect is provided a composition for the manufacture of a medicament for the treatment of a skin condition in a subject, wherein the one or more botulinum toxin type is botulinum toxin type G. In another aspect is provided a composition for the manufacture of a medicament for the treatment of a skin condition in a subject, wherein the skin condition in the subject is selected from one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles. In another aspect is provided a composition for the manufacture of a medicament for the treatment of a skin condition in a subject, wherein the skin condition in the subject is acne vulgaris. In another aspect is provided a composition for the manufacture of a medicament for the treatment of a skin condition in a subject, wherein the skin condition in the subject is acne rosacea type 1. In another aspect is provided a composition for the manufacture of a medicament for the treatment of a skin condition in a subject, wherein the skin condition in the subject is acne rosacea type 2. In another aspect is provided a composition for the manufacture of a medicament for the treatment of a skin condition in a subject, wherein the skin condition in the subject is psoriasis. In another aspect is provided a composition for the manufacture of a medicament for the treatment of a skin condition in a subject, wherein the skin condition in the subject is hyperhidrosis. In another aspect is provided a composition for the manufacture of a medicament for the treatment of a skin condition in a subject, wherein the second composition is selected from onabotulinumtoxinA, abobotulinumtoxinA, incobotulinumtoxinA, prabotulinumtoxinA, EB-001A, and EB-001T, and the skin condition in the subject is one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles. In another aspect is provided a composition for the manufacture of a medicament for the treatment of a skin condition in a subject, wherein the second composition is onabotulinumtoxinA, and the skin condition in the subject is one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles.

In another aspect is provided a method of treating one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles in a subject, comprising applying to the skin of the subject a first composition comprising Spongilla, and a second composition comprising one or more botulinum toxins. In another aspect is provided any of the methods disclosed herein for treating the one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles, wherein the second composition comprises one or more botulinum toxin type selected from botulinum toxin type A, botulinum toxin type B, botulinum toxin type C1, botulinum toxin type C2, botulinum toxin type D, botulinum toxin type E, botulinum toxin type F and botulinum toxin type G. In another aspect is provided any of the methods disclosed herein for treating one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles, wherein the second composition comprises one or more botulinum toxin type selected from botulinum toxin type A. In another aspect is provided any of the methods disclosed herein for treating one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles, wherein the botulinum toxin type A is onabotulinumtoxinA. In another aspect is provided any of the methods disclosed herein for treating one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles, wherein the subject experiences at least a one-grade improvement or at least a measurable improvement in the skin condition following treatment compared to the subject's skin condition prior to treatment. Such improvement can be measured or determined as described herein or according to any suitable method. In another aspect is provided any of the methods disclosed herein for treating one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles, wherein the subject experiences at least a two-grade improvement in the score following treatment compared to the subject's score prior to treatment. In another aspect is provided any of the methods disclosed herein for treating one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles, wherein the subject experiences at least a three-grade improvement in the score following treatment compared to the subject's score prior to treatment. In another aspect is provided any of the methods disclosed herein for treating one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles, wherein the subject experiences a greater than 10% improvement (e.g., a reduction in condition or an increase in a positive outcome) following treatment compared to the subject's-measured condition prior to treatment. In another aspect is provided any of the methods disclosed herein for treating one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles, wherein the subject experiences a greater than 20%, 30%, 40%, 50%, 60%, 70%, 80%, 90%, or 95% improvement following treatment compared to the subject's measured condition prior to treatment. In another aspect is provided any of the methods disclosed herein for treating one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles, wherein the subject is treated once per month, twice per month, three times per month, four times per month, five times per month, six times per month, 7 times per month, 8 times per month, 9 times per month, 10 times per month, 11 times per month, 12 times per month, 13 times per month, 14 times per month, 15 times per month, 16 times per month, 17 times per month, 18 times per month, 19 times per month, 20 times per month, 21 times per month, 22 times per month, or 24 times per month. In another aspect is provided any of the methods disclosed herein for treating one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles, wherein the subject is treated twice per month. In another aspect is provided any of the methods disclosed herein for treating one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles, wherein the subject is treated three times per month. In another aspect is provided any of the methods disclosed herein for treating one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles, wherein the subject is treated once per week. In another aspect is provided any of the methods disclosed herein for treating one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles, wherein the subject is at least 18 years old. In another aspect is provided any of the methods disclosed herein for treating hyperhidrosis, wherein the subject is treated once per month, or once every two months, or once every three months, or once every four months, or once every five months, or once every six months, or once every seven months, or once every eight months, or once every nine months, or once every 10 months, or once every 11 months, or once every 12 months. In another aspect is provided any of the methods disclosed herein for treating one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles, wherein the subject is treated once per month. In another aspect is provided any of the methods disclosed herein for treating one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles, wherein the subject is treated once every two months. In another aspect is provided any of the methods disclosed herein for treating one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles, wherein the subject is treated once every three months. In another aspect is provided any of the methods disclosed herein for treating one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles, wherein the subject is treated once every four months. In another aspect is provided any of the methods disclosed herein for treating one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles, wherein the subject is treated once every five months. In another aspect is provided any of the methods disclosed herein for treating one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles, wherein the subject is treated once every six months. In another aspect is provided any of the methods disclosed herein for treating one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles, wherein the subject is treated once every seven months. In another aspect is provided any of the methods disclosed herein for treating one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles, wherein the subject is treated once every eight months. In another aspect is provided any of the methods disclosed herein for treating one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles, wherein the subject is treated once every nine months. In another aspect is provided any of the methods disclosed herein for treating one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles, wherein the subject is treated once every 10 months. In another aspect is provided any of the methods disclosed herein for treating one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles, wherein the subject is treated once every 11 months. In another aspect is provided any of the methods disclosed herein for treating one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles, wherein the subject is treated once every 12 months. In another aspect is provided any of the methods disclosed herein for treating one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles.

In another aspect is provided a method of treating hyperhidrosis in a subject, comprising applying to the skin of the subject a first composition comprising Spongilla, and a second composition comprising one or more botulinum toxins. In another aspect is provided any of the methods disclosed herein for treating hyperhidrosis, wherein the second composition comprises one or more botulinum toxin type selected from botulinum toxin type A, botulinum toxin type B, botulinum toxin type C1, botulinum toxin type C2, botulinum toxin type D, botulinum toxin type E, botulinum toxin type F and botulinum toxin type G. In another aspect is provided any of the methods disclosed herein for treating hyperhidrosis, wherein the second composition comprises one or more botulinum toxin type selected from botulinum toxin type A. In another aspect is provided any of the methods disclosed herein for treating hyperhidrosis, wherein the botulinum toxin type A is onabotulinumtoxinA. In another aspect is provided any of the methods disclosed herein for treating hyperhidrosis, wherein the subject experiences at least a at least a 4-point improvement from baseline in the weekly mean Axillary Sweating Daily Diary (ASDD) item #2 score compared to the subject's ASDD score prior to treatment. In another aspect is provided any of the methods disclosed herein for treating hyperhidrosis, wherein the subject experiences at least a at least a 4-point improvement from baseline in the weekly mean Axillary Sweating Daily Diary (ASDD) item #2 score at week four following treatment compared to the subject's ASDD score prior to treatment In another aspect is provided any of the methods disclosed herein for treating hyperhidrosis, wherein the subject experiences at least a two-grade improvement in the ASDD score following treatment compared to the subject's ASDD score prior to treatment. In another aspect is provided any of the methods disclosed herein for treating hyperhidrosis, wherein the subject experiences at least a three-grade improvement in the ASDD score following treatment compared to the subject's ASDD score prior to treatment. In another aspect is provided any of the methods disclosed herein for treating hyperhidrosis, wherein the subject experiences a greater than 10% reduction in gravimetrically-measured sweat production following treatment compared to the subject's gravimetrically-measured sweat production prior to treatment. In another aspect is provided any of the methods disclosed herein for treating hyperhidrosis, wherein the subject experiences a greater than 20%, 30%, 40%, 50%, 60%, 70%, 80%, 90%, or 95% reduction in gravimetrically-measured sweat production following treatment compared to the subject's gravimetrically-measured sweat production prior to treatment. In another aspect is provided any of the methods disclosed herein for treating hyperhidrosis, wherein the subject experiences a greater than 30% reduction in gravimetrically-measured sweat production following treatment compared to the subject's gravimetrically-measured sweat production prior to treatment. In another aspect is provided any of the methods disclosed herein for treating hyperhidrosis, wherein the subject experiences a greater than 40% reduction in gravimetrically-measured sweat production following treatment compared to the subject's gravimetrically-measured sweat production prior to treatment. In another aspect is provided any of the methods disclosed herein for treating hyperhidrosis, wherein the subject experiences a greater than 50% reduction in gravimetrically-measured sweat production following treatment compared to the subject's gravimetrically-measured sweat production prior to treatment. In another aspect is provided any of the methods disclosed herein for treating hyperhidrosis, wherein the subject experiences a greater than 60% reduction in gravimetrically-measured sweat production following treatment compared to the subject's gravimetrically-measured sweat production prior to treatment. In another aspect is provided any of the methods disclosed herein for treating hyperhidrosis, wherein the subject experiences a greater than 70% reduction in gravimetrically-measured sweat production following treatment compared to the subject's gravimetrically-measured sweat production prior to treatment. In another aspect is provided any of the methods disclosed herein for treating hyperhidrosis, wherein the subject experiences a greater than 80% reduction in gravimetrically-measured sweat production following treatment compared to the subject's gravimetrically-measured sweat production prior to treatment. In another aspect is provided any of the methods disclosed herein for treating hyperhidrosis, wherein the subject experiences a greater than 90% reduction in gravimetrically-measured sweat production following treatment compared to the subject's gravimetrically-measured sweat production prior to treatment. In another aspect is provided any of the methods disclosed herein for treating hyperhidrosis, wherein the subject experiences a greater than 95% reduction in gravimetrically-measured sweat production following treatment compared to the subject's gravimetrically-measured sweat production prior to treatment. In another aspect is provided any of the methods disclosed herein for treating hyperhidrosis, wherein the subject is treated once per month, twice per month, three times per month, four times per month, five times per month, six times per month, 7 times per month, 8 times per month, 9 times per month, 10 times per month, 11 times per month, 12 times per month, 13 times per month, 14 times per month, 15 times per month, 16 times per month, 17 times per month, 18 times per month, 19 times per month, 20 times per month, 21 times per month, 22 times per month, or 24 times per month. In another aspect is provided any of the methods disclosed herein for treating hyperhidrosis, wherein the subject is treated twice per month. In another aspect is provided any of the methods disclosed herein for treating hyperhidrosis, wherein the subject is treated three times per month. In another aspect is provided any of the methods disclosed herein for treating hyperhidrosis, wherein the subject is treated once per week. In another aspect is provided any of the methods disclosed herein for treating hyperhidrosis, wherein the subject is at least 18 years old. In another aspect is provided any of the methods disclosed herein for treating hyperhidrosis, wherein the subject is treated once per month, or once every two months, or once every three months, or once every four months, or once every five months, or once every six months, or once every seven months, or once every eight months, or once every nine months, or once every 10 months, or once every 11 months, or once every 12 months. In another aspect is provided any of the methods disclosed herein for treating hyperhidrosis, wherein the subject is treated once per month. In another aspect is provided any of the methods disclosed herein for treating hyperhidrosis, wherein the subject is treated once every two months. In another aspect is provided any of the methods disclosed herein for treating hyperhidrosis, wherein the subject is treated once every three months. In another aspect is provided any of the methods disclosed herein for treating hyperhidrosis, wherein the subject is treated once every four months. In another aspect is provided any of the methods disclosed herein for treating hyperhidrosis, wherein the subject is treated once every five months. In another aspect is provided any of the methods disclosed herein for treating hyperhidrosis, wherein the subject is treated once every six months. In another aspect is provided any of the methods disclosed herein for treating hyperhidrosis, wherein the subject is treated once every seven months. In another aspect is provided any of the methods disclosed herein for treating hyperhidrosis, wherein the subject is treated once every eight months. In another aspect is provided any of the methods disclosed herein for treating hyperhidrosis, wherein the subject is treated once every nine months. In another aspect is provided any of the methods disclosed herein for treating hyperhidrosis, wherein the subject is treated once every 10 months. In another aspect is provided any of the methods disclosed herein for treating hyperhidrosis, wherein the subject is treated once every 11 months. In another aspect is provided any of the methods disclosed herein for treating hyperhidrosis, wherein the subject is treated once every 12 months. In another aspect is provided any of the methods disclosed herein for treating hyperhidrosis, wherein the subject suffers from primary axillary hyperhidrosis.

In another aspect is provided any of the methods, compositions, compositions for use, and kits disclosed herein wherein the percentage of treated subjects having gravimetric sweat production of ≤50 mg per axilla at 4 weeks following the application of the composition comprising Spongilla and the composition comprising one or more botulinum toxins is about 10% of subjects, about 15% of subjects, about 20% of subjects, about 25% of subjects, about 30% of subjects, about 35% of subjects, about 40% of subjects, about 45% of subjects, about 50% of subjects, about 55% of subjects, about 60% of subjects, about 65% of subjects, about 70% of subjects, about 75% of subjects, about 80% of subjects, about 85% of subjects, about 90% of subjects, about 95% of subjects, or about 99% of subjects.

In another aspect is provided any of the methods, compositions, compositions for use, and kits, wherein the second composition comprises one or more botulinum toxin type selected from botulinum toxin type A, botulinum toxin type B, botulinum toxin type C1, botulinum toxin type C2, botulinum toxin type D, botulinum toxin type E, botulinum toxin type F and botulinum toxin type G. In another aspect is provided any of the methods, compositions, compositions for use, and kits, wherein the second composition comprises one or more botulinum toxin type selected from botulinum toxin type A. In another aspect is provided any of the methods, compositions, compositions for use, and kits, wherein the botulinum toxin type A is onabotulinumtoxinA. In another aspect is provided any of the methods, compositions, compositions for use, and kits, wherein the subject is treated once per month, twice per month, three times per month, four times per month, five times per month, six times per month, 7 times per month, 8 times per month, 9 times per month, 10 times per month, 11 times per month, 12 times per month, 13 times per month, 14 times per month, 15 times per month, 16 times per month, 17 times per month, 18 times per month, 19 times per month, 20 times per month, 21 times per month, 22 times per month, or 24 times per month. In another aspect is provided any of the methods, compositions, compositions for use, and kits, wherein the subject is treated twice per month. In another aspect is provided any of the methods, compositions, compositions for use, and kits, wherein the subject is treated three times per month. In another aspect is provided any of the methods, compositions, compositions for use, and kits, wherein the subject is treated once per week. In another aspect is provided any of the methods, compositions, compositions for use, and kits, wherein the subject is at least 18 years old. In another aspect is provided any of the methods, compositions, compositions for use, and kits, wherein the subject is treated once per month, or once every two months, or once every three months, or once every four months, or once every five months, or once every six months, or once every seven months, or once every eight months, or once every nine months, or once every 10 months, or once every 11 months, or once every 12 months. In another aspect is provided any of the methods, compositions, compositions for use, and kits, wherein the subject is treated once per month. In another aspect is provided any of the methods, compositions, compositions for use, and kits, wherein the subject is treated once every two months. In another aspect is provided any of the methods, compositions, compositions for use, and kits, wherein the subject is treated once every three months. In another aspect is provided any of the methods, compositions, compositions for use, and kits, wherein the subject is treated once every four months. In another aspect is provided any of methods, compositions, compositions for use, and kits, wherein the subject is treated once every five months. In another aspect is provided any of the methods, compositions, compositions for use, and kits, wherein the subject is treated once every six months. In another aspect is provided any of the methods, compositions, compositions for use, and kits, wherein the subject is treated once every seven months. In another aspect is provided any of methods, compositions, compositions for use, and kits, wherein the subject is treated once every eight months. In another aspect is provided any of methods, compositions, compositions for use, and kits, wherein the subject is treated once every nine months. In another aspect is provided any of the methods, compositions, compositions for use, and kits, wherein the subject is treated once every 10 months. In another aspect is provided any of the methods, compositions, compositions for use, and kits, wherein the subject is treated once every 11 months. In another aspect is provided any of the methods, compositions, compositions for use, and kits, wherein the subject is treated once every 12 months. In another aspect is provided any of the methods, compositions, compositions for use, and kits, wherein the subject suffers from and/or seeks to improve one or more luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles.

In another aspect is provided any of the methods disclosed herein for treating one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles, wherein the first composition comprises from about 0.25 grams to about 10 grams Spongilla. In another aspect is provided any of the methods disclosed herein for treating one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles, wherein the composition comprises Spongilla and hydrogen peroxide solution. In another aspect is provided any of the methods disclosed herein, wherein the hydrogen peroxide solution comprises about 3% hydrogen peroxide. In another aspect is provided any of the methods disclosed herein, wherein the first composition comprises about 2 grams of Spongilla and about 6 mL of 3% hydrogen peroxide or about 6 mL of saline.

In another aspect is provided any of the methods disclosed herein, wherein the first composition comprises Spongilla in the form of a powder. Materials comprising Spongilla may be prepared in powdered form having particles of substantially the same size, using techniques known to those having ordinary skill in the art, such as grinding and sieving. In another aspect is provided any of the methods disclosed herein, wherein the Spongilla is in the form of a powder comprising particles that are substantially uniform in size. In another aspect is provided any of the methods disclosed herein, wherein not less than about 50% of the particles comprising the Spongilla powder pass through a US 70-mesh screen. In another aspect is provided any of the methods disclosed herein, wherein not less than about 60%, or about 70%, or about 75%, or about 80%, or about 85%, or about 90%, or about 95%, or about 96%, or about 97%, or about 98%, or about 99% of the particles comprising the Spongilla powder pass through a US 70-mesh screen. In another aspect is provided any of the methods disclosed herein, wherein not less than about 95%, or about 96%, or about 97%, or about 98%, or about 99% of the particles comprising the Spongilla powder pass through a US 70-mesh screen. In another aspect is provided any of the methods disclosed herein, wherein not less than about 95% of the particles comprising the Spongilla powder pass through a US 70-mesh screen. In another aspect is provided any of the methods disclosed herein, wherein not less than about 96% of the particles comprising the Spongilla powder pass through a US 70-mesh screen. In another aspect is provided any of the methods disclosed herein, wherein not less than about 97% of the particles comprising the Spongilla powder pass through a US 70-mesh screen. In another aspect is provided any of the methods disclosed herein, wherein not less than about 98% of the particles comprising the Spongilla powder pass through a US 70-mesh screen. In another aspect is provided any of the methods disclosed herein, wherein not less than about 99% of the particles comprising the Spongilla powder pass through a US 70-mesh screen. The particles of Spongilla may be manufactured or produced from Spongilla materials that are harvested by procedures known to those of ordinary skill in the art, such as determining the appropriate harvest period, removal of foreign materials, drying, milling and grinding using equipment known to those of ordinary skill in the art.

In another aspect is provided any of the methods disclosed herein, wherein the particles comprising the Spongilla powder have an average length of from about 50 µm to about 500

µm. In another aspect is provided any of the methods disclosed herein, wherein the particles comprising the Spongilla powder have an average length of from about 50 µm to about 400 µm, or from about 50 µm to about 350 µm, or from about 50 µm to about 300 µm, or from about 50 µm to about 250 µm, or from about 50 µm to about 200 µm, or from about 75 µm to about 500 µm, or from about 75 µm to about 450 µm, or from about 80 µm to about 450 µm, or from about 80 µm to about 400 µm, or from about 85 µm to about 450 µm, or from about 85 µm to about 400 µm, or from about 90 µm to about 450 µm, or from about 90 µm to about 400 µm, or from about 90 µm to about 350 µm, or from about 100 µm to about 450 µm, or from about 100 µm to about 400 µm, or from about 100 µm to about 350 µm, or from about 100 µm to about 300 µm, or from about 100 µm to about 250 µm, or from about 100 µm to about 200 µm, or from about 150 µm to about 500 µm, or from about 150 µm to about 450 µm, or from about 150 µm to about 400 µm, or from about 150 µm to about 350 µm, or from about 150 µm to about 350 µm, or from about 150 µm to about 300 µm, or from about 150 µm to about 250 µm, or from about 150 µm to about 200 µm, or from about 175 µm to about 450 µm, or from about 175 µm to about 400 µm, or from about 175 µm to about 350 µm, or from about 175 µm to about 300 µm, or from about 175 µm to about 250 µm, or from about 175 µm to about 200 µm. In another aspect is provided any of the methods disclosed herein, wherein the particles comprising the Spongilla powder have an average length of about 50 µm, or about 75 µm, or about 80 µm, or about 85 µm, or about 90 µm, or about 100 µm, or about 125 µm, or about 150 µm, or about 175 µm, or about 200 µm, or about 225 µm, or about 250 µm, or about 300 µm, or about 350 µm, or about 400 µm, or about 450 µm, or about 500 µm. In another aspect is provided any of the methods disclosed herein, wherein the particles comprising the Spongilla powder have an average length of about 200 µm. The particles comprising the Spongilla powder may be manufactured or produced from Spongilla materials that are harvested by procedures known to those of ordinary skill in the art, such as milling and grinding using equipment known to those of ordinary skill in the art. The average length of particles comprising the Spongilla powder may be measured using analytical methods known to those of ordinary skill in the art, such as, for example, scanning electron microscopy (SEM) and sieve analysis. Sieve analysis may also be used to determine the particle size distribution of the particles comprising the Spongilla powder.

In another aspect is provided any of the methods disclosed herein, wherein the particles comprising the Spongilla powder have an average diameter of from about 5 µm to about 50 µm. In another aspect is provided any of the methods disclosed herein, wherein the particles comprising the Spongilla powder have an average diameter of from about 5 µm to about 45 µm, or from about 5 µm to about 40 µm, from about 5 µm to about 35 µm, from about 5 µm to about 30 µm, from about 5 µm to about 25 µm, from about 5 µm to about 20 µm, from about 10 µm to about 50 µm, from about 10 µm to about 45 µm, from about 10 µm to about 40 µm, from about 10 µm to about 35 µm, from about 10 µm to about 30 µm, from about 10 µm to about 25 µm, from about 10 µm to about 20 µm. In another aspect is provided any of the methods disclosed herein, wherein the particles comprising the Spongilla powder have an average diameter of about 5 µm, or about 10 µm, or about 15 µm, or about 20 µm, or about 25 µm, or about 30 µm, or about 35 µm, or about 40 µm, or about 45 µm, or about 50 µm. The particles comprising the Spongilla powder may be manufactured or produced from Spongilla materials that are harvested by procedures known to those of ordinary skill in the art, such as milling and grinding using equipment known to those of ordinary skill in the art. The average diameter of particles comprising the Spongilla powder may be measured using analytical methods known to those of ordinary skill in the art, such as, for example, scanning electron microscopy (SEM) and sieve analysis. Sieve analysis may also be used to determine the particle size distribution of the particles comprising the Spongilla powder In another aspect is provided any of the methods disclosed herein, wherein the particles comprising the Spongilla powder have an aspect ratio of from about 1 to about 100. In another aspect is provided any of the methods disclosed herein, wherein the particles comprising the Spongilla powder have an aspect ratio of from about 1 to about 75, or from about 1 to about 50, or from about 1 to about 25, or from about 1 to about 20, or from about 1 to about 15, or from about 5 to about 100, or from about 5 to about 75, or from about 5 to about 50, or from about 5 to about 40, or from about 5 to about 35, or from about 5 to about 30, or from about 5 to about 25, or from about 5 to about 20, or from about 5 to about 15, or from about 7 to about 50, or from about 7 to about 45, or from about 7 to about 40, or from about 7 to about 35, or from about 7 to about 30, or from about 7 to about 25, or from about 10 to about 50, or from about 10 to about 45, or from about 10 to about 40, or from about 10 to about 35, or from about 10 to about 30, or from about 10 to about 25, from about 10 to about 20, or from about 10 to about 15. In another aspect is provided any of the methods disclosed herein, wherein the particles comprising the Spongilla powder have an aspect ratio of about 5, or about 6, or about 7, or about 8, or about 9, or about 10, or about 11, or about 12, or about 13, or about 14, or about 15, or about 16, or about 17, or about 18, or about 19, or about 20, or about 21, or about 22, or about 23, or about 24, or about 25, or about 26, or about 27, or about 28, or about 29, or about 30, or about 35, or about 40, or about 45, or about 50, or about 75, or about 100. The particles comprising the Spongilla powder may be manufactured or produced from Spongilla materials that are harvested by procedures known to those of ordinary skill in the art, such as milling and grinding using equipment known to those of ordinary skill in the art. The aspect ratio of particles comprising the Spongilla powder may be measured using analytical methods known to those of ordinary skill in the art, such as, for example, scanning electron microscopy (SEM) and sieve analysis. Sieve analysis may also be used to determine the particle size distribution of the particles comprising the Spongilla powder Materials comprising Spongilla may be processed and dried, using techniques known to those having ordinary skill in the art, such as the use of drying ovens, to provide materials having a desired residual moisture content. In another aspect is provided any of the methods disclosed herein, wherein the first composition comprising Spongilla has a residual moisture content of not more than about 20%. In another aspect is provided any of the methods disclosed herein, wherein the first composition has a residual moisture content of not more than about 15%, or not more than about 10%, or not more than about 9%, or not more than about 8%, or not more than about 7%, or not more than about 6%, or not more than about 5%, or not more than about 4%, or not more than about 3%, or not more than about 2%, or not more than 1%. In another aspect is provided any of the methods disclosed herein, wherein the first composition has a residual moisture content of not more than about 5%. In another aspect is provided any of the methods disclosed herein, wherein the first composition has a residual moisture content of not more than about 4%. In another aspect is provided any of the methods disclosed herein, wherein the first composition has a residual moisture content of not more than about 3%. In another aspect is provided any of the methods disclosed herein, wherein the first composition has a residual moisture content of not more than about 2%. In another aspect is provided any of the methods disclosed herein, wherein the first composition has a residual moisture content of not more than about 1%. The moisture content of the Spongilla materials can be reduced by heating the raw Spongilla materials using methods known to those of ordinary skill in the art, such as by open-air drying, or by use of a conventional oven dryer or a vacuum dryer, using equipment known to those of ordinary skill in the art. For example, raw Spongilla materials may be placed into a tray and heated in a drying oven at a temperature range from about 30° C. to about 200° C., for example to about 70° C., for a period of time necessary to reduce the residual moisture content to the desired level. The level of residual moisture of the materials may be measured using methods known to those of ordinary skill in the art such as those described in the United States Pharmacopeia methods USP <731> (Loss on Drying) and USP <921> (Water Determination).

Materials comprising Spongilla may be treated in order to reduce the bioburden, such as aerobic and anaerobic microbes, yeast and mold, Coliform bacteria, *Salmonella, Pseudomonas aeruginosa*, and *Staphylococcus aureus*, of the materials prior to their packaging and use, such as by use of heat treatment or irradiation, such as the use of gamma irradiation.

In another aspect is provided any of the methods disclosed herein, wherein the first composition has a combined aerobic and anaerobic microbial content of not more than about 25 $\times 10^4$ colony-forming units per gram (CFU/g). In another aspect is provided any of the methods disclosed herein, wherein the first composition has a combined aerobic and anaerobic microbial content of not more than about $10 \times 10^4$ CFU/g, or not more than about $5 \times 10^4$ CFU/g, or not more than about $1 \times 10^4$ CFU/g, or not more than about $5 \times 10^3$ CFU/g, or not more than about $1 \times 10^3$ CFU/g, or not more than about 10,000 CFU/g, or not more than about 7,500 CFU/g, or not more than about 5,000 CFU/g, or not more than about 2,500 CFU/g, or not more than about 2,000 CFU/g, or not more than about 1,500 CFU/g, or not more than about 1,000 CFU/g, or not more than about 750 CFU/g, or not more than about 500 CFU/g, or not more than about 250 CFU/g, or not more than about 200 CFU/g, or not more than about 150 CFU/g, or not more than about 100 CFU/g, or not more than about 75 CFU/g, or not more than about 50 CFU/g, or not more than about 25 CFU/g, or not more than about 15 CFU/g, or not more than about 10 CFU/g, or not more than about 5 CFU/g, or not more than about 1 CFU/g. In another aspect is provided any of the methods disclosed herein, wherein the first composition has a combined aerobic and anaerobic microbial content of not more than about 1,000 CFU/g. In another aspect is provided any of the methods disclosed herein, wherein the first composition has a combined aerobic and anaerobic microbial content of not more than about 750 CFU/g. In another aspect is provided any of the methods disclosed herein, wherein the first composition has a combined aerobic and anaerobic microbial content of not more than about 500 CFU/g. In another aspect is provided any of the methods disclosed herein, wherein the first composition has a combined aerobic and anaerobic microbial content of not more than about 250 CFU/g. In another aspect is provided any of the methods disclosed herein, wherein the first composition has a combined aerobic and anaerobic microbial content of not more than about 200 CFU/g. In another aspect is provided any of the methods disclosed herein, wherein the first composition has a combined aerobic and anaerobic microbial content of not more than about 150 CFU/g. In another aspect is provided any of the methods disclosed herein, wherein the first composition has a combined aerobic and anaerobic microbial content of not more than about 100 CFU/g. In another aspect is provided any of the methods disclosed herein, wherein the first composition has a combined aerobic and anaerobic microbial content of not more than about 75 CFU/g. In another aspect is provided any of the methods disclosed herein, wherein the first composition has a combined aerobic and anaerobic microbial content of not more than about 50 CFU/g. In another aspect is provided any of the methods disclosed herein, wherein the first composition has a combined aerobic and anaerobic microbial content of not more than about 25 CFU/g. In another aspect is provided any of the methods disclosed herein, wherein the first composition has a combined aerobic and anaerobic microbial content of not more than about 20 CFU/g. In another aspect is provided any of the methods disclosed herein, wherein the first composition has a combined aerobic and anaerobic microbial content of not more than about 10 CFU/g. In another aspect is provided any of the methods disclosed herein, wherein the first composition has a combined aerobic and anaerobic microbial content of not more than about 1 CFU/g. The combined aerobic and anaerobic microbial content of the Spongilla materials may be reduced by physical or chemical methods known to those of ordinary skill in the art, such as physical treatment of the materials with heat in the form of steam or dry heat, or chemical treatment in the form of exposure to ethylene oxide gas or treatment by ionizing radiation for a sufficient amount of time to reduce the microbial content to the desired levels. The combined aerobic and anaerobic microbial content of the Spongilla materials may be measured by methods known to those of ordinary skill in the art, such as those described in the United States Pharmacopeia method USP <61> (Microbial Enumeration Tests).

In another aspect is provided any of the methods disclosed herein, wherein the first composition comprising Spongilla has a combined yeast and mold content of not more than about $25 \times 10^4$ colony-forming units per gram (CFU/g). In another aspect is provided any of the methods disclosed herein, wherein the first composition has a combined yeast and mold content of not more than about or not more than about $5 \times 10^4$ CFU/g, or not more than about $1 \times 10^4$ CFU/g, or not more than about $5 \times 10^3$ CFU/g, or not more than about $1 \times 10^3$ CFU/g, or not more than about 10,000 CFU/g, or not more than about 7,500 CFU/g, or not more than about 5,000 CFU/g, or not more than about 2,500 CFU/g, or not more than about 2,000 CFU/g, or not more than about 1,500 CFU/g, or not more than about 1,000 CFU/g, or not more than about 750 CFU/g, or not more than about 500 CFU/g, or not more than about 250 CFU/g, or not more than about 200 CFU/g, or not more than about 150 CFU/g, or not more than about 100 CFU/g, or not more than about 75 CFU/g, or not more than about 50 CFU/g, or not more than about 25 CFU/g, or not more than about 15 CFU/g, or not more than about 10 CFU/g, or not more than about 5 CFU/g, or not more than about 1 CFU/g. In another aspect is provided any of the methods disclosed herein, wherein the first composition has a combined yeast and mold content of not more than about 1,000 CFU/g. In another aspect is provided any of the methods disclosed herein, wherein the first composition has a combined yeast and mold content of not more than about 750 CFU/g. In another aspect is provided any of the methods disclosed herein, wherein the first composition has a combined yeast and mold content of not more than about 500 CFU/g. In another aspect is provided any of the methods disclosed herein, wherein the first composition has a combined yeast and mold content of not more than about 250 CFU/g. In another aspect is provided any of the methods disclosed herein, wherein the first composition has a combined yeast and mold content of not more than about 200 CFU/g. In another aspect is provided any of the methods disclosed herein, wherein the first composition has a combined yeast and mold content of not more than about 150 CFU/g. In another aspect is provided any of the methods disclosed herein, wherein the first composition has a combined yeast and mold content of not more than about 100 CFU/g. In another aspect is provided any of the methods disclosed herein, wherein the first composition has a combined yeast and mold content of not more than about 75 CFU/g. In another aspect is provided any of the methods disclosed herein, wherein the first composition has a combined yeast and mold content of not more than about 50 CFU/g. In another aspect is provided any of the methods disclosed herein, wherein the first composition has a combined yeast and mold content of not more than about 25 CFU/g. In another aspect is provided any of the methods disclosed herein, wherein the first composition has a combined yeast and mold content of not more than about 20 CFU/g. In another aspect is provided any of the methods disclosed herein, wherein the first composition has a combined yeast and mold content of not more than about 10 CFU/g. In another aspect is provided any of the methods disclosed herein, wherein the first composition has a combined yeast and mold content of not more than about 1 CFU/g. The combined yeast and mold content of the Spongilla materials may be reduced by physical or chemical methods known to those of ordinary skill in the art, such as physical treatment of the materials with heat in the form of steam or dry heat, or chemical treatment in the form of exposure to ethylene oxide gas or treatment by ionizing radiation for a sufficient amount of time to reduce the microbial content to the desired levels. The combined yeast and mold content of the Spongilla materials may be measured by methods known to those of ordinary skill in the art, such as those described in the United States Pharmacopeia method USP <61> (Microbial Enumeration Tests).

In another aspect is provided any of the methods disclosed herein, wherein the amount of Coliform bacteria in the first composition is not more than about $25 \times 10^4$ colony-forming units per gram (CFU/g). In another aspect is provided any of the methods disclosed herein, wherein the amount of Coliform bacteria in the first composition is not more than about $5 \times 10^4$ CFU/g, or not more than about $1 \times 10^4$ CFU/g, or not more than about $5 \times 10^3$ CFU/g, or not more than about $1 \times 10^3$ CFU/g, or not more than about 10,000 CFU/g, or not more than about 7,500 CFU/g, or not more than about 5,000 CFU/g, or not more than about 2,500 CFU/g, or not more than about 2,000 CFU/g, or not more than about 1,500 CFU/g, or not more than about 1,000 CFU/g, or not more than about 750 CFU/g, or not more than about 500 CFU/g, or not more than about 250 CFU/g, or not more than about 200 CFU/g, or not more than about 150 CFU/g, or not more than about 100 CFU/g, or not more than about 75 CFU/g, or not more than about 50 CFU/g, or not more than about 25 CFU/g, or not more than about 15 CFU/g, or not more than about 10 CFU/g, or not more than about 5 CFU/g, or not more than about 1 CFU/g. In another aspect is provided any of the methods disclosed herein, wherein the first composition has a Coliform bacteria content of not more than about 1,000 CFU/g. In another aspect is provided any of the methods disclosed herein, wherein the first composition has a Coliform bacteria content of not more than about 750 CFU/g. In another aspect is provided any of the methods disclosed herein, wherein the first composition has a Coliform bacteria content of not more than about 500 CFU/g. In another aspect is provided any of the methods disclosed herein, wherein the first composition has a Coliform bacteria content of not more than about 250 CFU/g. In another aspect is provided any of the methods disclosed herein, wherein the first composition has a Coliform bacteria content of not more than about 200 CFU/g. In another aspect is provided any of the methods disclosed herein, wherein the first composition has a Coliform bacteria content of not more than about 150 CFU/g. In another aspect is provided any of the methods disclosed herein, wherein the first composition has a Coliform bacteria content of not more than about 100 CFU/g. In another aspect is provided any of the methods disclosed herein, wherein the first composition has a Coliform bacteria content of not more than about 75 CFU/g. In another aspect is provided any of the methods disclosed herein, wherein the first composition has a Coliform bacteria content of not more than about 50 CFU/g. In another aspect is provided any of the methods disclosed herein, wherein the first composition has a Coliform bacteria content of not more than about 25 CFU/g. In another aspect is provided any of the methods disclosed herein, wherein the first composition has a Coliform bacteria content of not more than about 20 CFU/g. In another aspect is provided any of the methods disclosed herein, wherein the first composition has a Coliform bacteria content of not more than about 10 CFU/g. In another aspect is provided any of the methods disclosed herein, wherein the first composition has a Coliform bacteria content of not more than about 1 CFU/g. In another aspect is provided any of the methods disclosed herein, wherein the first composition has no detectable Coliform bacterial content. The Coliform bacteria content of the Spongilla materials may be reduced by physical or chemical methods known to those of ordinary skill in the art, such as physical treatment of the materials with heat in the form of steam or dry heat, or chemical treatment in the form of exposure to ethylene oxide gas or treatment by ionizing radiation for a sufficient amount of time to reduce the microbial content to the desired levels. The Coliform bacteria content of the Spongilla materials may be measured by methods known to those of ordinary skill in the art, such as those described in the United States Pharmacopeia method USP <62> (Tests for Specified Microorganisms).

In another aspect is provided any of the methods disclosed herein, wherein the amount of *Salmonella* in the first composition is not more than about $25 \times 10^4$ colony-forming units per gram (CFU/g). In another aspect is provided any of the methods disclosed herein, wherein the amount of *Salmonella* in the first composition is not more than about $5 \times 10^4$ CFU/g, or not more than about $1 \times 10^4$ CFU/g, or not more than about $5 \times 10^3$ CFU/g, or not more than about $1 \times 10^3$ CFU/g, or not more than about 10,000 CFU/g, or not more than about 7,500 CFU/g, or not more than about 5,000 CFU/g, or not more than about 2,500 CFU/g, or not more than about 2,000 CFU/g, or not more than about 1,500 CFU/g, or not more than about 1,000 CFU/g, or not more than about 750 CFU/g, or not more than about 500 CFU/g, or not more than about 250 CFU/g, or not more than about 200 CFU/g, or not more than about 150 CFU/g, or not more than about 100 CFU/g, or not more than about 75 CFU/g, or not more than about 50 CFU/g, or not more than about 25 CFU/g, or not more than about 15 CFU/g, or not more than about 10 CFU/g, or not more than about 5 CFU/g, or not more than about 1 CFU/g. In another aspect is provided any of the methods disclosed herein, wherein the first composition has a *Salmonella* content of not more than about 1,000 CFU/g. In another aspect is provided any of the methods disclosed herein, wherein the first composition has a *Salmonella* content of not more than about 750 CFU/g. In another aspect is provided any of the methods disclosed herein, wherein the first composition has a *Salmonella* content of not more than about 500 CFU/g. In another aspect is provided any of the methods disclosed herein, wherein the first composition has a *Salmonella* content of not more than about 250 CFU/g. In another aspect is provided any of the methods disclosed herein, wherein the first composition has a *Salmonella* content of not more than about 200 CFU/g. In another aspect is provided any of the methods disclosed herein, wherein the first composition has a *Salmonella* content of not more than about 150 CFU/g. In another aspect is provided any of the methods disclosed herein, wherein the first composition has a *Salmonella* content of not more than about 100 CFU/g. In another aspect is provided any of the methods disclosed herein, wherein the first composition has a *Salmonella* content of not more than about 75 CFU/g. In another aspect is provided any of the methods disclosed herein, wherein the first composition has a *Salmonella* content of not more than about 50 CFU/g. In another aspect is provided any of the methods disclosed herein, wherein the first composition has a *Salmonella* content of not more than about 25 CFU/g. In another aspect is provided any of the methods disclosed herein, wherein the first composition has a *Salmonella* content of not more than about 20 CFU/g. In another aspect is provided any of the methods disclosed herein, wherein the first composition has a *Salmonella* content of not more than about 10 CFU/g. In another aspect is provided any of the methods disclosed herein, wherein the first composition has a *Salmonella* content of not more than about 1 CFU/g. In another aspect is provided any of the methods disclosed herein, wherein the first composition has no detectable *Salmonella* content. The *Salmonella* content of the Spongilla materials may be reduced by physical or chemical methods known to those of ordinary skill in the art, such as physical treatment of the materials with heat in the form of steam or dry heat, or chemical treatment in the form of exposure to ethylene oxide gas or treatment by ionizing radiation for a sufficient amount of time to reduce the microbial content to the desired levels. The *Salmonella* content of the Spongilla materials may be measured by methods known to those of ordinary skill in the art, such as those described in the United States Pharmacopeia method USP <62> (Tests for Specified Microorganisms).

In another aspect is provided any of the methods disclosed herein, wherein the amount of *Pseudomonas aeruginosa* bacteria in the first composition is not more than about $25 \times 10^4$ colony-forming units per gram (CFU/g). In another aspect is provided any of the methods disclosed herein, wherein the amount of *Pseudomonas aeruginosa* bacteria in the first composition is not more than about $5 \times 10^4$ CFU/g, or not more than about $1 \times 10^4$ CFU/g, or not more than about $5 \times 10^3$ CFU/g, or not more than about $1 \times 10^3$ CFU/g, or not more than about 10,000 CFU/g, or not more than about 7,500 CFU/g, or not more than about 5,000 CFU/g, or not more than about 2,500 CFU/g, or not more than about 2,000 CFU/g, or not more than about 1,500 CFU/g, or not more than about 1,000 CFU/g, or not more than about 750 CFU/g, or not more than about 500 CFU/g, or not more than about 250 CFU/g, or not more than about 200 CFU/g, or not more than about 150 CFU/g, or not more than about 100 CFU/g, or not more than about 75 CFU/g, or not more than about 50 CFU/g, or not more than about 25 CFU/g, or not more than about 15 CFU/g, or not more than about 10 CFU/g, or not more than about 5 CFU/g, or not more than about 1 CFU/g. In another aspect is provided any of the methods disclosed herein, wherein the first composition has a *Pseudomonas aeruginosa* bacteria content of not more than about 1,000 CFU/g. In another aspect is provided any of the methods disclosed herein, wherein the first composition has a *Pseudomonas aeruginosa* bacteria content of not more than about 750 CFU/g. In another aspect is provided any of the methods disclosed herein, wherein the first composition has a *Pseudomonas aeruginosa* bacteria content of not more than about 500 CFU/g. In another aspect is provided any of the methods disclosed herein, wherein the first composition has a *Pseudomonas aeruginosa* bacteria content of not more than about 250 CFU/g. In another aspect is provided any of the methods disclosed herein, wherein the first composition has a *Pseudomonas aeruginosa* bacteria content of not more than about 200 CFU/g. In another aspect is provided any of the methods disclosed herein, wherein the first composition has a *Pseudomonas aeruginosa* bacteria content of not more than about 150 CFU/g. In another aspect is provided any of the methods disclosed herein, wherein the first composition has a *Pseudomonas aeruginosa* bacteria content of not more than about 100 CFU/g. In another aspect is provided any of the methods disclosed herein, wherein the first composition has a *Pseudomonas aeruginosa* bacteria content of not more than about 75 CFU/g. In another aspect is provided any of the methods disclosed herein, wherein the first composition has a *Pseudomonas aeruginosa* bacteria content of not more than about 50 CFU/g. In another aspect is provided any of the methods disclosed herein, wherein the first composition has a *Pseudomonas aeruginosa* bacteria content of not more than about 25 CFU/g. In another aspect is provided any of the methods disclosed herein, wherein the first composition has a *Pseudomonas aeruginosa* bacteria content of not more than about 20 CFU/g. In another aspect is provided any of the methods disclosed herein, wherein the first composition has a *Pseudomonas aeruginosa* bacteria content of not more than about 10 CFU/g. In another aspect is provided any of the methods disclosed herein, wherein the first composition has a *Pseudomonas aeruginosa* bacteria content of not more than about 1 CFU/g. In another aspect is provided any of the methods disclosed herein, wherein the first composition has no detectable *Pseudomonas aeruginosa* bacteria content. The *Pseudomonas aeruginosa* bacteria content of the Spongilla materials may be reduced by physical or chemical methods known to those of ordinary skill in the art, such as physical treatment of the materials with heat in the form of steam or dry heat, or chemical treatment in the form of exposure to ethylene oxide gas or treatment by ionizing radiation for a sufficient amount of time to reduce the microbial content to the desired levels. The *Pseudomonas aeruginosa* bacteria content of the Spongilla materials may be measured by methods known to those of ordinary skill in the art, such as those described in the United States Pharmacopeia method USP <62> (Tests for Specified Microorganisms).

In another aspect is provided any of the methods disclosed herein, wherein the amount of *Staphylococcus aureus* bacteria in the first composition is not more than about $25\times10^4$ colony-forming units per gram (CFU/g). In another aspect is provided any of the methods disclosed herein, wherein the amount of *Staphylococcus aureus* bacteria in the first composition is not more than about $5\times10^4$ CFU/g, or not more than about $1\times10^4$ CFU/g, or not more than about $5\times10^3$ CFU/g, or not more than about $1\times10^3$ CFU/g, or not more than about 10,000 CFU/g, or not more than about 7,500 CFU/g, or not more than about 5,000 CFU/g, or not more than about 2,500 CFU/g, or not more than about 2,000 CFU/g, or not more than about 1,500 CFU/g, or not more than about 1,000 CFU/g, or not more than about 750 CFU/g, or not more than about 500 CFU/g, or not more than about 250 CFU/g, or not more than about 200 CFU/g, or not more than about 150 CFU/g, or not more than about 100 CFU/g, or not more than about 75 CFU/g, or not more than about 50 CFU/g, or not more than about 25 CFU/g, or not more than about 15 CFU/g, or not more than about 10 CFU/g, or not more than about 5 CFU/g, or not more than about 1 CFU/g. In another aspect is provided any of the methods disclosed herein, wherein the first composition has a *Staphylococcus aureus* bacteria content of not more than about 1,000 CFU/g. In another aspect is provided any of the methods disclosed herein, wherein the first composition has a *Staphylococcus aureus* bacteria content of not more than about 750 CFU/g. In another aspect is provided any of the methods disclosed herein, wherein the first composition has a *Staphylococcus aureus* bacteria content of not more than about 500 CFU/g. In another aspect is provided any of the methods disclosed herein, wherein the first composition has a *Staphylococcus aureus* bacteria content of not more than about 250 CFU/g. In another aspect is provided any of the methods disclosed herein, wherein the first composition has a *Staphylococcus aureus* bacteria content of not more than about 200 CFU/g. In another aspect is provided any of the methods disclosed herein, wherein the first composition has a *Staphylococcus aureus* bacteria content of not more than about 150 CFU/g. In another aspect is provided any of the methods disclosed herein, wherein the first composition has a *Staphylococcus aureus* bacteria content of not more than about 100 CFU/g. In another aspect is provided any of the methods disclosed herein, wherein the first composition has a *Staphylococcus aureus* bacteria content of not more than about 75 CFU/g. In another aspect is provided any of the methods disclosed herein, wherein the first composition has a *Staphylococcus aureus* bacteria content of not more than about 50 CFU/g. In another aspect is provided any of the methods disclosed herein, wherein the first composition has a *Staphylococcus aureus* bacteria content of not more than about 25 CFU/g. In another aspect is provided any of the methods disclosed herein, wherein the first composition has a *Staphylococcus aureus* bacteria content of not more than about 20 CFU/g. In another aspect is provided any of the methods disclosed herein, wherein the first composition has a *Staphylococcus aureus* bacteria content of not more than about 10 CFU/g. In another aspect is provided any of the methods disclosed herein, wherein the first composition has a *Staphylococcus aureus* bacteria content of not more than about 1 CFU/g. In another aspect is provided any of the methods disclosed herein, wherein the first composition has no detectable *Staphylococcus aureus* bacteria content. The *Staphylococcus aureus* bacteria content of the Spongilla materials may be reduced by physical or chemical methods known to those of ordinary skill in the art, such as physical treatment of the materials with heat in the form of steam or dry heat, or chemical treatment in the form of exposure to ethylene oxide gas or treatment by ionizing radiation for a sufficient amount of time to reduce the microbial content to the desired levels. The *Staphylococcus aureus* bacteria content of the Spongilla materials may be measured by methods known to those of ordinary skill in the art, such as those described in the United States Pharmacopeia method USP <62> (Tests for Specified Microorganisms).

In another aspect is provided any of the methods disclosed herein, wherein the first composition is packaged prior to use. In another aspect is provided any of the methods disclosed herein, wherein the first composition is prepared by heating to at least about 70° C. prior to being packaged in order to reduce the bioburden. In another aspect is provided any of the methods disclosed herein, wherein the first composition is prepared by heating to at least about 50° C., or at least about 60° C., or at least about 75° C., or at least about 80° C., or at least about 85° C., or at least about 90° C., or at least about 100° C., or at least about 110° C., or at least about 115° C., or at least about 120° C., or at least about 125° C., or at least about 130° C., or at least about 135° C., or at least about 140° C., or at least about 150° C., or at least about 160° C., or at least about 170° C., or at least about 180° C., or at least about 190° C., or at least about 200° C. prior to being packaged.

In another aspect is provided any of the methods disclosed herein, wherein the first composition comprising Spongilla is heated to at least about 70° C. for at least about 5 minutes prior being packaged. In another aspect is provided any of the methods disclosed herein, wherein the first composition is heated to at least about 70° C. for at least about 10 minutes, or at least about 15 minutes, or at least about 20 minutes, or at least about 25 minutes, or at least about 30 minutes, or at least about 35 minutes, or at least about 40 minutes, or at least about 45 minutes, or at least about 50 minutes, or at least about 55 minutes, or at least about 60 minutes, or at least about 75 minutes, or at least about 90 minutes, or at least about 120 minutes, or at least about 180 minutes, or at least about 4 hours, or at least about 5 hours, or at least about 6 hours, or at least about 7 hours, or at least about 8 hours, or at least about 9 hours, or at least about 10 hours, or at least about 11 hours, or at least about 12 hours, or at least about 24 hours prior being packaged.

In another aspect is provided any of the methods disclosed herein, wherein the first composition comprising Spongilla is prepared by treating with ionizing radiation, such as gamma radiation, prior to being packaged or after packaging. For example, gamma irradiation may be performed on the raw Spongilla material prior to grinding to reduce the particle size, following grinding to reduce the particle size, the materials packaged in bulk and or the materials following packaging in unit dose containers. The materials may be treated with ionizing radiation, such as gamma radiation, using methods and equipment known to those of ordinary skill in the art, such as gamma irradiators or electron beam irradiators. In another aspect is provided any of the methods disclosed herein, wherein the first composition is prepared by treating with ionizing radiation, such as gamma radiation, to deliver an absorbed radiation dose between about 1 kGy and about 50 kGy prior to being packaged. In another aspect is provided any of the methods disclosed herein, wherein the first composition is prepared by treating with ionizing radiation, such as gamma radiation, to deliver an absorbed radiation dose between about 1 kGy and about 45 kGy, or between about 1 kGy and about 40 kGy, between about 1 kGy and about 35 kGy, between about 1 kGy and about 30 kGy, or between about 1 kGy and about 25 kGy or between about 5 kGy and about 50 kGy, or between about 5 kGy and about 45 kGy, or between about 5 kGy and about 40 kGy, or between about 5 kGy and about 35 kGy, or between about 5 kGy and about 30 kGy, or between about 5 kGy and about 25 kGy, or between about 10 kGy and about 50 kGy, or between about 10 kGy and about 45 kGy, or between about 10 kGy and about 40 kGy, or between about 10 kGy and about 35 kGy, or between about 10 kGy and about 30 kGy, or between about 10 kGy and about 25 kGy, or between about 15 kGy and about 50 kGy, or between about 15 kGy and about 45 kGy, or between about 15 kGy and about 40 kGy, or between about 15 kGy and about 35 kGy, or between about 15 kGy and about 30 kGy, or between about 15 kGy and about 25 kGy. In another aspect is provided any of the methods disclosed herein, wherein the first composition is prepared by treating with ionizing radiation, such as gamma radiation, to deliver an absorbed radiation dose of about 1 kGy, or about 5 kGy, or about 10 kGy, 11 kGy, or about 12 kGy, or about 13 kGy, or about 14 kGy, or about 15 kGy, or about 16 kGy, or about 17 kGy, or about 18 kGy, or about 19 kGy, or about 20 kGy, or about 21 kGy, or about 22 kGy, or about 23 kGy, or about 24 kGy, or about 25 kGy, or about 26 kGy, or about 27 kGy, or about 28 kGy, or about 29 kGy, or about 30 kGy, or about 31 kGy, or about 32 kGy, or about 33 kGy, or about 34 kGy, or about 35 kGy, or about 36 kGy, or about 37 kGy, or about 38 kGy, or about 39 kGy, or about 40 kGy, or about 41 kGy, or about 42 kGy, or about 43 kGy, or about 44 kGy, or about 45 kGy, or about 46 kGy, or about 47 kGy, or about 48 kGy, or about 49 kGy, or about 50 kGy.

In another aspect is provided any of the methods disclosed herein, wherein the first composition is applied to the skin of the subject in the form of a paste. In another aspect is provided any of the methods disclosed herein, wherein the paste further comprises water or saline. In another aspect is provided any of the methods disclosed herein, wherein the paste is prepared by mixing a composition comprising Spongilla and an aqueous solution comprising hydrogen peroxide. In another aspect is provided any of the methods disclosed herein, wherein the hydrogen peroxide is at a concentration of from about 0.1% w/w to about 50% w/w, or from about 0.1% w/w to about 45% w/w, or from about 0.1% w/w to about 40% w/w, or from about 0.1% w/w to about 35% w/w, or from about 0.1% w/w to about 30% w/w, or from about 0.1% w/w to about 25% w/w, or from about 0.1% w/w to about 20% w/w, or from about 0.1% w/w to about 15% w/w, or from about 0.1% w/w to about 10% w/w, or from about 0.1% w/w to about 9% w/w, or from about 0.1% w/w to about 8% w/w, or from about 0.1% w/w to about 7% w/w, or from about 0.1% w/w to about 6% w/w, or from about 0.1% w/w to about 5% w/w, or from about 0.1% w/w to about 4% w/w, or from about 0.1% w/w to about 3% w/w, or from about 0.1% w/w to about 2% w/w, or from about 0.1% w/w to about 1% w/w, or from about 0.5% w/w to about 45% w/w, or from about 1% w/w to about 45% w/w, or from about 1% w/w to about 40% w/w, or from about 1% w/w to about 35% w/w, or from about 1% w/w to about 30% w/w, or from about 1% w/w to about 25% w/w, or from about 1% w/w to about 20% w/w, or from about 1% w/w to about 15% w/w, or from about 1% w/w to about 10% w/w, or from about 1% w/w to about 9% w/w, or from about 1% w/w to about 8% w/w, or from about 1% w/w to about 7% w/w, or from about 1% w/w to about 6% w/w, or from about 1% w/w to about 5% w/w, or from about 1% w/w to about 4% w/w, or from about 1% w/w to about 3% w/w, or from about 1% w/w to about 2% w/w, or from about 2% w/w to about 45% w/w, or from about 2% w/w to about 40% w/w, or from about 2% w/w to about 35% w/w, or from about 2% w/w to about 30% w/w, or from about 2% w/w to about 25% w/w, or from about 2% w/w to about 20% w/w, or from about 2% w/w to about 15% w/w, or from about 2% w/w to about 10% w/w, or from about 2% w/w to about 9% w/w, or from about 2% w/w to about 8% w/w, or from about 1% w/w to about 7% w/w, or from about 2% w/w to about 6% w/w, or from about 2% w/w to about 5% w/w, or from about 2% w/w to about 4% w/w, or from about 2% w/w to about 3% w/w. In another aspect is provided any of the methods disclosed herein, wherein the hydrogen peroxide is at a concentration of about 0.1% w/w, or about 0.5% w/w, or about 1% w/w, or about 2% w/w, or about 3% w/w, or about 4% w/w, or about 5% w/w, or about 6% w/w, or about 7% w/w, or about 8% w/w, or about 9% w/w, or about 10% w/w, or about 15% w/w, or about 20% w/w, or about 25% w/w, or about 30% w/w, or about 35% w/w, or about 40% w/w, or about 45% w/w, or about 50% w/w. In another aspect is provided any of the methods disclosed herein, wherein the hydrogen peroxide is at a concentration of about 3% w/w. Aqueous hydrogen peroxide solutions that may be useful in treating skin conditions in a subject as disclosed herein are commercially available or may be prepared by methods known to those of ordinary skill in the art.

In another aspect is provided any of the methods disclosed herein, wherein the first composition and/or the second composition may be used in combination with a gel or cream, which gel or cream may or may not further comprise hydrogen peroxide. In another aspect is provided any of the methods disclosed herein, wherein the first composition and/or the second composition may be used in combination with a gel or cream, which gel or cream does not further comprise hydrogen peroxide. In another aspect is provided any of the methods disclosed herein, wherein the first composition and/or the second composition may be used in combination with a gel or cream, which gel or cream further comprises hydrogen peroxide. Such gels or creams are generally commercially available any may contain from about 0.5% w/w to about 50% w/w hydrogen peroxide. For example, a gel containing about 1% w/w, or about 2% w/w, or about 3% w/w, or about 4% w/w, or about 5% w/w, or about 6% w/w, or about 7% w/w, or about 8% w/w, or about 9% w/w, or about 10% w/w, or about 15% w/w, or about 20% w/w, or about 25% w/w, or about 30% w/w, or about 40% w/w, or about 45% w/w, or about 50% w/w hydrogen peroxide may be used in any of the methods disclosed herein in combination with the first composition and the second composition.

In another aspect is provided any of the methods disclosed herein, wherein the method further comprises applying a third composition to the skin of the subject. In another aspect is provided any of the methods disclosed herein, wherein the third composition comprises hydrogen peroxide. In another aspect is provided any of the methods disclosed herein, wherein the hydrogen peroxide is at a w/w concentration of about 3%. In another aspect is provided any of the methods disclosed herein, wherein the hydrogen peroxide is at a w/w concentration of about 0.1% w/w to about 50% w/w, or from about 0.1% w/w to about 45% w/w, or from about 0.1% w/w to about 40% w/w, or from about 0.1% w/w to about 35% w/w, or from about 0.1% w/w to about 30% w/w, or from about 0.1% w/w to about 25% w/w, or from about 0.1% w/w to about 20% w/w, or from about 0.1% w/w to about 15% w/w, or from about 0.1% w/w to about 10% w/w, or from about 0.1% w/w to about 9% w/w, or from about 0.1% w/w to about 8% w/w, or from about 0.1% w/w to about 7% w/w, or from about 0.1% w/w to about 6% w/w, or from about 0.1% w/w to about 5% w/w, or from about 0.1% w/w to about 4% w/w, or from about 0.1% w/w to about 3% w/w, or from about 0.1% w/w to about 2% w/w, or from about 0.1% w/w to about 1% w/w, or from about 0.5% w/w to about 45% w/w, or from about 1% w/w to about 45% w/w, or from about 1% w/w to about 40% w/w, or from about 1% w/w to about 35% w/w, or from about 1% w/w to about 30% w/w, or from about 1% w/w to about 25% w/w, or from about 1% w/w to about 20% w/w, or from about 1% w/w to about 15% w/w, or from about 1% w/w to about 10% w/w, or from about 1% w/w to about 9% w/w, or from about 1% w/w to about 8% w/w, or from about 1% w/w to about 7% w/w, or from about 1% w/w to about 6% w/w, or from about 1% w/w to about 5% w/w, or from about 1% w/w to about 4% w/w, or from about 1% w/w to about 3% w/w, or from about 1% w/w to about 2% w/w, or from about 2% w/w to about 45% w/w, or from about 2% w/w to about 40% w/w, or from about 2% w/w to about 35% w/w, or from about 2% w/w to about 30% w/w, or from about 2% w/w to about 25% w/w, or from about 2% w/w to about 20% w/w, or from about 2% w/w to about 15% w/w, or from about 2% w/w to about 10% w/w, or from about 2% w/w to about 9% w/w, or from about 2% w/w to about 8% w/w, or from about 1% w/w to about 7% w/w, or from about 2% w/w to about 6% w/w, or from about 2% w/w to about 5% w/w, or from about 2% w/w to about 4% w/w, or from about 2% w/w to about 3% w/w. In another aspect is provided any of the methods disclosed herein, wherein the hydrogen peroxide is at a concentration of about 0.1% w/w, or about 0.5% w/w, or about 1% w/w, or about 2% w/w, or about 3% w/w, or about 4% w/w, or about 5% w/w, or about 6% w/w, or about 7% w/w, or about 8% w/w, or about 9% w/w, or about 10% w/w, or about 15% w/w, or about 20% w/w, or about 25% w/w, or about 30% w/w, or about 35% w/w, or about 40% w/w, or about 45% w/w, or about 50% w/w. In another aspect is provided any of the methods disclosed herein, wherein the hydrogen peroxide is at a concentration of about 3% w/w. Aqueous hydrogen peroxide solutions that may be useful in treating skin conditions in a subject as disclosed herein are commercially available or may be prepared by methods known to those of ordinary skill in the art.

In another aspect is provided any of the methods disclosed herein, wherein the Spongilla is Spongilla *lacustris*.

The presence of botulinum toxin in vivo can be determined by measuring the presence of the proteolytic cleavage products derived from various SNARE proteins (Soluble NSF (N-ethylmaleimide-sensitive factor) Attachment Protein) Receptor). It known to those of ordinary skill in the art that botulinum toxins target one or more of three SNARE (Soluble NSF Attachment Protein Receptor) proteins VAMP (vesicle associated membrane protein, also known as synaptobrevin), SNAP-25 (synaptosomal-associated protein 25) and syntaxin (STX). BoNT/B cleaves the Q76 (P1 site)-F77 (P1' site) (human numbering from here following) peptide bond of VAMP-2, BoNT/D and/DC cleave the K59-L60 bond, BoNT/F1 cleaves the Q58-K59 bond, and BoNT/G cleaves the A81-A82 bond. BoNT/F5 and BoNT/FA (also known as BoNT/H) hydrolyses the L54-E55 bond of VAMP-2, and BoNT/X cleaves R66-A67. BoNT/A cleaves the Q197-R198 bond at the C-terminus of SNAP-25, whereas BoNT/E hydrolyses the R180-1181 peptide bond. BoNT/C cleaves SNAP-25 (at R198-A199), STX-1A (at K253-A254), and STX-1B (at K252-A253). For example, the in vivo presence of BoNT/A may be determined by measuring the presence of the cleavage product of SNAP25 using an appropriate assay, such as an ELISA assay that utilizes one or more monoclonal antibodies. For example, the in vivo presence of OnabotulinumtoxinA may be determined using one or more mAbs such anti-SNAP-25 monoclonal antibody 4F3-2C1 (available from available from MyBioSource, Inc., San Diego, California, United States of America) and/or anti-SNAP-25 biotinylated antibody MBS423684 (available from MyBioSource, Inc., San Diego, California, United States of America).

In another aspect is provided any of the methods disclosed herein, wherein the second composition comprising one or more botulinum toxins is applied topically to the skin of the subject. In another aspect is provided any of the methods disclosed herein, wherein the second composition is applied to the skin of the subject in the form of a solution. In another aspect is provided any of the methods disclosed herein, wherein the second composition comprising one or more botulinum toxins is applied to the skin of the subject in the form of an aqueous solution. Solutions of botulinum toxins, including aqueous solutions, may be prepared by methods known to those of ordinary skill in the art. For example, a botulinum toxin product may be available in the form of a vacuum-dried or lyophilized solid packaged in a vial that contain appropriate excipients, such as human albumin, sodium chloride, sucrose, and sodium succinate. The vacuum-dried or lyophilized material may be prepared for use according to the methods disclosed herein by reconstitution with an appropriate diluent, such as preservative-free 0.9% sodium chloride injection USP, by slowly injecting the diluent into the vial and mixing the diluent and the vacuum-dried material by rotating the vial. Alternatively, a first aliquot of an appropriate diluent, such as preservative-free 0.9% sodium chloride injection USP, may be injected in the container containing the vacuum-dried materials and mixed to provide a first solution. A second aliquot of an appropriate diluent, such as preservative-free 0.9% sodium chloride injection USP, may be drawn into a syringe, followed by a given amount of the reconstituted toxin solution, followed by mixing the two aliquots in the syringe to provide a resulting solution having the desired concentration of the toxin. Generally, the date and time of reconstitution should be recorded and the reconstituted materials should generally be used within 24 hours after reconstitution. Any reconstituted materials should be stored under appropriate. conditions, such as storage at a temperature of from about 2° C. to 8° C., following reconstitution and prior to use. Generally, reconstituted materials should be clear, colorless and free or particulate matter prior to use. Alternatively, the toxin product may be available as a pre-formed solution of a given concentration. The solution of toxin may be topically applied to the skin of a subject by drawing an appropriate amount of reconstituted solution from the container, such as a vial, by a syringe and then applying the reconstituted solution to the skin of the subject by an appropriate method, such as by means of a swab or a brush.

In another aspect is provided any of the methods disclosed herein, wherein the second composition comprises one or more botulinum toxin type selected from botulinum toxin type A, botulinum toxin type B, botulinum toxin type C1, botulinum toxin type C2, botulinum toxin type D, botulinum toxin type E, botulinum toxin type F and botulinum toxin type G. In another aspect is provided any of the methods disclosed herein, the one or more botulinum toxin type is selected from botulinum toxin type A and botulinum toxin type B. In another aspect is provided any of the methods disclosed herein, wherein the one or more botulinum toxin type is botulinum toxin type A. In another aspect is provided any of the methods disclosed herein, wherein the botulinum toxin type A is selected from onabotulinumtoxinA, abobotulinumtoxinA, and incobotulinumtoxinA. In another aspect is provided any of the methods disclosed herein, wherein the botulinum toxin type A is onabotulinumtoxinA. In another aspect is provided any of the methods disclosed herein, wherein the botulinum toxin type A is abobotulinumtoxinA. In another aspect is provided any of the methods disclosed herein, wherein the botulinum toxin type A is incobotulinumtoxinA. In another aspect is provided any of the methods disclosed herein, wherein the botulinum toxin type A is prabotulinumtoxinA. In another aspect is provided any of the methods disclosed herein, wherein the one or more botulinum toxin type is botulinum toxin type B. In another aspect is provided any of the methods disclosed herein, wherein the one or more botulinum toxin type B is rimabotulinumtoxinB. In another aspect is provided any of the methods disclosed herein, wherein the one or more botulinum toxin type is botulinum toxin type C1. In another aspect is provided any of the methods disclosed herein, wherein the one or more botulinum toxin type is botulinum toxin type C2. In another aspect is provided any of the methods disclosed herein, wherein the one or more botulinum toxin type is botulinum toxin type D. In another aspect is provided any of the methods disclosed herein, wherein the one or more botulinum toxin type is botulinum toxin type E. In another aspect is provided any of the methods. disclosed herein, wherein the one or more botulinum toxin type E is EB-001A or EB-001T. In another aspect is provided any of the methods disclosed herein, wherein the one or more botulinum toxin type E is EB-001A. In another aspect is provided any of the methods disclosed herein, wherein the one or more botulinum toxin type E is EB-001T. In another aspect is provided any of the methods disclosed herein, wherein the one or more botulinum toxin type is botulinum toxin type F. In another aspect is provided any of the methods disclosed herein, wherein the one or more botulinum toxin type is botulinum toxin type G.

In another aspect is provided any of the methods disclosed herein, wherein the number of potency units of the second composition comprising one or more botulinum toxins applied to the skin of the subject is from about 1 to about 400 potency units. In another aspect is provided any of the methods disclosed herein, wherein the number of potency units of the second composition comprising one or more botulinum toxins applied to the skin of the subject is from about 10 units to about 400 units, or about 10 units to about 375 units, or from about 10 units to about 350 units, or from about 10 units to about 325 units, or from about 10 units to about 300 units, or from about 10 units to about 275 units, or from about 10 units to about 250 units, or from about 10 units to about 225 units, or from about 10 units to about 200 units, or from about 10 units to about 175 units, or from about 10 units to about 150 units, or from about 10 units to about 125 units, or from about 10 units to about 100 units, or from about 10 units to about 75 units, or from about 10 units to about 50 units, or from about 10 units to about 40 units, or from about 10 units to about 35 units, or from about 10 units to about 30 units, or from about 10 units to about 25 units, or from about 5 units to about 75 units, or from about 5 units to 50 units, or from about 5 units to about 45 units, or from about 5 units to about 40 units, or from about 5 units to about 35 units, or from about 5 units to about 30 units, or from about 5 units to about 25 units, or from about 5 units to about 20 units, or from about 5 units to about 15 units, or from about 5 units to about 10 units, or from about 15 units to about 100 units, or from about 20 units to about 100 units, or from about 25 units to about 100 units, or from about 35 units to about 100 units, or from about 40 units to about 100 units, or from about 50 units to about 100 units, or from about 60 units to about 100 units, or from about 70 units to about 100 units, or from about 80 units to about 100 units, or from about 90 units to about 100 units. In another aspect is provided any of the methods disclosed herein, wherein the number of potency units of the second composition comprising one or more botulinum toxins applied to the skin of the subject is about 1 unit, or about 2 units, or about 3 units, or about 4 units, or about 5 units, or about 6 units, or about 7 units, or about 8 units, or about 9 units, or about 10 units, or about 11 units, or about 12 units, or about 13 units, or about 14 units, or about 15 units, or about 20 units, or about 25 units, or about 30 units, or about 35 units, or about 40 units, or about 45 units, or about 50 units, or about 60 units, or about 70 units, or about 80 units, or about 90 units, or about 100 units. The number of potency units of the composition comprising at least one botulinum toxin that may be used according to the methods and kits disclosed herein may be determined by those of ordinary skill in the art. The potency of an individual botulinum toxin composition may be determined by methods known to those of ordinary skill in the art (see, for example, Fernandez-Salas et al., PLOS ONE, vol. 7, pp. e49516 (2012)), such as by an appropriate cell-based assay, use of a mouse LD50 (mLD50) bioassay, localized muscle paralysis (abdominal apoptosis) (see, for example, Sesardic et al., Pharmacol. Toxicol., vol. 78, pp. 283 to 288 (1996)), Digit Abduction Score assays (see, for example, Aoki et al., Toxicon., vol. 39, pp. 1815-1820 (2001)), rat or mouse phrenic nerve diaphragm (see, for example, Goschel et al., Exp Neurol., vol. 147, pp. 96-102 (1997)), rat intercostal muscle strip assays (see, for example, Huber et al., Altern Lab Anim., vol. 36, pp. 141-152 (2008)), and Rasetti-Escargucil et al., Toxicon., vol. 53, pp. 503-511 (2009)).

In another aspect is provided any of the methods disclosed herein, wherein the amount of the first composition comprising Spongilla applied to the skin of the subject is from about 0.5 grams to about 50 grams. In one aspect is provided any of the methods disclosed herein, wherein the amount of the first composition is measured as a dry weight. In another aspect is provided any of the methods disclosed herein, wherein the amount of the first composition comprising Spongilla applied to the skin of the subject is from about 0.5 grams to about 40 grams, or from about 0.5 grams to about 35 grams, or from about 0.5 grams to about 30 grams, or from about 0.5 grams to about 25 grams, or from about 0.5 grams to about 20 grams, or from about 0.5 grams to about 15 grams, or from about 0.5 grams to about 10 grams, or from about 0.75 grams to about 20 grams, or from about 0.75 grams to about 15 grams, or from about 0.75 grams to about 10 grams, or from about 1 gram to about 20 grams, or from about 1 gram to about 15 grams, or from about 1 gram to about 10 grams, or from about 1 gram to about 9 grams, or from about 1 gram to about 8 grams, or from about 1 gram to about 7 grams, or from about 1 gram to about 6 grams, or from about 1 gram to about 5 grams, or from about 1 gram to about 4 grams, or from about 1 gram to about 3 grams, or from about 1 gram to 2 grams. In another aspect is provided any of the methods disclosed herein wherein the amount of Spongilla applied to the skin, such as those disclosed above, are each measured as a dry weight.

In another aspect is provided any of the methods disclosed herein, wherein the amount of the first composition comprising Spongilla applied to the skin of the subject is about 0.5 grams, or about 0.75 grams, or about 1 gram, or about 1.25 grams, or about 1.5 grams, or about 1.75 grams, or about 2 grams, or about 2.25 grams, or about 2.5 grams, or about 2.75 grams, or about 3 grams, or about 3.25 grams, or about 3.5 grams, or about 3.75 grams, or about 4 grams, or about 4.25 grams, or about 4.5 grams, or about 4.75 grams, or about 5 grams, or about 5.25 grams, or about 5.5 grams, or about 5.75 grams, or about 6 grams, or about 6.25 grams, or about 6.5 grams, or about 7 grams, or about 7.25 grams, or about 7.5 grams, or about 7.75 grams, or about 8 grams, or about 8.25 grams, or about 8.5 grams, or about 8.75 grams, or about 9 grams, or about 9.25 grams, or about 9.5 grams, or about 9.75 grams, or about 10 grams, or about 11 grams, or about 12 grams, or about 13 grams, or about 14 grams, or about 15 grams, or about 16 grams, or about 17 grams, or about 18 grams, or about 19 grams, or about 20 grams, or about 25 grams, or about 35 grams, or about 40 grams, or about 45 grams, or about 50 grams, or about 75 grams, or about 100 grams, or about 250 grams, or about 500 grams, or about 750 grams, or about 1000 grams, in each case measured as a dry weight.

In another aspect is provided any of the methods disclosed herein, wherein the first composition is applied to the skin of the subject prior to the second composition being applied to the skin of the subject. In another aspect is provided any of the methods disclosed herein, wherein the first composition is applied to the skin of the subject and is permitted to dry on the skin of the subject prior to application of the second composition to the skin of the subject. In another aspect is provided any of the methods disclosed herein, wherein the first composition is applied to the skin of the subject in the form of an aqueous paste, wherein the aqueous component may be water or saline. In another aspect is provided any of the methods disclosed herein, wherein the aqueous paste further comprises hydrogen peroxide. In another aspect is provided any of the methods disclosed herein, wherein an aqueous solution of hydrogen peroxide is applied to the face of the subject following application of the first composition to the skin of the subject and prior to the application of the second composition to the skin of the subject. In another aspect is provided any of the methods disclosed herein, wherein the first composition further comprises hydrogen peroxide. In another aspect is provided any of the methods disclosed herein, wherein the hydrogen peroxide is an aqueous solution. In another aspect is provided any of the methods disclosed herein, wherein the aqueous solution comprises hydrogen peroxide at a w/w concentration of about 3%. In another aspect is provided any of the methods disclosed herein, wherein the second composition is permitted to dry on the skin of the subject following application to the skin of the subject.

In another aspect is provided any of the methods disclosed herein, wherein the second composition is applied to the skin of the subject prior to the first composition being applied to the skin of the subject. In another aspect is provided any of the methods disclosed herein, wherein the second composition is permitted to dry on the skin of the subject prior to the first composition being applied to the skin of the subject. In another aspect is provided any of the methods disclosed herein, wherein the first composition is applied to the skin of the subject in the form of an aqueous paste, wherein the aqueous portion may be derived from water or saline. In another aspect is provided any of the methods disclosed herein, wherein the aqueous paste further comprises hydrogen peroxide. In another aspect is provided any of the methods disclosed herein, wherein an aqueous solution of hydrogen peroxide is applied to the face of the subject following application of the first composition to the skin of the subject. In another aspect is provided any of the methods disclosed herein, wherein the hydrogen peroxide is an aqueous solution. In another aspect is provided any of the methods disclosed herein, wherein the aqueous solution comprises hydrogen peroxide at a w/w concentration of about 3%. In another aspect is provided any of the methods disclosed herein, wherein the first composition is permitted to dry on the skin of the subject.

In another aspect is provided any of the methods disclosed herein, wherein the first composition and the second composition are mixed together and the resulting mixture is applied to the skin of the subject. In another aspect is provided any of the methods disclosed herein, wherein the first composition is mixed with an aqueous solution of hydrogen peroxide prior to mixing with the second composition. In another aspect is provided any of the methods disclosed herein, wherein the mixture of the first composition and the second composition is further mixed with an aqueous solution of hydrogen peroxide prior to application to the skin of the subject. In another aspect is provided any of the methods disclosed herein, wherein the aqueous solution comprises hydrogen peroxide at a w/w concentration of about 3%. In another aspect is provided any of the methods disclosed herein, wherein the first composition comprising Spongilla and the second composition comprising one or more botulinum toxins is applied to the skin of the subject once per week.

In another aspect is provided any of the methods disclosed herein, wherein the subject applies the second composition comprising one or more botulinum toxins to the skin no more than once every 4 weeks.

In another aspect is provided any of the methods disclosed herein, wherein the first composition comprising Spongilla is applied to the skin of the subject at least once per week for at least one week. In another aspect is provided any of the methods disclosed herein, wherein the first composition comprising Spongilla is applied to the skin of the subject at least two times per week for at least one week, at least three times per week for at least one week, at least 4 times per week for at least one week, at least 5 times per week for at least one week, at least 6 times per week for at least one week, or at least 7 times per week for at least one week.

In another aspect is provided any of the methods disclosed herein, wherein the first composition comprising Spongilla is applied to the skin of the subject at least once per week for at least two weeks. In another aspect is provided any of the methods disclosed herein, wherein the first composition comprising Spongilla is applied to the skin of the subject at least at once per week for at least two weeks, at once per week for at least three weeks, at least once per week for at least 4 weeks, at least once per week for at least 5 weeks, at least once per week for at least 6 weeks, at least once per week for at least 7 weeks, at least once per week for at least 8 weeks, at least once per week for at least 9 weeks, at least once per week for at least 10 weeks, at least once per week for at least 11 weeks, at least once per week for at least 12 weeks, at least once per week for at least 13 weeks, at least once per week for at least 14 weeks, at least once per week for at least 15 weeks, at least once per week for at least 16 weeks, at least once per week for at least 17 weeks, at least once per week for at least 18 weeks, at least once per week for at least 19 weeks, at least once per week for at least 20 weeks, at least once per week for at least 21 weeks, at least once per week for at least 22 weeks, at least once per week for at least 23 weeks, at least once per week for at least 24 weeks. In another aspect is provided any of the methods disclosed herein, wherein the first composition comprising Spongilla is applied to the skin of the subject once per week for 6 weeks.

In another aspect is provided any of the methods disclosed herein, wherein the first composition comprising Spongilla is applied to the skin of the subject once per week for 24 weeks, and the second composition comprising one or more botulinum toxins is applied to the skin of the subject only during the first week of treatment. In another aspect is provided any of the methods disclosed herein, wherein the first composition comprising Spongilla is applied to the skin of the subject once per week for 20 weeks, and the second composition comprising one or more botulinum toxins is applied to the skin of the subject only during the first week of treatment. In another aspect is provided any of the methods disclosed herein, wherein the first composition comprising Spongilla is applied to the skin of the subject once per week for 16 weeks, and the second composition comprising one or more botulinum toxins is applied to the skin of the subject only during the first week of treatment. In another aspect is provided any of the methods disclosed herein, wherein the first composition comprising Spongilla is applied to the skin of the subject once per week for 12 weeks, and the second composition comprising one or more botulinum toxins is applied to the skin of the subject only during the first week of treatment. In another aspect is provided any of the methods disclosed herein, wherein the first composition comprising Spongilla is applied to the skin of the subject once per week for 8 weeks, and the second composition comprising one or more botulinum toxins is applied to the skin of the subject only during the first week of treatment. In another aspect is provided any of the methods disclosed herein, wherein the first composition comprising Spongilla is applied to the skin of the subject once per week for 6 weeks, and the second composition comprising one or more botulinum toxins is applied to the skin of the subject only during the first week of treatment. In another aspect is provided any of the methods disclosed herein, wherein the first composition comprising Spongilla is applied to the skin of the subject once per week for 4 weeks, and the second composition comprising one or more botulinum toxins is applied to the skin of the subject only during the first week of treatment.

In another aspect is provided any of the methods disclosed herein, wherein the first composition comprising Spongilla and the second composition comprising one or more botulinum toxins is applied to the skin of the subject on at least one of the subject's face, back and chest. In another aspect is provided any of the methods disclosed herein, wherein the first composition comprising Spongilla and the second composition comprising one or more botulinum toxins is applied to the skin of the subject on the subject's face. In another aspect is provided any of the methods disclosed herein, wherein the first composition comprising Spongilla and the second composition comprising one or more botulinum toxins is applied to the skin of the subject on the subject's back. In another aspect is provided any of the methods disclosed herein, wherein the first composition comprising Spongilla and the second composition comprising one or more botulinum toxins is applied to the skin of the subject on the subject's chest.

In another aspect is provided any of the methods disclosed herein, wherein the skin of the subject is cleaned using a non-comedogenic cleanser, water, or a combination of a non-comedogenic cleanser and water following application of the first composition comprising Spongilla. In another aspect is provided any of the methods disclosed herein, wherein the skin of the subject is cleaned using a non-comedogenic cleanser, water, or a combination of a non-comedogenic cleanser and water following application of the second composition comprising one or more botulinum toxins to the skin of the subject. Non-comedogenic cleansers are those formulated not to cause blocked pores in the skin of subjects to which such cleansers are applied.

In another aspect is provided any of the methods disclosed herein, wherein the skin condition in the subject is selected from one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, forehead wrinkles, acne vulgaris, acne rosacea type 1, acne rosacea type 2, psoriasis, hyperhidrosis, alopecia areata, androgenic alopecia, keloids, and hypertrophic scars, hidradenitis suppurativa, Raynaud phenomenon, post-herpetic neuralgia, Hailey-Hailey disease, IgA bullous dermatosis, epidermolysis bullosa Simplex Weber-Cockane, Darier disease, pachyonchia congenita, aquagenic keratoderma, notalgia paresthetic, pompholyx (dyshidrotic eczema), chromhidrosis and bromhidrosis, eccrine nevus, facial rhytides, atrophic acne scars, and melasma. In another aspect is provided any of the methods disclosed herein, wherein the skin condition in the subject is selected from one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles. In another aspect is provided any of the methods disclosed herein, wherein the skin condition in the subject is acne vulgaris. In another aspect is provided any of the methods disclosed herein, wherein the skin condition in the subject is acne rosacea type 1. In another aspect is provided any of the methods disclosed herein, wherein the skin condition in the subject is acne rosacea type 2. In an other aspect is provided any of the methods disclosed herein, wherein the skin condition in the subject is psoriasis. In another aspect is provided any of the methods disclosed herein, wherein the skin condition in the subject is hyperhidrosis.

Acne vulgaris is a common chronic skin disease involving blockage and/or inflammation of pilosebaceous units (hair follicles and their accompanying sebaceous gland). Acne can present as noninflammatory lesions, inflammatory lesions, or a mixture of both, affecting mostly the face but also the back and chest. The efficacy of a treatment regimen in a subject having acne vulgaris can be measured by methods known to those of ordinary skill in the art, such as by measurement of lesion counts and the investigator global assessment on the face in a subject such as found below:

| Score | Grade | Description |
|---|---|---|
| 0 | None | No evidence of facial acne vulgaris |
| 1 | Minimal | Few non-inflammatory lesions (comedones) are present; a few inflammatory lesions (papules/pustules) may be present; no nodulo-cystic lesions are allowed |

-continued

| Score | Grade | Description |
|---|---|---|
| 2 | Mild | Several to many non-inflammatory lesions (comedones) are present; a few inflammatory lesions (papules/pustules) are present; no nodulo-cystic lesions are allowed |
| 3 | Moderate | Many non-inflammatory lesions (comedones) and inflammatory lesions (papules/pustules) are present; no nodulo-cystic lesions are allowed |
| 4 | Severe | Significant degree of inflammatory disease; papules/pustules are a predominate feature; a few nodulo-cystic lesions may be present; comedones may be present |

Rosacea is well recognized as a chronic cutaneous disorder primarily of the convexities of the central face (checks, chin, nose, and central forehead), often characterized by remissions and exacerbations. Based on present knowledge, it is considered a syndrome, or typology, encompassing various combinations of such cutaneous signs as flushing, erythema, telangiectasia, edema, papules, pustules, ocular lesions, and rhinophyma. In most cases, some rather than all of these *stigmata* appear in any given subject. Acne rosacea type-1, or erythematotelangiectatic rosacea, is mainly characterized by flushing and persistent central facial erythema. The appearance of telangiectases is common but not essential for a diagnosis of this subtype. Central facial edema, stinging and burning sensations, and roughness or scaling may also be reported. A history of flushing alone is common among subjects presenting with erythematotelangiectatic rosacea. The efficacy of a treatment regimen in a subject having acne rosacea type-1 can be measured by methods known to those of ordinary skill in the art, such as by use of the Clinician Erythema Assessment (CEA), a 5-point grading scale of facial erythema severity, and Subject Self-Assessment (SSA) shown below:

| Grade | Category | Description |
|---|---|---|
| 0 | None | Clear skin with no signs of erythema |
| 1 | Minimal | Almost clear of erythema, slight redness |
| 2 | Mild | Mild erythema, definite redness |
| 3 | Moderate | Moderate erythema, marked redness |
| 4 | Severe | Severe erythema, fiery redness |

| Grade | Category | Description |
|---|---|---|
| 0 | None | Clear of redness |
| 1 | Minimal | Almost clear of redness |
| 2 | Mild | Somewhat more redness than preferred |
| 3 | Moderate | More redness than preferred |
| 4 | Severe | Completely unacceptable redness |

Acne rosacea type 2 (papulopustular) is characterized by persistent central facial erythema with transient papules or pustules or both in a central facial distribution. However, papules and pustules also may occur periorificially (that is, they may occur in the perioral, perinasal, or periocular areas). The papulopustular subtype resembles acne vulgaris, except that comedones are absent. Rosacea and acne may occur concomitantly, and such subjects may have comedones as well as the papules and pustules of rosacea.

Burning and stinging sensations may be reported by subjects with papulopustular rosacea. This subtype has often been seen after or in combination with subtype 1, including the presence of telangiectases. The telangiectases may be obscured by persistent erythema, papules, or pustules, and tend to become more visible after successful treatment of these masking components. The efficacy of a treatment regimen in a subject having acne rosacea type-2 can be measured by methods known to those of ordinary skill in the art, such as by total lesion counts in the area of the skin of the subject undergoing treatment and an investigator global assessment as shown below:

| Grade | Category | Description |
|---|---|---|
| 0 | Clear | No papules and/or pustules |
| 1 | Almost Clear | Rare papules and/or pustules |
| 2 | Mild | Few papules and/or pustules |
| 3 | Moderate | Pronounced number of papules and/or pustules (but less than numerous papules and/or pustules) |
| 4 | Severe | Numerous papules and/or pustules, occasionally with confluent areas of inflamed lesions |

Psoriasis is a skin condition that speeds up the life cycle of skin cells. It causes cells to build up rapidly on the surface of the skin. The extra skin cells form scales and red patches that are itchy and sometimes painful. The symptoms a subject having psoriasis may present include red patches of skin covered with thick, silvery scales, small scaling spots (commonly seen in children), dry, cracked skin that may bleed, itching, burning or soreness, thickened, pitted or ridged nails, and swollen and stiff joints. The efficacy of a treatment regimen in a subject having acne psoriasis can be measured by methods known to those of ordinary skill in the art, such as by use of the Psoriasis Area and Severity Index (PASI). Use of PASI involves dividing the body of the subject into four sections (head (H) (10% of a person's skin); arms (A) (20%); trunk (T) (30%); legs (L) (40%)). Each of these areas is scored by itself, and then the four scores are combined into the final PASI. For each section, the percent of area of skin involved, is estimated and then transformed into a grade from 0 to 6 as in the table below. Within each area, the severity is estimated by three clinical signs: erythema (redness), induration (thickness) and desquamation (scaling). Severity parameters are measured on a scale of 0 to 4, from none to maximum. The sum of all three severity parameters is then calculated for each section of skin, multiplied by the area score for that area and multiplied by weight of respective section (0.1 for head, 0.2 for arms, 0.3 for body and 0.4 for legs).

| Score | Description |
|---|---|
| 0 | 0% of involved area |
| 1 | <10% of involved area |
| 2 | 10-29% of involved area |
| 3 | 30-49% of involved area |
| 4 | 50-69% of involved area |
| 5 | 70-89% of involved area |
| 6 | 90-100% of involved area |

Hyperhidrosis is a condition characterized by abnormally increased sweating, generally in excess of that required for regulation of body temperature. Although primarily a physical burden, hyperhidrosis can deteriorate quality of life from a psychological, emotional, and social perspective. The efficacy of a treatment regimen in a subject having hyperhidrosis can be measured by methods known to those of ordinary skill in the art, such as by use of the hyperhidrosis disease severity scale (HDSS), which is a 4-point scale designed to assess the severity of primary axillary hyperhidrosis in everyday clinical practice or in clinical research. The HDSS can be administered by an interviewer or self-completed by the subject. The HDSS assesses subject severity based on the extent of excessive sweating-related impairment of daily activities. Subjects rate the severity as: 1=my underarm sweating is never noticeable and never interferes with my daily activities; 2=my underarm sweating is tolerable but sometimes interferes with my daily activities; 3=my underarm sweating is barely tolerable and frequently interferes with my daily activities; or 4=my underarm sweating is intolerable and always interferes with my daily activities.

The efficacy of a treatment regimen in a subject having hyperhidrosis may also be measured by use of the Axillary Sweating Daily Diary (ASDD), Item 2, and/or the Axillary Sweating Daily Diary-Children (ASDD-C), which are validated patient-reported outcome measure to assess axillary hyperhidrosis sweating severity. The ADSS Item 2 asks subjects to rate their underarm sweating during the last 24-hour period at its worst using a 10-point scale, in which a score of zero (0) represents "no sweating at all," and a score of ten (10) represents "worst possible sweating." See Glaser et. al., *J. Am. Acad. Dermatol.*, 2018, Supplemental FIG. 1 for a description of the ASDD, including Item 2, and the ASDD-C.

Alopecia areata is an autoimmune skin disease, causing hair loss on the scalp, face and sometimes on other areas of the body. In fact, it affects as many as 6.8 million people in the U.S. The efficacy of a treatment regimen in a subject having alopecia areata can be measured by methods known to those of ordinary skill in the art, such as by use fixed hair counts, and loose hair counts on a subject's pillow.

Androgenic alopecia is a genetically determined disorder characterized by the gradual conversion of terminal hairs into indeterminate, and finally into vellus, hairs. It is an extremely common disease that affects men and women. Subjects suffering from androgenic alopecia generally display symptoms such as a gradual onset of hair loss, increased hair shedding, transition in the involved areas from large, thick, pigmented terminal hairs to thinner, shorter, indeterminate hairs and finally to short, wispy, nonpigmented vellus hairs, the end result of which may be an area of total denudation; this area varies from subject to subject and is usually most marked at the vertex. The efficacy of a treatment regimen in a subject having androgenic alopecia can be measured by methods known to those of ordinary skill in the art, such as by use fixed hair counts, and loose hair counts on a subject's pillow.

Keloids are raised, reddish nodules that develop at the site of an injury. After a wound has occurred to the skin both skin cells and connective tissue cells (fibroblasts) begin multiplying to repair the damage. A scar is made up of 'connective tissue', gristle-like fibers deposited in the skin by the fibroblasts to hold the wound closed. With keloids, the fibroblasts continue to multiply even after the wound is filled in. Thus, keloids project above the surface of the skin and form large mounds of scar tissue. Keloids may form on any part of the body, although the upper chest, shoulders and upper back are especially prone to keloid formation. Symptoms include pigmentation of the skin, itchiness, redness, unusual sensations and pain, Darkly pigmented people seem to be more prone to forming keloids. Men and women are equally affected. Keloids are considered a benign tumor, but they are mainly a cosmetic nuisance and never become malignant. Operating on a keloid usually stimulates more scar tissue to form; so many subjects having keloids may be told that there are no available treatments. Hypertrophic scars appear like, and are more common than, keloids, although they do not generally grow as large as keloids, may fade with time, and occur in all racial groups. The efficacy of a treatment regimen in a subject having keloids and/or hypertrophic scars can be measured by methods known to those of ordinary skill in the art, such as by the use the Vancouver Scar Scale (VSS), Manchester Scar Scale (MSS), Subject and Observer Scar Assessment Scale (POSAS), Visual Analog Scale (VAS), and Stony Brook Scar Evaluation Scale (SBSES).

Hidradenitis suppurativa is a disease that usually begins as pimple-like bumps on the skin, which tend to develop in places that everyday pimples do not appear and is most common on the underarms and groin. If hidradenitis suppurativa worsens, the pimple-like bumps can grow deep into the skin and become painful and can rupture. As the deep bumps heal, scars can form, and some subjects develop tunnel-like tracts under their skin, forming scars, which can thicken. When thick scars form in the underarm, moving the arm can be difficult. Thick scars in the groin area can make walking difficult. The efficacy of a treatment regimen in a subject suffering from hidradenitis suppurativa can be measured by methods known to those of ordinary skill in the art, such as by the visual count of lesion counts in the affected areas of a subject's skin.

Raynaud's phenomenon is a type of vascular disease characterized by a pale to blue to red sequence of color changes of the digits, most commonly after exposure to cold. The cause of Raynaud's phenomenon is unknown, although abnormal nerve control of blood-vessel diameter and nerve sensitivity to cold are suspected of being involved. Symptoms of Raynaud's phenomenon depend on the severity, frequency, and duration of the blood-vessel spasm. The efficacy of a treatment regimen in a subject suffering from Raynaud's phenomenon can be measured by methods known to those of ordinary skill in the art, such as measurements of digital pulp temperature, photographic assessment of the affected areas, and a visual analogue scale for pain in the affected areas.

Post-herpetic neuralgia is generally considered a complication of shingles, which is caused by the chickenpox (herpes zoster) virus. Postherpetic neuralgia affects nerve fibers and skin, causing burning pain that lasts long after the rash and blisters of shingles disappear. The signs and symptoms of postherpetic neuralgia are generally limited to the area in a subject's skin where the shingles outbreak first occurred. Signs and symptoms of post-herpetic neuralgia may include pain that lasts 3 months or longer after the shingles rash has healed sensitivity to light touch, and itching and numbness in the affected area. The efficacy of a treatment regimen in a subject suffering from post-herpetic neuralgia can be measured by methods known to those of ordinary skill in the art, use of a visual analogue scale for pain in the affected areas.

Hailey-Hailey Disease (familial benign pemphigus) is a genetic disorder that causes blisters to form on the skin and is characterized by outbreaks of rashes and blisters in the skin, usually in the folds of the skins, but also often over large areas of the body. The painful blisters break and sometimes become infected and raw; with new blisters forming over raw skin in a sometimes seemingly unending cycle of outbreaks. The cause of the disease is a haploinsufficiency of the enzyme ATP2C1, which encodes the protein hSPCA1. A mutation on one copy of the gene causes only half of this necessary protein to be made and the cells of the skin do not adhere together properly due to malformation of intercellular desmosomes, causing acantholysis, blisters and rashes. The efficacy of a treatment regimen in a subject suffering from Hailey-Hailey Disease can be measured by methods known to those of ordinary skill in the art, such as counting the total lesion counts in a subject, wherein a reduction in the total lesion count indicates the treatment regimen is having a positive effect.

Linear IgA bullous dermatosis (LABD) is a rare subepidermal blistering disease due to an autoimmune reaction against basement membrane proteins such as the lamina *lucida* and sublamina *densa*. The basement membrane anchors the epidermis to the dermis and helps to stabilize the skin. When IgA antibodies target such proteins, the basement membrane destabilizes resulting in tense blister formation. In the majority of LABD cases, the cause is unknown or idiopathic. Furthermore, more than half of all childhood cases tend to remit over a mean course of two to four years. Adults may have a more protracted course and LABD has been shown to occur in those with internal malignancy, infection, and other autoimmune diseases like rheumatoid arthritis or dermatomyositis. Other cases of LABD are drug-induced often due to vancomycin and subjects can break out as early after the first dose of vancomycin in some cases. The efficacy of a treatment regimen in a subject suffering from LABD can be measured by methods known to those of ordinary skill in the art, such as counting the total lesion counts in a subject, wherein a reduction in the total lesion count indicates the treatment regimen is having a positive effect.

Epidermolysis bullosa simplex (EBS) is a chronic vesicular disorder with characteristic manifestations, from birth to infancy, of intraepidermal vesicle and milia formation on the hand, elbow, or knee due to minimal trauma. It is a genetic disorder that is caused by a dominant-negative mutation in either the keratin 5 (KRT5) or the keratin 14 (KRT14) gene. EBS is sub-categorized by its clinical manifestation into the systemic (Koebner), localized (Weber-Cockayne), and herpetiform (Dowling-Meara) 1 types. The localized type of EBS is the mildest form of the subtypes that involves easy development of vesicles on the palms and soles from minimal mechanical trauma. According to molecular genetic studies of EBS, there are mutations in KRT5 and KRT14, which contribute to skeletons on hemidesmosome in keratinocytes located in the basal layer near the dermo-epidermal junction. Mutations in each subtype of EBS vary in location and severity. The efficacy of a treatment regimen in a subject suffering from EBS can be measured by methods known to those of ordinary skill in the art, such as counting the total lesion counts in a subject, wherein a reduction in the total lesion count indicates the treatment regimen is having a positive effect.

Darier Disease is a skin condition characterized by wart-like blemishes on the body. The blemishes are usually yellowish in color, hard to the touch, mildly greasy, and can emit a strong odor. The most common sites for blemishes are the scalp, forehead, upper arms, chest, back, knees, elbows, and behind the ear. The mucous membranes can also be affected, with blemishes on the roof of the mouth (palate), tongue, inside of the cheek, gums, and throat. Other features of Darier disease include nail abnormalities, such as red and white streaks in the nails with an irregular texture, and small pits in the palms of the hands and soles of the feet. The wart-like blemishes characteristic of Darier disease usually appear in late childhood to early adulthood. The severity of the disease varies over time; affected people experience flare-ups alternating with periods when they have fewer blemishes. The appearance of the blemishes is influenced by environmental factors. Most people with Darier disease will develop more blemishes during the summertime when they are exposed to heat and humidity. UV light; minor injury or friction, such as rubbing or scratching; and ingestion of certain medications can also cause an increase in blemishes. The efficacy of a treatment regimen in a subject suffering from Darier Disease can be measured by methods known to those of ordinary skill in the art, such as counting the total lesion counts and measuring the size of the lesions in a subject, wherein a reduction in the total lesion count indicates the treatment regimen is having a positive effect.

Pachyonchia Congenita is a condition that primarily affects the nails and skin. The signs and symptoms of this condition in a subject usually become apparent within the first few months of a subject's life. Almost everyone with pachyonychia congenita has hypertrophic nail dystrophy, which causes the fingernails and toenails to become thick and abnormally shaped. Many affected children also develop very painful blisters and calluses on the soles of the feet and, less commonly, on the palms of the hands. This condition is known as palmoplantar keratoderma. Severe blisters and calluses on the feet can make it painful or impossible to walk. Pachyonychia congenita can have several additional features, which vary among affected individuals. These features include thick, white patches on the tongue and inside of the cheeks (oral leukokeratosis); bumps called follicular keratoses that develop around hair follicles on the elbows, knees, and waistline; cysts in the armpits, groin, back, or scalp; and excessive sweating on the palms and soles (palmoplantar hyperhidrosis). Some affected individuals also develop widespread cysts called steatocystomas, which are filled with an oily substance called sebum that normally lubricates the skin and hair. Some babies with pachyonychia congenita have prenatal or natal teeth, which are teeth that are present at birth or in early infancy. Rarely, pachyonychia congenita can affect the voice box (larynx), potentially leading to hoarseness or breathing problems. The efficacy of a treatment regimen in a subject suffering from pachyonychia congenita can be measured by methods known to those of ordinary skill in the art, such as counting the total number of blisters and measuring the size of the blisters in the affected area on a subject.

Aquagenic keratoderma (AK) is a skin disorder also known as acquired aquagenic palmoplantar keratoderma, transient reactive papulotranslucent acrokeratoderma, aquagenic wrinkling of the palms or aquagenic syringeal acrokeratoderma. The main characteristic of the disorder is skin wrinkling with edema of palms/soles, whitish papules, pruritus, burning, and pain after contact with water. Prolongation of water exposure and temperature of the water affect the rate and intensity of lesion development; however, the pathogenesis of AK is poorly understood. The efficacy of a treatment regimen in a subject suffering from AK can be measured by methods known to those of ordinary skill in the art, such as counting the total number of lesions in a subject, the visual analogue pain score, and the visual analogue pruritis score.

Notalgia paresthetic is a sensory neuropathic syndrome of the midback skin, classically described as the unilateral infrascapular area. It is primarily a localized pruritus and dysesthesia syndrome, and it may present with episodic itching or pain on a small patch of the mid back, usually an area of skin just past easy reach. The correlation of notalgia paraesthetica localization with corresponding degenerative changes in the spine suggest that spinal nerve impingement may be a contributing cause, but subjects may have other conditions that predispose them to peripheral neuropathies, such as nerve damage. The efficacy of a treatment regimen in a subject suffering from notalgia paraesthetica can be measured by methods known to those of ordinary skill in the art, such as counting the total number of lesions in a subject, the visual analogue pain score, and the visual analogue pruritis score.

Pompholyx (dyshidrotic eczema) is a skin condition in which very small, fluid-filled blisters appear on the palms of a subject's hands, sides of the fingers, and soles of the feet. The blisters that occur in dyshidrosis may cause intense itching and, once dried, may cause a subject's skin to appear scaly. The blisters typically recur, sometimes before a subject's skin heals completely from the previous blisters. The efficacy of a treatment regimen in a subject suffering from dyshidrotic eczema can be measured by methods known to those of ordinary skill in the art, such as observing the signs and symptoms of eczema, the visual analogue pain score, and the visual analogue pruritis score.

Chromhidrosis is a condition characterized by the secretion of colored sweat and is caused by the deposition of lipofuscin in the sweat glands. It normally affects the apocrine glands, mainly on the face and underarms. The efficacy of a treatment regimen in a subject suffering from chromhidrosis can be measured by methods known to those of ordinary skill in the art, such as observing the signs of sweat and the odor of sweat in an affected subject.

Bromhidrosis, also known as osmidrosis, is a condition of abnormal or offensive body odor, largely determined by apocrine gland secretion, although other sources may play a role. Sudoriferous (sweat) glands are divided into two types: apocrine and eccrine and there is some crossover in some subjects. The efficacy of a treatment regimen in a subject suffering from bromhidrosis can be measured by methods known to those of ordinary skill in the art, such as observing the odor of sweat in an affected subject.

Eccrine nevus is a disease, which may be present at birth or at an early age. It is more often associated with localized hyperhidrosis, while cases not associated have also been reported. It is usually characterized histologically by the increase in number or size of structurally normal eccrine glands. The efficacy of a treatment regimen in a subject suffering from eccrine nevus can be measured by methods known to those of ordinary skill in the art, use of the Hyperhidrosis Disease Severity Scale (HDSS), and measuring the number sweat episodes per month in an affected subject.

Facial rhytides is a condition in subjects that is associated with moderate to severe glabellar lines associated with corrugator and/or procerus muscle activity, moderate to severe lateral canthal lines associated with orbicularis oculi activity, and/or moderate to severe forehead lines associated with *frontalis* muscle activity. The efficacy of a treatment regimen in a subject having facial rhytides can be measured by methods known to those of ordinary skill in the art, including a 4-point Facial Wrinkle Scale (FWS; 0=none, 1=mild, 2-moderate, 3=severe).

Atrophic acne scarring can occur in subjects suffering from acne. The efficacy of a treatment regimen in a subject suffering from atrophic acne scarring can be measured by methods known to those of ordinary skill in the art, including the Self-assessment of Clinical Acne-Related Scars (SCARS) and the Facial Acne Scar Quality of Life (FASQOL) tools.

In another aspect is provided a method of treating a skin condition in a subject, comprising applying to the skin of the subject a first composition comprising Spongilla, and a second composition comprising one or more botulinum toxins, wherein (a) the second composition is comprises one or more botulinum toxin type selected from botulinum toxin type A, botulinum toxin type B, botulinum toxin type C1, botulinum toxin type C2, botulinum toxin type D, botulinum toxin type E, botulinum toxin type F and botulinum toxin type G; and (b) the skin condition in the subject is selected from one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, forehead wrinkles, acne vulgaris, acne rosacea type 1, acne rosacea type 2, psoriasis, hyperhidrosis, alopecia areata, androgenic alopecia, keloids, and hypertrophic scars, hidradenitis suppurativa, Raynaud phenomenon, post-herpetic neuralgia, Hailey-Hailey disease, IgA bullous dermatosis, epidermolysis bullosa Simplex Weber-Cockane, Darier disease, pachyonchia congenita, aquagenic keratoderma, notalgia paresthetic, pompholyx (dyshidrotic eczema), chromhidrosis and bromhidrosis, eccrine nevus, facial rhytides, atrophic acne scars, and melasma. In another embodiment are methods, wherein the one or more botulinum toxin type is selected from botulinum toxin type A and botulinum toxin type B. In another embodiment are methods, wherein the one or more botulinum toxin type is botulinum toxin type A. In another embodiment are methods, wherein the botulinum toxin type A is selected from onabotulinumtoxinA, abobotulinumtoxinA, incobotulinumtoxinA, prabotulinumtoxinA, and daxibotulinumtoxinA. In another embodiment are methods, wherein the botulinum toxin type A is onabotulinumtoxinA. In another embodiment are methods, wherein the botulinum toxin type A is abobotulinumtoxinA. In another embodiment are methods, wherein the botulinum toxin type A is incobotulinumtoxinA. In another aspect is provided any of the methods disclosed herein, wherein the botulinum toxin type A is prabotulinumtoxinA. In another aspect is provided any of the methods disclosed herein, wherein the botulinum toxin type A is daxibotulinumtoxinA. In another embodiment are methods, wherein the one or more botulinum toxin type is botulinum toxin type B. In another aspect is provided any of the methods disclosed herein, wherein the one or more botulinum toxin type B is rimabotulinumtoxinB. In another embodiment are methods, wherein the skin condition in the subject is selected from one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles. In another aspect is provided any of the methods disclosed herein, wherein the one or more botulinum toxin type is botulinum toxin type E. In another aspect is provided any of the methods disclosed herein, wherein the one or more botulinum toxin type E is EB-001A or EB-001T. In another aspect is provided any of the methods disclosed herein, wherein the one or more botulinum toxin type E is EB-001A. In another aspect is provided any of the methods disclosed herein, wherein the one or more botulinum toxin type E is EB-001T. In another embodiment are methods, wherein the skin condition in the subject is selected from acne vulgaris, acne rosacea type 1, acne rosacea type 2, psoriasis, and hyperhidrosis. In another embodiment are methods, wherein the skin condition in the subject is acne vulgaris. In another embodiment are methods, wherein the skin condition in the subject is acne rosacea type 1. In another embodiment are methods, wherein the skin condition in the subject is acne rosacea type 2. In another embodiment are methods, wherein the skin condition in the subject is psoriasis. In another embodiment are methods, wherein the skin condition in the subject is hyperhidrosis. In another embodiment are methods, wherein the Spongilla is Spongilla *lacustris*. In another embodiment are methods, wherein the second composition comprising one or more botulinum toxins is applied topically to the skin of the subject. In another embodiment are methods, wherein the second composition comprising one or more botulinum toxins is in the form of an aqueous solution. In another embodiment are methods, wherein the second composition is applied to the skin of the subject in the form of a solution. In another embodiment are methods, wherein the second composition is in the form of an aqueous solution. In another embodiment are methods, wherein the amount of the first composition comprising Spongilla applied to the skin of the subject is from about 0.5 grams to about 50 grams, measured as a dry weight. In another embodiment are methods, wherein the first composition is applied to the skin of the subject in the form of a paste. In another embodiment are methods, wherein the paste further comprises water or saline. In another embodiment are methods, wherein the paste is prepared by mixing a powder comprising Spongilla and an aqueous solution comprising hydrogen peroxide. In another embodiment are methods, wherein the aqueous solution comprises hydrogen peroxide at a w/w concentration of about 3%. In another embodiment are methods, wherein the first composition is applied to the skin of the subject prior to the second composition being applied to the skin of the subject. In another embodiment are methods, wherein the first composition is applied to the skin of the subject and is permitted to dry on the skin of the subject prior to application of the second composition to the skin of the subject. In another embodiment are methods, wherein the first composition is applied to the skin of the subject in the form of an aqueous paste, wherein the aqueous portion is derived from water or saline. In another embodiment are methods, wherein the aqueous paste further comprises hydrogen peroxide. In another embodiment are methods, wherein an aqueous solution of hydrogen peroxide is applied to the face of the subject following application of the first composition to the skin of the subject and prior to the application of the second composition to the skin of the subject. In another embodiment are methods, wherein the first composition further comprises hydrogen peroxide. In another embodiment are methods, wherein the hydrogen peroxide is an aqueous solution. In another embodiment are methods, wherein the aqueous solution comprises hydrogen peroxide at a w/w concentration of about 3%. In another embodiment are methods, wherein the second composition is permitted to dry on the skin of the subject following application to the skin of the subject. In another embodiment are methods, wherein the second composition is applied to the skin of the subject prior to the first composition being applied to the skin of the subject. In another embodiment are methods, wherein the second composition is permitted to dry on the skin of the subject prior to the first composition being applied to the skin of the subject. In another embodiment are methods, wherein the first composition is applied to the skin of the subject in the form of an aqueous paste, wherein the aqueous portion is derived from water or saline. In another embodiment are methods, wherein the aqueous paste further comprises hydrogen peroxide. In another embodiment are methods, wherein an aqueous solution of hydrogen peroxide is applied to the face of the subject following application of the first composition to the skin of the subject. In another embodiment are methods, wherein the hydrogen peroxide is an aqueous solution. In another embodiment are methods, wherein the aqueous solution comprises hydrogen peroxide at a w/w concentration of about 3%. In another embodiment are methods, wherein the first composition is permitted to dry on the skin of the subject. In another embodiment are methods, wherein the first composition and the second composition are mixed together, and the resulting mixture is applied to the skin of the subject. In another embodiment are methods, wherein the first composition is mixed with an aqueous solution of hydrogen peroxide prior to mixing with the second composition. In another embodiment are methods, wherein the mixture of the first composition and the second composition is further mixed with an aqueous solution of hydrogen peroxide prior to application to the skin of the subject. In another embodiment are methods, wherein the aqueous solution comprises hydrogen peroxide at a w/w concentration of about 3%. In another embodiment are methods, wherein the first composition and the second composition are applied to the skin of the subject once per week. In another embodiment are methods, wherein the second composition is applied to the skin of the subject no more than once every 4 weeks. In another embodiment are methods, wherein the first composition is applied to the skin of the subject at least once per week for at least one week. In another embodiment are methods, wherein the first composition is applied to the skin of the subject once per week for 6 weeks. In another embodiment are methods, wherein the first composition and the second composition are applied to the skin of the subject on at least one of the subject's face, back and chest. In another embodiment are methods, wherein the first composition and the second composition are applied to the skin of the subject on the subject's face. In another embodiment are methods, wherein the first composition and the second composition are applied to the skin of the subject on the subject's back. In another embodiment are methods, wherein the first composition c and the second composition comprising are applied to the skin of the subject on the subject's chest.

In one aspect is provided a method of treating a skin condition in a subject, comprising applying to the skin of the subject a first composition and a second composition, wherein (a) the first composition comprises Spongilla powder; (b) the second composition is comprises one or more botulinum toxin type selected from botulinum toxin type A, and botulinum toxin type B; and (c) the skin condition in the subject is selected from one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, forehead wrinkles, acne vulgaris, acne rosacea type 1, acne rosacea type 2, psoriasis, hyperhidrosis, alopecia areata, androgenic alopecia, keloids and hypertrophic scars, hidradenitis suppurativa, Raynaud phenomenon, post-herpetic neuralgia, Hailey-Hailey disease, IgA bullous dermatosis, epidermolysis bullosa Simplex Weber-Cockane, Darier disease, pachyonchia congenita, aquagenic keratoderma, notalgia paresthetic, pompholyx (dyshidrotic eczema), chromhidrosis and bromhidrosis, eccrine nevus, facial rhytides, atrophic acne scars, and melasma. In another embodiment are methods, wherein the one or more botulinum toxin type is botulinum toxin type A. In another embodiment are methods, wherein the botulinum toxin type A is selected from onabotulinumtoxinA, abobotulinumtoxinA, incobotulinumtoxinA, prabotulinumtoxinA, and daxibotulinumtoxinA. In another embodiment are methods, wherein the botulinum toxin type A is onabotulinumtoxinA. In another embodiment are methods, wherein the botulinum toxin type A is abobotulinumtoxinA. In another embodiment are methods, wherein the botulinum toxin type A is incobotulinumtoxinA. In another aspect is provided any of the methods disclosed herein, wherein the botulinum toxin type A is prabotulinumtoxinA. In another aspect is provided any of the methods disclosed herein, wherein the botulinum toxin type A is daxibotulinumtoxinA. In another embodiment are methods, wherein the one or more botulinum toxin type is botulinum toxin type B. In another aspect is provided any of the methods disclosed herein, wherein the one or more botulinum toxin type B is rimabotulinumtoxinB. In another embodiment are methods, wherein the one or more botulinum toxin type is botulinum toxin type E. In another aspect is provided any of the methods disclosed herein, wherein the one or more botulinum toxin type E is EB-001A or EB-001T. In another aspect is provided any of the methods disclosed herein, wherein the one or more botulinum toxin type E is EB-001A. In another aspect is provided any of the methods disclosed herein, wherein the one or more botulinum toxin type E is EB-001T. In another embodiment are methods, wherein the skin condition in the subject is selected from acne vulgaris, acne rosacea type 1, acne rosacea type 2, psoriasis, and hyperhidrosis. In another embodiment are methods, wherein the skin condition in the subject is acne vulgaris. In another embodiment are methods, wherein the skin condition in the subject is acne rosacea type 1. In another embodiment are methods, wherein the skin condition in the subject is acne rosacea type 2. In another embodiment are methods, wherein the skin condition in the subject is psoriasis. In another embodiment are methods, wherein the skin condition in the subject is hyperhidrosis. In another embodiment are methods, wherein the Spongilla is Spongilla *lacustris*. In another embodiment are methods, wherein the second composition comprising one or more botulinum toxins is applied topically to the skin of the subject. In another embodiment are methods, wherein the second composition comprising one or more botulinum toxins is in the form of an aqueous solution. In another embodiment are methods, wherein the second composition is applied to the skin of the subject in the form of a solution. In another embodiment are methods, wherein the second composition is in the form of an aqueous solution. In another embodiment are methods, wherein the amount of the first composition comprising Spongilla applied to the skin of the subject is from about 0.5 grams to about 50 grams, measured as a dry weight. In another embodiment are methods, wherein the first composition is applied to the skin of the subject in the form of a paste. In another embodiment are methods, wherein the paste further comprises water or saline, In another embodiment are methods, wherein the paste is prepared by mixing a powder comprising Spongilla and an aqueous solution comprising hydrogen peroxide. In another embodiment are methods, wherein the aqueous solution comprises hydrogen peroxide at a w/w concentration of about 3%. In another embodiment are methods, wherein the first composition is applied to the skin of the subject prior to the second composition being applied to the skin of the subject. In another embodiment are methods, wherein the first composition is applied to the skin of the subject and is permitted to dry on the skin of the subject prior to application of the second composition to the skin of the subject. In another embodiment are methods, wherein the first composition is applied to the skin of the subject in the form of an aqueous paste, wherein the aqueous portion is derived from water or saline. In another embodiment are methods, wherein the aqueous paste further comprises hydrogen peroxide. In another embodiment are methods, wherein an aqueous solution of hydrogen peroxide is applied to the face of the subject following application of the first composition to the skin of the subject and prior to the application of the second composition to the skin of the subject. In another embodiment are methods, wherein the first composition further comprises hydrogen peroxide. In another embodiment are methods, wherein the hydrogen peroxide is an aqueous solution. In another embodiment are methods, wherein the aqueous solution comprises hydrogen peroxide at a w/w concentration of about 3%. In another embodiment are methods, wherein the second composition is permitted to dry on the skin of the subject following application to the skin of the subject. In another embodiment are methods, wherein the second composition is applied to the skin of the subject prior to the first composition being applied to the skin of the subject. In another embodiment are methods, wherein the second composition is permitted to dry on the skin of the subject prior to the first composition being applied to the skin of the subject. In another embodiment are methods, wherein the first composition is applied to the skin of the subject in the form of an aqueous paste, wherein the aqueous portion is derived from water or saline. In another embodiment are methods, wherein the aqueous paste further comprises hydrogen peroxide. In another embodiment are methods, wherein an aqueous solution of hydrogen peroxide is applied to the face of the subject following application of the first composition to the skin of the subject. In another embodiment are methods, wherein the hydrogen peroxide is an aqueous solution. In another embodiment are methods, wherein the aqueous solution comprises hydrogen peroxide at a w/w concentration of about 3%. In another embodiment are methods, wherein the first composition is permitted to dry on the skin of the subject. In another embodiment are methods, wherein the first composition and the second composition are mixed together, and the resulting mixture is applied to the skin of the subject. In another embodiment are methods, wherein the first composition is mixed with an aqueous solution of hydrogen peroxide prior to mixing with the second composition. In another embodiment are methods, wherein the mixture of the first composition and the second composition is further mixed with an aqueous solution of hydrogen peroxide prior to application to the skin of the subject. In another embodiment are methods, wherein the aqueous solution comprises hydrogen peroxide at a w/w concentration of about 3%. In another embodiment are methods, wherein the first composition and the second composition are applied to the skin of the subject once per week. In another embodiment are methods, wherein the second composition is applied to the skin of the subject no more than once every 4 weeks. In another embodiment are methods, wherein the first composition is applied to the skin of the subject at least once per week for at least one week. In another embodiment are methods, wherein the first composition is applied to the skin of the subject once per week for 6 weeks. In another embodiment are methods, wherein the first composition and the second composition are applied to the skin of the subject on at least one of the subject's face, back and chest. In another embodiment are methods, wherein the first composition and the second composition are applied to the skin of the subject on the subject's face. In another embodiment are methods, wherein the first composition and the second composition are applied to the skin of the subject on the subject's back. In another embodiment are methods, wherein the first composition c and the second composition comprising are applied to the skin of the subject on the subject's chest.

In one aspect is provided a method of treating a skin condition in a subject, comprising applying to the skin of the subject a first composition and a second composition, wherein (a) the first composition comprises Spongilla *lacustris* powder; (b) the second composition comprises one or more botulinum toxin type selected from botulinum toxin type A; and (c) the skin condition in the subject is selected from one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles. In another embodiment are methods, wherein the botulinum toxin type A is selected from onabotulinumtoxinA, abobotulinumtoxinA, incobotulinumtoxinA, prabotulinumtoxinA, and daxibotulinumtoxinA. In another embodiment are methods, wherein the botulinum toxin type A is onabotulinumtoxinA. In another embodiment are methods, wherein the botulinum toxin type A is abobotulinumtoxinA. In another embodiment are methods, wherein the botulinum toxin type A is incobotulinumtoxinA. In another aspect is provided any of the methods disclosed herein, wherein the botulinum toxin type A is prabotulinumtoxinA. In another aspect is provided any of the methods disclosed herein, wherein the botulinum toxin type A is daxibotulinumtoxinA. In another embodiment are methods, wherein the skin condition in the subject is acne vulgaris. In another embodiment are methods, wherein the skin condition in the subject is acne rosacea type 1. In another embodiment are methods, wherein the skin condition in the subject is acne rosacea type 2. In another embodiment are methods, wherein the skin condition in the subject is psoriasis. In another embodiment are methods, wherein the skin condition in the subject is hyperhidrosis. In another embodiment are methods, wherein the second composition comprising one or more botulinum toxins is applied topically to the skin of the subject. In another embodiment are methods, wherein the second composition comprising one or more botulinum toxins is in the form of an aqueous solution. In another embodiment are methods, wherein the second composition is applied to the skin of the subject in the form of a solution. In another embodiment are methods, wherein the second composition is in the form of an aqueous solution. In another embodiment are methods, wherein the amount of the first composition comprising Spongilla applied to the skin of the subject is from about 0.5 grams to about 50 grams, measured as a dry weight. In another embodiment are methods, wherein the first composition is applied to the skin of the subject in the form of a paste. In another embodiment are methods, wherein the paste further comprises water or saline. In another embodiment are methods, wherein the paste is prepared by mixing a powder comprising Spongilla and an aqueous solution comprising hydrogen peroxide. In another embodiment are methods, wherein the aqueous solution comprises hydrogen peroxide at a w/w concentration of about 3%. In another embodiment are methods, wherein the first composition is applied to the skin of the subject prior to the second composition being applied to the skin of the subject. In another embodiment are methods, wherein the first composition is applied to the skin of the subject and is permitted to dry on the skin of the subject prior to application of the second composition to the skin of the subject. In another embodiment are methods, wherein the first composition is applied to the skin of the subject in the form of an aqueous paste, wherein the aqueous portion is derived from water or saline. In another embodiment are methods, wherein the aqueous paste further comprises hydrogen peroxide. In another embodiment are methods, wherein an aqueous solution of hydrogen peroxide is applied to the face of the subject following application of the first composition to the skin of the subject and prior to the application of the second composition to the skin of the subject. In another embodiment are methods, wherein the first composition further comprises hydrogen peroxide. In another embodiment are methods, wherein the hydrogen peroxide is an aqueous solution. In another embodiment are methods, wherein the aqueous solution comprises hydrogen peroxide at a w/w concentration of about 3%. In another embodiment are methods, wherein the second composition is permitted to dry on the skin of the subject following application to the skin of the subject. In another embodiment are methods, wherein the second composition is applied to the skin of the subject prior to the first composition being applied to the skin of the subject. In another embodiment are methods, wherein the second composition is permitted to dry on the skin of the subject prior to the first composition being applied to the skin of the subject. In another embodiment are methods, wherein the first composition is applied to the skin of the subject in the form of an aqueous paste, wherein the aqueous portion is derived from water or saline. In another embodiment are methods, wherein the aqueous paste further comprises hydrogen peroxide. In another embodiment are methods, wherein an aqueous solution of hydrogen peroxide is applied to the face of the subject following application of the first composition to the skin of the subject. In another embodiment are methods, wherein the hydrogen peroxide is an aqueous solution. In another embodiment are methods, wherein the aqueous solution comprises hydrogen peroxide at a w/w concentration of about 3%. In another embodiment are methods, wherein the first composition is permitted to dry on the skin of the subject. In another embodiment are methods, wherein the first composition and the second composition are mixed together, and the resulting mixture is applied to the skin of the subject. In another embodiment are methods, wherein the first composition is mixed with an aqueous solution of hydrogen peroxide prior to mixing with the second composition. In another embodiment are methods, wherein the mixture of the first composition and the second composition is further mixed with an aqueous solution of hydrogen peroxide prior to application to the skin of the subject. In another embodiment are methods, wherein the aqueous solution. comprises hydrogen peroxide at a w/w concentration of about 3%. In another embodiment are methods, wherein the first composition and the second composition are applied to the skin of the subject once per week. In another embodiment are methods, wherein the second composition is applied to the skin of the subject no more than once every 4 weeks. In another embodiment are methods, wherein the first composition is applied to the skin of the subject at least once per week for at least one week. In another embodiment are methods, wherein the first composition is applied to the skin of the subject once per week for 6 weeks. In another embodiment are methods, wherein the first composition and the second composition are applied to the skin of the subject on at least one of the subject's face, back and chest. In another embodiment are methods, wherein the first composition and the second composition are applied to the skin of the subject on the subject's face. In another embodiment are methods, wherein the first composition and the second composition are applied to the skin of the subject on the subject's back. In another embodiment are methods, wherein the first composition c and the second composition comprising are applied to the skin of the subject on the subject's chest.

In one aspect is provided a method of treating a skin condition in a subject, comprising applying to the skin of the subject a first composition and a second composition, wherein (a) the first composition comprises Spongilla *lacustris* powder; (b) the second composition comprises one or more botulinum toxin type selected from botulinum toxin type A; and (c) the skin condition in the subject is selected from one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, forehead wrinkles, acne vulgaris, acne rosacea type 1, acne rosacea type 2, psoriasis, and hyperhidrosis. In another embodiment are methods, wherein the second composition comprises onabotulinumtoxinA, and the skin condition in the subject is acne vulgaris. In another embodiment are methods, wherein the second composition comprises onabotulinumtoxinA, and the skin condition in the subject is acne rosacea type 1. In another embodiment are methods, wherein the second composition comprises onabotulinumtoxinA, and the skin condition in the subject is acne rosacea type 2. In another embodiment are methods, wherein the second composition comprises onabotulinumtoxinA, and the skin condition in the subject is psoriasis. In another embodiment are methods, wherein the second composition comprises onabotulinumtoxinA, and the skin condition in the subject is hyperhidrosis. In another embodiment are methods, wherein the second composition comprises abobotulinumtoxinA. In another embodiment are methods, wherein the second composition comprises abobotulinumtoxinA, and the skin condition in the subject is acne vulgaris. In another embodiment are methods, wherein the second composition comprises abobotulinumtoxinA, and the skin condition in the subject is acne rosacea type 1. In another embodiment are methods, wherein the second composition comprises abobotulinumtoxinA, and the skin condition in the subject is acne rosacea type 2. In another embodiment are methods, wherein the second composition comprises abobotulinumtoxinA, and the skin condition in the subject is psoriasis. In another embodiment are methods, wherein the second composition comprises abobotulinumtoxinA, and the skin condition in the subject is hyperhidrosis. In another embodiment are methods, wherein the second composition comprises incobotulinumtoxinA. In another embodiment are methods, wherein the second composition comprises incobotulinumtoxinA, and the skin condition in the subject is acne vulgaris. In another embodiment are methods, wherein the second composition comprises incobotulinumtoxinA, and the skin condition in the subject is acne rosacea type 1. In another embodiment are methods, wherein the second composition comprises incobotulinumtoxinA, and the skin condition in the subject is acne rosacea type 2. In another embodiment are methods, wherein the second composition comprises incobotulinumtoxinA, and the skin condition in the subject is psoriasis. In another embodiment are methods, wherein the second composition comprises incobotulinumtoxinA, and the skin condition in the subject is hyperhidrosis. In another embodiment are methods, wherein the second composition comprises prabotulinumtoxinA. In another embodiment are methods, wherein the second composition comprises prabotulinumtoxinA, and the skin condition in the subject is acne vulgaris. In another embodiment are methods, wherein the second composition comprises prabotulinumtoxinA, and the skin condition in the subject is acne rosacea type 1. In another embodiment are methods, wherein the second composition comprises prabotulinumtoxinA, and the skin condition in the subject is acne rosacea type 2. In another embodiment are methods, wherein the second composition comprises prabotulinumtoxinA, and the skin condition in the subject is psoriasis. In another embodiment are methods, wherein the second composition comprises prabotulinumtoxinA, and the skin condition in the subject is hyperhidrosis. In another embodiment are methods, wherein the second composition comprises daxibotulinumtoxinA. In another embodiment are methods, wherein the second composition comprises daxibotulinumtoxinA, and the skin condition in the subject is acne vulgaris. In another embodiment are methods, wherein the second composition comprises daxibotulinumtoxinA, and the skin condition in the subject is acne rosacea type 1. In another embodiment are methods, wherein the second composition comprises daxibotulinumtoxinA, and the skin condition in the subject is acne rosacea type 2. In another embodiment are methods, wherein the second composition comprises daxibotulinumtoxinA, and the skin condition in the subject is psoriasis. In another embodiment are methods, wherein the second composition comprises daxibotulinumtoxinA, and the skin condition in the subject is hyperhidrosis.

In another embodiment are methods, wherein the second composition comprises EB-001A. In another embodiment are methods, wherein the second composition comprises EB-001A, and the skin condition in the subject is acne vulgaris. In another embodiment are methods, wherein the second composition comprises EB-001A, and the skin condition in the subject is acne rosacea type 1. In another embodiment are methods, wherein the second composition comprises EB-001A, and the skin condition in the subject is one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, forehead wrinkles, acne rosacea type 2. In another embodiment are methods, wherein the second composition comprises EB-001A, and the skin condition in the subject is psoriasis. In another embodiment are methods, wherein the second composition comprises EB-001A, and the skin condition in the subject is hyperhidrosis. In another embodiment are methods, wherein the second composition comprises EB-001T. In another embodiment are methods, wherein the second composition comprises EB-001T, and the skin condition in the subject is acne vulgaris. In another embodiment are methods, wherein the second composition comprises EB-001T, and the skin condition in the subject is acne rosacea type 1. In another embodiment are methods, wherein the second composition comprises EB-001T, and the skin condition in the subject is acne rosacea type 2. In another embodiment are methods, wherein the second composition comprises EB-001T, and the skin condition in the subject is psoriasis. In another embodiment are methods, wherein the second composition comprises EB-001T, and the skin condition in the subject is hyperhidrosis.

In another embodiment are methods, wherein the second composition comprising one or more botulinum toxins is applied topically to the skin of the subject. In another embodiment are methods, wherein the second composition comprising one or more botulinum toxins is in the form of an aqueous solution. In another embodiment are methods, wherein the second composition is applied to the skin of the subject in the form of a solution. In another embodiment are methods, wherein the second composition is in the form of an aqueous solution. In another embodiment are methods, wherein the amount of the first composition comprising Spongilla applied to the skin of the subject is from about 0.5 grams to about 50 grams, measured as a dry weight. In another embodiment are methods, wherein the first composition is applied to the skin of the subject in the form of a paste. In another embodiment are methods, wherein the paste further comprises water or saline. In another embodiment are methods, wherein the paste is prepared by mixing a powder comprising Spongilla and an aqueous solution comprising hydrogen peroxide. In another embodiment are methods, wherein the aqueous solution comprises hydrogen peroxide at a w/w concentration of about 3%. In another embodiment are methods, wherein the first composition is applied to the skin of the subject prior to the second composition being applied to the skin of the subject. In another embodiment are methods, wherein the first composition is applied to the skin of the subject and is permitted to dry on the skin of the subject prior to application of the second composition to the skin of the subject. In another embodiment are methods, wherein the first composition is applied to the skin of the subject in the form of an aqueous paste, wherein the aqueous portion is derived from water or saline. In another embodiment are methods, wherein the aqueous paste further comprises hydrogen peroxide. In another embodiment are methods, wherein an aqueous solution of hydrogen peroxide is applied to the face of the subject following application of the first composition to the skin of the subject and prior to the application of the second composition to the skin of the subject. In another embodiment are methods, wherein the first composition further comprises hydrogen peroxide. In another embodiment are methods, wherein the hydrogen peroxide is an aqueous solution. In another embodiment are methods, wherein the aqueous solution comprises hydrogen peroxide at a w/w concentration of about 3%. In another embodiment are methods, wherein the second composition is permitted to dry on the skin of the subject following application to the skin of the subject. In another embodiment are methods, wherein the second composition is applied to the skin of the subject prior to the first composition being applied to the skin of the subject. In another embodiment are methods, wherein the second composition is permitted to dry on the skin of the subject prior to the first composition being applied to the skin of the subject. In another embodiment are methods, wherein the first composition is applied to the skin of the subject in the form of an aqueous paste, wherein the aqueous portion is derived from water or saline. In another embodiment are methods, wherein the aqueous paste further comprises hydrogen peroxide. In another embodiment are methods, wherein an aqueous solution of hydrogen peroxide is applied to the face of the subject following application of the first composition to the skin of the subject. In another embodiment are methods, wherein the hydrogen peroxide is an aqueous solution. In another embodiment are methods, wherein the aqueous solution comprises hydrogen peroxide at a w/w concentration of about 3%. In another embodiment are methods, wherein the first composition is permitted to dry on the skin of the subject. In another embodiment are methods, wherein the first composition and the second composition are mixed together, and the resulting mixture is applied to the skin of the subject. In another embodiment are methods, wherein the first composition is mixed with an aqueous solution of hydrogen peroxide prior to mixing with the second composition. In another embodiment are methods, wherein the mixture of the first composition and the second composition is further mixed with an aqueous solution of hydrogen peroxide prior to application to the skin of the subject. In another embodiment are methods, wherein the aqueous solution comprises hydrogen peroxide at a w/w concentration of about 3%.

In another aspect is provided a kit, comprising a first composition and a second composition, wherein (a) the first composition comprises a Spongilla; and (b) the second composition comprises one or more botulinum toxins. In another aspect is provided any of the kits described herein, further comprising instructions for use in treating the first and the second composition in the treatment in a subject having a skin condition. In another aspect is provided any of the kits described herein, wherein the first composition comprises Spongilla in the form of a powder. In another aspect is provided any of the kits described herein, wherein the Spongilla is in the form of a powder comprising particles that are substantially uniform in size.

In another aspect is provided any of the kits described herein, wherein not less than 50% of the particles comprising the Spongilla powder pass through a US 70-mesh screen.

In another aspect is provided any of the kits described herein, wherein not less than about 50% of the particles comprising the Spongilla powder pass through a US 70-mesh screen. In another embodiment are methods, wherein not less than about 60%, or about 70%, or about 75%, or about 80%, or about 85%, or about 90%, or about 95%, or about 96%, or about 97%, or about 98%, or about 99% of the particles comprising the Spongilla powder pass through a US 70-mesh screen. In another aspect is provided any of the kits disclosed herein, wherein not less than about 95%, or about 96%, or about 97%, or about 98%, or about 99% of the particles comprising the Spongilla powder pass through a US 70-mesh screen. In another aspect is provided any of the kits disclosed herein, wherein not less than about 95% of the particles comprising the Spongilla powder pass through a US 70-mesh screen. In another aspect is provided any of the kits disclosed herein, wherein not less than about 96% of the particles comprising the Spongilla powder pass through a US 70-mesh screen. In another aspect is provided any of the kits disclosed herein, wherein not less than about 97% of the particles comprising the Spongilla powder pass through a US 70-mesh screen. In another aspect is provided any of the kits disclosed herein, wherein not less than about 98% of the particles comprising the Spongilla powder pass through a US 70-mesh screen. In another aspect is provided any of the kits disclosed herein, wherein not less than about 99% of the particles comprising the Spongilla powder pass through a US 70-mesh screen.

In another aspect is provided any of the kits disclosed herein, wherein the particles comprising the Spongilla powder have an average length of from about 50 μm to about 500 μm. In another aspect is provided any of the kits disclosed herein, wherein the particles comprising the Spongilla powder have an average length of from about 50 μm to about 400 μm, or from about 50 μm to about 350 μm, or from about 50 μm to about 300 μm, or from about 50 μm to about 250 μm, or from about 50 μm to about 200 μm, or from about 75 μm to about 500 μm, or from about 75 μm to about 450 μm, or from about 80 μm to about 450 μm, or from about 80 μm to about 400 μm, or from about 85 μm to about 450 μm, or from about 85 μm to about 400 μm, or from about 90 μm to about 450 μm, or from about 90 μm to about 400 μm, or from about 90 μm to about 350 μm, or from about 100 μm to about 450 μm, or from about 100 μm to about 400 μm, or from about 100 μm to about 350 μm, or from about 100 μm to about 300 μm, or from about 100 μm to about 250 μm, or from about 100 μm to about 200 μm, or from about 150 μm to about 500 μm, or from about 150 μm to about 450 μm, or from about 150 μm to about 400 μm, or from about 150 μm to about 350 μm, or from about 150 μm to about 350 μm, or from about 150 μm to about 300 μm, or from about 150 μm to about 250 μm, or from about 150 μm to about 200 μm, or from about 175 μm to about 450 μm, or from about 175 μm to about 400 μm, or from about 175 μm to about 350 μm, or from about 175 μm to about 300 μm, or from about 175 μm to about 250 μm, or from about 175 μm to about 200 μm. In another aspect is provided any of the kits disclosed herein, wherein the particles comprising the Spongilla powder have an average length of about 50 μm, or about 75 μm, or about 80 μm, or about 85 μm, or about 90 μm, or about 100 μm, or about 125 μm, or about 150 μm, or about 175 μm, or about 200 μm, or about 225 μm, or about 250 μm, or about 300 μm, or about 350 μm, or about 400 μm, or about 450 μm, or about 500 μm. In another aspect is provided any of the kits disclosed herein, wherein the particles comprising the Spongilla powder have an average length of about 200 μm.

In another aspect is provided any of the kits disclosed herein, wherein the particles comprising the Spongilla powder have an average diameter of from about 5 μm to about 50 μm. In another aspect is provided any of the kits disclosed herein, wherein the particles comprising the Spongilla powder have an average diameter of from about 5 μm to about 45 μm, or from about 5 μm to about 40 μm, from about 5 μm to about 35 μm, from about 5 μm to about 30 μm, from about 5 μm to about 25 μm, from about 5 μm to about 20 μm, from about 10 μm to about 50 μm, from about 10 μm to about 45 μm, from about 10 μm to about 40 μm, from about 10 μm to about 35 μm, from about 10 μm to about 30 μm, from about 10 μm to about 25 μm, from about 10 μm to about 20 μm. In another aspect is provided any of the kits disclosed herein, wherein the particles comprising the Spongilla powder have an average diameter of about 5 μm, or about 10 μm, or about 15 μm, or about 20 μm, or about 25 μm, or about 30 μm, or about 35 μm, or about 40 μm, or about 45 μm, or about 50 μm.

In another aspect is provided any of the kits disclosed herein, wherein the particles comprising the Spongilla powder have an aspect ratio of from about 1 to about 100. In another aspect is provided any of the kits disclosed herein, wherein the particles comprising the Spongilla powder have an aspect ratio of from about 1 to about 75, or from about 1 to about 50, or from about 1 to about 25, or from about 1 to about 20, or from about 1 to about 15, or from about 5 to about 100, or from about 5 to about 75, or from about 5 to about 50, or from about 5 to about 40, or from about 5 to about 35, or from about 5 to about 30, or from about 5 to about 25, or from about 5 to about 20, or from about 5 to about 15, or from about 7 to about 50, or from about 7 to about 45, or from about 7 to about 40, or from about 7 to about 35, or from about 7 to about 30, or from about 7 to about 25, or from about 10 to about 50, or from about 10 to about 45, or from about 10 to about 40, or from about 10 to about 35, or from about 10 to about 30, or from about 10 to about 25, or from about 10 to about 15. In another aspect is provided any of the kits disclosed herein, wherein the particles comprising the Spongilla powder have an aspect ratio of about 5, or about 6, or about 7, or about 8, or about 9, or about 10, or about 11, or about 12, or about 13, or about 14, or about 15, or about 16, or about 17, or about 18, or about 19, or about 20, or about 21, or about 22, or about 23, or about 24, or about 25, or about 26, or about 27, or about 28, or about 29, or about 30, or about 35, or about 40, or about 45, or about 50, or about 75, or about 100.

In another aspect is provided any of the kits disclosed herein, wherein the first composition has a residual moisture content of not more than about 20%. In another aspect is provided any of the kits disclosed herein, wherein the first composition has a residual moisture content of not more than about 15%, or not more than about 10%, or not more than about 9%, or not more than about 8%, or not more than about 7%, or not more than about 6%, or not more than about 5%, or not more than about 4%, or not more than about 3%, or not more than about 2%, or not more than 1%. In another aspect is provided any of the kits disclosed herein, wherein the first composition has a residual moisture content of not more than about 5%. In another aspect is provided any of the kits disclosed herein, wherein the first composition has a residual moisture content of not more than about 4%. In another aspect is provided any of the kits disclosed herein, wherein the first composition has a residual moisture content of not more than about 3%. In another aspect is provided any of the kits disclosed herein, wherein the first composition has a residual moisture content of not more than about 2%. In another aspect is provided any of the kits disclosed herein, wherein the first composition has a residual moisture content of not more than about 1%.

In another aspect is provided any of the kits disclosed herein, wherein the first composition has a combined aerobic and anaerobic microbial content of not more than about 25 $\times 10^4$ colony-forming units per gram (CFU/g). In another aspect is provided any of the kits disclosed herein, wherein the first composition has a combined aerobic and anaerobic microbial content of not more than about $10 \times 10^4$ CFU/g, or not more than about $5 \times 10^4$ CFU/g, or not more than about $1 \times 10^4$ CFU/g, or not more than about $5 \times 10^3$ CFU/g, or not more than about $1 \times 10^3$ CFU/g, or not more than about 10,000 CFU/g, or not more than about 7,500 CFU/g, or not more than about 5,000 CFU/g, or not more than about 2,500 CFU/g, or not more than about 2,000 CFU/g, or not more than about 1,500 CFU/g, or not more than about 1,000 CFU/g, or not more than about 750 CFU/g, or not more than about 500 CFU/g, or not more than about 250 CFU/g, or not more than about 200 CFU/g, or not more than about 150 CFU/g, or not more than about 100 CFU/g, or not more than about 75 CFU/g, or not more than about 50 CFU/g, or not more than about 25 CFU/g, or not more than about 15 CFU/g, or not more than about 10 CFU/g, or not more than about 5 CFU/g, or not more than about 1 CFU/g. In another aspect is provided any of the kits disclosed herein, wherein the first composition has a combined aerobic and anaerobic microbial content of not more than about 1,000 CFU/g. In another aspect is provided any of the kits disclosed herein, wherein the first composition has a combined aerobic and anaerobic microbial content of not more than about 750 CFU/g. In another aspect is provided any of the kits disclosed herein, wherein the first composition has a combined aerobic and anaerobic microbial content of not more than about 500 CFU/g. In another aspect is provided any of the kits disclosed herein, wherein the first composition has a combined aerobic and anaerobic microbial content of not more than about 250 CFU/g. In another aspect is provided any of the kits disclosed herein, wherein the first composition has a combined aerobic and anaerobic microbial content of not more than about 200 CFU/g. In another aspect is provided any of the kits disclosed herein, wherein the first composition has a combined aerobic and anaerobic microbial content of not more than about 150 CFU/g. In another aspect is provided any of the kits disclosed herein, wherein the first composition has a combined aerobic and anaerobic microbial content of not more than about 100 CFU/g. In another aspect is provided any of the kits disclosed herein, wherein the first composition has a combined aerobic and anaerobic microbial content of not more than about 75 CFU/g. In another aspect is provided any of the kits disclosed herein, wherein the first composition has a combined aerobic and anaerobic microbial content of not more than about 50 CFU/g. In another aspect is provided any of the kits disclosed herein, wherein the first composition has a combined aerobic and anaerobic microbial content of not more than about 25 CFU/g. In another aspect is provided any of the kits disclosed herein, wherein the first composition has a combined aerobic and anaerobic microbial content of not more than about 20 CFU/g. In another aspect is provided any of the kits disclosed herein, wherein the first composition has a combined aerobic and anaerobic microbial content of not more than about 10 CFU/g. In another aspect is provided any of the kits disclosed herein, wherein the first composition has a combined aerobic and anaerobic microbial content of not more than about 1 CFU/g. In another aspect is provided any of the kits disclosed herein, wherein the first composition has a combined aerobic and anaerobic microbial content of not more than about $25 \times 10^4$ colony-forming units per gram (CFU/g). In another aspect is provided any of the kits disclosed herein, wherein the first composition has a combined aerobic and anaerobic microbial content of not more than about $10 \times 10^4$ CFU/g, or not more than about $5 \times 10^4$ CFU/g, or not more than about $1 \times 10^4$ CFU/g, or not more than about $5 \times 10^3$ CFU/g, or not more than about $1 \times 10^3$ CFU/g.

In another aspect is provided any of the kits disclosed herein, wherein the first composition has a combined yeast and mold content of not more than about 25×10⁴ colony-forming units per gram (CFU/g). In another aspect is provided any of the kits disclosed herein, wherein the first composition has a combined yeast and mold content of not more than about or not more than about 5×10⁴ CFU/g, or not more than about 1×10⁴ CFU/g, or not more than about 5×10³ CFU/g, or not more than about 1×10³ CFU/g, or not more than about 10,000 CFU/g, or not more than about 7,500 CFU/g, or not more than about 5,000 CFU/g, or not more than about 2,500 CFU/g, or not more than about 2,000 CFU/g, or not more than about 1,500 CFU/g, or not more than about 1,000 CFU/g, or not more than about 750 CFU/g, or not more than about 500 CFU/g, or not more than about 250 CFU/g, or not more than about 200 CFU/g, or not more than about 150 CFU/g, or not more than about 100 CFU/g, or not more than about 75 CFU/g, or not more than about 50 CFU/g, or not more than about 25 CFU/g, or not more than about 15 CFU/g, or not more than about 10 CFU/g, or not more than about 5 CFU/g, or not more than about 1 CFU/g. In another aspect is provided any of the kits disclosed herein, wherein the first composition has a combined yeast and mold content of not more than about 1,000 CFU/g. In another aspect is provided any of the kits disclosed herein, wherein the first composition has a combined yeast and mold content of not more than about 750 CFU/g. In another aspect is provided any of the kits disclosed herein, wherein the first composition has a combined yeast and mold content of not more than about 500 CFU/g. In another aspect is provided any of the kits disclosed herein, wherein the first composition has a combined yeast and mold content of not more than about 250 CFU/g. In another aspect is provided any of the kits disclosed herein, wherein the first composition has a combined yeast and mold content of not more than about 200 CFU/g. In another aspect is provided any of the kits disclosed herein, wherein the first composition has a combined yeast and mold content of not more than about 150 CFU/g. In another aspect is provided any of the kits disclosed herein, wherein the first composition has a combined yeast and mold content of not more than about 100 CFU/g. In another aspect is provided any of the kits disclosed herein, wherein the first composition has a combined yeast and mold content of not more than about 75 CFU/g. In another aspect is provided any of the kits disclosed herein, wherein the first composition has a combined yeast and mold content of not more than about 50 CFU/g. In another aspect is provided any of the kits disclosed herein, wherein the first composition has a combined yeast and mold content of not more than about 25 CFU/g. In another aspect is provided any of the kits disclosed herein, wherein the first composition has a combined yeast and mold content of not more than about 20 CFU/g. In another aspect is provided any of the kits disclosed herein, wherein the first composition has a combined yeast and mold content of not more than about 10 CFU/g. In another aspect is provided any of the kits disclosed herein, wherein the first composition has a combined yeast and mold content of not more than about 1 CFU/g. In another aspect is provided any of the kits disclosed herein, wherein the first composition has a combined yeast and mold content of not more than about 25×10⁴ colony-forming units per gram (CFU/g). In another aspect is provided any of the kits disclosed herein, wherein the first composition has a combined yeast and mold content of not more than about or not more than about 5×10⁴ CFU/g, or not more than about 1×10⁴ CFU/g, or not more than about 5×10³ CFU/g, or not more than about 1×10³ CFU/g.

In another aspect is provided any of the kits disclosed herein, wherein the amount of Coliform bacteria in the first composition is not more than about 25×10⁴ colony-forming units per gram (CFU/g). In another aspect is provided any of the kits disclosed herein, wherein the amount of Coliform bacteria in the first composition is not more than about 5×10⁴ CFU/g, or not more than about 1×10⁴ CFU/g, or not more than about 5×10³ CFU/g, or not more than about 1×10³ CFU/g, or not more than about 10,000 CFU/g, or not more than about 7,500 CFU/g, or not more than about 5,000 CFU/g, or not more than about 2,500 CFU/g, or not more than about 2,000 CFU/g, or not more than about 1,500 CFU/g, or not more than about 1,000 CFU/g, or not more than about 750 CFU/g, or not more than about 500 CFU/g, or not more than about 250 CFU/g, or not more than about 200 CFU/g, or not more than about 150 CFU/g, or not more than about 100 CFU/g, or not more than about 75 CFU/g, or not more than about 50 CFU/g, or not more than about 25 CFU/g, or not more than about 15 CFU/g, or not more than about 10 CFU/g, or not more than about 5 CFU/g, or not more than about 1 CFU/g. In another aspect is provided any of the kits disclosed herein, wherein the first composition has a Coliform bacteria content of not more than about 1,000 CFU/g. In another aspect is provided any of the kits disclosed herein, wherein the first composition has a Coliform bacteria content of not more than about 750 CFU/g. In another aspect is provided any of the kits disclosed herein, wherein the first composition has a Coliform bacteria content of not more than about 500 CFU/g. In another aspect is provided any of the kits disclosed herein, wherein the first composition has a Coliform bacteria content of not more than about 250 CFU/g. In another aspect is provided any of the kits disclosed herein, wherein the first composition has a Coliform bacteria content of not more than about 200 CFU/g. In another aspect is provided any of the kits disclosed herein, wherein the first composition has a Coliform bacteria content of not more than about 150 CFU/g. In another aspect is provided any of the kits disclosed herein, wherein the first composition has a Coliform bacteria content of not more than about 100 CFU/g. In another aspect is provided any of the kits disclosed herein, wherein the first composition has a Coliform bacteria content of not more than about 75 CFU/g. In another aspect is provided any of the kits disclosed herein, wherein the first composition has a Coliform bacteria content of not more than about 50 CFU/g. In another aspect is provided any of the kits disclosed herein, wherein the first composition has a Coliform bacteria content of not more than about 25 CFU/g. In another aspect is provided any of the kits disclosed herein, wherein the first composition has a Coliform bacteria content of not more than about 20 CFU/g. In another aspect is provided any of the kits disclosed herein, wherein the first composition has a Coliform bacteria content of not more than about 10 CFU/g. In another aspect is provided any of the kits disclosed herein, wherein the first composition has a Coliform bacteria content of not more than about 1 CFU/g. In another aspect is provided any of the kits disclosed herein, wherein the first composition has no detectable Coliform bacterial content. In another aspect is provided any of the kits disclosed herein, wherein the amount of Coliform bacteria in the first composition is not more than about 25×10⁴ colony-forming units per gram (CFU/g). In another aspect is provided any of the kits disclosed herein, wherein the amount of Coliform bacteria in the first composition is not more than about 5×10⁴ CFU/g, or not more than about 1×10⁴ CFU/g, or not more than about 5×10³ CFU/g, or not more than about 1×10³ CFU/g.

In another aspect is provided any of the kits disclosed herein, wherein the amount of *Salmonella* in the first composition is not more than about 25×10⁴ colony-forming units per gram (CFU/g). In another aspect is provided any of the kits disclosed herein, wherein the amount of *Salmonella* in the first composition is not more than about $5 \times 10^4$ CFU/g, or not more than about $1 \times 10^4$ CFU/g, or not more than about $5 \times 10^3$ CFU/g, or not more than about $1 \times 10^3$ CFU/g, or not more than about 10,000 CFU/g, or not more than about 7,500 CFU/g, or not more than about 5,000 CFU/g, or not more than about 2,500 CFU/g, or not more than about 2,000 CFU/g, or not more than about 1,500 CFU/g, or not more than about 1,000 CFU/g, or not more than about 750 CFU/g, or not more than about 500 CFU/g, or not more than about 250 CFU/g, or not more than about 200 CFU/g, or not more than about 150 CFU/g, or not more than about 100 CFU/g, or not more than about 75 CFU/g, or not more than about 50 CFU/g, or not more than about 25 CFU/g, or not more than about 15 CFU/g, or not more than about 10 CFU/g, or not more than about 5 CFU/g, or not more than about 1 CFU/g. In another aspect is provided any of the kits disclosed herein, wherein the first composition has a *Salmonella* content of not more than about 1,000 CFU/g. In another aspect is provided any of the kits disclosed herein, wherein the first composition has a *Salmonella* content of not more than about 750 CFU/g. In another aspect is provided any of the kits disclosed herein, wherein the first composition has a *Salmonella* content of not more than about 500 CFU/g. In another aspect is provided any of the kits disclosed herein, wherein the first composition has a *Salmonella* content of not more than about 250 CFU/g. In another aspect is provided any of the kits disclosed herein, wherein the first composition has a *Salmonella* content of not more than about 200 CFU/g. In another aspect is provided any of the kits disclosed herein, wherein the first composition has a *Salmonella* content of not more than about 150 CFU/g. In another aspect is provided any of the kits disclosed herein, wherein the first composition has a *Salmonella* content of not more than about 100 CFU/g. In another aspect is provided any of the kits disclosed herein, wherein the first composition has a *Salmonella* content of not more than about 75 CFU/g. In another aspect is provided any of the kits disclosed herein, wherein the first composition has a *Salmonella* content of not more than about 50 CFU/g. In another aspect is provided any of the kits disclosed herein, wherein the first composition has a *Salmonella* content of not more than about 25 CFU/g. In another aspect is provided any of the kits disclosed herein, wherein the first composition has a *Salmonella* content of not more than about 20 CFU/g. In another aspect is provided any of the kits disclosed herein, wherein the first composition has a *Salmonella* content of not more than about 10 CFU/g. In another aspect is provided any of the kits disclosed herein, wherein the first composition has a *Salmonella* content of not more than about 1 CFU/g. In another aspect is provided any of the kits disclosed herein, wherein the first composition has no detectable *Salmonella* content. In another aspect is provided any of the kits disclosed herein, wherein the amount of *Salmonella* in the first composition is not more than about 25×10⁴ colony-forming units per gram (CFU/g). In another aspect is provided any of the kits disclosed herein, wherein the amount of *Salmonella* in the first composition is not more than about $5 \times 10^4$ CFU/g, or not more than about $1 \times 10^4$ CFU/g, or not more than about $5 \times 10^3$ CFU/g, or not more than about $1 \times 10^3$ CFU/g.

In another aspect is provided any of the kits disclosed herein, wherein the amount of *Pseudomonas aeruginosa* bacteria in the first composition is not more than about 25×10⁴ colony-forming units per gram (CFU/g). In another aspect is provided any of the kits disclosed herein, wherein the amount of *Pseudomonas aeruginosa* bacteria in the first composition is not more than about $5 \times 10^4$ CFU/g, or not more than about $1 \times 10^4$ CFU/g, or not more than about $5 \times 10^3$ CFU/g, or not more than about $1 \times 10^3$ CFU/g, or not more than about 10,000 CFU/g, or not more than about 7,500 CFU/g, or not more than about 5,000 CFU/g, or not more than about 2,500 CFU/g, or not more than about 2,000 CFU/g, or not more than about 1,500 CFU/g, or not more than about 1,000 CFU/g, or not more than about 750 CFU/g, or not more than about 500 CFU/g, or not more than about 250 CFU/g, or not more than about 200 CFU/g, or not more than about 150 CFU/g, or not more than about 100 CFU/g, or not more than about 75 CFU/g, or not more than about 50 CFU/g, or not more than about 25 CFU/g, or not more than about 15 CFU/g, or not more than about 10 CFU/g, or not more than about 5 CFU/g, or not more than about 1 CFU/g. In another aspect is provided any of the kits disclosed herein, wherein the first composition has a *Pseudomonas aeruginosa* bacteria content of not more than about 1,000 CFU/g. In another aspect is provided any of the kits disclosed herein, wherein the first composition has a *Pseudomonas aeruginosa* bacteria content of not more than about 750 CFU/g. In another aspect is provided any of the kits disclosed herein, wherein the first composition has a *Pseudomonas aeruginosa* bacteria content of not more than about 500 CFU/g. In another aspect is provided any of the kits disclosed herein, wherein the first composition has a *Pseudomonas aeruginosa* bacteria content of not more than about 250 CFU/g. In another aspect is provided any of the kits disclosed herein, wherein the first composition has a *Pseudomonas aeruginosa* bacteria content of not more than about 200 CFU/g. In another aspect is provided any of the kits disclosed herein, wherein the first composition has a *Pseudomonas aeruginosa* bacteria content of not more than about 150 CFU/g. In another aspect is provided any of the kits disclosed herein, wherein the first composition has a *Pseudomonas aeruginosa* bacteria content of not more than about 100 CFU/g. In another aspect is provided any of the kits disclosed herein, wherein the first composition has a *Pseudomonas aeruginosa* bacteria content of not more than about 75 CFU/g. In another aspect is provided any of the kits disclosed herein, wherein the first composition has a *Pseudomonas aeruginosa* bacteria content of not more than about 50 CFU/g. In another aspect is provided any of the kits disclosed herein, wherein the first composition has a *Pseudomonas aeruginosa* bacteria content of not more than about 25 CFU/g. In another aspect is provided any of the kits disclosed herein, wherein the first composition has a *Pseudomonas aeruginosa* bacteria content of not more than about 20 CFU/g. In another aspect is provided any of the kits disclosed herein, wherein the first composition has a *Pseudomonas aeruginosa* bacteria content of not more than about 10 CFU/g. In another aspect is provided any of the kits disclosed herein, wherein the first composition has a *Pseudomonas aeruginosa* bacteria content of not more than about 1 CFU/g. In another aspect is provided any of the kits disclosed herein, wherein the first composition has no detectable *Pseudomonas aeruginosa* bacteria content. In another aspect is provided any of the kits disclosed herein, wherein the amount of *Pseudomonas aeruginosa* bacteria in the first composition is not more than about 25×10⁴ colony-forming units per gram (CFU/g). In another aspect is provided any of the kits disclosed herein, wherein the amount of *Pseudomonas aeruginosa* bacteria in the first composition is not more than about $5\times10^4$ CFU/g, or not more than about $1\times10^4$ CFU/g, or not more than about $5\times10^3$ CFU/g, or not more than about $1\times10^3$ CFU/g.

In another aspect is provided any of the kits disclosed herein, wherein the amount of *Staphylococcus aureus* bacteria in the first composition is not more than about $25\times10^4$ colony-forming units per gram (CFU/g). In another aspect is provided any of the kits disclosed herein, wherein the amount of *Staphylococcus aureus* bacteria in the first composition is not more than about $5\times10^4$ CFU/g, or not more than about $1\times10^4$ CFU/g, or not more than about $5\times10^3$ CFU/g, or not more than about $1\times10^3$ CFU/g, or not more than about 10,000 CFU/g, or not more than about 7,500 CFU/g, or not more than about 5,000 CFU/g, or not more than about 2,500 CFU/g, or not more than about 2,000 CFU/g, or not more than about 1,500 CFU/g, or not more than about 1,000 CFU/g, or not more than about 750 CFU/g, or not more than about 500 CFU/g, or not more than about 250 CFU/g, or not more than about 200 CFU/g, or not more than about 150 CFU/g, or not more than about 100 CFU/g, or not more than about 75 CFU/g, or not more than about 50 CFU/g, or not more than about 25 CFU/g, or not more than about 15 CFU/g, or not more than about 10 CFU/g, or not more than about 5 CFU/g, or not more than about 1 CFU/g. In another aspect is provided any of the kits disclosed herein, wherein the first composition has a *Staphylococcus aureus* bacteria content of not more than about 1,000 CFU/g. In another aspect is provided any of the kits disclosed herein, wherein the first composition has a *Staphylococcus aureus* bacteria content of not more than about 750 CFU/g. In another aspect is provided any of the kits disclosed herein, wherein the first composition has a *Staphylococcus aureus* bacteria content of not more than about 500 CFU/g. In another aspect is provided any of the kits disclosed herein, wherein the first composition has a *Staphylococcus aureus* bacteria content of not more than about 250 CFU/g. In another aspect is provided any of the kits disclosed herein, wherein the first composition has a *Staphylococcus aureus* bacteria content of not more than about 200 CFU/g. In another aspect is provided any of the kits disclosed herein, wherein the first composition has a *Staphylococcus aureus* bacteria content of not more than about 150 CFU/g. In another aspect is provided any of the kits disclosed herein, wherein the first composition has a *Staphylococcus aureus* bacteria content of not more than about 100 CFU/g. In another aspect is provided any of the kits disclosed herein, wherein the first composition has a *Staphylococcus aureus* bacteria content of not more than about 75 CFU/g. In another aspect is provided any of the kits disclosed herein, wherein the first composition has a *Staphylococcus aureus* bacteria content of not more than about 50 CFU/g. In another aspect is provided any of the kits disclosed herein, wherein the first composition has a *Staphylococcus aureus* bacteria content of not more than about 25 CFU/g. In another aspect is provided any of the kits disclosed herein, wherein the first composition has a *Staphylococcus aureus* bacteria content of not more than about 20 CFU/g. In another aspect is provided any of the kits disclosed herein, wherein the first composition has a *Staphylococcus aureus* bacteria content of not more than about 10 CFU/g. In another aspect is provided any of the kits disclosed herein, wherein the first composition has a *Staphylococcus aureus* bacteria content of not more than about 1 CFU/g. In another aspect is provided any of the kits disclosed herein, wherein the first composition has no detectable *Staphylococcus aureus* bacteria content. In another aspect is provided any of the kits disclosed herein, wherein the amount of *Staphylo-*

*coccus aureus* bacteria in the first composition is not more than about $25\times10^4$ colony-forming units per gram (CFU/g). In another aspect is provided any of the kits disclosed herein, wherein the amount of *Staphylococcus aureus* bacteria in the first composition is not more than about $5\times10^4$ CFU/g, or not more than about $1\times10^4$ CFU/g, or not more than about $5\times10^3$ CFU/g, or not more than about $1\times10^3$ CFU/g.

In another aspect is provided any of the kits disclosed herein, wherein the first composition is packaged prior to use. In another aspect is provided any of the kits disclosed herein, wherein the first composition is prepared by heating to at least about 70° C. prior to being packaged. In another aspect is provided any of the kits disclosed herein, wherein the first composition is prepared by heating to at least about 50° C., or at least about 60° C., or at least about 75° C., or at least about 80° C., or at least about 85° C., or at least about 90° C., or at least about 100° C., or at least about 110° C., or at least about 115° C., or at least about 120° C., or at least about 125° C., or at least about 130° C., or at least about 135° C., or at least about 140° C., or at least about 150° C., or at least about 160° C., or at least about 170° C., or at least about 180° C., or at least about 190° C., or at least about 200° C. prior to being packaged.

In another aspect is provided any of the kits disclosed herein, wherein the first composition is heated to at least about 70° C. for at least about 5 minutes prior being packaged. In another aspect is provided any of the kits disclosed herein, wherein the first composition is heated to at least about 70° C. for at least about 10 minutes, or at least about 15 minutes, or at least about 20 minutes, or at least about 25 minutes, or at least about 30 minutes, or at least about 35 minutes, or at least about 40 minutes, or at least about 45 minutes, or at least about 50 minutes, or at least about 55 minutes, or at least about 60 minutes, or at least about 75 minutes, or at least about 90 minutes, or at least about 120 minutes, or at least about 180 minutes, or at least about 4 hours, or at least about 5 hours, or at least about 6 hours, or at least about 7 hours, or at least about 8 hours, or at least about 9 hours, or at least about 10 hours, or at least about 11 hours, or at least about 12 hours, or at least about 24 hours prior being packaged.

In another aspect is provided any of the kits disclosed herein, wherein the first composition is prepared by treatment with ionizing radiation, such as gamma radiation, prior to being packaged or after packaging. For example, gamma irradiation may be performed on the raw Spongilla material prior to grinding to reduce the particle size, following grinding to reduce the particle size, the materials packaged in bulk and or the materials following packaging in unit dose containers. The materials comprising the kits disclosed herein may be treated with ionizing radiation, such as gamma radiation, using methods and equipment known to those of ordinary skill in the art, such as gamma irradiators or electron beam irradiators. In another aspect is provided any of the kits disclosed herein, wherein the first composition is prepared by treating with ionizing radiation, such as gamma radiation, to deliver an absorbed radiation dose between about 1 kGy and about 50 kGy prior to being packaged. In another aspect is provided any of the kits disclosed herein, wherein the first composition is prepared by treating with ionizing radiation, such as gamma radiation, to deliver an absorbed radiation dose between about 1 kGy and about 45 kGy, or between about 1 kGy and about 40 kGy, between about 1 kGy and about 35 kGy, between about 1 kGy and about 30 kGy, or between about 1 kGy and about 25 kGy or between about 5 kGy and about 50 kGy, or between about 5 kGy and about 45 kGy, or between about 5 kGy and about 40 kGy, or between about 5 kGy and about 35 kGy, or between about 5 kGy and about 30 kGy, or between about 5 kGy and about 25 kGy, or between about 10 kGy and about 50 kGy, or between about 10 kGy and about 45 kGy, or between about 10 kGy and about 40 kGy, or between about 10 kGy and about 35 kGy, or between about 10 kGy and about 30 kGy, or between about 10 kGy and about 25 kGy, or between about 15 kGy and about 50 kGy, or between about 15 kGy and about 45 kGy, or between about 15 kGy and about 40 kGy, or between about 15 kGy and about 35 kGy, or between about 15 kGy and about 30 kGy, or between about 15 kGy and about 25 kGy. In another aspect is provided any of the methods disclosed herein, wherein the first composition is prepared by treating with ionizing radiation, such as gamma radiation, to deliver an absorbed radiation dose of about 1 kGy, or about 5 kGy, or about 10 kGy, 11 kGy, or about 12 kGy, or about 13 kGy, or about 14 kGy, or about 15 kGy, or about 16 kGy, or about 17 kGy, or about 18 kGy, or about 19 kGy, or about 20 kGy, or about 21 kGy, or about 22 kGy, or about 23 kGy, or about 24 kGy, or about 25 kGy, or about 26 kGy, or about 27 kGy, or about 28 kGy, or about 29 kGy, or about 30 kGy, or about 31 kGy, or about 32 kGy, or about 33 kGy, or about 34 kGy, or about 35 kGy, or about 36 kGy, or about 37 kGy, or about 38 kGy, or about 39 kGy, or about 40 kGy, or about 41 kGy, or about 42 kGy, or about 43 kGy, or about 44 kGy, or about 45 kGy, or about 46 kGy, or about 47 kGy, or about 48 kGy, or about 49 kGy, or about 50 kGy.

In another aspect is provided any of the kits disclosed herein, wherein the first composition further comprises an aqueous solution of hydrogen peroxide. In another aspect is provided any of the kits disclosed herein, wherein the hydrogen peroxide is at a concentration of from about 0.1% w/w to about 50% w/w, or from about 0.1% w/w to about 45% w/w, or from about 0.1% w/w to about 40% w/w, or from about 0.1% w/w to about 35% w/w, or from about 0.1% w/w to about 30% w/w, or from about 0.1% w/w to about 25% w/w, or from about 0.1% w/w to about 20% w/w, or from about 0.1% w/w to about 15% w/w, or from about 0.1% w/w to about 10% w/w, or from about 0.1% w/w to about 9% w/w, or from about 0.1% w/w to about 8% w/w, or from about 0.1% w/w to about 7% w/w, or from about 0.1% w/w to about 6% w/w, or from about 0.1% w/w to about 5% w/w, or from about 0.1% w/w to about 4% w/w, or from about 0.1% w/w to about 3% w/w, or from about 0.1% w/w to about 2% w/w, or from about 0.1% w/w to about 1% w/w, or from about 0.5% w/w to about 45% w/w, or from about 1% w/w to about 45% w/w, or from about 1% w/w to about 40% w/w, or from about 1% w/w to about 35% w/w, or from about 1% w/w to about 30% w/w, or from about 1% w/w to about 25% w/w, or from about 1% w/w to about 20% w/w, or from about 1% w/w to about 15% w/w, or from about 1% w/w to about 10% w/w, or from about 1% w/w to about 9% w/w, or from about 1% w/w to about 8% w/w, or from about 1% w/w to about 7% w/w, or from about 1% w/w to about 6% w/w, or from about 1% w/w to about 5% w/w, or from about 1% w/w to about 4% w/w, or from about 1% w/w to about 3% w/w, or from about 1% w/w to about 2% w/w, or from about. 2% w/w to about 45% w/w, or from about 2% w/w to about 40% w/w, or from about 2% w/w to about 35% w/w, or from about 2% w/w to about 30% w/w, or from about 2% w/w to about 25% w/w, or from about 2% w/w to about 20% w/w, or from about 2% w/w to about 15% w/w, or from about 2% w/w to about 10% w/w, or from about 2% w/w to about 9% w/w, or from about 2% w/w to about 8% w/w, or from about 1% w/w to about 7% w/w, or from about 2% w/w to about 6% w/w, or from about 2% w/w to about 5% w/w, or from about 2% w/w to about 4% w/w, or from about 2% w/w to about 3% w/w. In another aspect is provided any of the kits disclosed herein, wherein the hydrogen peroxide is at a concentration of about 0.1% w/w, or about 0.5% w/w, or about 1% w/w, or about 2% w/w, or about 3% w/w, or about 4% w/w, or about 5% w/w, or about 6% w/w, or about 7% w/w, or about 8% w/w, or about 9% w/w, or about 10% w/w, or about 15% w/w, or about 20% w/w, or about 25% w/w, or about 30% w/w, or about 35% w/w, or about 40% w/w, or about 45% w/w, or about 50% w/w. In another aspect is provided any of the methods disclosed herein, wherein the hydrogen peroxide is at a concentration of about 3% w/w. Aqueous hydrogen peroxide solutions that may be useful in treating skin conditions in a subject as disclosed herein are commercially available or may be prepared by methods known to those of ordinary skill in the art.

In another aspect is provided any of the kits disclosed herein, further comprising a gel or cream comprising hydrogen peroxide. Such gels or creams are generally commercially available any may contain from about 0.5% w/w to about 50% w/w hydrogen peroxide. For example, a gel containing about 1% w/w, or about 2% w/w, or about 3% w/w, or about 4% w/w, or about 6% w/w, or about 7% w/w, or about 8% w/w, or about 9% w/w, or about 10% w/w, or about 15% w/w, or about 20% w/w, or about 25% w/w, or about 30% w/w, or about 40% w/w, or about 45% w/w, or about 50% w/w hydrogen peroxide may be used in any of the methods and kits disclosed herein in combination with the first composition and the second composition.

In another aspect is provided any of the kits disclosed herein, wherein the Spongilla is Spongilla *lacustris.*

In another aspect is provided any of the kits described herein, wherein the second composition comprises one or more botulinum toxin type selected from botulinum toxin type A, botulinum toxin type B, botulinum toxin type C1, botulinum toxin type C2, botulinum toxin type D, botulinum toxin type E, botulinum toxin type F and botulinum toxin type G. In another aspect is provided any of the kits described herein, wherein the one or more botulinum toxin type is selected from botulinum toxin type A and botulinum toxin type B. In another aspect is provided any of the kits described herein, wherein the one or more botulinum toxin type is botulinum toxin type A. In another aspect is provided any of the kits described herein, wherein the botulinum toxin type A is selected from onabotulinumtoxinA, abobotulinumtoxinA, incobotulinumtoxinA, prabotulinumtoxinA, and daxibotulinumtoxinA. In another aspect is provided any of the kits described herein, wherein the botulinum toxin type A is onabotulinumtoxinA. In another aspect is provided any of the kits described herein, wherein the botulinum toxin type A is abobotulinumtoxinA. In another aspect is provided any of the kits described herein, wherein the botulinum toxin type A is incobotulinumtoxinA. In another aspect is provided any of the kits described herein, wherein the botulinum toxin type A is prabotulinumtoxinA. In another aspect is provided any of the kits described herein, wherein the botulinum toxin type A is daxibotulinumtoxinA. In another aspect is provided any of the kits described herein, wherein the one or more botulinum toxin type is botulinum toxin type B. In another aspect is provided any of the methods disclosed herein, wherein the one or more botulinum toxin type B is rimabotulinumtoxinB. In another aspect is provided any of the kits described herein, wherein the one or more botulinum toxin type is botulinum toxin type C1. In another aspect is provided any of the kits described herein, wherein the one or more botulinum toxin type is botulinum toxin type C2. In another aspect is provided any of the kits described herein, wherein the one or more botulinum toxin type is botulinum toxin type D. In another aspect is provided any of the kits described herein, wherein the one or more botulinum toxin type is botulinum toxin type E.

In another aspect is provided any of the methods disclosed herein, wherein the one or more botulinum toxin type E is EB-001A or EB-001T. In another aspect is provided any of the methods disclosed herein, wherein the one or more botulinum toxin type E is EB-001A. In another aspect is provided any of the methods disclosed herein, wherein the one or more botulinum toxin type E is EB-001T. In another aspect is provided any of the kits described herein, wherein the one or more botulinum toxin type is botulinum toxin type F. In another aspect is provided any of the kits described herein, wherein the one or more botulinum toxin type is botulinum toxin type G.

In another aspect is provided any of the kits described herein, wherein the kit is used for the treatment of a skin condition in a subject. In another aspect is provided any of the kits described herein, wherein the kit is for use in the treatment of a skin condition in a subject. In another aspect is provided any of the kits described herein, wherein the skin condition in the subject is selected from one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, forehead wrinkles, acne vulgaris, acne rosacea type 1, acne rosacea type 2, psoriasis, hyperhidrosis, alopecia areata, androgenic alopecia, keloids, and hypertrophic scars, hidradenitis suppurativa, Raynaud phenomenon, post-herpetic neuralgia, Hailey-Hailey disease, IgA bullous dermatosis, epidermolysis bullosa Simplex Weber-Cockane, Darier disease, pachyonchia congenita, aquagenic keratoderma, notalgia paresthetic, pompholyx (dyshidrotic eczema), chromhidrosis and bromhidrosis, eccrine nevus, facial rhytides, atrophic acne scars, and melasma. In another aspect is provided any of the kits described herein, wherein the skin condition in the subject is selected from acne vulgaris, acne rosacea type 1, acne rosacea type 2, psoriasis, and hyperhidrosis. In another aspect is provided any of the kits described herein, wherein the skin condition in the subject is acne vulgaris. In another aspect is provided any of the kits described herein, wherein the skin condition in the subject is acne rosacea type 1. In another aspect is provided any of the kits described herein, wherein the skin condition in the subject is acne rosacea type 2. In another aspect is provided any of the kits described herein, wherein the skin condition in the subject is psoriasis. In another aspect is provided any of the kits described herein, wherein the skin condition in the subject is hyperhidrosis.

In another embodiment are provided methods to treat, reduce the symptoms of, ameliorate the symptoms of, delay the onset of, or otherwise pharmaceutically address one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, forehead wrinkles, acne vulgaris, acne rosacea type 1, acne rosacea type 2, psoriasis, hyperhidrosis, alopecia areata, androgenic alopecia, keloids, and hypertrophic scars, hidradenitis suppurativa, Raynaud phenomenon, post-herpetic neuralgia, Hailey-Hailey disease, IgA bullous dermatosis, epidermolysis bullosa Simplex Weber-Cockane, Darier disease, pachyonchia congenita, aquagenic keratoderma, notalgia paresthetic, pompholyx (dyshidrotic eczema), chromhidrosis and bromhidrosis, eccrine nevus, facial rhytides, atrophic acne scars, and melasma.

The compositions disclosed herein, such as the first composition comprising Spongilla, may further comprise one or more conventional pharmaceutical carriers or excipients. Suitable pharmaceutical carriers and excipients include inert diluents, binders (such as starches), fillers (such as colloidal silicon dioxide, sugars, including lactose, sucrose, mannitol, or sorbitol; and cellulose preparations, for example, maize starch, wheat starch, rice starch, potato starch, gelatin, gum, methyl cellulose, hydroxypropylmethyl cellulose, sodium carboxymethylcellulose, or polyvinylpyrrolidone (PVP)), bulking agents, lubricants (such as magnesium stearate, sodium lauryl sulfate and talc), coloring matters or dyes and, if desired, emulsifying agents or suspending agents, together with diluents such as water, saline, ethanol, propylene glycol, glycerin, or combinations thereof.

The pharmaceutical compositions disclosed herein may be in unit dosage forms suitable for single administration of precise dosages. In another aspect is provided any of the methods or kits disclosed herein, wherein the unit dosage forms of the first compositions and/or the second composition are suitable for two administrations, three administrations, four administrations, five administrations, six administrations, seven administrations, eight administrations, nine administrations, 10 administrations, 11 administrations, 12 administrations, 13 administrations, 14 administrations, 15 administrations, 16 administrations, 17 administrations, 18 administrations, 19 administrations, 20 administrations, 21 administrations, 22 administrations, 23 administrations, 24 administrations, 25 administrations, 26 administrations, 27 administrations, 28 administrations, 29 administrations, 30 administrations, administrations for two months, administrations for three months, administrations for four months, administrations for five months, administrations for six months, administrations for seven months, administrations for eight months, administrations for nine months, administrations for ten months, administrations for eleven months, or administrations for 12 months.

It will be appreciated that the actual dosages of the compositions disclosed herein, may vary according to the composition being used, the mode of administration, and the particular site of the subject being treated, and the skin condition being treated. Those skilled in the art using conventional dosage-determination tests in view of the experimental data for a given composition may ascertain optimal dosages for a given set of conditions. This amount will vary depending upon a variety of factors, including but not limited to the characteristics of the compositions and formulations disclosed herein (including activity, pharmacokinetics, pharmacodynamics, and bioavailability thereof), the physiological condition of the subject treated (including age, sex, disease type and stage, general physical condition, responsiveness to a given dosage, and type of medication) or cells, the nature of the pharmaceutically acceptable carrier mg/kg or carriers in the formulation, and the route of administration. Further, an effective or therapeutically effective amount may vary depending on whether the one or more compositions and formulations disclosed herein is administered alone or in combination with other drug(s), other therapy/therapies or other therapeutic method(s) or modality/modalities. One skilled in the clinical and pharmacological arts will be able to determine an effective amount or therapeutically effective amount through routine experimentation, namely by monitoring a cell's or subject's response to administration of the one or more compositions and formulations disclosed herein and adjusting the dosage accordingly.

Dosage regimens using the first composition and the second composition may be adjusted to provide the optimum desired response. Dosage unit form, as used herein, refers to physically discrete units suited as unitary dosages for the subjects to be treated; each unit containing a predetermined quantity of the compositions disclosed herein, calculated to produce the desired therapeutic effect in association with the required pharmaceutical carrier. The specification for the dosage unit forms of the compositions disclosed herein are dictated by and directly dependent on (a) the characteristics of the composition and the particular therapeutic or prophylactic effect to be achieved, and (b) the limitations inherent in the art of compounding such a composition for the treatment a particular condition in a subject.

Thus, the skilled artisan would appreciate, based upon the disclosure provided herein, that the dose and dosing regimen using the compositions disclosed herein may be adjusted in accordance with methods well known in the therapeutic arts. That is, the maximum tolerable dose can be readily established, and the effective amount providing a detectable therapeutic benefit to a subject may also be determined, as can the temporal requirements for administering each agent to provide a detectable therapeutic benefit to the subject. Accordingly, while certain dose and administration regimens are exemplified herein, these examples in no way limit the dose and administration regimen that may be provided to a subject in practicing the presently disclosed methods.

It is to be noted that dosage values may vary with the type and severity of the condition to be alleviated and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition. For example, doses may be adjusted based on pharmacokinetic or pharmacodynamic parameters, which may include clinical effects such as toxic effects and/or laboratory values. The embodiments disclosed herein are intended to encompass intra-subject dose-escalation as determined by the skilled artisan. Determining appropriate dosages and regimens for administration of the chemotherapeutic agent are well-known in the relevant art and would be understood to be encompassed by the skilled artisan once provided the teachings disclosed herein.

In some embodiments, the compositions may be used in combination with one or more additional compositions useful in treating skin conditions in a subject which are described below. When a combination therapy is used, the one or more additional compositions may be administered sequentially or simultaneously with the first composition and/or the second composition disclosed herein. In some embodiments, the additional compositions is administered to a subject prior to, at the same time as, or following administration of the first composition and/or the second composition disclosed herein. In some embodiments, the additional composition is administered to the subject prior to the administration of the first composition and/or the second composition disclosed herein. In some embodiments, the additional composition is administered to the subject at the same time the first composition and/or the second composition disclosed herein are administered to the subject. In some embodiments, the additional composition is administered to the subject following to the administration of the first composition and/or the second composition disclosed herein. Among the additional compositions that may be used according to any of the methods disclosed herein include, but are not limited to, cromolyn sodium (also known as sodium cromoglycate), topical alpha agonists (including, but not limited to, oxymetazoline hydrochloride, clonidine hydrochloride, apraclonidine hydrochloride, and brimonidine tartrate), topical antibiotics (including, but not limited to, tetracyclines [tetracycline, doxycycline, minocycline, sarecycline], clindamycin, and erythromycin), benzoyl peroxide, salicylic acid, azelaic acid, retinoids, topical anticholinergics (including, but not limited to, oxybutynin, glycopyrrolate, propantheline), topical prostaglandin analogs (including, but not limited to, latanoprost, bimatoprost, travoprost, and tafluprost), and topical hydroquinone or a combination of fluocinolone acetonide, hydroquinone, and tretinoin (sold as Tri-Luma® cream).

In another aspect is provided any of the methods disclosed herein, wherein the Spongilla is Spongilla *lacustris*. In another aspect is provided any of the kits disclosed herein, wherein the Spongilla is Spongilla *lacustris*.

In another aspect is provided any of the methods, compositions and kits disclosed herein wherein the first composition is derived from one or more sponges. In another aspect, the one or more sponges may be marine sponges or freshwater sponges. In another aspect, the one or more sponges is a marine sponge. In another aspect, the sponge is a freshwater sponge. In another aspect, the compositions are derived from sponges of the phylum Porifera. In another aspect, the compositions are derived from sponges of the class Demospongiae. In another aspect, the compositions are derived from sponges of the order Spongdilla. In another aspect, the compositions are derived from sponges of the family Spongillidae. In another aspect, the compositions are derived from sponges of the genus Spongilla. In another aspect, the compositions are derived from sponges of the species Spongilla *lacustris*. In another aspect, the compositions are derived from sponges of the order Haplosclerida. In another aspect, the compositions are derived from sponges of the family Chalinidea. In another aspect, the compositions are derived from sponges of the genus Halciona.

As will be understood by one skilled in the art, for all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

Headings, e.g., (a), (b), (i) etc., are presented merely for ease of reading the specification and claims. The use of headings in the specification or claims does not require the steps or elements be performed in alphabetical or numerical order or the order in which they are presented.

The preparations and examples of a number of embodiments disclosed herein are intended to be illustrative and not limiting. All starting materials are available commercially or are described in the literature. All temperatures are reported in ° C.

Example 1: Regimen 1

Week 1: The subject's skin is washed and dried with a non-comedogenic cleanser. A container comprising botulinum toxin (botulinum toxin type A, botulinum toxin type B, botulinum toxin type C1, botulinum toxin type C2, botulinum toxin type D, botulinum toxin type E, botulinum toxin type F and botulinum toxin type G, onabotulinumtoxinA, abobotulinumtoxinA, incobotulinumtoxinA, prabotulinumtoxinA, daxibotulinumtoxinA, rimabotulinumtoxinB, EB-001A, or EB-001T) is reconstituted with 10 mL of 0.9% sterile saline and the reconstituted solution is set aside. Three-percent (3%) hydrogen peroxide USP 9 (6 mL) is added to 3 grams (dry weight) of Spongilla powder, and the resulting mixture is stirred until thoroughly mixed. The Spongilla mixture is applied to the affected area of the subject's skin taking care to avoid mucous membranes (e.g., eyes, mouth, and nostrils). Additional Spongilla materials may be applied to areas on the subject's skin where lesions and hyperpigmentation are present. The Spongilla composition is allowed to dry on subject's skin to which it was applied and is then removed using non-comedogenic wipes or water and a non-comedogenic cleanser. The reconstituted botulinum toxin composition is then applied to the skin of the subject in the affected areas and in the areas in which the Spongilla composition was applied taking care to avoid mucous membranes (e.g., eyes, mouth, and nostrils). The botulinum toxin composition is allowed to dry on the application area and is then cleaned using non-comedogenic wipes or water and a non-comedogenic cleanser.

Weeks 2 through 6: Three-percent (3%) hydrogen peroxide USP (6 mL) are added to 3 grams (dry weight) of Spongilla powder composition and the resulting mixture is stirred until thoroughly mixed. The Spongilla mixture is applied to the affected area of the subject's skin taking care to avoid mucous membranes (e.g., eyes, mouth, and nostrils). Additional Spongilla materials may be applied to areas on the subject's skin where lesions and hyperpigmentation are present. The Spongilla composition is allowed to dry on subject's skin to which it was applied and is then removed using non-comedogenic wipes or water and a non-comedogenic cleanser.

Maintenance Regimen: After the 6-week treatment regimen is complete, the subject can apply the composition comprising Spongilla and/or Spongilla and 3% hydrogen peroxide to the affected areas monthly. The application of the composition comprising botulinum toxin may be repeated as indicated by the symptoms of the subject, but no sooner than 3 months since the immediately prior treatment using the composition comprising the botulinum toxin.

Example 2

Week 1: The subject's skin is washed and dried with a non-comedogenic cleanser. A container comprising botulinum toxin (botulinum toxin type A, botulinum toxin type B, botulinum toxin type C1, botulinum toxin type C2, botulinum toxin type D, botulinum toxin type E, botulinum toxin type F and botulinum toxin type G, onabotulinumtoxinA, abobotulinumtoxinA, incobotulinumtoxinA, prabotulinumtoxinA, daxibotulinumtoxinA, rimabotulinumtoxinB, EB-001A, or EB-001T) is reconstituted with 10 mL of 0.9% sterile saline and the reconstituted solution is set aside. Three percent (3%) hydrogen peroxide USP (6 mL) is added to 3 grams (dry weight) of Spongilla powder, and the resulting mixture is stirred thoroughly mixed. The reconstituted botulinum toxin composition is then applied to the skin of the subject in the affected areas and in the areas in which the Spongilla composition was applied taking care to avoid mucous membranes (e.g., eyes, mouth, and nostrils). The Spongilla mixture is applied to the affected area of the subject's skin taking care to avoid mucous membranes (e.g., eyes, mouth, and nostrils). Additional Spongilla materials may be applied to areas on the subject's skin where lesions and hyperpigmentation are present. The compositions are allowed to dry on subject's skin to which they were applied and is then removed using non-comedogenic wipes or water and a non-comedogenic cleanser.

Weeks 2 through 6: Three percent (3%) hydrogen peroxide USP (6 mL) are added to 3 grams (dry weight) of Spongilla powder composition and the resulting mixture is stirred thoroughly mixed. The Spongilla mixture is applied to the affected area of the subject's skin taking care to avoid mucous membranes (e.g., eyes, mouth, and nostrils). Additional Spongilla materials may be applied to areas on the subject's skin where lesions and hyperpigmentation are present. The Spongilla composition is allowed to dry on subject's skin to which it was applied and is then removed using non-comedogenic wipes or water and a non-comedogenic cleanser.

Maintenance Regimen: After the 6-week treatment regimen is complete, the subject can apply the composition comprising Spongilla and/or Spongilla and 3% hydrogen peroxide to the affected areas monthly. The application of the composition comprising botulinum toxin may be repeated as indicated by the symptoms of the subject, but no sooner than 3 months since the immediately prior treatment using the composition comprising the botulinum toxin.

Example 3

Week 1: The subject's skin is washed and dried with a non-comedogenic cleanser. A container comprising botulinum toxin (botulinum toxin type A, botulinum toxin type B, botulinum toxin type C1, botulinum toxin type C2, botulinum toxin type D, botulinum toxin type E, botulinum toxin type F and botulinum toxin type G, onabotulinumtoxinA, abobotulinumtoxinA, incobotulinumtoxinA, prabotulinumtoxinA, daxibotulinumtoxinA, rimabotulinumtoxinB, EB-001A, or EB-001T) is reconstituted with 10 mL of 0.9% sterile saline and the reconstituted solution is set aside. Three percent (3%) hydrogen peroxide USP (6 mL) is added to 3 grams (dry weight) of Spongilla powder, and the resulting mixture is stirred thoroughly mixed. A portion of the reconstituted botulinum toxin composition is added to the Spongilla mixture and the resulting mixture is applied to the skin of the subject in the affected areas, taking care to avoid mucous membranes (e.g., eyes, mouth, and nostrils). The compositions are allowed to dry on subject's skin to which they were applied and is then removed using non-comedogenic wipes or water and a non-comedogenic cleanser.

Weeks 2 through 6: Three percent (3%) hydrogen peroxide USP (6 mL) are added to 3 grams (dry weight) of Spongilla powder composition and the resulting mixture is stirred thoroughly mixed. The Spongilla mixture is applied to the affected area of the subject's skin taking care to avoid mucous membranes (e.g., eyes, mouth, and nostrils). Additional Spongilla materials may be applied to areas on the subject's skin where lesions and hyperpigmentation are present. The Spongilla composition is allowed to dry on subject's skin to which it was applied and is then removed using non-comedogenic wipes or water and a non-comedogenic cleanser.

Maintenance Regimen: After the 6-week treatment regimen is complete, the subject can apply the composition comprising Spongilla and/or Spongilla and 3% hydrogen peroxide to the affected areas monthly. The application of the composition comprising botulinum toxin may be repeated as indicated by the symptoms of the subject, but no sooner than 3 months since the immediately prior treatment using the composition comprising the botulinum toxin.

Example 4

Week 1: The subject's skin is washed and dried with a non-comedogenic cleanser. A container comprising botulinum toxin (botulinum toxin type A, botulinum toxin type B, botulinum toxin type C1, botulinum toxin type C2, botulinum toxin type D, botulinum toxin type E, botulinum toxin type F and botulinum toxin type G, onabotulinumtoxinA, abobotulinumtoxinA, incobotulinumtoxinA, prabotulinumtoxinA, daxibotulinumtoxinA, rimabotulinumtoxinB, EB-001A, or EB-001T) is reconstituted with 10 mL of 0.9% sterile saline and the reconstituted solution is set aside. A portion of the reconstituted botulinum toxin composition is added to the Spongilla mixture and the resulting mixture is applied to the to the skin of the subject in the affected areas, taking care to avoid mucous membranes (e.g., eyes, mouth, and nostrils). The compositions are allowed to dry on subject's skin to which they were applied and is then removed using non-comedogenic wipes or water and a non-comedogenic cleanser.

Weeks 2 through 6: Three percent (3%) hydrogen peroxide USP (6 mL) are added to 3 grams (dry weight) of Spongilla powder composition and the resulting mixture is stirred thoroughly mixed. The Spongilla mixture is applied to the affected area of the subject's skin taking care to avoid mucous membranes (e.g., eyes, mouth, and nostrils). Additional Spongilla materials may be applied to areas on the subject's skin where lesions and hyperpigmentation are present. The Spongilla composition is allowed to dry on subject's skin to which it was applied and is then removed using non-comedogenic wipes or water and a non-comedogenic cleanser.

Maintenance Regimen: After the 6-week treatment regimen is complete, the subject can apply the composition comprising Spongilla and/or Spongilla and 3% hydrogen peroxide to the affected areas monthly. The application of the composition comprising botulinum toxin may be repeated as indicated by the symptoms of the subject, but no sooner than 3 months since the immediately prior treatment using the composition comprising the botulinum toxin.

Example 5

Week 1: The subject's skin is washed and dried with a non-comedogenic cleanser. A container comprising botulinum toxin (botulinum toxin type A, botulinum toxin type B, botulinum toxin type C1, botulinum toxin type C2, botulinum toxin type D, botulinum toxin type E, botulinum toxin type F and botulinum toxin type G, onabotulinumtoxinA, abobotulinumtoxinA, incobotulinumtoxinA, prabotulinumtoxinA, daxibotulinumtoxinA, rimabotulinumtoxinB, EB-001A, or EB-001T) is reconstituted with 10 mL of 0.9% sterile saline and the reconstituted solution is set aside. A composition comprising Spongilla powder is applied to the affected area of the subject's skin taking care to avoid mucous membranes (e.g., eyes, mouth, and nostrils). Additional Spongilla materials may be applied to areas on the subject's skin where lesions and hyperpigmentation are present. The Spongilla composition is allowed to dry on subject's skin to which it was applied and is then removed using non-comedogenic wipes or water and a non-comedogenic cleanser. The reconstituted botulinum toxin composition is then applied to the skin of the subject in the affected areas and in the areas in which the Spongilla composition was applied taking care to avoid mucous membranes (e.g., eyes, mouth, and nostrils). The botulinum toxin composition is allowed to dry on the application area and is then cleaned using non-comedogenic wipes or water and a non-comedogenic cleanser.

Weeks 2 through 6: Three percent (3%) hydrogen peroxide USP (6 mL) are added to 3 grams (dry weight) of Spongilla powder composition and the resulting mixture is stirred thoroughly mixed. The Spongilla mixture is applied to the affected area of the subject's skin taking care to avoid mucous membranes (e.g., eyes, mouth, and nostrils). Additional Spongilla materials may be applied to areas on the subject's skin where lesions and hyperpigmentation are present. The Spongilla composition is allowed to dry on subject's skin to which it was applied and is then removed using non-comedogenic wipes or water and a non-comedogenic cleanser.

Maintenance Regimen: After the 6-week treatment regimen is complete, the subject can apply the composition comprising Spongilla and/or Spongilla and 3% hydrogen peroxide to the affected areas monthly. The application of the composition comprising botulinum toxin may be repeated as indicated by the symptoms of the subject, but no sooner than 3 months since the immediately prior treatment using the composition comprising the botulinum toxin.

Example 6

Week 1: The subject's skin is washed and dried with a non-comedogenic cleanser. A container comprising botulinum toxin (botulinum toxin type A, botulinum toxin type B, botulinum toxin type C1, botulinum toxin type C2, botulinum toxin type D, botulinum toxin type E, botulinum toxin type F and botulinum toxin type G, onabotulinumtoxinA, abobotulinumtoxinA, incobotulinumtoxinA, prabotulinumtoxinA, daxibotulinumtoxinA, rimabotulinumtoxinB, EB-001A, or EB-001T) is reconstituted with 10 mL of 0.9% sterile saline and the reconstituted solution is set aside. The reconstituted botulinum toxin composition is then applied to the skin of the subject in the affected areas, taking care to avoid mucous membranes (e.g., eyes, mouth, and nostrils). A composition comprising Spongilla powder is then applied to the affected area of the subject's skin taking care to avoid mucous membranes (e.g., eyes, mouth, and nostrils). Additional Spongilla materials may be applied to areas on the subject's skin where lesions and hyperpigmentation are present. The Spongilla composition is allowed to dry on subject's skin to which it was applied and is then removed using non-comedogenic wipes or water and a non-comedogenic cleanser.

Weeks 2 through 6: Three percent (3%) hydrogen peroxide USP (6 mL) are added to 3 grams (dry weight) of Spongilla powder composition and the resulting mixture is stirred thoroughly mixed. The Spongilla mixture is applied to the affected area of the subject's skin, taking care to avoid mucous membranes (e.g., eyes, mouth, and nostrils). Additional Spongilla materials may be applied to areas on the subject's skin where lesions and hyperpigmentation are present. The Spongilla composition is allowed to dry on subject's skin to which it was applied and is then removed using non-comedogenic wipes or water and a non-comedogenic cleanser.

Maintenance Regimen: After the 6-week treatment regimen is complete, the subject can apply the composition comprising Spongilla and/or Spongilla and 3% hydrogen peroxide to the affected areas monthly. The application of the composition comprising botulinum toxin may be repeated as indicated by the symptoms of the subject, but no sooner than 3 months since the immediately prior treatment using the composition comprising the botulinum toxin.

Example 7: Treatment of Subjects Having Moderate to Severe Facial Acne Vulgaris with a Combination of Spongilla *Lacustris* and onabotulinumtoxinA The objective of the study is to evaluate the tolerability, safety, and efficacy of powdered Spongilla *lacustris* administered with onabotulinumtoxinA (BOTOX®) 100U following 6 weeks of topical administration (comprising one topical treatment using onabotulinumtoxinA and once-weekly topical treatment of Spongilla *lacustris* in male and female subjects with moderate to severe facial acne vulgaris.

The study is an open-label, parallel-group study of approximately 12 weeks duration (day 1 treatment to day 85 study exit). The study groups will receive treatment with a combination of powdered Spongilla *lacustris*, that is mixed with 3% H2O2 or water prior to administration, and onabotulinumtoxinA (BOTOX®) 100U. Powdered Spongilla *lacustris* is administered to the entire face of the subject for once weekly for 6 weeks and onabotulinumtoxinA (BOTOX®) 100U is administered topically to the face of the subject on study day 1. On day 1, subjects are randomly assigned to 1 of 6 treatment groups in a 1:1:1:1:1:1 ratio to receive one of six regimens as summarized in Table 1.

TABLE 1

Treatment Allocation

| Treatment Regimen | Study Treatment |
|---|---|
| 1 | Topical application of a first composition comprising *Spongilla lacustris* powder mixed with 3% H2O2, followed by topical application of a second composition comprising onabotulinumtoxinA (BOTOX ®) 100 U |
| 2 | Topical application of a first composition comprising onabotulinumtoxinA (BOTOX ®) 100 U, followed by topical application of a second composition comprising *Spongilla lacustris* powder mixed with 3% H2O2 |
| 3 | Topical application of a single composition comprising onabotulinumtoxinA (BOTOX ®) 100 U and *Spongilla lacustris* powder mixed with 3% H2O2 |
| 4 | Topical application of a first composition comprising *Spongilla lacustris* powder mixed with water, followed by topical application of a second composition comprising onabotulinumtoxinA (BOTOX ®) 100 U |

TABLE 1-continued

Treatment Allocation

| Treatment Regimen | Study Treatment |
|---|---|
| 5 | Topical application of a first composition comprising onabotulinumtoxinA (BOTOX ®) 100 U, followed by topical application of a second composition comprising *Spongilla lacustris* powder mixed with water |
| 6 | Topical application of a single composition comprising onabotulinumtoxinA (BOTOX ®) 100 U and *Spongilla lacustris* powder mixed with water |

Study Population

Male and female subjects 12 years or older with moderate to severe acne vulgaris with facial involvement who are in otherwise good health are enrolled.

Inclusion Criteria

Each subject has moderate to severe acne vulgaris defined as meeting all of the following criteria: (a) a minimum of 20 but not more than 150 inflammatory lesions (papules and pustules) on the face; (b) a minimum of 20 but not more than 300 noninflammatory lesions (open comedones and closed comedones) on the face; (c) not more than 2 nodules on the face above the mandibular line; and (d) an investigator's Global Assessment (IGA) score of 3 or 4 as assessed by the investigator (the area considered for the IGA must be confined to the face)

Exclusion Criteria:

Subjects are excluded from the study if they have a known allergy or sensitivity to any botulinum toxin preparation, or if they have any medical condition that may put them at increased risk with exposure to onabotulinumtoxinA (BOTOX®) 100U, including diagnosed myasthenia gravis, Eaton-Lambert syndrome, or amyotrophic lateral sclerosis Measurement of Efficacy:

Efficacy is measured by lesion counts (inflammatory and noninflammatory) on the face of each subject and by use of an Investigator's Global Assessment using the scores in Table 2, below. Three analysis populations will be used as follows: (a) the intent-to-treat (ITT) population will consist of all randomized subjects; (b) the per protocol (PP) population will consist of all randomized subjects with no significant protocol violations during the study that would affect the efficacy analyses (the PP population will be determined prior to database lock); and (c) the safety population will consist of all subjects who receive at least 1 dose of study medication in the study.

All efficacy analyses will be performed using the ITT and PP population. For lesion counts, absolute and percent change from baseline in lesion counts will be summarized using descriptive statistics. A frequency distribution will be used to analyze the proportion of subjects with a complete or partial response.

TABLE 2

Investigator's Global Assessment (IGA)

| Score | Grade | Description |
|---|---|---|
| 0 | None | No evidence of facial acne vulgaris |
| 1 | Minimal | Few noninflammatory lesions (comedones) are present; a few inflammatory lesions (papules/ pustules) may be present; no nodulo-cystic lesions are allowed) |

TABLE 2-continued

| | Investigator's Global Assessment (IGA) | |
|---|---|---|
| Score | Grade | Description |
| 2 | Mild | Several to many noninflammatory lesions (comedones) are present; a few inflammatory lesions (papules/pustules) are present; no nodulo-cystic lesions are allowed |
| 3 | Moderate | Many noninflammatory (comedones) and inflammatory lesions (papules/pustules) are present; no nodulo-cystic lesions are allowed |
| 4 | Severe | Significant degree of inflammatory disease; papules/pustules are a predominant feature; a few nodulo-cystic lesions may be present; comedones may be present |

The safety of the treatment regimens is evaluated by measuring the number of any events that are determined to be treatment-related adverse events, directed physical examination, measurement of vital signs (including height, weight, body temperature, pulse rate, respiratory rate, and blood pressure), and local (dermal) tolerability (as measured by the investigator's assessment of the dryness, scaling and/or erythema of a subject's skin in the treatment area). All adverse events will be coded from the verbatim text to the lower level term and mapped to preferred term (PT) and primary system organ class (SOC) using the Medical Dictionary for Regulatory Activities.b Data will be summarized with descriptive statistics with 95% confidence intervals, frequency tables, and data listings.

Sample Size Calculation:

Approximately 60 subjects will be entered into the study. When the sample size is 10 per group, a two-sided 95.0% confidence interval for a single proportion using the binomial approximation will extend 0.262 to 0.878 for an expected proportion of 0.600 of IGA responders. When the sample size is 10 per group, a two-sided 95.0% confidence interval for the mean change from baseline lesion counts using the normal approximation will extend −7.85 to −22.15 assuming a mean change from baseline of −15 and a standard deviation of 10.

The application of Spongilla *lacustris* and onabotulinum-toxinA (BOTOX®) 100U has an acceptable response rate and decreases the total number of lesions in the treatment area in subjects with acne vulgaris after 6 weeks of topical administration (one topical treatment of onabotulinum-toxinA (BOTOX®) 100U and once-weekly topical treatment with Spongilla), measured by both investigator's global assessment (IGA), and total lesion counts (nodules, cysts, inflammatory and non-inflammatory).

Example 8: Preparation of Spongilla Materials

Spongilla raw material was treated with heat or gamma irradiation to reduce bioburden to acceptable levels. The resulting materials were milled and sieved to obtain a material having a particle size of no larger than 200 μm. The sized material was dried using a low temperature tray dryer at a temperature of about 40° C. to obtain a target moisture content of less than 1%. A representative batch of materials was irradiated as follows using Nordion Cobalt-60 Batch JS 8900 Irradiator #139, ON-STD; processing start time=10: 57:38 am; processing end time: 01:31:14 μm; minimum specified dose (kGy): 25.0; maximum specified dose (kGy):

32.5; minimum delivered dose (kGy): 26.2; maximum delivered dose (kGy): 31.2. The resulting material was filled and sealed into high-density polyethylene jars that were packaged into foil laminate pouches containing desiccant packets. The packaged product may be further gamma irradiated if the material does not otherwise meet the microbial limits set forth in USP <1111>. The resulting materials were stored at a temperature of below 30° C. and were protected from light and moisture prior to use.

Example 9: Treatment of Subjects Having Hyperhidrosis with a Combination of Spongilla *Lacustris* and onabotulinumtoxinA The objective of the study was to evaluate the tolerability, safety, and efficacy of (a) Spongilla powder mixed with 3% hydrogen peroxide USP, or (b) Spongilla powder, mixed with 0.9% sodium chloride USP, followed by topical administration of BOTOX® (onabotulinumtoxinA) Purified Neurotoxin complex to the axilla in subjects with primary axillary hyperhidrosis. The study was structured as a single center, two arm, open label, study of approximately 4 weeks (day 1 treatment to day 29 study exit).

To be enrolled in the study, each subject had diagnosis of primary, axillary hyperhidrosis within 6 months of baseline (study day 1) and a HDSS score of 3 or 4 (based on both axillae) using the criteria in Table 3. The subject must also have had sweat production of at least 50 mg over about 5 minutes in each axilla assessed gravimetrically.

TABLE 3

| | HYPERHIDROSIS DISEASE SEVERITY SCALE (HDSS) |
|---|---|
| Score | Description |
| 1 | My underarm sweating is never noticeable and never interferes with my daily activities |
| 2 | My underarm sweating is tolerable and sometimes interferes with my daily activities |
| 3 | My underarm sweating is barely tolerable and frequently interferes with my daily activities |
| 4 | My underarm sweating is intolerable and always interferes with my daily activities |

All subjects received active therapy in both right and left axillae on day one of the study. Each subject received Spongilla powder mixed with 3% hydrogen peroxide USP in one axilla and Spongilla powder mixed with 0.9% sodium chloride for injection USP in the contralateral axilla. The investigational products were as set forth in Table 4.

TABLE 4

| | Description of Investigational Products |
|---|---|
| IP Name: | *Spongilla* topical powder plus hydrogen peroxide |
| Active Ingredient: | 2 gm of *Spongilla* powder |
| Other Ingredients: | 6 mL of 3% hydrogen peroxide USP |
| IP Name: | *Spongilla* topical powder plus sodium chloride solution |
| Active Ingredient: | 2 gm of *Spongilla* powder |
| Other Ingredients: | 6 mL of 0.9% sodium chloride for Injection USP |
| IP Name: | BOTOX ® (Botulinum Toxin Type A) Purified Neurotoxin Complex |
| Active Ingredient: | 100 units (U) of Clostridium botulinum toxin Type A |
| Other Ingredients: | 0.5 mg albumin (human), and 0.9 mg sodium chloride |

The choice of diluent (3% hydrogen peroxide USP or 0.9% sodium chloride) was randomly allocated to right and left axillae for each subject. After approximately 10 minutes, the composition containing Spongilla was removed from the subject's skin with Cetaphil® wipes and onabotulinum-toxinA 100U was massaged into the axilla. Reconstituted onabotulinumtoxinA 100U was applied to each axilla and massaged into the skin of the axilla. The onabotulinum-toxinA composition was allowed to remain on the skin for approximately 15 minutes, then the subject's skin was cleaned with a pre-moistened cleaning wipe (e.g., Cetaphil® wipe) and then the area was gently dried. Treatments were applied once, on study day 1.

Gravimetric sweat production in each subject was measured (a) prior to day one of the study; (b) on study day one in which the treatment is applied to the subject; and (c) on study day 29±3. The measurement of gravimetric sweat production was performed on each axilla at the Screening, Day 1, and 29/early exit visits. Gravimetric assessment were conducted after about 15 minutes at rest in a sitting position. All tests were performed in the same room at a room temperature of about 25° C. The axillae were thoroughly cleaned with an absorbent paper before gravimetry. A 90-mm diameter round filter paper was weighed with a microbalance and the weight recorded. The filter paper was placed under the axilla and a plastic bag was placed under the filter paper, to avoid evaporation of sweat. After about 5 minutes, the round filter paper was reweighed, and the difference between the 2 weights was taken as sweat production in milligrams over about 5 minutes. Each subject's overall severity of hyperhidrosis was also evaluated by a 4-point HDSS assessment that is self-assessment by the subject and was completed (a) at screening; (b) on study day one; (c) and on study day 29±3 or earlier if the subject did not complete the 29-day study.

Treatment efficacy was measured as the percentage of subjects with a >2-grade improvement in the Hyperhidrosis Disease Severity Scale (HDSS) from baseline 4 weeks following treatment. Another measure of treatment efficacy was the percentage of subjects having >50% reduction in gravimetrically measured sweat production from baseline in the 4 weeks following treatment. Another measure of treatment efficacy was the mean absolute change from baseline in gravimetrically-measured sweat production in subjects in the 4 weeks following treatment. Three analysis populations were used as follows: (1) the intent-to-treat (ITT) population will consist of all enrolled subjects; (2) the per protocol (PP) population will consist of all enrolled subjects with no significant protocol violations during the study that would affect the efficacy analyses. The PP population was determined prior to database lock; and (3) the safety population consisted of all subjects who receive at least 1 dose of study medication in the study. Efficacy Analysis: All efficacy analyses were performed using the ITT and PP population. For continuous variables, (e.g., change from baseline in gravimetric sweat production) data was summarized using descriptive statistics by treatment group with 95% confidence intervals. For categorical variables, a frequency distribution was used to analyze the proportion of subjects with a response (e.g., % of subjects with >50% reduction in gravimetric sweat production).

TABLE 5

Summary of Sweat Gravimetric Sweat Production and Hyperhidrosis Disease Severity Scale (HDSS)

| Subject No. | Day 1 Gravimetric Test | | Day 2 Gravimetric Test | | Day 1 HDSS | | Day 29 HDSS | |
| --- | --- | --- | --- | --- | --- | --- | --- | --- |
| | Left axilla | Right Axilla | Left axilla | Right Axilla | Left axilla | Right Axilla | Left axilla | Right Axilla |
| 001-001 | 83 mg (0.9% saline) | 110 mg (H2O2) | 5 mg (0.9% saline) | 1 mg (H2O2) | 3 | 3 | 3 | 3 |
| 001-006 | 90 mg (H2O2) | 60 mg (0.9% saline) | 34 mg (H2O2) | 28 mg (0.9% saline) | 4 | 3 | 2 | 2 |
| 001-008 | 275 mg (H2O2) | 310 mg (0.9% saline) | 183 mg (H2O2) | 284 mg (0.9% saline) | 4 | 4 | 4 | 4 |
| 001-011 | 55 mg (0.9% saline) | 73 mg (H2O2) | 4 mg (0.9% saline) | 4 mg (H2O2) | 4 | 4 | 4 | 4 |
| 001-012 | 230 mg (H2O2) | 165 mg (0.9% saline) | 15.7 mg (H2O2) | 36.6 mg (0.9% saline) | 3 | 3 | 3 | 3 |
| 001-013 | 122 mg (H2O2) | 151 mg (0.9% saline) | 5.7 mg (H2O2) | 9.1 mg (0.9% saline) | 3 | 3 | 2 | 2 |
| 001-014 | 100 mg (0.9% saline) | 103 mg (H2O2) | 41.1 mg (0.9% saline) | 53 mg (H2O2) | 4 | 4 | 3 | 3 |
| 001-016 | 231 mg (0.9% saline) | 280 mg (H2O2) | 3 mg (0.9% saline) | 11 mg (H2O2) | 3 | 3 | 3 | 3 |
| 001-025 | 274 mg (0.9% saline) | 208 mg (H2O2) | 22 mg (0.9% saline) | 10 mg (H2O2) | 3 | 3 | 3 | 3 |
| 001-027 | 61 mg (H2O2) | 133 mg (0.9% saline) | 40 mg (H2O2) | 31 mg (0.9% saline) | 3 | 3 | 3 | 3 |

TABLE 6

Summary of Response Rate in Subjects (0.9% saline and H2O2 arms combined)

Total No. Axilla = 20 (10 subjects each contributed 2 axilla that received treatment)

| | Response Rate | Z-score | p-value |
|---|---|---|---|
| Decrease in gravimetric sweat production ≥ 50% at Week 4 | 80% | 2.26 | 0.024 |
| Gravimetric sweat production < 50 mg at Week 4 | 85% | 2.58 | 0.009 |

In Table 6, the Z-score is from a one sample test for a single proportion. Assumption for the analysis is that the observed proportion is not different from 40% (Placebo Response Rate) (Fleiss, D. B. 1981. Statistical Methods for Rates and Proportions, 2nd Ed. Wiley and Sons, p. 13-14).

TABLE 7

Mean Change in Gravimetric Sweat Production

| | Saline Arm | Hydrogen peroxide | p-value |
|---|---|---|---|
| No. of Subjects | 10 | 10 | |
| Mean change in gravimetric sweat | −109.82 | −119.46 | 0.791 |
| Percent change in gravimetric sweat | −0.746 | −0.752 | 0.965 |

TABLE 8

Summary of Gravimetric Sweat Production in Subjects (0.9% saline and H2O2 arms combined)

| | Gravimetric Measurements (mg sweat) by Time | | |
|---|---|---|---|
| | Total No. Axilla = 20 (10 subjects each contributed 2 axilla that received treatment) | t-score | p-value |
| Baseline sweat production (mean) | 155.7 mg | | |
| Sweat production in week 4 following treatment (mean) | 41.0 mg | | |
| Mean change in sweat production from baseline in week 4 following treatment (mg) | −114.64 mg | 2.44 | 0.024 |
| Mean Percent Change from Baseline | −75% | 8.93 | <0.001 |

In table 8, the t-score of 2.44 is from a one sample test for a single mean and assumes for the analysis is that the observed mean change is not different from 72 mg. In table 8, the t-score of 8.93 is from a one sample test for a single mean and assumes for the analysis is that the observed mean percent change is not different from 21%.

TABLE 9

Treatment Emergent Adverse Events

| Adverse Event | No. Subjects (% out of 10 subjects in study) |
|---|---|
| Subjects reporting at least one AE | 2 (20%) |
| Skin and subcutaneous tissue disorders | 1 (10%) |
| Irritant Dermatitis | 1 (10%) |
| Renal and Urinary Disorders | 1 (10%) |
| Urinary Tract Infection | 1 (10%) |

Subject 01-016 experienced dermatitis of the right axilla 2 days post treatment with DMT410 plus hydrogen peroxide. Subject applied ice and aloe vera gel to the affected are and the event resolved completely within 24 hours.

Example 10: A Study of the Tolerability, Safety, and Efficacy of DMT310 for the Treatment of Lateral Canthal Lines Protocol Summary.

The objective of the study is to evaluate the tolerability, safety, and efficacy of DMT310 administered to the facial skin followed by BOTOX® in patients with moderate to severe glabellar lines, forehead lines, and lateral canthal lines. The clinical hypothesis is that DMT310 administered to the facial skin followed by BOTOX 64U has an acceptable response rate at 4 weeks post administration, and that DMT310 followed by BOTOX 64U has an acceptable tolerability and safety profile at 4 weeks post administration. The study compounds used are DMT310 (Spongilla powder, mixed with 0.9% sterile saline) and BOTOX® (Botulinum Toxin Type A) Purified Neurotoxin complex. The study design includes a single center, one arm, open label study, with a duration of approximately 16 weeks (day 1 treatment to day 112 study exit). The study treatment group is DMT310 followed by BOTOX 64U, and there is no control group. Regarding dosage/dose regimen, DMT310 will be administered to the skin of the upper face, in the clinic, by trained study staff. After approximately 10 minutes, DMT310 will be removed with Neutrogena® wipes and BOTOX 64U will be massaged into the skin. Treatments will be applied once, on study day 1. The visit schedule used is as follows: visit 1 (Day-28 to −1) Screening; visit 2 (Day 1) Baseline, enrollment, and treatment initiation; visit 3 (Day 15) follow-up visit; visit 4 (Day 29) follow-up visit; visit 5 (Day 57) follow-up visit; visit 6 (Day 85) follow-up visit; visit 7 (Day 112 [successful completion of study] or early discontinuation) Exit. The study will be conducted in compliance with International Conference on Harmonisation (ICH) Good Clinical Practices (GCPs).

Study Population.

Approximately 10 patients will be enrolled at one center. Male and female patients with moderate to severe lateral canthal lines (LCL) at maximum smile, moderate to severe glabellar lines (GL) at maximum frown, and moderate to severe symmetrical horizontal forehead lines (FHL) at maximum eyebrow elevation will be included. Approximately 10 patients will be entered into the study. Each patient will receive DMT310 mixed with 0.9% sterile saline USP. DMT310 application will be followed by topical application of BOTOX 64U. This sample size was determined empirically for this proof of concept study and no hypothesis testing will be conducted. However, BOTOX has been shown to demonstrate a treatment response of up to 90% (BOTOX Package Insert), thus when the sample size is 10 per group, a two-sided 95.0% confidence interval for a single proportion using the large sample normal approximation will extend 0.186 from the observed proportion for an expected proportion of 0.900.

Key inclusion criteria include the following: the patient is a male or non-pregnant female, 18 years of age or older at the time of consent; the patient has moderate to severe GL at maximum frown and moderate to severe LCL at maximum smile and symmetrical horizontal FHL of moderate to severe at maximum contraction (maximum eyebrow elevation) assessed by both the investigator and patient using the FWS (investigator and patient ratings for LCL must be the same at randomization); and the patient must have sufficient visual acuity without the use of eyeglasses (contact lens use acceptable), to accurately assess their facial lines, in the opinion of the investigator. Key exclusion criteria include the following: the patient has had prior treatment with any botulinum toxin (e.g., Botox®) for facial lines or chronic migraine within 1 year of Baseline (study day 1); the patient has had prior treatment with DMT310. Additional key exclusion criteria is that the patient has had any of the following procedures or treatments occurring in the specified period before enrollment (day 1): any facial non-ablative resurfacing laser or light treatment, microdermabrasion, or superficial peels within 3 months; any facial cosmetic procedure with medium depth or deep depth chemical peels (eg, trichloroacetic acid and phenol); periorbital, mid-facial, or upper-facial skin resurfacing; or permanent make-up in the mid-facial (extending from inferior orbital margin to level of the nasal base) or upper facial areas within 6 months; or any periorbital, mid-facial, or upper-facial treatment with nonpermanent soft tissue fillers, or treatment with oral retinoids within 12 months. Further key exclusion criteria include the following: the patient has had prior periorbital surgery, facial lift (full face or mid-face), thread lift, brow lift, or related procedures (eg, eyelid [blepharoplasty] and/or eyebrow surgery); the patient has had prior periorbital, mid-facial, or upper-facial treatment with permanent soft tissue fillers, synthetic implantation (eg, Gore-Tex®), and/or autologous fat transplantation; the patient has marked facial asymmetry, dermatochalasis, deep dermal scarring, excessively thick sebaceous skin, or the inability to substantially lessen facial lines even by physically spreading them apart, determined by the investigator; the patient has any eyebrow or eyelid ptosis, as determined by the investigator; the patient has been immunized for any botulinum serotype; and the patient has a known allergy or sensitivity to any botulinum preparation and/or shellfish.
Response Measures.

Primary and secondary efficacy measures are as follows. Primary: Investigators' and patients' assessments of LCL severity at maximum smile and at rest using the facial wrinkle scale (5-grade scale: 0=none, 1=almost none, 2=mild, 3=moderate, 4=severe). Secondary: Investigators' and patients' assessments of GL severity at maximum smile and at rest using the facial wrinkle scale (5-grade scale: 0=none, 1=almost none, 2=mild, 3=moderate, 4=severe). Secondary: Investigators' and patients' assessments of FHL severity at maximum eyebrow elevation and at rest using the facial wrinkle scale (5-grade scale: 0=none, 1-almost none, 2=mild, 3-moderate, 4=severe). Secondary: luminosity, brightness, pore size, sebum production, Global Aesthetic Improvement, laxity under the eye and fine lines under the eye. Safety measures are as follows. Adverse events, directed physical examination, vital signs (height, weight, body temperature, pulse rate, respiratory rate, and blood pressure), urine pregnancy test for females of childbearing potential, local (dermal) tolerability, investigator's or trained designee's assessment of dryness, scaling and erythema, and patient's assessment of stinging/burning. Other response measures are skin phototype and facial photography.
Statistical Methods.

Three analysis populations will be used as follows. The intent-to-treat (ITT) population will consist of all enrolled patients. The per protocol (PP) population will consist of all enrolled patients with no significant protocol violations during the study that would affect the efficacy analyses. The PP population will be determined prior to database lock. The safety population will consist of all patients who receive at least 1 dose of study medication in the study. All efficacy analyses will be performed using the ITT and PP population. For continuous variables, (e.g., change from Baseline in sebum production) data will be summarized using descriptive statistics by treatment group with 95% confidence intervals. For categorical variables, a frequency distribution will be used to analyze the proportion of patients with a response (e.g., proportion of patients with achieving a none or mild LCL using the facial wrinkle scale). All adverse events will be coded from the verbatim text to the lower level term and mapped to preferred term (PT) and primary system organ class (SOC) using the Medical Dictionary for Regulatory Activities. Data will be summarized with descriptive statistics with 95% confidence intervals, frequency tables, and data listings.
Disease Background GL are deep furrows in the glabellar area of the face and LCL are horizontal "smile lines" by the sides of the eyes. These types of facial lines result from the repetitive functional action of the underlying mimetic facial musculature during animation (Blitzer et al, 1993). When injected at therapeutic doses, botulinum toxin produces partial chemical denervation of the muscle, resulting in localized reduction in muscle activity. Because GL, FHL, and LCL result from muscular activity, the muscle relaxation leads to a temporary flattening of the mechanical component causing the facial lines. While it was previously thought that these facial lines were structural and permanent, the effects of these injections demonstrate the lines are part functional and remain because of constant muscle tone (Garcia and Fulton, 1996).

The development of facial lines (such as GL, FHL and LCL) is an age-related change of the face that occurs because of the repetitive muscle contractions that are associated with common facial expressions. Thus, these facial lines can be observed with contraction (dynamic rhytides) or in more severe cases in repose (static rhytides). Increasing severity in the appearance of facial lines has been associated with a patient's perception of reduced attractiveness and a negative effect on self-esteem and sense of well-being (Koblenzer, 2005). Furthermore, the appearance of these facial lines can lead to a miscommunication of an emotional state of anger, anxiety, disapproval, or sadness (Khan, 2001) causing distress and affecting social interactions (Cox and Finn, 2005). The popularity of BoNT/A cosmetic treatment of GL, FHL and LCL in adults is related to its proven efficacy for reducing moderate to severe facial lines (Beer, 2006); well documented safety profile (Brin, 2009); and positive impact on psychological well-being and the resulting psychosocial benefits (Cox and Finn, 2005).

However, the skin penetration, and volume effects from botulinum toxin treatment may produce injection site pain. Injection site pain may be a barrier to treatment when injections have to be placed in sensitive skin areas, such as the temples (Alam et al, 2002). Thus, a topical product with potential anti-microbial effects, a simple usage paradigm, which would allow for penetration of botulinum toxin past the stratum corneum and into the dermis, may exhibit greater comfort and adoption due to improved tolerability of the treatment.

Compound Background

DMT310 is a powdered mixture that contains a unique variant of Spongilla *lacustris*, a fresh water sponge species of the Genus Spongilla. DMT310 powder is mixed with 0.9% Sodium Chloride USP, which is used a fluidizing agent, allowing for ease of topical application.

DMT310 is comprised of inorganic siliceous spicules which are approximately 200 μm in length and 15 μm in diameter. It is believed that the spicules penetrate the stratum corneum during application. The structure of the spicule is shown in FIG. 1. Topical application of Spongilla has been practiced in Central Europe and Asia for decades for the treatment of inflammatory conditions. According to the Russian Ministry of Health, approximately 1.5 million patients per year use the Badyaga with no registered side effects of the medicine (see Letter from Russian Ministry of Health).

Throughout its many years of use as a folk medicine, Spongilla has demonstrated its potential for the treatment of skin, and other inflammatory, diseases.

Botulinum Toxin Type A inhibits vesicle-bound neurotransmitters at the neuromuscular junction, including acetylcholine. The rationale for the use of BOTOX® to treat facial lines is that by inhibiting the release of the neurotransmitter acetylcholine at peripheral cholinergic nerve endings, the overactivity of the muscles responsible for LCL (bilateral orbicularis oculi), FHL (*frontalis*) and GL (the corrugators and procerus muscles) can be reduced, thus eliminating or diminishing the appearance of excessive facial lines. Botulinum toxin has been approved by US FDA for the treatment of glabellar lines and lateral canthal lines.

Rationale

Botulinum toxin type A is approved for the treatment of glabellar lines, forehead lines and lateral canthal lines, but the injections can be painful, which may lead to poor adoption of this therapy. Thus, for the treatment of upper facial lines, it would be desirable to have a needle free method that could provide a convenient topical approach to botulinum toxin administration.

A small study was conducted in ten patients with primary axillary hyperhidrosis with at least 50 mg of gravimetric sweat production in 15 minutes. DMT310 was applied to the axillary skin, after 15 minutes of contact time, the DMT310 was washed from the axilla. BOTOX (OnabotulinumtoxinA) was reconstituted with 0.9% sterile saline and the reconstituted liquid was applied directly to the axillary skin and massaged until absorbed. 30 days post-treatment, there was evidence of reduction in the mean gravimetric sweat production with a large proportion (80%) of patients having a treatment response (>50% reduction in sweat production). These results suggest that topical administration of DMT310 and botulinum toxin may result in delivery of the botulinum toxin past the stratum corneum without the use of a needle. This study will be the first to test Spongilla powder with botulinum toxin type A in this disease, and thus provide data on the relative benefit-risk profile of this treatment.

This is an open label study of DMT310 in patients 18 years and older with moderate to severe glabellar lines, lateral canthal lines and forehead lines. All patients will receive active therapy. Each patient will receive DMT310 mixed with 0.9% Sodium Chloride for Injection USP. DMT310 will be removed with Neutrogena® wipes and reconstituted BOTOX 64U will be massaged into the skin. It is hypothesized that the spicules contained in the product will allow for penetration of BOTOX past the stratum corneum (see FIG. 2). Thus, the commercially available, standard formulation of BOTOX may be used. The key design elements of the study were chosen based on historical experience with studies of this type.

The volume of DMT310 was chosen based on historical information regarding the use of this medicine. The dose of BOTOX® is the labeled dose used for OnabotulinumtoxinA in patients with upper facial lines. One treatment will be applied as OnabotulinumtoxinA exhibits clinical efficacy for at least three months (BOTOX® Package Insert).

Study Objectives and Endpoints

The objective of the study is to evaluate the tolerability, safety, and efficacy of DMT310 administered to the upper face followed by BOTOX 64U in patients with moderate to severe glabellar lines, lateral canthal lines and forehead lines. Table 1 below lists the study endpoints.

TABLE 1

| Study endpoints. | | | |
|---|---|---|---|
| Endpoints | Name | Description | Timeframe |
| Efficacy | Facial Wrinkle Scale<br>0 = None<br>1 = Almost None<br>2 = Mild<br>3 = Moderate<br>4 = Severe | Proportion of subjects achieving a grade of none or mild on the investigator's assessment of LCL severity at maximum smile, based on the FWS | Day 29, 57, 85, 112 |
| | | Proportion of subjects achieving a grade of none or mild on the investigator's assessment of GL severity at maximum frown, based on the FWS | Day 29, 57, 85, 112 |
| | | Proportion of subjects achieving a grade of none or mild on the investigator's assessment of FHL severity at maximum contraction, based on the FWS | Day 29, 57, 85, 112 |
| | | Proportion of subjects achieving a grade of none or mild on the patient's assessment of LCL severity at maximum smile, based on the FWS | Day 29, 57, 85, 112 |
| | | Proportion of subjects achieving a grade of none or mild on the patient's assessment of GL severity at maximum frown, based on the FWS | Day 29, 57, 85, 112 |
| | | Proportion of subjects achieving a grade of none or mild on the patient's assessment of FHL severity at maximum contraction, based on the FWS | Day 29, 57, 85, 112 |
| | | Proportion of subjects achieving a 2-grade improvement in the FWS from baseline on the physician's assessment of LCL | Day 29, 57, 85, 112 |

TABLE 1-continued

| | | Study endpoints. | |
| --- | --- | --- | --- |
| Endpoints | Name | Description | Timeframe |
| | | and GL, and FHL at both rest and maximum contraction | |
| | | Proportion of subjects achieving a 2-grade improvement in the FWS from baseline on the patient's assessment of LCL and GL, and FHL at both rest and maximum contraction | Day 29, 57, 85, 112 |
| | Luminosity and Brightness (Visual Analog Scales) | Mean and Percent change from baseline | Day 29, 57, 85, 112 |
| | Skin Pore Size Global Aesthetic Improvement Scale (GAIS): 0 = No Improvement 1 = ≤ 25% Improvement (mild) 2 = 26-50% Improvement (moderate) 3 = 51-75% Improvement (good) 4 = 76-100% Improvement (excellent). | Proportion of subjects achieving improvement on the physician's assessment of pore size improvement, based on the GAIS | Day 29, 57, 85, 112 |
| | Sebum Production | Mean and Percent change from baseline | Day 29, 57, 85, 112 |
| | Facial Wrinkle Scale 0 = None 1 = Almost None 2 = Mild 3 = Moderate 4 = Severe | Proportion of subjects achieving a two grade improvement on the physician's assessment of fine lines under the eye at maximum contraction, based on the FWS | Day 29, 57, 85, 112 |
| | Facial Laxity Rating Scale (Eyelid fold) 0 = Absent 1 = Perceivable 2 = Well Defined 3 = Partially folding 4 = Folding 5 = Well-defined fold, still separated from eyelid border 6 = Partially on eyelid border 7 = Completely on eyelid border 8 = Pushing eyelid border downward 9 = interfering with pupil | Proportion of subjects achieving a two grade improvement on the physician's assessment of laxity severity based on the FLRS | Day 29, 57, 85, 112 |
| | Overall Skin Quality Global Aesthetic Improvement Scale (GAIS): 0 = No Improvement 1 = ≤ 25% Improvement (mild) 2 = 26-50% Improvement (moderate) 3 = 51-75% Improvement (good) 4 = 76-100% Improvement (excellent). | Proportion of subjects achieving improvement on the physician's assessment of overall skin quality, based on the GAIS | Day 29, 57, 85, 112 |
| Safety | Adverse Events (AEs) | Incidence (severity and causality) of any local and systemic Treatment Emergent AEs | Up to Day 112 |

TABLE 1-continued

| | | Study endpoints. | |
| --- | --- | --- | --- |
| Endpoints | Name | Description | Timeframe |
| | Physical Exam | Change from Baseline | Day 15, 29, 57, 85, 112 |
| | Vital Signs | Change from Baseline | Day 112 |

Study Design.

This is a single center, randomized, open-label study to evaluate the tolerability, safety, and efficacy of DMT310 administered to the upper face followed by BOTOX 64U in male and female patients with moderate to severe glabellar lines, forehead lines, and lateral canthal lines. Approximately 10 patients will be enrolled. Each patient will receive DMT310 mixed with 0.9% Sodium Chloride for Injection, USP. DMT310 application will be followed by topical application of BOTOX 64U. Eligible patients must have an FWS rating of moderate or severe as rated by both the patient and the investigator on study day 1. The investigator and patient ratings for LCL must be the same at randomization. There will be a single, open label, treatment group: DMT310 Spongilla powder mixed with 0.9% Sodium Chloride for Injection USP. Each treatment will be followed by topical application of BOTOX 64U (reconstituted with 2.5 mL of Sodium Chloride for Injection per label) massaged into the skin of the upper face.

Patients will have up to 7 clinic visits. Safety will be assessed by directed physical exams, vital signs (heart rate, respiration rate, blood pressure, and body temperature), and AEs. Efficacy will be assessed by the investigator and patient assessments of the facial wrinkle scale. The study will be conducted in compliance with the International Council on Harmonisation (ICH) of Technical Requirements for Registration of Pharmaceuticals for Human Use/Good Clinical Practice (GCP) and applicable regulatory requirements. Each patient may participate in the study for up to approximately 16 weeks. Patients will have 28 days to meet study criteria (i.e., Screening) before entering the 112 day treatment period. The End of Trial is defined as the date of the last visit of the last patient to complete the study.

Study Population.

Patients must satisfy the following criteria to be enrolled in the study. Patient must be a male or non-pregnant female, 18 years of age or older at the time of consent. Females of childbearing potential (FCBP) must satisfy the following criteria. FCBP is defined as a female who: 1) has achieved menarche at some point, 2) has not undergone a total hysterectomy, bilateral tubal ligation, or bilateral oophorectomy, or 3) has not been naturally postmenopausal (amenorrhea following cancer therapy does not rule out childbearing potential) for at least 12 consecutive months (ie, had menses at any time in the preceding 12 consecutive months. FCBP must have negative pregnancy tests as verified by the Investigator prior to starting study therapy. Patient must agree to pregnancy testing after end of study treatment. This applies even if the patient practices true abstinence from heterosexual contact. True abstinence is acceptable when this is in line with the preferred and usual lifestyle of the patient. Periodic abstinence (e.g., calendar, ovulation, sympothermal, post-ovulation methods) and withdrawal are not acceptable methods of contraception. FCBP must either commit to true abstinence from heterosexual contact (which must be source documented) or agreed to use, and be able to comply with, effective contraception without interruption, prior to starting the investigational product (IP) as detailed below, during study period. For FCBP who may participate in the study, the following methods of contraception, if properly used, are generally considered reliable with the following wait periods prior to having relations (Trussel, 2011): oral contraceptives; vaginal contraceptive ring and patch contraceptives (one full cycle; e.g., 4 to 8 weeks); injection contraceptives (more than 7 days); intrauterine device or implantable hormone contraceptives (more than 7 days); surgical sterilization (hysterectomy, bilateral tubal ligation, or bilateral oophorectomy) or a vasectomized partner (each, more than 6 months); male condom with intravaginal spermicide or diaphragm/cervical cap with spermicide (effective with proper use without a waiting period). Male patients must practice true abstinence (which must be source documented) or agree to use a condom with intravaginal spermicide during sexual contact with a pregnant female or a FCBP while participating in this study, during dose interruptions, and for at least 30 days following IP discontinuation, unless patient has undergone a successful vasectomy.

Patient must have provided written informed consent. Patient must have moderate to severe GL at maximum frown and moderate to severe LCL at maximum smile and symmetrical horizontal FHL of moderate to severe at maximum contraction (maximum eyebrow elevation) assessed by both the investigator and patient using the FWS (investigator and patient ratings for LCL must be the same) at randomization. Patients must have sufficient visual acuity without the use of eyeglasses (contact lens use acceptable), to accurately assess their facial lines, in the opinion of the investigator. Patient must be willing and able to refrain from physical activity (eg, sports, running) that would result in excessive sweating for 24 hours post treatment. Patient must be willing and able to comply with study instructions and commit to all follow-up visits for the duration of the study. Written informed consent must have been obtained from the patient prior to any study related procedures. In the investigator's opinion, patient must be in good general health and is free of any disease state or physical condition that exposes the patient to an unacceptable risk by study participation or impairs the evaluation of the patient or IP by participating in the study.

The presence of any of the following will exclude a patient from enrollment. Patient is pregnant, lactating, or is planning to become pregnant during the study. Patient has had prior treatment with any botulinum toxin (e.g., Botox®) for facial lines or chronic migraine within 1 year of Baseline (study day 1). Patient has had any of the following procedures or treatments occurring in the specified period before enrollment (day 1): any facial non-ablative resurfacing laser or light treatment, microdermabrasion, or superficial peels within 3 months; any facial cosmetic procedure with medium depth or deep depth chemical peels (eg, trichloroacetic acid and phenol); periorbital, mid-facial, or upper-facial skin resurfacing; or permanent make-up in the mid-facial (extending from inferior orbital margin to level of the nasal base) or upper facial areas within 6 months; any periorbital, mid-facial, or upper-facial treatment with non-permanent soft tissue fillers, or treatment with oral retinoids within 12 months. Patient has had prior periorbital surgery, facial lift (full face or mid-face), thread lift, brow lift, or related procedures (eg, eyelid [blepharoplasty] and/or eyebrow surgery). Patient has had prior periorbital, mid-facial, or upper-facial treatment with permanent soft tissue fillers, synthetic implantation (eg, Gore-Tex®), and/or autologous fat transplantation. Patient has marked facial asymmetry, dermatochalasis, deep dermal scarring, excessively thick sebaceous skin, or the inability to substantially lessen facial lines even by physically spreading them apart, determined by the investigator. Patient has any eyebrow or eyelid ptosis, as determined by the investigator. Patient has been immunized for any botulinum serotype. Patient has a known allergy or sensitivity to any botulinum preparation. Patient has a known allergy or sensitivity to shellfish. Patient has any medical condition that may put the patient at increased risk with exposure to BOTOX including diagnosed myasthenia gravis, Eaton Lambert syndrome, and amyotrophic lateral sclerosis. In the opinion of the investigator, the patient has skin pathology or condition that could interfere with the evaluation of the test products or requires the use of interfering topical or systemic therapy during the study. Skin abnormalities or other physical characteristics in or around the application sites that could confound the study results based on the investigator's judgment. Patient is currently enrolled in another investigational drug or device study OR is using or has used an investigational drug or investigational device treatment within 30 days of Day 1. Patient has any acute illness (eg, infection) within 48 hours of Day 1, which, in the investigator's opinion, is considered significant. Patient has a history of sensitivity to any of the ingredients in the intraperitoneal investigational product (IP). Patient is known to be noncompliant or is unlikely to comply with the requirements of the study protocol (eg, due to alcoholism, drug dependency, mental incapacity) in the opinion of the investigator.

Table 2 below shows the table of events. FCBP=females of childbearing potential. The following superscripts are used in Table 2: $^a$all assessments, including photography, before study treatment; $^b$or early discontinuation from the study; $^c$vital sign measurements include height, weight, pulse rate, respiration rate, blood pressure (systolic and diastolic), and body temperature, and must be performed before study treatment; $^d$FCBP must have a negative urine pregnancy test (UPT) before study treatment, the investigator may ask the patient to perform a UPT at any visit, and compliance with contraceptives should be discussed with all FCBP at each visit; $^e$patients will be contacted via telephone or electronic communication 24-48 hours after treatment to assess any potential signs/symptoms of ocular/periocular adverse reactions and distant spread of botulinum toxin, and patients reporting a TEAE will have an in-person clinic visit scheduled to assess the event.

TABLE 2

| | | | | | |
|---|---|---|---|---|---|
| | Table of events. | | | | |
| | | Visit | | | |
| | Visit 1 Screening | Visit 2 Random-ization | Visit 3 Follow-Up | Visit 4, 5, 6 Follow-Up | Visit 7 Study Exit |
| | | | Study Period | | |
| Visit Windows | Days −28 to −1 | Day 1$^a$ | Day 15 ±3 days | Days 29, 57, 85 ±7 days | Day 112$^b$ ±7 days |
| Informed Consent | X | | | | |
| Demographics | X | | | | |
| Inclusion/ Exclusion Criteria | X | Reconfirm | | | |
| Medical/ Dermatological History | X | | | | |

TABLE 2-continued

Table of events.

| | Visit | | | | |
|---|---|---|---|---|---|
| | Visit 1 Screening | Visit 2 Random- ization | Visit 3 Follow- Up Study Period | Visit 4, 5, 6 Follow-Up | Visit 7 Study Exit |
| Visit Windows | Days −28 to −1 | Day 1[a] | Day 15 ±3 days | Days 29, 57, 85 ±7 days | Day 112[b] ±7 days |
| Fitzpatrick Skin Phototype | X | | | | |
| Brief Physical Examination | X | X | X | X | X |
| Vital Sign Measurements[c] | X | X | | | X |
| UPT for FCBP[d] | X | X | | | X |
| Photography | | X | X | X | X |
| Clinical Evaluations | | X | | X | X |
| Local Tolerability | | X | X | X | X |
| Dosing | | X | | | |
| IP Accountability | | X | | | X |
| Adverse Events[e] | X | X | X | X | X |
| Concomitant Medications/ Therapies | X | X | X | X | X |

Procedures

Screening period (day-28 to −1). Patients can be screened for the study up to 28 days before Baseline. If applicable, qualified patients can washout from prohibited medications or treatments prior to Baseline (after obtaining consent). Patients who require washout for longer than 28 days will be re-consented. Patients who do not require washout may be randomized on the same day as screening, provided all screening procedures are performed and the patient meets all other entry criteria. At Screening, the investigator or designee will perform the following. Obtain a signed, written informed consent. Record demographics. Confirm inclusion/exclusion criteria. Record medical/dermatological history. Record the prior and/or concomitant medications and therapies. Perform Fitzpatrick skin phototype assessment. Perform directed physical exam. Record any findings in the medical/dermatological history. Perform vital signs (heart rate, respiration rate, blood pressure, and body temperature) and height/weight. Perform UPT for FCBP. Results must be negative for the patient to be enrolled in the study. Perform clinical evaluations GL, LCL, and FHL using facial wrinkle scale. Schedule the Baseline Visit.

Treatment period. Visit 2 (Day 1) baseline/randomization. At Baseline, the investigator or designee will perform the following. Query the patient about any changes in health status since the previous visit including concomitant medications and therapies, and document the findings. Re-confirm eligibility. Patients who do not meet inclusion/exclusion criteria at this visit will be classified as screen failures. Perform vital signs (heart rate, respiration rate, blood pressure, and body temperature). Perform directed physical exam. Record any findings that have worsened as AEs. Perform UPT for FCBP. Results must be negative for the patient to be enrolled in the study. Perform clinical evaluations GL, LCL, and FHL using facial wrinkle scale. Perform assessment of luminosity and brightness. Measure sebum production. Perform assessment of fine lines under the eye using the facial wrinkle scale. Perform assessment of laxity under the eye using the Facial Laxity Rating Scale (FLRS). Take facial photography. Perform the application of the IP, ensuring that the IP is correctly applied to the treatment area. Document IP accountability. Document any AEs. Assess Local Tolerability approximately 15 minutes post-application. Schedule a follow-up visit.

Visit 3 (Day 15±3) follow-up. At this visit, the investigator or designee will perform the following. Query the patient about changes in health status since the previous visit, including concomitant medications and therapies, and document the findings. Take facial photography. Perform directed physical exam. Record any findings that have worsened as AEs. Document any AEs. Assess Local Tolerability. Schedule the next visit.

Visits 4, 5, 6 (Days 29, 57, 85±7) follow-up. At this visit, the investigator or designee will perform the following. Query the patient about changes in health status since the previous visit, including concomitant medications and therapies, and document the findings. Take facial photography. Perform directed physical exam (Section 6.3.1). Record any findings that have worsened as AEs. Perform clinical evaluations GL, LCL, and FHL using facial wrinkle scale. Perform assessment of luminosity and brightness. Perform assessment of improvement in skin pore size using GAIS. Perform assessment of improvement in skin quality using GAIS. Measure sebum production. Perform assessment of laxity under the eye using the Facial Laxity Rating Scale (FLRS). Perform assessment of fine lines under the eye using the facial wrinkle scale. Document any AEs. Assess Local Tolerability.

Visit 7 (Day 112±7) end of study. If the patient reaches this timepoint or discontinues early from the study, the Visit 7 procedures should be followed. At this visit, the investigator or designee will perform the following. Query the patient about changes in health status since the previous visit, including concomitant medications and therapies, and document the findings. Perform directed physical exam. Record any findings that have worsened as AEs. Perform vital signs (heart rate, respiration rate, blood pressure, and body temperature). Perform UPT for FCBP. Take facial photography. Perform clinical evaluations GL, LCL, and FHL using facial wrinkle scale. Perform assessment of luminosity and brightness. Perform assessment of improvement in skin pore size using GAIS. Perform assessment of improvement in skin quality using GAIS. Measure sebum production. Perform assessment of laxity under the eye using the Facial Laxity Rating Scale (FLRS). Perform assessment of fine lines under the eye using the facial wrinkle scale. Document any AEs. Assess Local Tolerability. Collect all containers of IP and prepare for final IP accountability by CRA, as applicable. Exit the patient from the study.

Safety Assessments

Directed physical examinations will be performed at all clinic visits. Assessments will include examination of head and neck (including assessment of cranial nerves, cardiovascular, respiratory, gastrointestinal (abdomen), and gross motor and gait. Findings at Screening and Day 1 will be recorded as medical history. Any new or worsening findings at Days 15, 29, 57, 85, or 112 will be recorded as AEs. Vital signs including heart rate, respiration rate, blood pressure (systolic and diastolic), and body temperature will be assessed at Screening, Baseline/Randomization, and Day 112. Height and weight will also be measured at Screening.

UPTs will be performed on all FCBP at Screening, Baseline, and Day 112. FCBP include any female who has experienced menarche and who has not undergone successful surgical sterilization (hysterectomy, bilateral tubal ligation, or bilateral oophorectomy) or is not postmenopausal [defined as amenorrhea ≥12 consecutive months in women 50 years of age and older]. UPT must have a minimum sensitivity of 25 mIU ß-hCG/mL.

The UPTs will be performed at the study site, if the site is registered and conforms to CLIA regulations for such testing (possesses a current valid CLIA Certificate of Waiver), or at an appropriately registered reference laboratory. The investigator will report the UPT results on the CRFs, in the patient's medical records, and in independent records maintained at the study site.

In the event the patient experiences a skin reaction of such nature or severity that a contact allergy is suspected, the patient should discontinue the study medication. The event should be documented as an adverse event. The patient should be rechallenged using the assigned study medication to confirm or rule out contact dermatitis. If the diagnosis of allergic contact dermatitis is confirmed, the patient may have an additional patch test with the study medication and the individual study medication ingredients. The physician investigator should contact the medical monitor and discuss whether a patch test is warranted. If deemed appropriate, the patch test should be performed at least 2 weeks after discontinuation of the study medication. Patches will be applied to untreated areas on the back for 48 hours. Readings will be performed approximately 15 to 30 minutes and 48 hours following the removal of the patches. At the investigator's discretion, a facultative additional reading might be performed at 96 or 120 hours after removal of the patches if an equivocal reaction is observed at the previous reading.

Local (dermal) tolerability examination (only on the face) will be performed at the time points given in Table 2, and will include assessments of stinging/burning (rated by the patient), dryness, scaling, and erythema (rated by the investigator or appropriately trained designee). Dryness, scaling, and erythema must be assessed by the same person throughout the study whenever possible. Local tolerability on the face will be rated as none, mild, moderate, or severe and a detailed description is provided below. On study day 1, the patient rating of Stinging/Burning should be assessed within 15 minutes after dosing, the remaining measures of tolerability should be assessed by the physician investigator within 15 minutes after dosing. At subsequent visits, the patient rating of Stinging/Burning as well as the physician rated measures can be assessed at any time during the visit since there is a single application of IP in this study.

Patient Rated. Stinging/Burning (prickling pain sensation): None (0)=No stinging/burning; Mild (1)=Slight warm, tingling/stinging sensation; not really bothersome; Moderate (2)=Definite warm, tingling/stinging sensation that is somewhat bothersome; Severe (3)=Hot, tingling/stinging sensation that has caused definite discomfort.

Investigator Rated (or designee). Dryness (brittle and/or tight sensation): None (0)=No dryness; Mild (1)=Slight but definite roughness; Moderate (2)=Moderate roughness; Severe (3)=Marked roughness. Scaling (abnormal shedding of the stratum corneum): None (0)=No scaling; Mild (1)=Barely perceptible shedding, noticeable only on light scratching or rubbing; Moderate (2)=Obvious but not profuse shedding; Severe (3)=Heavy scale production. Erythema (abnormal redness of the skin): None (0)=No erythema; Mild (1)-Slight pinkness present; Moderate (2)=Definite redness, easily recognized; Severe (3)=Intense redness. If any sign or symptom is judged to be an adverse event in the opinion of the investigator, it will be captured on the patient's adverse event source document and eCRF.

Investigators and patients will assess GL and LCL severity using the FWS independently of each other, and these assessments will be the basis for several efficacy measures described in this section. These assessments will be done at rest and at maximum contraction (frown for GL and smile for LCL). For all assessments, the FWS uses the following scale for each treatment area separately: 0=None; 1=Almost None; 2=Mild; 3=Moderate; 4=Severe.

The investigator or designee will document the patient's skin phototype (I-VI) at screening using the Fitzpatrick Skin Type Assessment (see Table 3 below).

TABLE 3

Fitzpatrick skin type.

| Skin Phototype | Typical Features | Tanning Ability |
|---|---|---|
| I | Pale white skin, blue/hazel eyes, blond/red hair | Always burns, does not tan |
| II | Fair skin, blue eyes | Burns easily, tans poorly |
| III | Darker white skin | Tans after initial burn |
| IV | Light brown skin | Burns minimally, tans easily |
| V | Brown skin | Rarely burns, tans darkly easily |
| VI | Dark brown or black skin | Never burns, always tans darkly |

Patients' GL, FHL, and LCL wrinkle severity will be evaluated by both the physician and the patient using a 4-point FWS as shown in Table 4. The FWS will be performed at Screening, Days 1, 29, 57, 85 and Day 112/early exit. This is a static morphological scale that refers to a point in time and not a comparison to Baseline. Patients must have an investigator and physician rated FWS score of 3 or 4 at Baseline (study day 1) and both the investigator and patient score must match.

For each patient, investigator FWS evaluations should be performed by the same trained evaluator throughout the study whenever possible. If it is not possible to use the same evaluator to follow the patient throughout the study, then evaluations should overlap between the evaluators (ie, examine the patient together and discuss findings) for at least 1 visit.

TABLE 4

Facial wrinkle scale.

| Score | Wrinkle Severity | Description |
|---|---|---|
| 0 | None | No visible wrinkles |
| 1 | Almost None | Minimal wrinkles |
| 2 | Mild | Shallow wrinkles |
| 3 | Moderate | Moderately deep wrinkles |
| 4 | Severe | Very deep wrinkles |

Digital photographs are required to be taken during the study. Patients who refuse to have photographs taken will not be enrolled. Study Sponsor shall have full ownership rights to any photographs derived from the study.

Using standardized photographic equipment provided by Canfield Scientific Inc., full frontal pictures of the face will be obtained at rest and at maximum contraction (frown for GL, eyebrow raise for FHL, and smile for LCL). Site personnel will be trained and certified by Canfield Scientific Inc. on the use of the photographic equipment. Photographs will be performed at the time points given in Table 2. Photographs will be retained for research purposes, and will be assessed by an independent physician reviewer using the FWS.

Note: Patients may decline to have photographs taken during the conduct of the study. If a patient initially consents to photographs, then declines further photography, the Sponsor may use the photographs taken under consent for the purposes noted above.

Patients skin luminosity and brightness in the treated area will be evaluated by the physician. Skin luminosity is defined as the intensity of the light areas reflected on the treated areas of the face, while skin brightness is defined as the combined uniformity of skin coloring and skin texture. The visual evaluation of luminosity and brightness will be made using visual analogical scales that range from "no luminosity/brightness" (0) to "maximum luminosity/brightness/transparency" (10) (Musnier et al. 2004).

The physician will evaluate the degree of improvement in pore size reduction, according to the Global Aesthetic Improvement Scale (GAIS): (0=No Improvement, 1=≤25% Improvement [mild], Feb. 26, 1950% Improvement [moderate], 3=51-75% Improvement [good], 4=76-100% Improvement [excellent]). Sebum measurements will be taken from the central forehead using a.calibrated sebum measurement device Details of the procedures are provided in the DMT310-004 study manual. The physician will evaluate the degree of improvement in overall skin quality, according to the Global Aesthetic Improvement Scale (GAIS): (0=No Improvement, 1=≤25% Improvement [mild], Feb. 26, 1950% Improvement [moderate], 3=51-75% Improvement [good], 4-76-100% Improvement [excellent]).

Patients' eyelid laxity severity will be evaluated by the physician a 10-point FLRS as shown in Table 5 below. The FLRS will be performed at Screening, Days 1, 29, 57, 85 and Day 112/early exit. This is a static morphological scale that refers to a point in time and not a comparison to Baseline.

For each patient, investigator FLRS evaluations should be performed by the same trained evaluator throughout the study whenever possible. If it is not possible to use the same evaluator to follow the patient throughout the study, then evaluations should overlap between the evaluators (ie, examine the patient together and discuss findings) for at least 1 visit.

TABLE 5

Facial laxity rating scale.

| Score | Description |
| --- | --- |
| 0 | Absent |
| 1 | Perceivable |
| 2 | Well Defined |
| 3 | Partially Folding |
| 4 | Folding |
| 5 | Well-defined fold, still separated from eyelid border |
| 6 | Partially on eyelid border |
| 7 | Completely on eyelid border |
| 8 | Pushing eyelid border downward |
| 9 | Interfering with pupil |

The severity of patients' fine lines under the eye will be evaluated by the physician using a 5-point FWS as shown in Table 4. The FWS will be performed at Screening, Days 1, 29, 57, 85 and Day 112/early exit. This is a static morphological scale that refers to a point in time and not a comparison to Baseline.

For each patient, investigator FWS evaluations should be performed by the same trained evaluator throughout the study whenever possible. If it is not possible to use the same evaluator to follow the patient throughout the study, then evaluations should overlap between the evaluators (ie, examine the patient together and discuss findings) for at least 1 visit.

Description of Study Treatments

DMT310, contains Spongilla lacustris powder, and is used after addition of 0.9% Sodium Chloride for Injection USP. Patients will also receive BOTOX 64U applied topically. Blinding of the Investigational Product (IP) is not required as this is an open label study.

TABLE 6

Investigational products

| IP Name | DMT310 Topical Powder |
| --- | --- |
| Active Ingredient | 2 gm of Spongilla powder |
| Other Ingredients | 6 mL of 0.9% Sodium Chloride for Injection USP |
| IP Name | BOTOX ® (Botulinum Toxin Type A) Purified Neurotoxin Complex |
| Active Ingredient | 64 units (U) of Clostridium botulinum toxin Type A |
| Other Ingredients | 0.5 mg albumin (human), and 0.9 mg sodium chloride |

The IP will be applied to the face once on study day 1. The IP will be applied in the clinic at study day 1 by the study staff. After facial photographs have been taken, trained study staff will wash the patient's face with mild cleanser (eg, Cetaphil®) and water and then gently dry the area. Study staff will mix the liquid portion of the IP into the powder portion of the IP and then apply the IP to the upper face. Allow the IP to remain on the skin for approximately 10-15 minutes (until dry), then remove excess material from the patient's with face pre-moistened cleaning wipe (eg, Neutrogena® wipe) and then gently dry the area. Study staff will be provided with written information and trained on how to mix and apply the IP.

The patient should rest comfortably in the supine position prior for approximately 10-15 minutes before the reconstituted BOTOX is applied to the upper face, this 10-15 minutes includes the time the patient had DMT310 on the upper face. While the patient is resting in the supine position, the BOTOX vial should be reconstituted as instructed in the DMT310-004 Pharmacy Manual and in Appendix B: Preparation of BOTOX®. Reconstituted BOTOX 64U should be applied to the upper face as described in the Pharmacy Manual and massaged into the skin. in 0.2 ml increments until it is completely absorbed into the skin. Care should be taken to ensure that the reconstituted BOTOX does not come into contact with the eyes or mouth. The patient should remain in the supine position for approximately 15 minutes, then clean the patient's face with a pre-moistened cleaning wipe (eg, Neutrogena® wipe) and then gently dry the area. Dispose of all materials that have come into contact with BOTOX. Patients should not apply anything (eg, moisturizers, sunscreen, make-up) to the treatment area for the remainder of the day. Since this study requires only a single application of IP, dose modifications are highly unlikely. If a patient cannot tolerate or complete the day 1 study treatment, an additional patient may be enrolled at the discretion of the Sponsor.

The IPs are for topical use only. Care should be taken to avoid contact with eyes and all mucous membranes. If contact with eyes occurs, rinse thoroughly with water. Patients with a known sensitivity to any of the ingredients in the IP should not participate in this study. Should skin irritation or rash develop on the face, discontinue use. In case of accidental ingestion, patients should contact the investigator immediately. The effects of the IP in nursing mothers, pregnant women, and their unborn children are unknown. FCBP must not be pregnant or planning a pregnancy during the study period. The IP should be kept out of reach of children and pets. Refer to the BOTOX Package Insert for Warnings, Precautions and Contraindications.

On Day 1 of the study, (Baseline) before treatment, each patient who provides informed consent will be assigned a patient number that will serve as the patient identification number on all study documents. Before administering study treatment, the study staff must ensure the patient meets all eligibility criteria. The following will be provided by the Sponsor: Containers to mix DMT310; Pre-Moistened (eg, Neutrogena®) wipes. The study site will be responsible for providing the following supplies: Sterile saline (0.9%) USP for reconstitution of study medication; Needles and syringes for reconstitution of study medication; BOTOX® (botulinum toxin type A) 100 U vials; All supplies needed for urine pregnancy testing.

The DMT310 powder will be packaged and labeled in sealed packets. The IP will be identified as an investigational compound. The study number and lot number will be identified on the unit label. Commercially available 0.9% Sodium Chloride for Injection USP, and BOTOX 100U vials will be in their approved packaging and labeling. The IP must be stored in a secure area and administered only to patients entered into the clinical study, at no cost to the patient, in accordance with the conditions specified in this protocol. DMT310 powder must be stored in a secure area at a temperature not exceeding 30° C. Refer to the Study Reference Manual for guidelines on acceptable variances and instructions for reporting to the sponsor. Storage conditions at the clinical site will be documented. The BOTOX must be stored in a refrigerator at a temperature of between 2 and 80° C. Refer to the Pharmacy Manual for guidelines on acceptable variances and instructions for reporting to the sponsor. Reconstituted BOTOX must also be stored in a refrigerator between a temperature of 2° C. and 80° C. and is to be used within 4 hours following reconstitution. Storage conditions will be documented. If not used within 4 hours of reconstitution, study medication should be disposed of as described in DMT310-004 Pharmacy Manual.

The IP must be dispensed only to study patients and only at study sites specified on the form FDA 1572 by authorized personnel as required by applicable regulations and guidelines. The designee will review with the Investigator and relevant site personnel the process for investigational product return, disposal, and/or destruction. It is the responsibility of the investigator to ensure that a current record of IP disposition is maintained. The date of the IP application will be recorded on the appropriate CRF. Any changes from the application specified in the protocol (e.g., missed applications, investigator directed reduction in application time, etc.) will also be recorded on a CRF.

Concomitant Medications and Procedures

Current medications and any medications taken in the 28 days prior to the start of the study (Baseline) will be recorded as prior/concomitant medications with corresponding indication. The medications to be recorded include prescription and OTC medications, and vitamins, minerals, and dietary supplements being taken for a therapeutic indication. All medications taken on a regular basis should be recorded on the CRF prior to commencing the use of the IP.

Therapies (medication and non-medication therapies) not restricted by the protocol may be used during the study for the treatment or prevention of disease or to maintain good health. Non-prohibited chronic therapies being used at Baseline may be continued, but must be recorded.

Over the course of this study, additional medications may be required to manage aspects of the disease state of the patients, including side effects from trial treatments or disease progression. Supportive care may be administered at the discretion of the Investigator. Any changes to concomitant medications or therapies during the study must be recorded. The reason for any change in concomitant medications and/or therapies should be evaluated and, if appropriate, reported as, or in conjunction with, an AE.

Therapy considered necessary for the subject's welfare may be given at the discretion of the investigator. The subject's standard facial care hygiene (ie, moisturizers, skin creams, sunscreen), or dermatologic regimen should remain consistent throughout the study (ie, bleaching agents, hormone replacement therapy, prescription or over-the-counter products, and use of alpha hydroxy acid containing products). If the permissibility of a specific medication/treatment is in question, please contact the Sponsor.

No other facial cosmetic procedures are to be performed or new facial treatments started throughout the duration of the study. Prohibited facial treatments and procedures during study participation include, but are not limited to: Oral retinoids; New regimen or change in regimen of topical retinoid and/or hormone cream to the face; Microdermabrasion; Dermarollers or micro-needling; Laser surgery or resurfacing; Phototherapy to the face; Facial lift (mid or full face); Blepharoplasty; Synthetic implantation (eg, Gore-Tex®); Autologous fat transplantation; Dermal fillers; and Medium depth to deep facial chemical peels, periorbital surgery, and/or permanent make-up to the periorbital area (eg, eyeliner, eyebrow). Concurrent treatment with botulinum toxin of any serotype for any indication (other than the study treatment) is prohibited. Co-administration of aminoglycosides or other agents that could interfere with neuromuscular transmission (eg, curare-like agents) should only be used with caution as the effects of the toxin, theoretically, could be potentiated. The decision to administer a prohibited medication/treatment is done with the safety of the study participant as the primary consideration. When possible, the Sponsor should be notified before a prohibited medication/treatment is administered. Patients may not use any investigational drug or device treatments within 30 days of Baseline. Prior to attending study visits, subjects must not apply facial cosmetics.

If needed, any moisturizers used in the treatment area must be hypoallergenic, and oil-free. Patients will be instructed that they must refrain from: intensively scratching their body around the area of treatment, swimming for up to 8 hours following study medication application; and tattooing their skin or body piercings to the areas of study medication application.

Statistical Considerations

Summary tables (descriptive statistics and/or frequency tables) will be provided for screening variables, baseline variables, efficacy variables, and safety variables. Continuous variables will be described by descriptive statistics (n, mean, median, standard deviation, minimum, and maximum). Frequency counts and percentage of patients within each category will be provided for categorical data.

The Safety population will include all enrolled patients who received the IP. The intent-to-treat (ITT) population will include all randomized patients in the group to which they were randomized regardless of treatment received. The per-protocol (PP) population will consist of a subset of the ITT population including all randomized patients who completed the study with no significant protocol violations during the study that would affect the efficacy analyses. The PP population will be determined prior to database lock.

Approximately 10 patients will be entered into the study. Each patient will receive DMT310 mixed with 0.9% Sodium Chloride for Injection USP. DMT310 application will be followed by topical application of reconstituted BOTOX 64U. Thus, the sample size will be 10. This sample size was determined empirically for this proof of concept study and no hypothesis testing will be conducted. However, BOTOX has been shown to demonstrate a treatment response of up to 90% (BOTOX Package Insert), thus when the sample size is 10 per group, a two-sided 95.0% confidence interval for a single proportion using the large sample normal approximation will extend 0.186 from the observed proportion for an expected proportion of 0.900.

Demographic information including age, ethnicity, race, and Fitzpatrick skin phototype will be summarized by treatment group for each analysis population. Medical history entries will be provided in a patient listing for the Safety population. Abnormalities noted during the physical examination will be recorded on the medical history (at Screening or as AEs, if applicable, on Day 15, 29, 57, 85, 112). Descriptive statistics will be provided for vital signs (heart rate, respiration rate, blood pressure, and body temperature), height, and weight for the Safety population. Descriptive statistics will be provided for the FWS for the ITT and PP populations. The number and percent of patients who were enrolled in the study, in each analysis population, who completed the study, who withdrew from the study and their reasons for discontinuation will be tabulated.

The analysis of safety will be conducted on the Safety population. The safety endpoints of the study will be as follows:

Adverse Events: All TEAEs reported during the study will be listed, documenting onset, severity, whether therapy was required, any change in IP dosing, investigator assessment of the relationship to the IP, and outcome. AEs will be coded from the verbatim term using the Medical Dictionary for Regulatory Activities (MedDRA) and mapped to preferred terms (PT) and system organ class (SOC). All TEAEs will be summarized by the number of patients reporting AEs, SOC, PT, severity, and relationship to IP.

Local tolerability: Severity of local tolerability will be summarized by frequency at each study visit. Local tolerability will be collected independently of AEs. Only local tolerability reactions that require medical intervention (e.g., prescription medication) or require withholding of the study medication will be documented as AEs. Any local tolerability reactions that are not listed will be recorded as AEs.

Physical Exams: Findings from the physical examinations will be recorded in medical history (from assessment at Screening) or as AEs, if applicable, (from assessment at Day 15, 29, 57, 85, and 112).

Vital Signs: Vital signs will be summarized with descriptive statistics at all visits. Clinically significant changes in vital signs from Baseline will be documented.

Urine Pregnancy Tests: UPT results (if applicable) at Baseline and Day 29 will be listed.

Concomitant Medications/Therapies: Concomitant medications and therapies will be listed.

The analysis of efficacy will be conducted on the ITT and PP populations. Efficacy endpoints will include: Proportion of subjects achieving a grade of none or mild on the investigator's assessment of LCL severity at maximum smile at day 29, based on the FWS; Proportion of subjects achieving a grade of none or mild on the investigator's assessment of GL severity at maximum frown at day 29, based on the FWS; Proportion of subjects achieving a grade of none or mild on the patient's assessment of LCL severity at maximum smile at day 29, based on the FWS; Proportion of subjects achieving a grade of none or mild on the patient's assessment of GL severity at maximum frown at day 29, based on the FWS.

All efficacy analyses will be performed using both the ITT and PP populations. Continuous data will be summarized using descriptive statistics and categorical data will be analyzed by constructing a frequency distribution. A detailed statistical analysis plan will be generated and finalized prior to database lock. An interim analysis will be conducted once all patient data have been collected for the Day 29 visit.

Adverse Events

An AE is any noxious, unintended, or untoward medical occurrence that may appear or worsen in a patient during the course of a study. It may be a new intercurrent illness, a worsening concomitant illness, an injury, or any concomitant impairment of the patient's health, including laboratory test values, regardless of etiology. Any worsening (i.e., any clinically significant adverse change in the frequency or intensity of a pre-existing condition) should be considered an AE.

AEs should only be recorded by an investigator or by a health-care provider qualified by training and experience. Patients should be asked in an open-ended manner about the occurrence of AEs. All AEs, regardless of whether or not ascribed to the investigational product, should be recorded in the eCRF.

It is generally not necessary to record both a diagnosis and its associated symptoms and laboratory abnormalities. For example, if "acute renal failure" is recorded as an AE, "creatinine 5 mg/dL" need not be recorded.

If an AE necessitates a procedure, the description of the event (e.g., appendicitis) rather than the procedure (appendectomy) should be listed as the AE. However, if a procedure is performed for a reason other than an AE, the name of the procedure should be used as the name of the event. Concomitant procedures should always be listed on the concomitant procedure CRF.

Abuse, withdrawal, sensitivity, or toxicity to an investigational product should be reported as an AE. Overdose, accidental or intentional, whether or not it is associated with an AE should be reported on the CRF. Any sequela of an accidental or intentional overdose of an investigational product should be reported as an AE on the AE CRF. If the sequela of an overdose is a serious adverse event (SAE), then the sequela must be reported on an SAE report form and on the AE CRF. The overdose resulting in the SAE should be identified as the cause of the event on the SAE report form and CRF but should not be reported as an SAE itself.

In the event of overdose, the patient should be monitored as appropriate and should receive supportive measures as necessary. There is no known specific antidote for DMT310 overdose. Actual treatment should depend on the severity of the clinical situation and the judgment and experience of the treating physician.

All patients will be monitored for AEs during the study. Assessments may include monitoring of any or all of the following parameters: the patient's clinical symptoms, laboratory, pathological, radiological or surgical findings, physical examination findings, or findings from other tests and/or procedures.

All AEs will be recorded by the Investigator from the time the patient signs informed consent until 28 days after the last dose of IP, as well as those SAEs made known to the Investigator at any time thereafter that are suspected of being related to IP. AEs and SAEs will be recorded on the AE page of the CRF and in the patient's source documents. All SAEs must be reported to the Medical Monitor within 24 hours of the Investigator's knowledge of the event by facsimile, or other appropriate method, using the SAE Report Form, or approved equivalent form.

The site will contact patients via telephone or electronic communication 24 to 48 hours after treatment to assess any potential signs/symptoms of ocular/periocular adverse reactions and distant spread of botulinum toxin. Patients reporting a TEAE will have an in-person clinic visit scheduled to assess the event.

An adverse event (AE) is any unfavorable and unintended sign, symptom, or disease experienced by a study participant while in a clinical study, whether or not considered related to the investigational product. Examples include: reactions or side effects, a preexisting condition that worsens in severity or frequency, a concurrent illness, an injury, or a clinically significant laboratory abnormality.

A serious adverse event is an AE that meets at least one of the following criteria: Is fatal; Is life-threatening (A life-threatening AE is an AE that places the patient at immediate risk of death from the reaction as it occurred. It does not include a reaction that, had it occurred in a more severe form, might have caused death); Requires inpatient hospitalization or prolongs an existing hospitalization (excluding emergency room visits); Results in persistent or significant disability/incapacity; Is a congenital anomaly/birth defect in the offspring of an exposed patient; Other important medical events that may not result in death, be life-threatening or require hospitalization may be considered SAEs when, based upon appropriate medical judgment, they may jeopardize the patient and may require medical or surgical intervention to prevent one of the outcomes listed in this definition. Examples of such medical events include allergic bronchospasm requiring intensive treatment in an emergency room or at home, blood dyscrasias, or convulsions that do not result in inpatient hospitalization, or the development of drug dependency or drug abuse.

The onset date of an SAE is defined as the date on which it met the criteria for an SAE (e.g., the date of admission to a hospital). The end date is the date on which it no longer met the criteria for an SAE (e.g., the date that the patient was discharged from a hospital).

Events not considered to be SAEs are hospitalizations for: a procedure that is planned (i.e., planned prior to start of treatment on study); must be documented in the source document and the CRF. However, hospitalization or prolonged hospitalization for a complication remains a reportable SAE; an elective treatment of or an elective procedure for a pre-existing condition, unrelated to the studied indication, that has not worsened from baseline; or emergency outpatient treatment or observation that does not result in admission, unless fulfilling other seriousness criteria above.

If an AE is considered serious, both the AE page/screen of the CRF and the SAE Report Form must be completed. For each SAE, the Investigator will provide information on severity, start and stop dates, relationship to the IP, action taken regarding the IP, and outcome. For both AEs and SAEs, the Investigator must assess the severity/intensity of the event. The severity of an AE should be defined evaluated using the following guidelines: 1=Mild AE: Awareness of symptom, but easily tolerated; usually transient requiring no special treatment; does not interfere with usual status or activities; 2=Moderate AE: May be ameliorated by simple therapeutic measures; may interfere with usual activities; 3=Severe AE: Incapacitating, inability to perform usual activities; 4=Life threatening or disabling AE; 5=Fatal AE.

The Investigator must determine the relationship between the administration of the IP and the occurrence of an AE/SAE as Not Related or Related as defined below:

Not Related: a causal relationship of the adverse event to IP administration is unlikely or remote, or other medications, therapeutic interventions, or underlying conditions provide a sufficient explanation for the observed event.

Related: there is a reasonable possibility that the administration of IP caused the adverse event. 'Reasonable possibility' means there is evidence to suggest a causal relationship between the IP and the adverse event.

Causality should be assessed and provided for every AE/SAE based on currently available information. Causality is to be reassessed and provided as additional information becomes available.

For both AEs and SAEs, the Investigator will provide a record of the start and stop dates of the event. The Investigator will report the action taken with IP as a result of an AE or SAE, as applicable (e.g., discontinuation, interruption, or dose reduction of IP, as appropriate) and report if concomitant and/or additional treatments were given for the event. The Investigator will report the outcome of the event for both AEs and SAEs. All SAEs that have not resolved upon discontinuation of the patient's participation in the study must be followed until recovered (returned to baseline), recovered with sequelae, or death (due to the SAE). All pregnancies or suspected pregnancies occurring in a female patient of childbearing potential are immediately reportable events.

Pregnancies and suspected pregnancies (including elevated βhCG or positive pregnancy test in a FCBP regardless of disease state) occurring while the patient is on IP, or within 28 days of the patient's last dose of IP, are considered immediately reportable events once they become known by the site. If the patient suspects that she may be pregnant (e.g., missed or late menstrual period), the patient must contact the investigator immediately and discontinued treatment immediately. The pregnancy, suspected pregnancy, or positive pregnancy test must be reported to the Medical Monitor immediately by email, phone or facsimile, or other appropriate method, using the Pregnancy Initial Report Form, or approved equivalent form. If pregnancy is confirmed, the patient must not receive or apply further IP, must be discontinued from the study, and the patient may be referred to an obstetrician-gynecologist, preferably one experienced in reproductive toxicity for further evaluation and counseling.

The Investigator will follow the female patient until completion of the pregnancy, and must notify Drug Safety immediately about the outcome of the pregnancy (either normal or abnormal outcome) using the Pregnancy Follow-up Report Form, or approved equivalent form.

If the outcome of the pregnancy was abnormal (e.g., spontaneous abortion), the Investigator should report the abnormal outcome as an AE. If the abnormal outcome meets any of the serious criteria, it must be reported as an SAE to Medical Monitor by phone and followed by written notification with a copy to the study project manager (e.g. facsimile, email, or other appropriate method), within 24 hours of the Investigator's knowledge of the event using the SAE Report Form, or approved equivalent form.

All neonatal deaths that occur within 28 days of birth should be reported, without regard to causality, as SAEs. In addition, any infant death after 28 days that the Investigator suspects is related to the in utero exposure to the IP should also be reported to Medical Monitor by facsimile, or other appropriate method, within 24 hours of the Investigator's knowledge of the event using the SAE Report Form, or approved equivalent form.

Any AE that meets any criterion for an SAE requires the completion of an SAE Report Form in addition to being recorded on the AE page/screen of the eCRF. All SAEs must be reported to Medical Monitor within 24 hours of the Investigator's knowledge of the event by facsimile, or other appropriate method (e.g., via email), using the SAE Report Form, or approved equivalent form. This instruction pertains to initial SAE reports as well as any follow-up reports.

The Investigator is required to ensure that the data on these forms is accurate and consistent. This requirement applies to all SAEs (regardless of relationship to IP) that occur during the study (from the time the patient signs informed consent until 28 days after the last dose of IP) or any SAE made known to the Investigator at any time thereafter that are suspected of being related to IP. SAEs occurring prior to treatment (after signing the informed consent form [ICF]) will be captured.

The SAE report should provide a detailed description of the SAE and include a concise summary of hospital records and other relevant documents. If a patient died and an autopsy has been performed, copies of the autopsy report and death certificate are to be sent to Medical Monitor as soon as these become available. Any follow-up data should be detailed in a subsequent SAE Report Form, or approved equivalent form, and sent to Medical Monitor.

Where required by local legislation, the Investigator is responsible for informing the Institutional Review Board/ Ethics Committee (IRB/EC) of the SAE and providing them with all relevant initial and follow-up information about the event. The Investigator must keep copies of all SAE information on file including correspondence with Study Sponsor and the IRB/EC. Queries pertaining to SAEs will be communicated from Medical Monitor to the site via facsimile or electronic mail. The response time is expected to be no more than five (5) business days. Urgent queries (e.g., missing causality assessment) may be handled by phone.

For the purpose of regulatory reporting, the Medical Monitor will determine the expectedness of events suspected of being related to DMT310 based on the Investigator Brochure. In the United States, all suspected unexpected serious adverse reactions (SUSARs) will be reported in an expedited manner in accordance with 21 CFR 312.32. Study Sponsor or its authorized representative shall notify the Investigator of the following information: Any AE suspected of being related to the use of IP in this study or in other studies that is both serious and unexpected (i.e., SUSAR); Any finding from tests in laboratory animals that suggests a significant risk for human patients including reports of mutagenicity, teratogenicity, or carcinogenicity.

Where required by local legislation, the Investigator shall notify his/her IRB/EC promptly of these new serious and unexpected AE(s) or significant risks to patients. The Investigator must keep copies of all pertinent safety information on file including correspondence with Study Sponsor and the IRB/EC.

Discontinuations

The following events are considered sufficient reasons for discontinuing a patient from the investigational product(s): Adverse Event; Pregnancy; Withdrawal by patient; Death; Lost to follow-up; Other.

The reason for discontinuation of treatment should be recorded in the eCRF and in the source documents. The decision to discontinue a patient from treatment remains the responsibility of the treating physician, which will not be delayed or refused by the Sponsor. However, prior to discontinuing a patient, the Investigator may contact the Medical Monitor and forward appropriate supporting documents for review and discussion.

The following events are considered sufficient reasons for discontinuing a patient from the study: AE; Death; Lack of efficacy; Lost to follow-up; Noncompliance with study drug; Physician decision; Pregnancy; Progressive disease; Protocol deviation; Study terminated by Sponsor; Withdrawal by patient (note: if the patient decides to withdraw from the study due to an AE then it should be classified as withdrawal due to an AE); Other (e.g., any other reason that may affect the outcome of the study or the safety of the patients). The reason for study discontinuation should be recorded in the eCRF and in the source documents.

TABLE 7

Abbreviations and Special Terms

| Abbreviation or Specialist Term | Explanation |
|---|---|
| AE | Adverse event |
| β-hCG | β-subunit of human chorionic gonadotropin |
| CFR | Code of Federal Regulations |
| CLIA | Clinical laboratory improvement amendments |
| CRF | Case report form |
| CRO | Contract research organization |
| EC | Ethics Committee |
| EMA | European Medicines Agency |
| FCBP | Female of Childbearing Potential |
| FDA | Food and Drug Administration |
| FHL | Forehead Lines |
| FLRS | Facial Laxity Rating Scale |
| FWS | Facial Wrinkle Scale |
| GAIS | Global Aesthetic Improvement Scale |
| GCP | Good Clinical Practice |
| GL | Glabellar Lines |
| ICF | Informed consent form |
| ICH | International Conference on Harmonisation |
| IND | Investigational New Drug |
| IP | Investigational Product |
| IRB | Institutional Review Board |
| ITT | Intent-to-treat |
| LCL | Lateral Canthal Lines |
| MedDRA | Medical Dictionary for Regulatory Activities |
| μm | Micrometer |
| mL | Milliliter |
| ms | Milliseconds |
| OTC | Over-the-counter |
| PP | Per protocol |
| PT | Preferred term |
| SAE | Serious adverse event |
| SNAP-25 | Syaptosomal nerve-associated protein 25 |
| SOC | System organ class |
| SUSAR | Suspected unexpected serious adverse reactions |

US 12,629,331 B2

147

TABLE 7-continued

Abbreviations and Special Terms

| Abbreviation or Specialist Term | Explanation |
| --- | --- |
| TEAE | Treatment emergent adverse event |
| UPT | Urine pregnancy test |

Preparation of BOTOX®

100U BOTOX® vials will be reconstituted based on the following table:

TABLE 8

Preparation of BOTOX®

| Vial | Volume of saline (mL) added to vial to reconstitute IP | Concentration of BOTOX® (U/mL) in vial | Volume of reconstituted BOTOX® drawn into dosing syringe (mL) | Total volume of solution in dosing syringe(mL) | Final concentration in Dosing syringe (U/mL) | Dose per syringe (Units) | Total volume to be administered to each patient | Total dose to be administered to each patient |
| --- | --- | --- | --- | --- | --- | --- | --- | --- |
| 1 | 2.5 | 40 | 1.6 | 1.6 | 40 | 64 | 1.6 | 64 |

When reconstituting IP for each patient, sterile, preservative-free, normal saline should be added to the BOTOX® vial with a new 10-ml syringe. The vacuum within the vial will draw in the diluent. Do not use the vial if a vacuum is not observed. Once the diluent has been drawn into the vial, the vial should be rotated gently to mix the contents. The reconstituted study medication should be clear, colorless and free of particulate matter. A new 10-ml syringe should be used to withdraw the required solution from the study medication vial. This will be the dosing syringe. A detailed step-by-step process for BOTOX® reconstitution will be provided in the DMT310-004 Pharmacy Manual.

Protocol Amendment Summary

Protocol amendment summary #1, protocol number DMT310-004, protocol version 2.0, amendment number 01, amendment date Mar. 11, 2020. Summary of changes: 1) Added inclusion criterion to ensure patients agree to refrain from excessive activity for 24 hours post treatment; 2) Added a telephone contact 24 to 48 hours post treatment to assess potential ocular/periocular adverse events; 3) Included cranial nerve assessment to the directed physical exam and increased the frequency of the physical exam to every in-clinic visit.

REFERENCES FOR EXAMPLE 10

Each of the following references, and all others mentioned herein, is incorporated herein by reference in its entirety for all of it disclosure, and can be combined in whole or in part with the embodiments described herein for compounds, compositions, components, methods, etc.

Beer K, Comparative evaluation of the safety and efficacy of botulinum toxin type A and topical creams for treating moderate-to-severe glabellar rhytides. Dermatol Surg. 2006 February;32 (2): 184-97.

Blitzer A, Brin M F, Keen M S, Aviv J E. Botulinum toxin for the treatment of hyperfunctional lines of the face. Arch Otolaryngol Head Neck Surg. 1993; 119:1018-1022.

Brin M Fl, Boodhoo T I, Pogoda J M, James L M, Demos G, Terashima Y, Gu J, Eadie N, Bowen B L. Safety and tolerability of onabotulinumtoxinA in the treatment of facial lines: a meta-analysis of individual patient data from global clinical registration studies in 1678 participants. J Am Acad Dermatol. 2009 December;61 (6): 961-70.

Cox S E, Finn J C. Social implications of hyperdynamic facial lines and patient satisfaction outcomes. International ophthalmology clinics. 2005; 45:13-24.

Garcia A, Fulton J. Cosmetic Denervation of the Muscles of Facial Expression with Botulinum Toxin A Dose-Response Study. Serm Surg. 1996; 22 (1): 39-43.

Hambleton P. Clostridium botulinum toxins: a general review of involvement in disease, structure, mode of action and preparation for clinical use. J Neurol 1992; 239:16-20.

Khan J A. Aesthetic surgery: diagnosing and healing the miscues of human facial expression. Ophthalmic plastic and reconstructive surgery. 2001; 17:4-6.

Koblenzer C. The emotional impact of chronic and disabling skin disease: a psychoanalytic perspective. Dermatol Clin. 2005 October;23 (4): 619-27.

Musnier C, Piquemal P, Beau P, Pittet J C. Visual evaluation in vivo of complexion radiance using the CLBT sensory methodology. Skin Res Technol. 2004; 10:50-6.

Trussell J. Contraceptive Efficacy. In: Hatcher R A, Trussell J, Nelson A L, Cates W, Kowal D, Policar M, editors. Contraceptive Technology: Twentieth Revised Edition. New York NY: Ardent Media; 2011; p. 779-863.

Example 11: A Study of the Tolerability, Safety, and Efficacy of DMT410 for the Treatment of Upper Facial Lines This study utilized a unique natural platform technology with dual method of action. The platform is a Spongilla-derived platform, also referred to as DMT410. DMT410 is a powdered mixture that contains a unique variant of Spongilla lacustris, a freshwater sponge. DMT410 is comprised of inorganic siliceous spicules, which are about 200 µm in length and 15 µm in diameter. It is believed that the spicules penetrate the stratum corneum during application. DMT410 powder is mixed with 0.9% Sodium Chloride allowing for ease of topical application.

Figure 2:
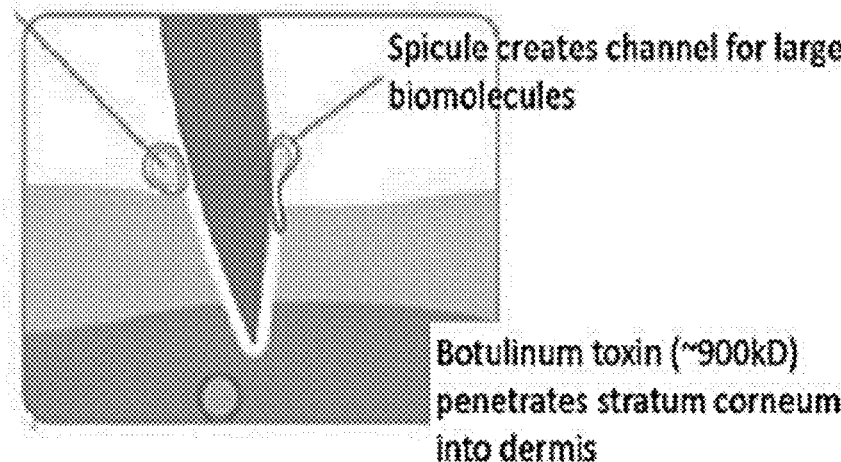
FIG. 2 is a schematic diagram of a spicule allowing for penetration of BOTOX past the stratum corneum into the dermis.

It is hypothesized that the spicules contained in the product will allow for penetration of botulinum toxin past the stratum corneum (see FIG. 2). It is thus postulated that DMT410 may be able to deliver botulinum toxin to the facial dermis and impact upper facial line severity as well as other aesthetic endpoints.

Study Design. Open-label, 1-arm study; subjects 18 and older with moderate to severe upper facial lines. One application of Spongilla mixture, followed by 1 topical application of 64 units of OnabotulinumtoxinA to the glabellar lines, lateral canthal lines, and forehead lines. Patients were assessed at 4 weeks, 8 weeks, 12 weeks, and 16 weeks post application.

Study Endpoints. Severity of glabellar, lateral canthal, and forehead lines; luminosity, brightness, pore size, sebum production; Investigator Global Aesthetic Improvement; laxity under the eye and fine lines under the eye. It is noted that one patient withdrew from study at the baseline visit prior to application of OnabotulinumtoxinA and thus is not included in the analysis. Table 1 below shows the demographics of study participants.

TABLE 1

Demographics.

|  | DMT410 (N = 10) N (%) |
| --- | --- |
| Sex-Female | 10 (100.0) |
| Race-White | 10 (100.0) |
| Ethnicity-Not Hispanic/Latino | 10 (100.0) |
| Age |  |
| Mean (range) | 57.2 (48-78) |
| Fitzpatrick Skin Type |  |
| Type I | 1 (10.0) |
| Type II | 2 (20.0) |
| Type III | 4 (40.0) |

TABLE 1-continued

Demographics.

|  | DMT410 (N = 10) N (%) |
| --- | --- |
| Type IV | 3 (30.0) |
| Type V | 0 (0.0) |
| Type VI | 0 (0.0) |

TABLE 2

Treatment Emergent Adverse Events.

| System Organ Class Preferred Term | DMT410 (N = 10) N (%) |
| --- | --- |
| Any Adverse Event | 0 (0.0) |
| Any Potential Distant Spread of Toxin Event | 0 (0.0) |
| General disorders and administration site conditions | 0 (0.0) |

FIGS. 3A-3D are graphs illustrating local tolerability of DMT410 at 15 minutes (FIG. 3A), 4 weeks (FIG. 3B), 8 weeks (FIG. 3C), and 12 weeks (FIG. 3D) after receiving a dose of DMT410. FIGS. 4A-4B are graphs illustrating mean improvement in skin brightness (FIG. 4A) and skin luminosity (FIG. 4B) over 112 days. Improvement ranged from 1 to 5 points. FIGS. 5A-5B are graphs illustrating mean improvement in pore size (FIG. 5A) and Global Aesthetic Score improvement. (FIG. 5B) over 112 days.

TABLE 3

Canfield VISIA Image Analysis Change from Baseline to Month 1.

| Measure | Forehead | | Left Temple | | Right Temple | |
| --- | --- | --- | --- | --- | --- | --- |
|  | Mean Change | Pct Change | Mean Change | Pct Change | Mean Change | Pct Change |
| Pore Count | −107.5 | −12.2% | −14.8 | −11.1% | −21.3 | −19.0% |
| Pore Area | −5.2 | −16.4% | −1.7 | −10.0% | −2.0 | −16.5% |
| Wrinkle Count | −12.2 | −11.6% | −3.2 | −18.9% | −3.4 | −19.0% |
| Wrinkle Area | −11.7 | −7.0% | −4.1 | −13.5% | −5.1 | −14.1% |

TABLE 4

Canfield PRIMOS Image Analysis Change from Baseline to Month 1.

| Measure (mm²) | Forehead | | Glabella | | Left Oblique | | Right Oblique[1] | |
| --- | --- | --- | --- | --- | --- | --- | --- | --- |
|  | Mean Change | Pct Change | Mean Change | Pct Change | Mean Change | Pct Change | Mean Change | Pct Change |
| Mean Line | −1.8 | −3.4% | −2.8 | −3.9% | −23.0 | −14.7% | −20.5 | −14.3% |
| Mean Roughness | −1.4 | −5.1% | −2.7 | −7.2% | −4.0 | −5.8% | −4.2 | −7.9% |

Figures 7A, 7B:
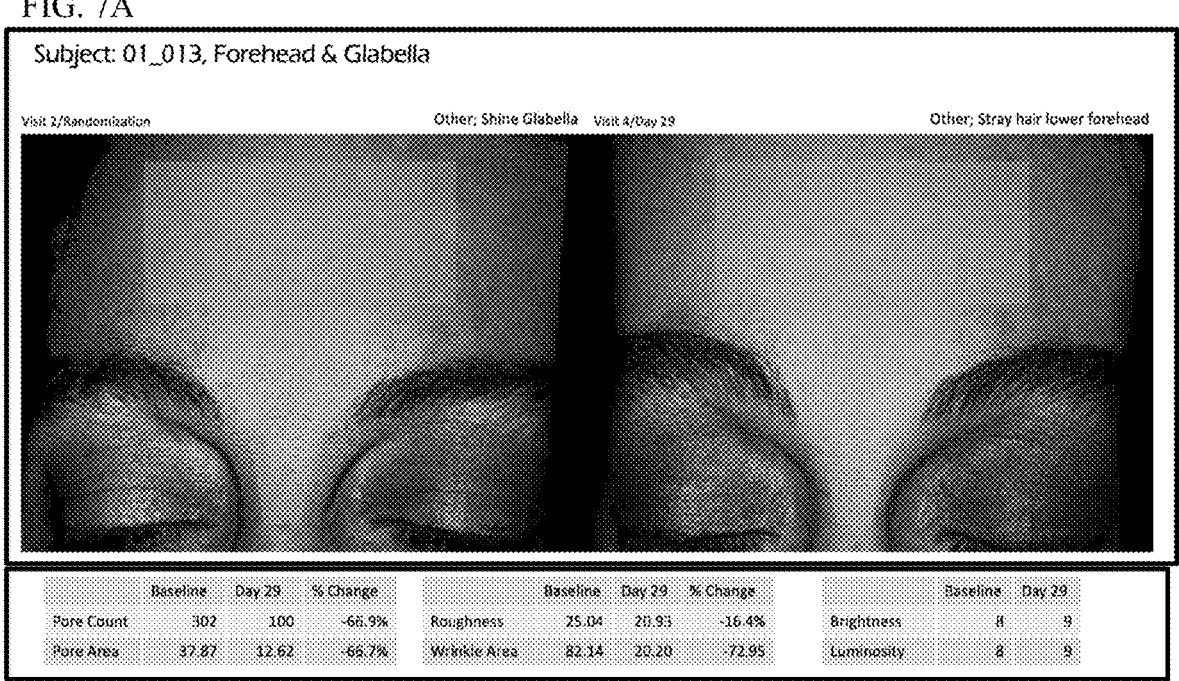
FIGS. 7A-7B are images (FIG. 7A) and tables (FIG. 7B) illustrating changes in pore count and area (FIG. 7B, left), skin roughness and wrinkle area (FIG. 7B, center), and skin brightness and luminosity (FIG. 7B, right), at a second visit (FIG. 7A, left panel) and a fourth visit (FIG. 7A, right panel) for treatment with compounds and formulations consistent with the present disclosure.
Figures 8A, 8B:
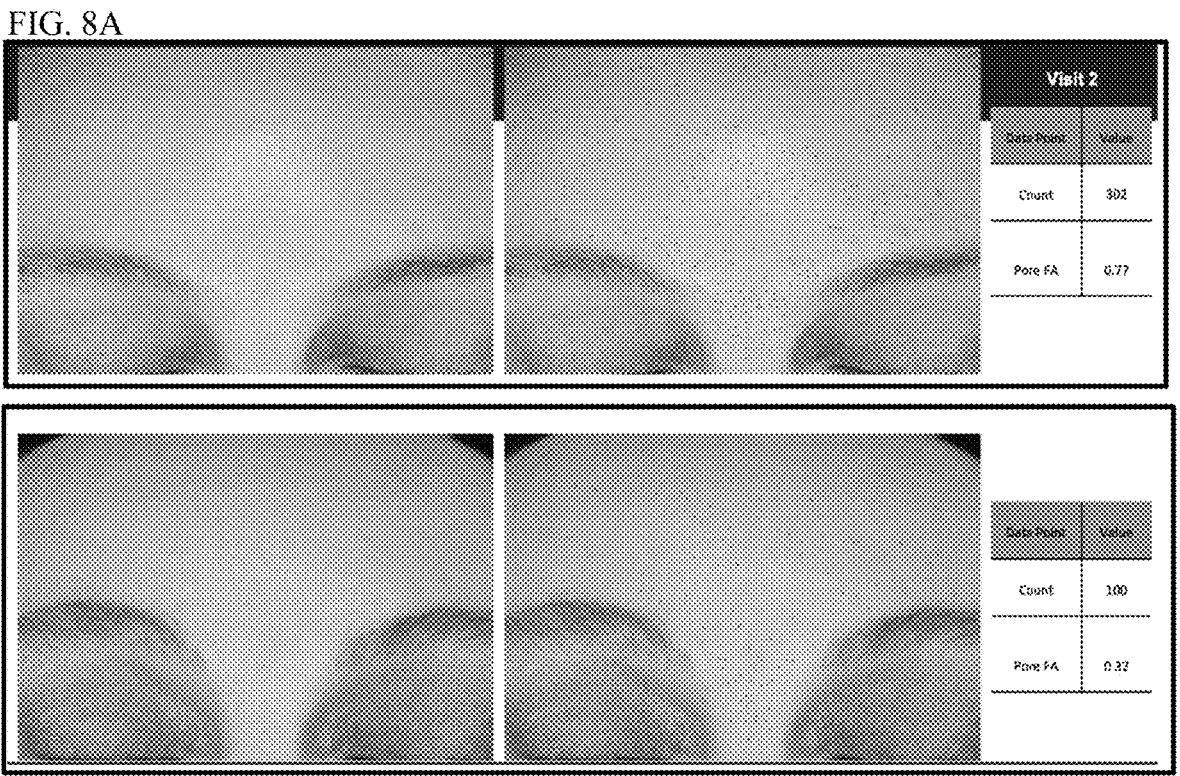
FIGS. 8A-8B are images and tables illustrating pore analysis at a second visit (FIG. 8A) and a fourth visit (FIG. 8B) for treatment with compounds and formulations consistent with the present disclosure.

FIGS. 6A-6B are images of study Subject 01_005, right lateral canthus. Wrinkle area and wrinkle count are tabulated at the bottom of the images. Scale for measurements 1-5 is given at the top right. FIG. 7A are images of study Subject 01_013, forehead and *glabella*. The tables of FIG. 7B show baseline and day 29 values, as well as percent change, for study parameters of pore count, pore area, skin roughness, and wrinkle area. Baseline and day 29 values are given for skin brightness and luminosity. FIGS. 8A-8B are images of a study Subject for pore analysis. Data points and values are given on the rightmost side of FIGS. 8A-8B.

Study Conclusions. DMT410 treatment appeared to be well tolerated and produced no potential distant spread of toxin adverse events. DMT410 treatment had a minimal effect on upper facial line improvement, suggesting most of the toxin remained in the dermis. Most patients demonstrated improvements in skin quality endpoints (e.g., brightness, luminosity and pore size) which peaked approximately 2-3 months after treatment. These results support the use of DMT410 and for skin quality improvement, including with regimens and doses that differ from those disclosed herein.

The invention claimed is:

1. A topical pharmaceutical composition for topically administering and treating hyperhidrosis in a subject in need thereof, comprising a combination comprising a first topical pharmaceutical composition and a second topical pharmaceutical composition, wherein (a) the first topical pharmaceutical composition comprises Spongilla particles, the particles consisting of Spongilla spicules having an aspect ratio of from 10 to 70, an average length of about 200 μm to about 350 μm, and an average diameter of about 5 μm to about 20 μm, wherein the Spongilla particles are irradiated and are manufactured from Spongilla *lacustris*; and (b) the second topical pharmaceutical composition comprises a topical formulation of one or more botulinum toxin complexes and optionally an excipient; wherein the topical pharmaceutical composition is formulated for treating hyperhidrosis in a subject in need thereof, and wherein the first and second topical pharmaceutical compositions are combined and in contact with each other.

2. The pharmaceutical composition according to claim 1, wherein the one or more botulinum toxin complexes are selected from botulinum toxin type A, botulinum toxin type B, botulinum toxin type C1, botulinum toxin type C2, botulinum toxin type D, botulinum toxin type E, botulinum toxin type F and botulinum toxin type G.

3. The pharmaceutical composition according to claim 2, wherein the one or more botulinum toxin complexes is botulinum toxin type A.

4. The pharmaceutical composition according to claim 3, wherein the botulinum toxin type A is onabotulinumtoxinA.

5. A kit, comprising a combination comprising a first topical pharmaceutical composition and a second topical pharmaceutical composition, wherein:
(a) the first topical pharmaceutical composition comprises Spongilla particles, the particles consisting of Spongilla spicules having an aspect ratio of from 10 to 70, an average length of about 200 μm to about 350 μm, and an average diameter of about 5 μm to about 20 μm, wherein the Spongilla particles are irradiated and are manufactured from Spongilla *lacustris*; and
(b) the second topical pharmaceutical composition comprises one or more botulinum toxin complexes and optionally an excipient;
wherein the topical pharmaceutical compositions are is formulated for treating hyperhidrosis in a subject in need thereof.

6. The kit according to claim 5, wherein the second topical pharmaceutical composition comprises an excipient and the topical pharmaceutical compositions are further formulated for use in the treatment of a subject having one or more of luminosity, brightness, skin pore size, skin pore count, sebum production, sebum composition, overall skin quality, eyelid laxity, fine lines under the eye, fine lines on the face, laxity on the face, perioral rhytids, moderate to severe facial folds and wrinkles such as nasolabial folds, moderate to severe facial wrinkles such as smile lines or marionette lines, age-related midface contour deficiencies, dorsal hand to correct volume deficit, glabellar lines, correction of facila depressions, either due to injury or age-related, perioral wrinkles, lip commissures, crow's feet, facial rhytides, and forehead wrinkles.

7. The kit according to claim 5, wherein the one or more botulinum toxin complexes is selected from botulinum toxin type A, botulinum toxin type B, botulinum toxin type C1, botulinum toxin type C2, botulinum toxin type D, botulinum toxin type E, botulinum toxin type F and botulinum toxin type G.

8. The kit according to claim 5, wherein the one or more botulinum toxin complexes is onabotulinumtoxinA.

9. The pharmaceutical composition of claim 1, wherein the first topical pharmaceutical composition comprises from about 0.25 grams to about 10 grams Spongilla.

10. The pharmaceutical composition of claim 1, wherein the second topical pharmaceutical composition comprises from about 1 potency units to about 400 potency units botulinum toxin.

11. The pharmaceutical composition of claim 1, wherein the first topical pharmaceutical composition comprises from about 0.25 grams to about 10 grams Spongilla, and the second topical pharmaceutical composition comprises from about 50 potency units to about 100 potency units botulinum toxin.

12. The pharmaceutical composition of claim 11, wherein the first topical pharmaceutical composition comprises about 2 grams Spongilla, and the second topical pharmaceutical composition comprises about 64 potency units botulinum toxin.

13. The pharmaceutical composition of claim 1, wherein the second topical pharmaceutical composition comprises from about 50 potency units to about 100 potency units botulinum toxin.

* * * * *